US008791066B2

(12) United States Patent
DeFrees

(10) Patent No.: US 8,791,066 B2
(45) Date of Patent: Jul. 29, 2014

(54) BRANCHED PEG REMODELING AND GLYCOSYLATION OF GLUCAGON-LIKE PEPTIDE-1 [GLP-1]

(75) Inventor: Shawn DeFrees, North Wales, PA (US)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/541,185

(22) Filed: Jul. 3, 2012

(65) Prior Publication Data

US 2013/0059780 A1  Mar. 7, 2013

Related U.S. Application Data

(63) Continuation of application No. 11/632,005, filed as application No. PCT/US2005/024781 on Jul. 13, 2005, now abandoned.

(60) Provisional application No. 60/587,738, filed on Jul. 13, 2004, provisional application No. 60/608,723, filed on Sep. 10, 2004.

(51) Int. Cl.
*A61P 3/10* (2006.01)
*A61P 7/12* (2006.01)

(52) U.S. Cl.
USPC .......................................... 514/7.2

(58) Field of Classification Search
None
See application file for complete search history.

(56) References Cited

U.S. PATENT DOCUMENTS

| | | | |
|---|---|---|---|
| 4,055,635 A | 10/1977 | Green et al. |
| 4,088,538 A | 5/1978 | Schneider |
| 4,179,337 A | 12/1979 | Davis et al. |
| 4,385,260 A | 5/1983 | Watts |
| 4,412,989 A | 11/1983 | Iwashita et al. |
| 4,414,147 A | 11/1983 | Klibanov et al. |
| 4,438,253 A | 3/1984 | Casey et al. |
| 4,451,566 A | 5/1984 | Spencer |
| 4,496,689 A | 1/1985 | Mitra |
| 4,565,653 A | 1/1986 | Ives et al. |
| 4,675,414 A | 6/1987 | DeFusco et al. |
| 4,767,702 A | 8/1988 | Cohenford |
| 4,806,595 A | 2/1989 | Noishiki et al. |
| 4,826,945 A | 5/1989 | Cohn et al. |
| 4,847,325 A | 7/1989 | Shadle et al. |
| 4,879,236 A | 11/1989 | Smith et al. |
| 4,918,009 A | 4/1990 | Nilsson |
| 4,925,796 A | 5/1990 | Bergh et al. |
| 4,980,502 A | 12/1990 | Felder et al. |
| 5,032,519 A | 7/1991 | Paulson et al. |
| 5,047,335 A | 9/1991 | Paulson et al. |
| 5,104,651 A | 4/1992 | Boone et al. |
| 5,122,614 A | 6/1992 | Zalipsky |
| 5,147,788 A | 9/1992 | Page et al. |
| 5,153,265 A | 10/1992 | Shadle et al. |
| 5,154,924 A | 10/1992 | Friden |
| 5,164,374 A | 11/1992 | Rademacher et al. |
| 5,166,322 A | 11/1992 | Shaw et al. |
| 5,169,933 A | 12/1992 | Anderson et al. |
| 5,180,674 A | 1/1993 | Roth |
| 5,182,107 A | 1/1993 | Friden |
| 5,194,376 A | 3/1993 | Kang |
| 5,202,413 A | 4/1993 | Spinu |
| 5,206,344 A | 4/1993 | Katre et al. |
| 5,219,564 A | 6/1993 | Zalipsky et al. |
| 5,272,066 A | 12/1993 | Bergh et al. |
| 5,278,299 A | 1/1994 | Wong et al. |
| 5,281,698 A | 1/1994 | Nitecki |
| 5,288,637 A | 2/1994 | Roth |
| 5,308,460 A | 5/1994 | Mazid et al. |
| 5,324,663 A | 6/1994 | Lowe |
| 5,324,844 A | 6/1994 | Zalipsky |
| 5,342,940 A | 8/1994 | Ono et al. |
| 5,346,696 A | 9/1994 | Kim et al. |
| 5,352,670 A | 10/1994 | Venot et al. |
| 5,369,017 A | 11/1994 | Wong et al. |
| 5,374,541 A | 12/1994 | Wong et al. |
| 5,374,655 A | 12/1994 | Kashem et al. |
| 5,384,249 A | 1/1995 | Sasaki et al. |
| 5,399,345 A | 3/1995 | Schumacher et al. |
| 5,405,753 A | 4/1995 | Brossmer et al. |
| 5,409,817 A | 4/1995 | Ito et al. |
| 5,410,016 A | 4/1995 | Hubbell et al. |
| 5,432,059 A | 7/1995 | Bean et al. |
| 5,446,090 A | 8/1995 | Harris |

(Continued)

FOREIGN PATENT DOCUMENTS

AU  1991/083760 A  3/1992
AU  1992/017052    12/1992

(Continued)

OTHER PUBLICATIONS

Office Action dated Sep. 20, 1994 in U.S. Appl. No. 08/215,727.
Office Action dated May 4, 1995 in U.S. Appl. No. 08/102,385.
Office Action dated Jun. 7, 1995 in U.S. Appl. No. 08/215,727.
Office Action dated Apr. 5, 1996 in U.S. Appl. No. 08/102,385.
Office Action dated Jun. 23, 1996 in U.S Appl. No. 08/447,435.
Office Action dated Jun. 28, 1996 in U.S. Appl. No. 08/447,783.
Office Action dated Aug. 28, 1996 in U.S. Appl. No. 08/478,140.
Office Action dated Oct. 15, 1996 in U.S. Appl. No. 08/102,385.
Office Action dated Feb. 24, 1997 in U.S. Appl. No. 08/447,435.
Office Action dated Feb. 24, 1997 in U.S. Appl. No. 08/447,783.
Office Action dated Apr. 12, 1997 in U.S. Appl. No. 08/215,727.
Office Action dated Jul. 23, 1997 in U.S. Appl. No. 08/102,385.

(Continued)

*Primary Examiner* — Thomas Heard
(74) *Attorney, Agent, or Firm* — Leydig, Voit & Mayer, Ltd.

(57) ABSTRACT

The present invention provides polypeptides that include an O-linked glycoconjugate in which a species such as a water-soluble polymer, a therapeutic agent of a biomolecule is covalently linked through an intact O-linked glycosyl residue to the polypeptide. The polypeptides of the invention include wild-type peptides and mutant peptides that include an O-linked glycosylation site that is not present in the wild-type peptide. Also provided are methods of making the peptides of the invention and methods, pharmaceutical compositions containing the peptides and methods of treating, ameliorating or preventing diseased in mammals by administering an amount of a peptide of the invention sufficient to achieve the desired response.

17 Claims, 1 Drawing Sheet

(56) References Cited

U.S. PATENT DOCUMENTS

| | | | |
|---|---|---|---|
| 5,492,821 | A | 2/1996 | Callstrom et al. |
| 5,492,841 | A | 2/1996 | Craig |
| 5,527,527 | A | 6/1996 | Friden |
| 5,529,914 | A | 6/1996 | Hubbell et al. |
| 5,545,553 | A | 8/1996 | Gotschlich |
| 5,567,422 | A | 10/1996 | Greenwald |
| 5,583,042 | A | 12/1996 | Roth |
| 5,595,900 | A | 1/1997 | Lowe |
| 5,605,793 | A | 2/1997 | Stemmer |
| 5,614,184 | A | 3/1997 | Sytkowski et al. |
| 5,621,039 | A | 4/1997 | Hallahan et al. |
| 5,629,384 | A | 5/1997 | Veronese et al. |
| 5,635,603 | A | 6/1997 | Hansen et al. |
| 5,643,575 | A | 7/1997 | Martinez et al. |
| 5,646,113 | A | 7/1997 | Attie et al. |
| 5,672,662 | A | 9/1997 | Harris et al. |
| 5,672,683 | A | 9/1997 | Friden et al. |
| 5,705,367 | A | 1/1998 | Gotschlich |
| 5,714,166 | A | 2/1998 | Tomalia et al. |
| 5,716,812 | A | 2/1998 | Withers et al. |
| 5,723,121 | A | 3/1998 | Takenaga et al. |
| 5,728,554 | A | 3/1998 | Bayer et al. |
| 5,739,208 | A | 4/1998 | Harris |
| 5,762,920 | A | 6/1998 | Yung et al. |
| 5,770,420 | A | 6/1998 | Lowe et al. |
| 5,798,233 | A | 8/1998 | Gotschlich |
| 5,811,238 | A | 9/1998 | Stemmer et al. |
| 5,824,778 | A | 10/1998 | Ishikawa et al. |
| 5,824,864 | A | 10/1998 | Fox et al. |
| 5,830,721 | A | 11/1998 | Stemmer et al. |
| 5,833,988 | A | 11/1998 | Friden |
| 5,834,251 | A | 11/1998 | Maras et al. |
| 5,837,458 | A | 11/1998 | Minshull et al. |
| 5,849,535 | A | 12/1998 | Cunningham et al. |
| 5,858,751 | A | 1/1999 | Paulson et al. |
| 5,858,752 | A | 1/1999 | Seed et al. |
| 5,861,374 | A | 1/1999 | Berkner et al. |
| 5,874,075 | A | 2/1999 | Collins et al. |
| 5,876,980 | A | 3/1999 | DeFrees et al. |
| 5,922,577 | A | 7/1999 | DeFrees et al. |
| 5,925,739 | A | 7/1999 | Spira et al. |
| 5,932,462 | A | 8/1999 | Harris et al. |
| 5,945,314 | A | 8/1999 | Prieto et al. |
| 5,945,322 | A | 8/1999 | Gotschlich |
| 5,955,347 | A | 9/1999 | Lowe |
| 5,962,294 | A | 10/1999 | Paulson et al. |
| 5,969,040 | A | 10/1999 | Hallahan et al. |
| 5,977,307 | A | 11/1999 | Friden et al. |
| 6,010,999 | A | 1/2000 | Daley et al. |
| 6,015,555 | A | 1/2000 | Friden |
| 6,030,815 | A | 2/2000 | DeFrees et al. |
| 6,034,223 | A | 3/2000 | Maddon et al. |
| 6,037,452 | A | 3/2000 | Minamino et al. |
| 6,048,720 | A | 4/2000 | Dalborg et al. |
| 6,057,292 | A | 5/2000 | Cunningham et al. |
| 6,075,134 | A | 6/2000 | Bertozzi et al. |
| 6,087,325 | A | 7/2000 | Meers et al. |
| 6,096,512 | A | 8/2000 | Elhammer et al. |
| 6,113,906 | A | 9/2000 | Greenwald et al. |
| 6,117,651 | A | 9/2000 | Schultz et al. |
| 6,127,153 | A | 10/2000 | Johnson et al. |
| 6,166,183 | A | 12/2000 | Ishikawa et al. |
| 6,183,738 | B1 | 2/2001 | Clark |
| 6,251,864 | B1 | 6/2001 | Dower et al. |
| 6,261,805 | B1 | 7/2001 | Wood |
| 6,268,193 | B1 | 7/2001 | Lowe |
| 6,319,695 | B1 | 11/2001 | Wong et al. |
| 6,340,742 | B1 | 1/2002 | Burg et al. |
| 6,342,382 | B1 | 1/2002 | Gotschlich |
| 6,348,558 | B1 | 2/2002 | Harris et al. |
| 6,361,977 | B1 | 3/2002 | Bauer et al. |
| 6,362,254 | B2 | 3/2002 | Harris et al. |
| 6,376,604 | B2 | 4/2002 | Kozlowski |
| 6,399,336 | B1 | 6/2002 | Paulson et al. |
| 6,399,337 | B1 | 6/2002 | Taylor et al. |
| 6,440,703 | B1 | 8/2002 | DeFrees |
| 6,458,937 | B1 | 10/2002 | Bertozzi et al. |
| 6,465,220 | B1 | 10/2002 | Hassan et al. |
| 6,495,365 | B1 | 12/2002 | Saito et al. |
| 6,531,121 | B2 | 3/2003 | Brines et al. |
| 6,555,346 | B1 | 4/2003 | Kretzdorn et al. |
| 6,555,660 | B2 | 4/2003 | Nissen et al. |
| 6,586,398 | B1 | 7/2003 | Kinstler et al. |
| 6,692,931 | B1 | 2/2004 | Reutter et al. |
| 6,693,183 | B2 | 2/2004 | Natsuka et al. |
| 6,716,626 | B1 | 4/2004 | Itoh et al. |
| 6,743,896 | B2 | 6/2004 | Filpula et al. |
| 6,780,624 | B2 | 8/2004 | Gotschlich |
| 6,800,740 | B1 | 10/2004 | Cunningham et al. |
| 6,949,372 | B2 | 9/2005 | Betenbaugh et al. |
| 7,094,530 | B1 | 8/2006 | Sasaki et al. |
| 7,125,843 | B2 | 10/2006 | DeFrees et al. |
| 7,138,371 | B2 | 11/2006 | DeFrees et al. |
| 7,157,277 | B2 | 1/2007 | DeFrees et al. |
| 7,173,003 | B2 | 2/2007 | DeFrees et al. |
| 7,179,617 | B2 | 2/2007 | DeFrees et al. |
| 7,199,223 | B2 | 4/2007 | Bossard et al. |
| 7,202,208 | B2 | 4/2007 | Papadimitriou |
| 7,214,660 | B2 | 5/2007 | DeFrees et al. |
| 7,226,903 | B2 | 6/2007 | DeFrees et al. |
| 7,229,962 | B2 | 6/2007 | Chung et al. |
| 7,235,638 | B2 | 6/2007 | Persson |
| 7,265,084 | B2 | 9/2007 | DeFrees et al. |
| 7,265,085 | B2 | 9/2007 | DeFrees et al. |
| 7,276,475 | B2 | 10/2007 | DeFrees et al. |
| 7,297,511 | B2 | 11/2007 | DeFrees et al. |
| 7,304,150 | B1 | 12/2007 | Egrie et al. |
| 7,338,933 | B2 | 3/2008 | DeFrees et al. |
| 7,368,108 | B2 | 5/2008 | DeFrees et al. |
| 7,399,613 | B2 | 7/2008 | DeFrees et al. |
| 7,405,198 | B2 | 7/2008 | DeFrees et al. |
| 7,416,858 | B2 | 8/2008 | DeFrees et al. |
| 7,439,043 | B2 | 10/2008 | DeFrees et al. |
| 7,473,680 | B2 | 1/2009 | DeFrees et al. |
| 7,524,813 | B2 | 4/2009 | Zundel et al. |
| 7,662,933 | B2 | 2/2010 | Kinstler et al. |
| 7,691,603 | B2 | 4/2010 | DeFrees |
| 7,696,163 | B2 | 4/2010 | DeFrees et al. |
| 7,795,210 | B2 | 9/2010 | DeFrees et al. |
| 7,803,777 | B2 | 9/2010 | DeFrees |
| 7,842,661 | B2 | 11/2010 | DeFrees et al. |
| 7,932,364 | B2 | 4/2011 | DeFrees et al. |
| 7,956,032 | B2 | 6/2011 | DeFrees et al. |
| 8,008,252 | B2 | 8/2011 | DeFrees et al. |
| 8,063,015 | B2 | 11/2011 | DeFrees et al. |
| 8,207,112 | B2 | 6/2012 | Hinderer et al. |
| 8,247,381 | B2 | 8/2012 | DeFrees |
| 8,268,967 | B2 | 9/2012 | DeFrees et al. |
| 8,361,961 | B2 | 1/2013 | DeFrees et al. |
| 8,633,157 | B2 | 1/2014 | DeFrees et al. |
| 2001/0041683 | A1 | 11/2001 | Schmitz et al. |
| 2001/0043929 | A1 | 11/2001 | Zalipsky et al. |
| 2002/0004483 | A1 | 1/2002 | Nissen et al. |
| 2002/0016003 | A1 | 2/2002 | Saxon et al. |
| 2002/0019342 | A1 | 2/2002 | Bayer |
| 2002/0037841 | A1 | 3/2002 | Papadimitriou |
| 2002/0068347 | A1 | 6/2002 | Taylor et al. |
| 2002/0115833 | A1 | 8/2002 | Burg et al. |
| 2002/0137134 | A1 | 9/2002 | Gerngross et al. |
| 2002/0142370 | A1 | 10/2002 | Paulson et al. |
| 2002/0142964 | A1 | 10/2002 | Nissen et al. |
| 2002/0148791 | A1 | 10/2002 | DeFrees |
| 2002/0150981 | A1 | 10/2002 | Canfield |
| 2002/0168323 | A1 | 11/2002 | Gonda |
| 2002/0182586 | A1 | 12/2002 | Morris et al. |
| 2003/0027257 | A1 | 2/2003 | Iatrou et al. |
| 2003/0040037 | A1 | 2/2003 | Bayer |
| 2003/0083251 | A1 | 5/2003 | Westenfelder |
| 2003/0096338 | A1 | 5/2003 | Pedersen et al. |
| 2003/0100075 | A1 | 5/2003 | Persson et al. |
| 2003/0119090 | A1 | 6/2003 | Wong |
| 2003/0124645 | A1 | 7/2003 | Paulson et al. |
| 2003/0166212 | A1 | 9/2003 | Taylor et al. |
| 2003/0166525 | A1 | 9/2003 | Hoffmann et al. |

(56) References Cited

U.S. PATENT DOCUMENTS

| | | |
|---|---|---|
| 2003/0170863 A1 | 9/2003 | Persson et al. |
| 2003/0180835 A1 | 9/2003 | Bayer |
| 2003/0186850 A1 | 10/2003 | Clausen et al. |
| 2003/0195338 A1 | 10/2003 | Chung et al. |
| 2003/0207406 A1 | 11/2003 | Johnson et al. |
| 2004/0020857 A1 | 2/2004 | Belew et al. |
| 2004/0043446 A1 | 3/2004 | DeFrees et al. |
| 2004/0063911 A1 | 4/2004 | DeFrees et al. |
| 2004/0077836 A1 | 4/2004 | DeFrees et al. |
| 2004/0082026 A1 | 4/2004 | DeFrees et al. |
| 2004/0102607 A1 | 5/2004 | Danishefsky et al. |
| 2004/0115168 A1 | 6/2004 | DeFrees et al. |
| 2004/0126838 A1 | 7/2004 | DeFrees et al. |
| 2004/0132640 A1 | 7/2004 | DeFrees et al. |
| 2004/0136955 A1 | 7/2004 | Barker et al. |
| 2004/0137557 A1 | 7/2004 | DeFrees et al. |
| 2004/0142856 A1 | 7/2004 | DeFrees et al. |
| 2004/0197875 A1 | 10/2004 | Hauser et al. |
| 2005/0026266 A1 | 2/2005 | Clausen et al. |
| 2005/0031584 A1 | 2/2005 | DeFrees et al. |
| 2005/0064540 A1 | 3/2005 | DeFrees et al. |
| 2005/0085631 A1 | 4/2005 | Boyle et al. |
| 2005/0100982 A1 | 5/2005 | DeFrees et al. |
| 2005/0106658 A1 | 5/2005 | DeFrees et al. |
| 2005/0113565 A1 | 5/2005 | Klausen et al. |
| 2005/0118672 A1 | 6/2005 | DeFrees et al. |
| 2005/0143292 A1 | 6/2005 | DeFrees et al. |
| 2005/0250678 A1 | 11/2005 | DeFrees et al. |
| 2005/0269265 A1 | 12/2005 | DeFrees |
| 2005/0271690 A1 | 12/2005 | Gotschlich |
| 2005/0288490 A1 | 12/2005 | Nakamoto et al. |
| 2006/0024286 A1 | 2/2006 | Glidden |
| 2006/0029573 A1 | 2/2006 | Shen et al. |
| 2006/0030521 A1 | 2/2006 | DeFrees et al. |
| 2006/0035224 A1 | 2/2006 | Johansen |
| 2006/0040856 A1 | 2/2006 | DeFrees et al. |
| 2006/0088906 A1 | 4/2006 | DeFrees et al. |
| 2006/0111279 A1 | 5/2006 | DeFrees et al. |
| 2006/0165728 A1 | 7/2006 | Young et al. |
| 2006/0177892 A1 | 8/2006 | DeFrees |
| 2006/0182714 A1 | 8/2006 | Behrens et al. |
| 2006/0183198 A1 | 8/2006 | Buechler et al. |
| 2006/0246544 A1 | 11/2006 | Kang et al. |
| 2006/0276618 A1 | 12/2006 | DeFrees et al. |
| 2006/0287223 A1 | 12/2006 | DeFrees et al. |
| 2006/0287224 A1 | 12/2006 | DeFrees et al. |
| 2007/0014759 A1 | 1/2007 | DeFrees et al. |
| 2007/0026485 A1 | 2/2007 | DeFrees et al. |
| 2007/0027068 A1 | 2/2007 | DeFrees et al. |
| 2007/0032405 A1 | 2/2007 | DeFrees et al. |
| 2007/0037966 A1 | 2/2007 | Rasmussen et al. |
| 2007/0042458 A1 | 2/2007 | DeFrees et al. |
| 2007/0059275 A1 | 3/2007 | DeFrees et al. |
| 2007/0105755 A1 | 5/2007 | DeFrees et al. |
| 2007/0111926 A1 | 5/2007 | Zundel et al. |
| 2007/0154992 A1 | 7/2007 | DeFrees |
| 2007/0254834 A1 | 11/2007 | DeFrees et al. |
| 2007/0254836 A1 | 11/2007 | DeFrees et al. |
| 2008/0015142 A1 | 1/2008 | DeFrees et al. |
| 2008/0039373 A1 | 2/2008 | Klausen et al. |
| 2008/0050772 A1 | 2/2008 | DeFrees et al. |
| 2008/0070275 A1 | 3/2008 | DeFrees et al. |
| 2008/0102083 A1 | 5/2008 | DeFrees et al. |
| 2008/0108557 A1 | 5/2008 | Behrens et al. |
| 2008/0146494 A1 | 6/2008 | DeFrees et al. |
| 2008/0146782 A1 | 6/2008 | DeFrees et al. |
| 2008/0176790 A1 | 7/2008 | DeFrees |
| 2008/0187955 A1 | 8/2008 | DeFrees et al. |
| 2008/0200651 A1 | 8/2008 | Ostergaard et al. |
| 2008/0206808 A1 | 8/2008 | DeFrees et al. |
| 2008/0206810 A1 | 8/2008 | Johnson et al. |
| 2008/0207487 A1 | 8/2008 | DeFrees et al. |
| 2008/0242607 A1 | 10/2008 | DeFrees |
| 2008/0242846 A1 | 10/2008 | DeFrees et al. |
| 2008/0248959 A1 | 10/2008 | DeFrees |
| 2008/0253992 A1 | 10/2008 | DeFrees et al. |
| 2008/0255026 A1 | 10/2008 | DeFrees et al. |
| 2008/0255040 A1 | 10/2008 | DeFrees |
| 2008/0274958 A1 | 11/2008 | DeFrees |
| 2008/0280818 A1 | 11/2008 | DeFrees |
| 2008/0300173 A1 | 12/2008 | DeFrees |
| 2008/0300175 A1 | 12/2008 | DeFrees et al. |
| 2008/0305518 A1 | 12/2008 | Klausen et al. |
| 2008/0305991 A1 | 12/2008 | DeFrees et al. |
| 2008/0305992 A1 | 12/2008 | DeFrees et al. |
| 2008/0318850 A1 | 12/2008 | DeFrees et al. |
| 2008/0319183 A1 | 12/2008 | DeFrees et al. |
| 2009/0028822 A1 | 1/2009 | DeFrees et al. |
| 2009/0048440 A1 | 2/2009 | Felo et al. |
| 2009/0053167 A1 | 2/2009 | DeFrees |
| 2009/0054623 A1 | 2/2009 | DeFrees |
| 2009/0055942 A1 | 2/2009 | Ostergaard et al. |
| 2009/0076237 A1 | 3/2009 | Turecek et al. |
| 2009/0081188 A1 | 3/2009 | DeFrees et al. |
| 2009/0093399 A1 | 4/2009 | DeFrees et al. |
| 2009/0124544 A1 | 5/2009 | DeFrees |
| 2009/0137763 A1 | 5/2009 | DeFrees et al. |
| 2009/0143292 A1 | 6/2009 | Hinderer et al. |
| 2009/0169509 A1 | 7/2009 | DeFrees et al. |
| 2009/0176967 A1 | 7/2009 | Stennicke |
| 2009/0203579 A1 | 8/2009 | DeFrees et al. |
| 2009/0227504 A1 | 9/2009 | Klausen et al. |
| 2009/0240028 A1 | 9/2009 | Behrens et al. |
| 2009/0247450 A1 | 10/2009 | Mack |
| 2009/0252720 A1 | 10/2009 | Ostergaard et al. |
| 2009/0253166 A1 | 10/2009 | Zundel et al. |
| 2009/0264366 A1 | 10/2009 | Johansen et al. |
| 2009/0292110 A1 | 11/2009 | DeFrees |
| 2009/0305967 A1 | 12/2009 | DeFrees et al. |
| 2010/0009902 A1 | 1/2010 | DeFrees |
| 2010/0015684 A1 | 1/2010 | DeFrees et al. |
| 2010/0028939 A1 | 2/2010 | Behrens et al. |
| 2010/0029555 A1 | 2/2010 | Tonon et al. |
| 2010/0035299 A1 | 2/2010 | DeFrees et al. |
| 2010/0041872 A1 | 2/2010 | DeFrees et al. |
| 2010/0048456 A1 | 2/2010 | DeFrees et al. |
| 2010/0056428 A1 | 3/2010 | Behrens |
| 2010/0075375 A1 | 3/2010 | DeFrees et al. |
| 2010/0081791 A1 | 4/2010 | DeFrees et al. |
| 2010/0113743 A1 | 5/2010 | DeFrees et al. |
| 2010/0120666 A1 | 5/2010 | Zopf et al. |
| 2010/0174056 A1 | 7/2010 | Gillies et al. |
| 2010/0174059 A1 | 7/2010 | DeFrees et al. |
| 2010/0210507 A9 | 8/2010 | DeFrees et al. |
| 2010/0286067 A1 | 11/2010 | DeFrees |
| 2010/0322940 A1 | 12/2010 | Bayer |
| 2010/0330645 A1 | 12/2010 | DeFrees et al. |
| 2010/0331489 A1 | 12/2010 | DeFrees |
| 2011/0003744 A1 | 1/2011 | DeFrees et al. |
| 2011/0177029 A1 | 7/2011 | DeFrees |
| 2011/0223646 A1 | 9/2011 | Schwartz et al. |
| 2011/0318780 A1 | 12/2011 | DeFrees |
| 2012/0016105 A1 | 1/2012 | DeFrees et al. |
| 2012/0083600 A1 | 4/2012 | Felo et al. |
| 2012/0107867 A1 | 5/2012 | DeFrees et al. |
| 2012/0172300 A1 | 7/2012 | DeFrees |
| 2012/0220517 A1 | 8/2012 | DeFrees et al. |
| 2013/0059780 A1 | 3/2013 | DeFrees |

FOREIGN PATENT DOCUMENTS

| | | |
|---|---|---|
| CA | 2131703 A1 | 9/1993 |
| CA | 2110543 A1 | 6/1994 |
| CA | 2324616 A1 | 9/1999 |
| CA | 2167521 | 10/2003 |
| CA | 2500389 A1 | 4/2004 |
| CA | 2511814 A1 | 7/2004 |
| DE | 2437388 | 2/1975 |
| DE | 19709787 | 9/1998 |
| DE | 19852729 A1 | 5/2000 |
| EP | 0119539 A2 | 9/1984 |
| EP | 0200421 A2 | 12/1986 |
| EP | 0370205 A2 | 5/1990 |
| EP | 0459630 A2 | 12/1991 |

(56) References Cited

FOREIGN PATENT DOCUMENTS

| | | | |
|---|---|---|---|
| EP | 0474313 | A2 | 3/1992 |
| EP | 0475354 | A2 | 3/1992 |
| EP | 0577580 | A2 | 1/1994 |
| EP | 0585109 | A2 | 3/1994 |
| EP | 0605963 | A2 | 7/1994 |
| EP | 0775711 | A1 | 5/1997 |
| EP | 0863154 | A1 | 9/1998 |
| EP | 1260582 | A1 | 11/2002 |
| EP | 1270642 | A1 | 1/2003 |
| EP | 1428878 | A1 | 6/2004 |
| EP | 1481985 | A1 | 12/2004 |
| FI | 922515 | A | 12/1992 |
| GB | 2256197 | A | 12/1992 |
| JP | S59172425 | A | 9/1984 |
| JP | H03-503759 | A | 8/1991 |
| JP | H06-086684 | A | 3/1994 |
| JP | H07-196925 | A | 8/1995 |
| JP | H07-223921 | A | 8/1995 |
| JP | H08-506023 | A | 7/1996 |
| JP | H09-503905 | A | 4/1997 |
| JP | H09-208461 | A | 8/1997 |
| JP | H10-307356 | A | 11/1998 |
| JP | 2000-501607 | A | 2/2000 |
| JP | 2001-508783 | A | 7/2001 |
| JP | 2001-519784 | A | 10/2001 |
| JP | 2003-521930 | A | 7/2003 |
| JP | 2005-521635 | A | 7/2005 |
| JP | 2005-328782 | A | 12/2005 |
| KR | 2002-0010363 | A | 2/2002 |
| KR | 10-0396983 | B1 | 8/2003 |
| NZ | 532027 | A | 9/2008 |
| NZ | 539415 | A | 12/2008 |
| NZ | 547554 | A | 9/2009 |
| RU | 2005/101348 | A | 8/2005 |
| SE | 9501285 | | 10/1996 |
| WO | WO 87/00056 | A1 | 1/1987 |
| WO | WO 87/05330 | A1 | 9/1987 |
| WO | WO 89/06546 | A1 | 7/1989 |
| WO | WO 89/10134 | A1 | 11/1989 |
| WO | WO 90/07572 | A1 | 7/1990 |
| WO | WO 90/08164 | A1 | 7/1990 |
| WO | WO 90/08823 | A1 | 8/1990 |
| WO | 90/12090 | A1 | 10/1990 |
| WO | WO 90/13540 | A1 | 11/1990 |
| WO | 91/06635 | A1 | 5/1991 |
| WO | 91/09122 | | 6/1991 |
| WO | WO 91/14697 | A1 | 10/1991 |
| WO | WO 92/01055 | A1 | 1/1992 |
| WO | 92/15686 | A1 | 9/1992 |
| WO | 92/16555 | A1 | 10/1992 |
| WO | 92/16640 | A1 | 10/1992 |
| WO | WO 92/18135 | A1 | 10/1992 |
| WO | WO 92/22310 | A1 | 12/1992 |
| WO | 93/08842 | A1 | 5/1993 |
| WO | 93/13198 | A1 | 7/1993 |
| WO | WO 93/15189 | A1 | 8/1993 |
| WO | 93/18787 | A1 | 9/1993 |
| WO | WO 94/04193 | A2 | 3/1994 |
| WO | WO 94/05332 | A2 | 3/1994 |
| WO | WO 94/09027 | A1 | 4/1994 |
| WO | WO 94/15625 | A1 | 7/1994 |
| WO | WO 94/17039 | A1 | 8/1994 |
| WO | WO 94/18247 | A1 | 8/1994 |
| WO | 94/25614 | A1 | 11/1994 |
| WO | 94/25615 | A1 | 11/1994 |
| WO | 94/26760 | A1 | 11/1994 |
| WO | 94/27631 | A1 | 12/1994 |
| WO | WO 94/28024 | A1 | 12/1994 |
| WO | WO 95/02421 | A1 | 1/1995 |
| WO | 95/05465 | A1 | 2/1995 |
| WO | WO 95/04278 | A1 | 2/1995 |
| WO | 96/10089 | A1 | 4/1996 |
| WO | WO 96/11953 | A1 | 4/1996 |
| WO | 96/12800 | A1 | 5/1996 |
| WO | WO 96/21468 | A1 | 7/1996 |
| WO | WO 96/21469 | A1 | 7/1996 |
| WO | 96/32492 | A1 | 10/1996 |
| WO | WO 96/32491 | A1 | 10/1996 |
| WO | WO 96/34015 | A1 | 10/1996 |
| WO | WO 96/36357 | A1 | 11/1996 |
| WO | WO 96/40731 | A1 | 12/1996 |
| WO | WO 96/40881 | A1 | 12/1996 |
| WO | WO 97/05330 | A1 | 2/1997 |
| WO | 97/21822 | A2 | 6/1997 |
| WO | 97/47651 | A1 | 12/1997 |
| WO | WO 98/05363 | A2 | 2/1998 |
| WO | 98/32466 | A1 | 7/1998 |
| WO | WO 98/31826 | A1 | 7/1998 |
| WO | WO 98/41562 | A1 | 9/1998 |
| WO | WO 98/51784 | A1 | 11/1998 |
| WO | WO 98/58964 | A1 | 12/1998 |
| WO | WO 99/00150 | A2 | 1/1999 |
| WO | 99/13063 | A1 | 3/1999 |
| WO | WO 99/14259 | A1 | 3/1999 |
| WO | WO 99/22764 | A1 | 5/1999 |
| WO | 99/28491 | A1 | 6/1999 |
| WO | 99/37779 | A1 | 7/1999 |
| WO | WO 99/34833 | A1 | 7/1999 |
| WO | WO 99/45964 | A1 | 9/1999 |
| WO | WO 99/48515 | A1 | 9/1999 |
| WO | 99/54342 | | 10/1999 |
| WO | WO 99/55376 | A1 | 11/1999 |
| WO | WO 00/23114 | A2 | 4/2000 |
| WO | 00/29558 | A1 | 5/2000 |
| WO | 00/29603 | A2 | 5/2000 |
| WO | WO 00/26354 | A1 | 5/2000 |
| WO | 00/44785 | A1 | 8/2000 |
| WO | 00/46379 | A1 | 8/2000 |
| WO | WO 00/65087 | A1 | 11/2000 |
| WO | WO 01/02017 | A2 | 1/2001 |
| WO | WO 01/05434 | A2 | 1/2001 |
| WO | 01/19955 | A2 | 3/2001 |
| WO | WO 01/39788 | A2 | 6/2001 |
| WO | WO 01/49830 | A2 | 7/2001 |
| WO | WO 01/51510 | A2 | 7/2001 |
| WO | WO 01/58493 | A1 | 8/2001 |
| WO | WO 01/58935 | A2 | 8/2001 |
| WO | WO 01/60411 | A1 | 8/2001 |
| WO | WO 01/76640 | A2 | 10/2001 |
| WO | 01/83725 | A1 | 11/2001 |
| WO | 01/87329 | A1 | 11/2001 |
| WO | 01/87925 | A2 | 11/2001 |
| WO | WO 01/88117 | A2 | 11/2001 |
| WO | WO 02/02597 | A2 | 1/2002 |
| WO | WO 02/02764 | A2 | 1/2002 |
| WO | WO 02/13843 | A2 | 2/2002 |
| WO | WO 02/13873 | A2 | 2/2002 |
| WO | 02/29025 | A2 | 4/2002 |
| WO | 02/49673 | A2 | 6/2002 |
| WO | 02/50099 | A2 | 6/2002 |
| WO | WO 02/44196 | A1 | 6/2002 |
| WO | WO 02/053580 | A2 | 7/2002 |
| WO | WO 02/074806 | A2 | 9/2002 |
| WO | 02/077218 | A1 | 10/2002 |
| WO | WO 02/092619 | A2 | 11/2002 |
| WO | 03/006501 | A2 | 1/2003 |
| WO | 03/011879 | A1 | 2/2003 |
| WO | WO 03/017949 | A2 | 3/2003 |
| WO | 03/029291 | A2 | 4/2003 |
| WO | WO 03/031464 | A2 | 4/2003 |
| WO | WO 03/045980 | A2 | 6/2003 |
| WO | WO 03/046150 | A2 | 6/2003 |
| WO | WO 03/093448 | A2 | 11/2003 |
| WO | WO 2004/000366 | A1 | 12/2003 |
| WO | WO 2004/009838 | A2 | 1/2004 |
| WO | WO 2004/010327 | A2 | 1/2004 |
| WO | 2004/014417 | A2 | 2/2004 |
| WO | WO 2004/022004 | A2 | 3/2004 |
| WO | 2004/029090 | A1 | 4/2004 |
| WO | 2004/029091 | A2 | 4/2004 |
| WO | WO 2004/033651 | A2 | 4/2004 |
| WO | 2004/047858 | A1 | 6/2004 |
| WO | WO 2004/046222 | A1 | 6/2004 |
| WO | WO 2004/067566 | A1 | 8/2004 |

(56) References Cited

FOREIGN PATENT DOCUMENTS

| | | | |
|---|---|---|---|
| WO | 2004/075923 A2 | 9/2004 |
| WO | WO 2004/083258 A2 | 9/2004 |
| WO | WO 2004/083259 A2 | 9/2004 |
| WO | WO 2004/091499 A2 | 10/2004 |
| WO | 2004/093823 A2 | 11/2004 |
| WO | 2004/101597 A2 | 11/2004 |
| WO | 2004/101740 A2 | 11/2004 |
| WO | WO 2004/093823 A2 | 11/2004 |
| WO | WO 2004/096148 A2 | 11/2004 |
| WO | WO 2004/099231 A2 | 11/2004 |
| WO | 2004/106373 A1 | 12/2004 |
| WO | WO 2004/103275 A2 | 12/2004 |
| WO | 2005/001025 A2 | 1/2005 |
| WO | 2005/003171 A2 | 1/2005 |
| WO | 2005/014024 A2 | 2/2005 |
| WO | 2005/014035 A2 | 2/2005 |
| WO | WO 2005/012484 A2 | 2/2005 |
| WO | WO 2005/025606 A1 | 3/2005 |
| WO | WO 2005/051327 A2 | 6/2005 |
| WO | WO 2005/055946 A2 | 6/2005 |
| WO | WO 2005/055950 A2 | 6/2005 |
| WO | WO 2005/056760 A2 | 6/2005 |
| WO | WO 2005/067601 A2 | 7/2005 |
| WO | WO 2005/070138 A2 | 8/2005 |
| WO | WO 2005/072371 A2 | 8/2005 |
| WO | 2005/079363 A2 | 9/2005 |
| WO | WO 2005/091944 A2 | 10/2005 |
| WO | WO 2005/121331 A2 | 12/2005 |
| WO | 2006/005058 A2 | 1/2006 |
| WO | WO 2006/010143 A2 | 1/2006 |
| WO | 2006/013202 A2 | 2/2006 |
| WO | 2006/018204 A1 | 2/2006 |
| WO | WO 2006/011839 A1 | 2/2006 |
| WO | WO 2006/014349 A2 | 2/2006 |
| WO | WO 2006/014466 A2 | 2/2006 |
| WO | WO 2006/020372 A2 | 2/2006 |
| WO | WO 2006/031811 A2 | 3/2006 |
| WO | 2006/035057 A1 | 4/2006 |
| WO | 2006/053299 A2 | 5/2006 |
| WO | WO 2006/050247 A2 | 5/2006 |
| WO | WO 2006/074279 A1 | 7/2006 |
| WO | WO 2006/074467 A2 | 7/2006 |
| WO | WO 2006/078645 A2 | 7/2006 |
| WO | WO 2006/082517 A1 | 8/2006 |
| WO | 2006/103298 A2 | 10/2006 |
| WO | WO 2006/105426 A2 | 10/2006 |
| WO | WO 2006/119987 A2 | 11/2006 |
| WO | WO 2006/121569 A2 | 11/2006 |
| WO | WO 2006/127910 A2 | 11/2006 |
| WO | 2006/134173 A2 | 12/2006 |
| WO | WO 2007/022512 A2 | 2/2007 |
| WO | WO 2007/056191 A2 | 5/2007 |
| WO | 2007/135182 A2 | 11/2007 |
| WO | WO 2008/011633 A2 | 1/2008 |
| WO | WO 2008/057683 A2 | 5/2008 |
| WO | WO 2008/060780 A2 | 5/2008 |
| WO | WO 2008/073620 A2 | 6/2008 |
| WO | WO 2008/124406 A2 | 10/2008 |
| WO | WO 2008/151258 A2 | 12/2008 |
| WO | WO 2008/154639 A2 | 12/2008 |
| WO | WO 2009/089396 A2 | 7/2009 |

OTHER PUBLICATIONS

Office Action dated Aug. 8, 1997 in U.S. Appl. No. 08/745,840.
Office Action dated Oct. 9, 1997 in U.S. Appl. No. 08/478,140.
Office Action dated Dec. 1, 1997 in U.S. Appl. No. 08/446,875.
Office Action dated Jan. 2, 1998 in U.S. Appl. No. 08/878,360.
Office Action dated Mar. 30, 1998 in U.S. Appl. No. 08/745,840.
Office Action dated Jun. 19, 1998 in U.S. Appl. No. 08/478,140.
Office Action dated Oct. 29, 1998 in U.S. Appl. No. 08/745,840.
Office Action dated Feb. 4, 1999 in U.S. Appl. No. 08/478,140.
Office Action dated Apr. 1, 1999 in U.S. Appl. No. 08/745,840.
Office Action dated Oct. 23, 1999 in U.S. Appl. No. 08/102,385.
Office Action dated Oct. 4, 2000 in U.S. Appl. No. 09/333,412.
Office Action dated Jan. 30, 2001 in U.S. Appl. No. 09/338,943.
Office Action dated Jun. 4, 2002 in U.S. Appl. No. 09/855,320.
Office Action dated Sep. 27, 2002 in U.S. Appl. No. 09/855,320.
Office Action dated Dec. 9, 2002 in U.S. Appl. No. 10/007,267.
Office Action dated Jun. 2, 2003 in U.S. Appl. No. 10/007,267.
Office Action dated Aug. 26, 2003 in U.S. Appl. No. 10/109,498.
Office Action dated Nov. 5, 2003 in U.S. Appl. No. 10/007,267.
Office Action dated Nov. 17, 2003 in U.S. Appl. No. 09/855,320.
Office Action dated Dec. 16, 2003 in U.S. Appl. No. 10/109,498.
Office Action dated Jun. 9, 2004 in U.S. Appl. No. 09/855,320.
Office Action dated Oct. 20, 2004 in U.S. Appl. No. 10/198,806.
Office Action dated Nov. 12, 2004 in U.S. Appl. No. 10/219,197.
Office Action dated Jan. 12, 2005 in U.S. Appl. No. 10/198,806.
Office Action dated Mar. 4, 2005 in U.S. Appl. No. 10/410,945.
Office Action dated Mar. 7, 2005 in U.S. Appl. No. 10/287,994.
Office Action dated Mar. 14, 2005 in U.S. Appl. No. 09/855,320.
Office Action dated Jun. 2, 2005 in U.S. Appl. No. 10/654,528.
Office Action dated Jun. 9, 2005 in U.S. Appl. No. 10/109,498.
Office Action dated Jun. 29, 2005 in U.S. Appl. No. 10/287,994.
Office Action dated Jul. 21, 2005 in U.S. Appl. No. 10/198,806.
Office Action dated Aug. 10, 2005 in U.S. Appl. No. 10/410,945.
Office Action dated Sep. 21, 2005 in U.S. Appl. No. 10/391,035.
Office Action dated Sep. 28, 2005 in U.S. Appl. No. 10/410,897.
Office Action dated Sep. 28, 2005 in U.S. Appl. No. 10/410,913.
Office Action dated Sep. 28, 2005 in U.S. Appl. No. 10/410,930.
Office Action dated Sep. 28, 2005 in U.S. Appl. No. 10/410,962.
Office Action dated Sep. 28, 2005 in U.S. Appl. No. 10/410,980.
Office Action dated Sep. 28, 2005 in U.S. Appl. No. 10/410,997.
Office Action dated Sep. 28, 2005 in U.S. Appl. No. 10/411,012.
Office Action dated Sep. 28, 2005 in U.S. Appl. No. 10/411,037.
Office Action dated Sep. 28, 2005 in U.S. Appl. No. 10/411,043.
Office Action dated Sep. 28, 2005 in U.S. Appl. No. 10/411,044.
Office Action dated Sep. 28, 2005 in U.S. Appl. No. 10/411,049.
Office Action dated Oct. 6, 2005 in U.S. Appl. No. 10/411,026.
Office Action dated Oct. 19, 2005 in U.S. Appl. No. 10/997,405.
Office Action dated Nov. 14, 2005 in U.S. Appl. No. 10/410,897.
Office Action dated Nov. 14, 2005 in U.S. Appll. No. 10/410,997.
Office Action dated Nov. 15, 2005 in U.S. Appl. No. 10/287,994.
Office Action dated Nov. 30, 2005 in U.S. Appl. No. 10/654,528.
Office Action dated Dec. 7, 2005 in U.S. Appl. No. 10/609,701.
Office Action dated Dec. 8, 2005 in U.S. Appl. No. 10/391,035.
Office Action dated Dec. 13, 2005 in U.S. Appl. No. 11/033,365.
Office Action dated Dec. 29, 2005 in U.S. Appl. No. 09/855,320.
Office Action dated Jan. 24, 2006 in U.S. Appl. No. 10/410,930.
Office Action dated Jan. 26, 2006 in U.S. Appl. No. 10/410,913.
Office Action dated Jan. 26, 2006 in U.S. Appl. No. 10/411,012.
Office Action dated Jan. 27, 2006 in U.S. Appl. No. 10/410,945.
Office Action dated Jan. 31, 2006 in U.S. Appl. No. 10/410,962.
Office Action dated Feb. 7, 2006 in U.S. Appl. No. 10/410,980.
Office Action dated Feb. 7, 2006 in U.S. Appl. No. 10/411,043.
Office Action dated Feb. 7, 2006 in U.S. Appl. No. 10/997,405.
Office Action dated Mar. 3, 2006 in U.S. Appl. No. 10/391,035.
Office Action dated Mar. 15, 2006 in U.S. Appl. No. 10/198,806.
Office Action dated Mar. 22, 2006 in U.S. Appl. No. 10/411,049.
Office Action dated Apr. 4, 2006 in U.S. Appl. No. 10/410,897.
Office Action dated Apr. 4, 2006 in U.S. Appl. No. 10/410,997.
Office Action dated Apr. 4, 2006 in U.S. Appl. No. 10/411,026.
Office Action dated Apr. 6, 2006 in U.S. Appl. No. 11/102,497.
Office Action dated May 2, 2006 in U.S. Appl. No. 11/144,223.
Office Action dated Jul. 28, 2006 in U.S. Appl. No. 10/109,498.
Office Action dated Aug. 24, 2006 in U.S. Appl. No. 10/492,261.
Office Action dated Aug. 30, 2006 in U.S. Appl. No. 11/102,497.
Office Action dated Oct. 6, 2006 in U.S. Appl. No. 10/497,284.
Office Action dated Oct. 17, 2006 in U.S. Appl. No. 11/339,752.
Office Action dated Nov. 1, 2006 in U.S. Appl. No. 11/183,205.
Office Action dated Nov. 1, 2006 in U.S. Appl. No. 11/183,218.
Office Action dated Nov. 15, 2006 in U.S. Appl. No. 10/411,026.
Office Action dated Nov. 28, 2006 in U.S. Appl. No. 11/144,223.
Office Action dated Dec. 8, 2006 in U.S. Appl. No. 10/997,405.
Office Action dated Dec. 13, 2006 in U.S. Appl. No. 10/410,980.
Office Action dated Dec. 13, 2006 in U.S. Appl. No. 10/411,043.
Office Action dated Dec. 13, 2006 in U.S. Appl. No. 10/497,284.
Office Action dated Dec. 18, 2006 in U.S. Appl. No. 09/855,320.

(56) References Cited

OTHER PUBLICATIONS

Office Action dated Dec. 21, 2006 in U.S. Appl. No. 11/183,205.
Office Action dated Dec. 21, 2006 in U.S. Appl. No. 11/183,218.
Office Action dated Dec. 29, 2006 in U.S. Appl. No. 11/033,365.
Office Action dated Jan. 22, 2007 in U.S. Appl. No. 10/198,806.
Office Action dated Jan. 24, 2007 in U.S. Appl. No. 11/404,266.
Office Action dated Jan. 31, 2007 in U.S. Appl. No. 10/497,283.
Office Action dated Feb. 27, 2007 in U.S. Appl. No. 10/609,701.
Office Action dated Feb. 28, 2007 in U.S. Appl. No. 10/492,261.
Office Action dated Apr. 5, 2007 in U.S. Appl. No. 10/485,892.
Office Action dated Apr. 6, 2007 in U.S. Appl. No. 11/339,752.
Office Action dated Apr. 12, 2007 in U.S. Appl. No. 10/497,283.
Office Action dated Apr. 16, 2007 in U.S. Appl. No. 10/410,980.
Office Action dated Apr. 26, 2007 in U.S. Appl. No. 11/033,365.
Office Action dated Apr. 27, 2007 in U.S. Appl. No. 11/183,205.
Office Action dated Apr. 30, 2007 in U.S. Appl. No. 11/183,218.
Office Action dated May 15, 2007 in U.S. Appl. No. 11/144,223.
Office Action dated May 31, 2007 in U.S. Appl. No. 11/395,784.
Office Action dated Jun. 1, 2007 in U.S. Appl. No. 11/102,497.
Office Action dated Jun. 11, 2007 in U.S. Appl. No. 11/514,484.
Office Action dated Jun. 25, 2007 in U.S. Appl. No. 10/411,043.
Office Action dated Jun. 26, 2007 in U.S. Appl. No. 10/411,026.
Office Action dated Jul. 13, 2007 in U.S. Appl. No. 11/440,839.
Office Action dated Jul. 26, 2007 in U.S. Appl. No. 11/395,784.
Office Action dated Aug. 16, 2007 in U.S. Appl. No. 10/497,283.
Office Action dated Aug. 17, 2007 in U.S. Appl. No. 10/492,261.
Office Action dated Aug. 30, 2007 in U.S. Appl. No. 10/497,284.
Office Action dated Sep. 4, 2007 in U.S. Appl. No. 11/144,223.
Office Action dated Sep. 18, 2007 in U.S. Appl. No. 09/855,320.
Office Action dated Oct. 1, 2007 in U.S. Appl. No. 10/411,043.
Office Action dated Oct. 2, 2007 in U.S. Appl. No. 11/166,028.
Office Action dated Oct. 3, 2007 in U.S. Appl. No. 11/514,484.
Office Action dated Oct. 16, 2007 in U.S. Appl. No. 11/183,205.
Office Action dated Oct. 16, 2007 in U.S. Appl. No. 11/183,218.
Office Action dated Oct. 30, 2007 in U.S. Appl. No. 11/580,669.
Office Action dated Nov. 1, 2007 in U.S. Appl. No. 11/339,752.
Office Action dated Nov. 15, 2007 in U.S. Appl. No. 11/166,404.
Office Action dated Nov. 28, 2007 in U.S. Appl. No. 11/102,497.
Office Action dated Dec. 7, 2007 in U.S. Appl. No. 10/530,972.
Office Action dated Dec. 11, 2007 in U.S. Appl. No. 11/440,839.
Office Action dated Dec. 17, 2007 in U.S. Appl. No. 10/497,284.
Office Action dated Dec. 27, 2007 in U.S. Appl. No. 11/396,215.
Office Action dated Dec. 28, 2007 in U.S. Appl. No. 11/402,105.
Office Action dated Dec. 28, 2007 in U.S. Appl. No. 10/565,331.
Office Action dated Jan. 3, 2008 in U.S. Appl. No. 10/549,528.
Office Action dated Jan. 9, 2008 in U.S. Appl. No. 11/144,223.
Office Action dated Jan. 11, 2008 in U.S. Appl. No. 10/485,892.
Office Action dated Jan. 30, 2008 in U.S. Appl. No. 10/411,043.
Office Action dated Feb. 6, 2008 in U.S. Appl. No. 11/395,784.
Office Action dated Mar. 3, 2008 in U.S. Appl. No. 11/166,404.
Office Action dated Mar. 4, 2008 in U.S. Appl. No. 09/855,320.
Office Action dated Mar. 7, 2008 in U.S. Appl. No. 11/580,669.
Office Action dated Mar. 10, 2008 in U.S. Appl. No. 10/497,284.
Office Action dated Mar. 13, 2008 in U.S. Appl. No. 10/411,026.
Office Action dated Mar. 20, 2008 in U.S. Appl. No. 10/411,044.
Office Action dated Mar. 31, 2008 in U.S. Appl. No. 10/549,528.
Office Action dated Apr. 3, 2008 in U.S. Appl. No. 11/166,028.
Office Action dated Apr. 7, 2008 in U.S. Appl. No. 11/344,767.
Office Action dated Apr. 28, 2008 in U.S. Appl. No. 11/402,105.
Office Action dated Apr. 29, 2008 in U.S. Appl. No. 10/565,331.
Office Action dated May 12, 2008 in U.S. Appl. No. 10/485,892.
Office Action dated Jun. 9, 2008 in U.S. Appl. No. 09/855,320.
Office Action dated Jun. 30, 2008 in U.S. Appl. No. 11/396,215.
Office Action dated Jul. 10, 2008 in U.S. Appl. No. 11/514,484.
Office Action dated Jul. 22, 2008 in U.S. Appl. No. 11/102,497.
Office Action dated Jul. 24, 2008 in U.S. Appl. No. 11/344,767.
Office Action dated Aug. 15, 2008 in U.S. Appl. No. 11/845,175.
Office Action dated Aug. 21, 2008 in U.S. Appl. No. 10/411,044.
Office Action dated Aug. 26, 2008 in U.S. Appl. No. 11/580,669.
Office Action dated Sep. 16, 2008 in U.S. Appl. No. 11/440,839.
Office Action dated Sep. 22, 2008 in U.S. Appl. No. 10/556,094.
Office Action dated Oct. 21, 2008 in U.S. Appl. No. 10/530,972.
Office Action dated Oct. 30, 2008 in U.S. Appl. No. 10/411,026.
Office Action dated Oct. 31, 2008 in U.S. Appl. No. 11/166,404.
Office Action dated Nov. 12, 2008 in U.S. Appl. No. 11/144,223.
Office Action dated Nov. 18, 2008 in U.S. Appl. No. 10/497,284.
Office Action dated Dec. 24, 2008 in U.S. Appl. No. 11/396,215.
Office Action dated Jan. 6, 2009 in U.S. Appl. No. 10/549,528.
Office Action dated Jan. 21, 2009 in U.S. Appl. No. 10/565,331.
Office Action dated Feb. 9, 2009 in U.S. Appl. No. 09/855,320.
Office Action dated Feb. 10, 2009 in U.S. Appl. No. 11/166,404.
Office Action dated Mar. 4, 2009 in U.S. Appl. No. 11/580,669.
Office Action dated Mar. 12, 2009 in U.S. Appl. No. 11/102,497.
Office Action dated Mar. 12, 2009 in U.S. Appl. No. 11/514,484.
Office Action dated Mar. 17, 2009 in U.S. Appl. No. 10/411,026.
Office Action dated Apr. 1, 2009 in U.S. Appl. No. 10/552,896.
Office Action dated Apr. 16, 2009 in U.S. Appl. No. 10/576,506.
Office Action dated May 11, 2009 in U.S. APpl. No. 10/411,044.
Office Action dated May 14, 2009 in U.S. Appl. No. 11/910,958.
Office Action dated May 22, 2009 in U.S. Appl. No. 11/166,404.
Office Action dated Jun. 1, 2009 in U.S. Appl. No. 12/201,705.
Office Action dated Jun. 3, 2009 in U.S. Appl. No. 10/549,520.
Office Action dated Jun. 17, 2009 in U.S. Appl. No. 11/934,700.
Office Action dated Jul. 2, 2009 in U.S. Appl. No. 10/497,284.
Office Action dated Jul. 21, 2009 in U.S. Appl. No. 11/440,839.
Office Action dated Jul. 21, 2009 in U.S. Appl. No. 10/549,528.
Office Action dated Aug. 7, 2009 in U.S. Appl. No. 10/556,094.
Office Action dated Aug. 7, 2009 in U.S. Appl. No. 10/579,621.
Office Action dated Aug. 11, 2009 in U.S. Appl. No. 10/549,445.
Office Action dated Aug. 13, 2009 in U.S. Appl. No. 09/855,320.
Office Action dated Aug. 17, 2009 in U.S. Appl. No. 10/581,538.
Office Action dated Sep. 18, 2009 in U.S. Appl. No. 11/652,467.
Office Action dated Sep. 23, 2009 in U.S. Appl. No. 12/201,705.
Office Action dated Sep. 28, 2009 in U.S. Appl. No. 11/910,958.
Office Action dated Sep. 29, 2009 in U.S. Appl. No. 11/645,839.
Office Action dated Sep. 29, 2009 in U.S. Appl. No. 11/714,874.
Office Action dated Oct. 2, 2009 in U.S. Appl. No. 11/781,900.
Office Action dated Oct. 2, 2009 in U.S. Appl. No. 11/781,902.
Office Action dated Oct. 14, 2009 in U.S. Appl. No. 10/549,528.
Office Action dated Oct. 14, 2009 in U.S. Appl. No. 10/565,331.
Office Action dated Oct. 23, 2009 in U.S. Appl. No. 11/396,215.
Office Action dated Oct. 27, 2009 in U.S. Appl. No. 11/402,105.
Office Action dated Nov. 2, 2009 in U.S. Appl. No. 11/659,942.
Office Action dated Nov. 2, 2009 in U.S. Appl. No. 11/866,969.
Office Action dated Nov. 4, 2009 in U.S. Appl. No. 10/549,445.
Office Action dated Nov. 20, 2009 in U.S. Appl. No. 11/580,669.
Office Action dated Nov. 24, 2009 in U.S. Appl. No. 11/781,888.
Office Action dated Nov. 27, 2009 in U.S. Appl. No. 11/781,885.
Office Action dated Dec. 10, 2009 in U.S. Appl. No. 11/144,223.
Office Action dated Dec. 12, 2009 in U.S. Appl. No. 12/418,530.
Office Action dated Dec. 14, 2009 in U.S. Appl. No. 11/102,497.
Office Action dated Dec. 17, 2009 in U.S. Appl. No. 10/581,538.
Office Action dated Dec. 17, 2009 in U.S. Appl. No. 11/781,896.
Office Action dated Dec. 22, 2009 in U.S. Appl. No. 09/855,320.
Office Action dated Dec. 28, 2009 in U.S. Appl. No. 12/371,156.
Office Action dated Jan. 6, 2010 in U.S. Appl. No. 11/656,643.
Office Action dated Jan. 19, 2010 in U.S. Appl. No. 11/597,258.
Office Action dated Jan. 26, 2010 in U.S. Appl. No. 11/166,404.
Office Action dated Jan. 27, 2010 in U.S. Appl. No. 11/440,839.
Office Action dated Feb. 4, 2010 in U.S. Appl. No. 12/201,705.
Office Action dated Feb. 5, 2010 in U.S. Appl. No. 11/584,743.
Office Action dated Feb. 5, 2010 in U.S. Appl. No. 11/657,441.
Office Action dated Feb. 8, 2010 in U.S. Appl. No. 12/184,956.
Office Action dated Feb. 19, 2010 in U.S. Appl. No. 11/981,483.
Office Action dated Feb. 19, 2010 in U.S. Appl. No. 11/982,273.
Office Action dated Mar. 3, 2010 in U.S. Appl. No. 10/579,620.
Office Action dated Mar. 3, 2010 in U.S. Appl. No. 11/917,772.
Office Action dated Mar. 4, 2010 in U.S. Appl. No. 09/855,320.
Office Action dated Mar. 8, 2010 in U.S. Appl. No. 11/652,467.
Office Action dated Mar. 11, 2010 in U.S. Appl. No. 12/101,389.
Office Action dated Mar. 15, 2010 in U.S. Appl. No. 10/497,284.
Office Action dated Mar. 29, 2010 in U.S. Appl. No. 11/514,484.
Office Action dated Mar. 30, 2010 in U.S. Appl. No. 12/496,595.

(56) References Cited

OTHER PUBLICATIONS

Office Action dated Apr. 2, 2010 in U.S. Appl. No. 11/701,949.
Office Action dated Apr. 5, 2010 in U.S. Appl. No. 10/556,094.
Office Action dated Apr. 5, 2010 in U.S. Appl. No. 10/579,621.
Office Action dated May 3, 2010 in U.S. Appl. No. 12/276,885.
Office Action dated May 13, 2010 in U.S. Appl. No. 11/781,888.
Office Action dated May 14, 2010 in U.S. Appl. No. 11/781,885.
Office Action dated May 24, 2010 in U.S. Appl. No. 10/581,538.
Office Action dated May 26, 2010 in U.S. Appl. No. 11/144,223.
Office Action dated May 26, 2010 in U.S. Appl. No. 11/659,942.
Office Action dated May 26, 2010 in U.S. Appl. No. 11/866,969.
Office Action dated May 27, 2010 in U.S. Appl. No. 10/565,331.
Office Action dated Jun. 16, 2010 in U.S. Appl. No. 11/843,588.
Office Action dated Jul. 1, 2010 in U.S. Appl. No. 11/981,483.
Office Action dated Jul. 2, 2010 in U.S. Appl. No. 11/632,005.
Office Action dated Jul. 6, 2010 in U.S. Appl. No. 10/579,620.
Office Action dated Jul. 6, 2010 in U.S. Appl. No. 11/917,772.
Office Action dated Jul. 8, 2010 in U.S. Appl. No. 11/867,553.
Office Action dated Jul. 15, 2010 in U.S. Appl. No. 11/664,199.
Office Action dated Jul. 15, 2010 in U.S. Appl. No. 11/701,949.
Office Action dated Jul. 20, 2010 in U.S. Appl. No. 11/652,467.
Office Action dated Jul. 22, 2010 in U.S. Appl. No. 12/201,705.
Office Action dated Jul. 27, 2010 in U.S. Appl. No. 11/656,643.
Office Action dated Aug. 5, 2010 in U.S. Appl. No. 12/496,595.
Office Action dated Aug. 17, 2010 in U.S. Appl. No. 11/632,005.
Office Action dated Aug. 19, 2010 in U.S. Appl. No. 11/665,908.
Office Action dated Aug. 20, 2010 in U.S. Appl. No. 11/144,223.
Office Action dated Sep. 10, 2010 in U.S. Appl. No. 11/867,553.
Office Action dated Sep. 14, 2010 in U.S. Appl. No. 12/371,156.
Office Action dated Sep. 22, 2010 in U.S. Appl. No. 11/982,273.
Office Action dated Oct. 1, 2010 in U.S. Appl. No. 11/166,404.
Office Action dated Oct. 1, 2010 in U.S. Appl. No. 11/597,258.
Office Action dated Oct. 1, 2010 in U.S. Appl. No. 11/644,014.
Office Action dated Oct. 1, 2010 in U.S. Appl. No. 11/910,958.
Office Action dated Oct. 4, 2010 in U.S. Appl. No. 12/302,167.
Office Action dated Oct. 5, 2010 in U.S. Appl. No. 11/579,401.
Office Action dated Oct. 12, 2010 in U.S. Appl. No. 12/066,619.
Office Action dated Oct. 13, 2010 in U.S. Appl. No. 11/792,610.
Office Action dated Oct. 14, 2010 in U.S. Appl. No. 11/781,885.
Office Action dated Oct. 15, 2010 in U.S. Appl. No. 11/664,199.
Office Action dated Oct. 15, 2010 in U.S. Appl. No. 11/781,888.
Office Action dated Nov. 24, 2010 in U.S. Appl. No. 11/866,969.
Office Action dated Nov. 26, 2010 in U.S. Appl. No. 11/981,483.
Office Action dated Dec. 16, 2010 in U.S. Appl. No. 10/579,620.
Office Action dated Dec. 16, 2010 in U.S. Appl. No. 11/701,949.
Office Action dated Dec. 17, 2010 in U.S. Appl. No. 11/658,218.
Office Action dated Dec. 21, 2010 in U.S. Appl. No. 11/632,005.
Office Action dated Dec. 27, 2010 in U.S. Appl. No. 11/144,223.
Office Action dated Jan. 10, 2011 in U.S. Appl. No. 11/659,942.
Office Action dated Jan. 18, 2011 in U.S. Appl. No. 12/444,380.
Office Action dated Jan. 20, 2011 in U.S. Appl. No. 10/586,166.
Office Action dated Jan. 21, 2011 in U.S. Appl. No. 11/843,588.
Office Action dated Feb. 1, 2011 in U.S. Appl. No. 11/867,553.
Office Action dated Feb. 3, 2011 in U.S. Appl. No. 11/794,555.
Office Action dated Feb. 3, 2011 in U.S. Appl. No. 11/914,104.
Office Action dated Feb. 3, 2011 in U.S. Appl. No. 12/443,428.
Office Action dated Feb. 4, 2011 in U.S. Appl. No. 11/794,560.
Office Action dated Feb. 15, 2011 in U.S. Appl. No. 12/496,595.
Office Action dated Feb. 22, 2011 in U.S. Appl. No. 12/820,926.
Office Action dated Feb. 23, 2011 in U.S. Appl. No. 12/092,563.
Office Action dated Mar. 2, 2011 in U.S. Appl. No. 12/201,705.
Office Action dated Mar. 11, 2011 in U.S. Appl. No. 11/982,273.
Office Action dated Mar. 16, 2011 in U.S. Appl. No. 11/665,908.
Office Action dated Mar. 17, 2011 in U.S. Appl. No. 11/597,258.
Office Action dated May 31, 2011 in U.S. Appl. No. 11/144,223.
Office Action dated Jun. 9, 2011 in U.S. Appl. No. 11/597,258.
Office Action dated Jul. 8, 2011 in U.S. Appl. No. 11/632,005.
Office Action dated Jul. 21, 2011 in U.S. Appl. No. 11/665,908.
Office Action dated Aug. 17, 2011 in U.S. Appl. No. 11/632,005.
Office Action dated Aug. 22, 2011 in U.S. Appl. No. 11/659,942.
Office Action dated Sep. 22, 2011 in U.S. Appl. No. 12/820,926.
Arslan et al., "Mobilization of Peripheral Blood Stem Cells," *Transf. Apher. Sci.*, 37: 179-185 (2007).
Broxmeyer et al., "Rapid Mobilization of Murine and Human Hematopoietic Stem and Progenitor Cells With AMD3100, A CXCR4 Antagonist," *J. Exp. Med.*, 201(8): 1307-1318 (2005).
Brumeanu et al., "Enzymatically Mediated, Glycosidic Conjugation of Immunoglobulins With Viral Epitopes," *J. Immunol. Meth.*, 183: 185-197 (1995).
Capoccia et al., "G-Csf and Amd3100 Mobilize Monocytes Into the Blood That Stimulate Angiogenesis In Vivo Through a Paracrine Mechanism," *Blood*, 108(7): 2438-2445 (2006).
Cashen et al., "Mobilizing Stem Cells From Normal Donors: Is It Possible to Improve Upon G-CSF," *Bone Marrow Trans.*, 39: 577-588 (2007).
Flomenberg et al., "The Use of AMD3100 plus G-CSF for Autologous Hematopoietic Progenitor Cell Mobilization is Superior to G-CSF Alone," *Blood*, 106(5): 1867-1874 (2005).
GE Healthcare, "Ion Exchange Chromatography & Chromatofocusing: Principles and Methods," Edition AA, Amersham Biosciences, pp. 7, 11-12, 16-17, 21-23, 26-36, 41, 89, 156, 160, 161 (2004).
Gross et al., "Enzymatic Introduction of a Fluorescent Sialic Acid Into Oligosaccharide Chains of Glycoproteins," *Eur. J. Biochem,.* 177(3): 583-589 (1988).
Guo et al., "Utilization of Glycosyltransferases to Change Oligosaccharide Structures," *Appl. Biochem. Biotechnol.*, 68(1-2): 1-20 (1997).
Hällgren et al., "An Animated GDP-Fucose Analog Useful in the Fucosyltransferase Catalyzed Addition of Biologocial Probes onto Oligosaccharide Chains," *J. Carb. Chem.*, 14(4-5): 453-464 (1995).
Hill et al., "Allogeneic Stem Cell Transplantation with peripheral Blood Stem Cells Mobilized by Pegylated G-CSF," *Biol. Blood Marrow Trans.*, 12: 603-607 (2006).
Hübel et al., "Clinical Applications of Granulocyte Colony-Stimulating Factor: an Update and Summary," *Ann. Hematol.*, 82: 207-213 (2003).
Kennedy, "Hydrophobic-Interaction Chromatography," in *Current Protocols in Protein Science*, pp. 8.4.1-8.4.21, Wiley (1995).
Kroschinsky et al., "The Role of Pegfilgrastim in Mobilization of Hematopoietic Stem Cells," *Trans. Apher. Sci.*, 38: 237-244 (2008).
Liles et al., "Augmented Mobilization and Collection of CD34+ Hematopoietic Cells From Normal Human Volunteers Stimulated With Granulocyte-Colony-Stimulating Factor by Single-Dose Administration of AMD3100, A CXCR4 Antagonist," *Transfusion*, 45: 295-300 (2005).
O'Shannessy et al., "Specific Conjugation Reactions of the Oligosaccharide Moieties of Immunoglobulins," *J. Appl. Biochem.*, 7: 347-355 (1985).
Perrin et al., "Common Physical Techniques Used in Purification," in *Purification of Laboratory Chemicals*, pp. 30-31, Pergamon (1980).
Rathnam et al., "Conjugation of a Fetuin Glycopeptide to Human Follicle-Stimulating Hormone and its Subunits by Photoactivation," *Biochim. Biophys. Acta*, 624(2): 436-442 (1980).
Schwarz et al., "Transfer of 131I and Fluoresceinyl Sialic Acid Derivatives into the Oligosaccharide Chains of IgG: a New Method for Site-Specific Labeling of Antibodies," *Nucl. Med. Biol.*, 26(4):383-388 (1999).
Song et al., "Enhanced Neuroprotective Effects of Basic Fibroblast Growth Factor in Regional Brain ischemia After Conjugation to a Blood-Brain Barrier Delivery Vector," *J. Pharmacol. Exp. Ther.*, 301(2): 605-610 (2002).
Srivastava et al., "Enzymatic Transfer of a Preassembled Trisaccharide Antigen to Cell Surfaces Using a Fucosyltransferase," *J. Biol. Chem.*, 267(31): 22356-22361 (1992).
Uptima, Detergents: Solubilization of Biomolecules, Internet page from www.interchim.com/interchim/bio/produits_uptima/product_line/p1p_detergents.htm, 2001, printed Nov. 14, 2011.
Yin et al., "Effects of Antioxidants on the Hydrogen Peroxide-Mediated Oxidation of Methionine Residues in Granulocyte Colony-Stimulating Factor and Human Parathyroid Hormone Fragment 13-34," *Pharm. Res.*, 21(12): 2377-2383 (2004).

(56) References Cited

OTHER PUBLICATIONS

Abeijon et al.,"3'-0-(4-Benzoyl)benzoylcytidine 5'—Triphosphate a Substrate and Photoaffinity Label for Cmp-N-Acetylneuraminic Acid Synthetase," *J. Biol. Chem.*, 261(24): 11374-11377 (1986).
Abuchowski et al., "Alteration of Immunological Properties of Bovine Serum Albumin by Covalent Attachment of Polyethylene Glycol," *J. Biol. Chem.*, 252(11): 3578-3581 (1977).
Abuchowski et al., "Effect of Covalent Attachment of Polyethylene Glycol on Immunogenicity and Circulating Life of Bovine Liver Catalase," *J. Biol. Chem.*, 252(11): 3582-3586 (1977).
Abuchowski et al.,"Cancer Therapy With Chemically Modified Enzymes. I. Antitumor . Properties of Polyethylene Glycol-Asparaginase Conjugates," *Cancer Biochem. Biophys.*, 7(2): 175-186 (1984).
Adelhorst et al.,"Structure-Activity Studies of Glucagon-like Peptide-1," *J. Biol. Chem.*, 269(9): 6275-6278 (1994).
Ailor et al., "N-Glycan Patterns of Human Transferrin Produced in *Trichoplusia Ni* Insect Cells: Effects of Mammalian Galactosyltransferase," *Glycobiology*, 10(8): 837-847 (2000).
Ajisaka et al., "Efficient Synthesis of O-linked Glycopeptide by a Transglycosylation Using Endo α-N-Acetylgalactosaminidase from *Streptomyces* sp.," *Biosci. Biotechnol. Biochem.*, 65(5): 1240-1243 (2001).
Alam et al., "Expression and Purification of a Mutant Human Growth Hormone That Is Resistant to Proteolytic Cleavage by Thrombin, Plasmin and Human Plasma In Vitro," *J. Biotechnol.*, 65(2-3): 183-190 (1998).
Allegre et al., "Cholesterol Removal by Nanofiltration: Applications in Nutraceutics and Nutritional Supplements," *J. Memb. Sci.*, 269(1-2): 109-117 (2006).
Altmann et al., "Insect Cells As Hosts for the Expression of Recombinant Glycoproteins," *Glycoconj. J.*, 16(2): 109-123 (1999).
Amersham Pharmacia Biotech, "Hydrophobic Interaction Chromatography: Principles and Methods," 104 pp. (2000).
Aplin et al., "Preparation, Properties, and Applications of Carbohydrate Conjugates of Proteins and Lipids," *CRC Crit. Rev. Biochem.*, 10(4): 259-306 (1981).
Barrios et al., "Length of the Antibody Heavy Chain Complementarity Determining Region 3 As a Specificity-Determining Factor," *J. Mol. Recognit.*, 17(4):332-338 (2004).
Beauchamp et al., "A New Procedure for the Synthesis of Polyethylene Glycol-Protein Adducts; Effects on Function, Receptor Recognition, and Clearance of Superoxide Dismutase, Lactoferrin, and α 2-Macroglobulin," *Anal. Biochem.*, 131(1): 25-33 (1983).
Bedard et al., "Maximization of Recombinant Protein Yield in the Insect Cel/baculovirus System by One-Time Addition of Nutrients to High-Density Batch Cultures," *Cytotechnology*, 15(1-3):129-138 (1994).
Bennett et al., "Cloning of a•Human UDP-N-Acetyl-α-D-Galactosamine:Polypeptide N-Acetylgalactosaminyltransferase That Complements Other GaINAc-Transferases in Complete O-Glycosylation of the Muc1 Tandem Repeat," *J. Biol. Chem.*, 273(46): 30472-30481 (1998).
Bennett et al., "A Novel Human UDP-N-Acetyl-D-Galactosamine:Polypeptide -N-Acetylgalactosaminyltransferase, GaINAc-T7, With Specificity for Partial GaINAc-Glycosylated Acceptor Substrates," *FEBS Lett.*, 460(2): 226-230 (1999).
Berger et al., "Preparation of Polyethylene Glycol-Tissue Plasminogen Activator Adducts That Retain Functional Activity: Characteristics and Behavior in Three Animal Species." *Blood*, 71(6): 1641-1647 (1988).
Berg-Fussman et al., "Human Acid ,B-Glucosidase N-Glycosylation Site Occupancy and the Effect of Glycosylation on Enzymatic Activity," *J. Biol. Chem.*, 268(20): 14861-14866 (1993).
Bhadra et al., "Pegnology: a-Review of PEG-ylated Systems," *Pharmazie*, 57(1): 5-29 (2002).
Bhatia et al., "Use of Thiol-Terminal Silanes and Heterobifunctional Crosslinkers for Immobilization of Antibodies on Silica Surfaces," *Anal. Biochem.*, 178(2): 408-413 (1989).

Bickel et al., "Delivery of Peptides and Proteins Through the Blood-Brain Barrier," *Adv. Drug Deliv. Rev.*, 46(1-3): 247-279 (2001).
Bijsterbosch et al., "Quantitative analysis of the targeting of mannose-terminal glucocerebrosidase: Predominant uptake by liver endothelial cells," *Eur. J. Biochem.*, 237(2): 344-349 (1996).
Bjoern et al., "Human Plasma and Recombinant Factor VII. Characterization of O-Glycosylations At Serine Residues 52 and 60 and Effects of Site-Directed Mutagenesis of Serine 52 to Alanine," *J. Biol. Chem.*, 266(17): 11051-11057 (1991).
Boccu et al., "Coupling of Monomethoxypolyethyleneglycols to Proteins Via Active Esters," *Z. Naturforsch.*, 38c: 94-99 (1983).
Boime et al., "Glycoprotein Hormone Structure-Function and Analog Design," *Recent Prog. Horm. Res.*, 54: 271-289 (1999).
Boissel et al., "Erythropoietin Structure-Function Relationships: Mutant Proteins That Test a Model of Tertiary Structure," *J. Biol. Chem.*, 268(21): 15983-15993 (1993).
Bork et al., "Go Hunting in Sequence Databases But Watch Out for the Traps," *Trends Genet.*, 12(10): 425-427 (1996).
Bork, "Powers and Pitfalls in Sequence Analysis: The 70% Hurdle," *Genome Res.*, 10(4): 398-400 (2000).
Bouizar et al., "Purification and Characterization of Calcitonin Receptors in Rat Kidney Membranes by Covalent Cross-Linking Techniques," *Eur. J. Biochem.*, 155(1): 141-147 (1986).
Boyd et al., "The Effect of the Removal of Sialic Acid, Galactose and Total Carbohydrate on the Functional Activity of Campath-1H," *Mol. Immunol.*, 32(17-18): 1311-1318 (1995).
Brenner, "Errors in Genome Annotation," *Trends Genet.*, 15(4): 132-133 (1999).
Brockhausen et al., "Glycoproteins and Their Relationship to Human Disease," *Acta Anatomica*, 161: 36-78 (1998).
Brockhausen et al., "Enzymatic Basis for Sialyl-Tn Expression in Human Colon Cancer Cells," *Glycoconj. J.*, 15: 595-603 (1998).
Broun et al., "Catalytic Plasticity of Fatty Acid Modification Enzymes Underlying Chemical Diversity of Plant Lipids," *Science*, 282(5392): 1315-1317 (1998).
Browning et al., "Studies on the Differing Effects of Tumor Necrosis Factor and Lymphotoxin on the Growth of Several Human Tumor Lines," *J. Immunol.*, 143(6): 1859-1867 (1989).
Bückmann et al., "Functionalization of Poly(Ethylene Glycol) and Monomethoxy-Poly(Ethylene Glycol)," *Makromol. Chem.*, 182(5): 1379-1384 (1981).
Burns et al., "Purification and Characterization of the Yeast-Expressed Erythropoietin Mutant Epo (R103A), A Specific Inhibitor of Human Primary Hematopoietic Cell Erythropoiesis," *Blood*, 99(12): 4400-4405 (2002).
Butnev et al., "Hormone-Specific Inhibitory Influence of Alpha-Subunit Asn56 Oligosaccharide on In Vitro Subunit Association and Follicle-Stimulating Hormone Receptor Binding of Equine Gonadotropins," *Biol. Reprod.*, 58(2): 458-469 (1998).
Byun et al., "Binding Kinetics of Thrombin and Antithrombin III With Immobilized Heparin Using a Spacer," *ASAIO J.*, 38(3): M649-M653 (1992).
Cantin et al., "Polyethylene Glycol Conjugation At Cys232 Prolongs The Half-Life of Alpha1 Proteinase Inhibitor," *Am. J. Respir. Cell Mol. Biol.*, 27(6): 659-665 (2002).
Casares et al., "Antigen-Specific Downregulation of T Cells by Doxorubicin Delivered Through a Recombinant MHC II—Peptide Chimera," *Nat. Biotechnol.*, 19(2): 142-147 (2001).
Chaffee et al., "Igg Antibody Response to Polyethylene Glycol-Modified Adenosine Deaminase in Patients With Adenosine Deaminase Deficiency," *J. Clin. Invest.*, 89(5): 1643-1651 (1992).
Charter et al., "Biosynthetic Incorporation of Unnatural Sialic Acids Into Polysialic Acid on Neural Cells," *Glycobiology*, 10(10): 1049-1056 (2000).
Chern et al., "Structural Role of Amino Acids 99-110 in Recombinant Human Erythropoietin," *Eur. J. Biochem.*, 202(2): 225-229 (1991).
Chiba et al., "Cloning and Expression of the Carboxypeptidase Gene From *Aspergillus saitoi* and Determination of the Catalytic Residues by Site-Directed Mutagenesis," *Biochem. J.*, 308(2): 405-409 (1995).
Chrisey et al., "Covalent Attachment of Synthetic DNA to Self-Assembled Monolayer Films," *Nucleic Acids Res.*, 24(15): 3031-3039 (1996).

(56) References Cited

OTHER PUBLICATIONS

Clark et al., "Long-Acting Growth Hormones Produced by Conjugation With Polyethylene Glycol," *J. Biol. Chem.*, 271(36): 21969-21977 (1996).
Cohn et al., "Biodegradable PEO/PLA Block Copolymers," *J. Biomed. Mater. Res,.* 22(11): 993-1009 (1988).
Cointe et al., "Unusual N-Glycosylation of a Recombinant Human Erythropoietin Expressed in a Human Lymphoblastoid Cell Line Does Not Alter Its Biological Properties," *Glycobiology*, 10(5): 511-519 (2000).
Conradt et al., "Structure of the Carbohydrate Moiety of Human Interferon-Beta Secreted by a Recombinant Chinese Hamster Ovary Cell Line," *J. Biol. Chem.*, 262(30): 14600-14605 (1987).
Cope et al., "Molecular Cloning of a Gene Involved in Lipooligosaccharide Biosynthesis and Virulence Expression by *Haemophilus influenzae* Type B," *Mol. Microbiol.*, 5(5): 1113-1124 (1991).
Copeland, "Enzymes: A Practical Introduction to Structure, Mechanism and Data Analysis" 2nd ed., Wiley-VCH, New York, pp. 146-150 (2000).
Costa et al., "Stable Expression of the Golgi Form and Secretory Variants of Human Fucosyltransferase III From BHK-21 Cells. Purification and Characterization of an Engineered Truncated Form From the Culture Medium," *J. Biol. Chem.*, 272(17): 11613-11621 (1997).
Crout et al., "Glycosidases and Glycosyl Transferases in Glycoside and Oligosaccharide Synthesis," *Curr. Opin. Chem. Biol.*, 2(1): 98-111 (1998).
Culajay et al., "Thermodynamic Characterization of Mutants of Human Fibroblast Growth Factor 1 With an Increased Physiological Half-Life," *Biochem.*, 39: 7153-7158 (2000).
Deacon, "Therapeutic Strategies Based on Glucagon-Like Peptide 1," *Diabetes*, 54: 2181-2189 (2004).
DeFrees et al., "Glycopegylation of Recombinant Therapeutic Proteins Produced in *Escherichia coli*," *Glycobiology*, 16(9): 833-843 (2006).
Delgado et al., "Coupling of Poly(Ethylene Glycol) to Albumin Under Very Mild Conditions by Activation With Tresyl Chloride: Characterization of the Conjugate by Partitioning in Aqueous Two-Phase Systems," *Biotechnol. Appl. Biochem.*, 12(2): 119-128 (1990).
Delgado et al., "The Uses and Properties of PEG-Linked Proteins," *Crit. Rev. Ther. Drug Carrier Syst.*, 9(3-4): 249-304 (1992).
De Vries et al, "Acceptor Specificity of Different Length Constructs of Human Recombinant Alpha 1,3/4-Fucosyltransferases: Replacement of the Stem Region and the Transmembrane Domain of Fucosyltransferase V by Protein a Results in an Enzyme With GDP-Fucose Hydrolyzing Activity," *J. Biol. Chem.*, 270(15): 8712-8722 (1995).
De Vries et al., "Acceptor Specificity of GDP-Fuc:Gal Beta 1→4glcnac-R Alpha 3-Fucosyltransferase VI (Fuct VI) Expressed in Insect Cells As Soluble, Secreted Enzyme," *Glycobiology*, 7(7): 921-927 (1997).
Dinter et al., "Glycosylation Engineering in Chinese Hamster Ovary Cells Using Tricistronic Vectors," *Biotechnol. Lett.*, 22(1): 25-30 (2000).
Doerks et al., "Protein Annotation: Detective Work for Function Prediction," *Trends Genet.*, 14(6): 248-250 (1998).
Douglas et al., "Polymer-Supported Solution Synthesis of Oligosaccharides," *J. Am. Chem. Soc.*, 113(13): 5095-5097 (1991).
Dubé et al., "Glycosylation At Specific Sites of Erythropoietin Is Essential for Biosynthesis, Secretion, and Biological Function," *J. Biol. Chem.*, 263(33): 17516-17521 (1988).
Dumas et al., "Enzymatic Synthesis of Sialyl Le$^x$ and Derivatives Based on a Recombinant Fucosyltransferase," *Bioorg. Med. Chem. Lett.*, 1(8): 425-428 (1991).
Dunn, 1991, "Polymeric Drugs and Drug Delivery Systems" Dunn et al. (eds.), Chapter 2 "Polymeric Matrices", pp. 11-23, ACS Symposium Series vol. 469, American Chemical Society, Washington D.C.
Durieux et al., "Synthesis of Biotinylated Glycosulfopeptides by Chemoselective Ligation," *Tetrahedron Lett.*, 42(12): 2297-2299 (2001).
Dwek et al., "Glycobiology: 'The Function of Sugar in the Igg Molecule'," *J. Anat.*, 187(Pt. 2): 279-292 (1995).
Eavarone et al., "Targeted Drug Delivery to C6 Glioma by Transferrin-Coupled Liposomes," *J. Biomed. Mater. Res.*, 51(1): 10-14 (2000).
Edge et al., "Deglycosylation of Glycoproteins by Trifluoromethanesulfonic Acid," *Anal. Biochem.*, 118(1): 131-137 (1981).
Elhalabi et al., "Synthesis and Applications for Unnatural Sugar Nucleotides,"*Curr. Med. Chem.*, 6(2): 93-116 (1999).
Espuelas et al., "Synthesis of an Amphiphilic Tetraantennary Mannosyl Conjugate and Incorporation Into Liposome Carriers," *Bioorg. Med. Chem. Lett.*, 13(15): 2557-2560 (2003).
Fairhall et al., "Growth Hormone (GH) Binding Protein and GH Interactions In Vivo in the Guinea Pig," *Endocrinology*, 131(4): 1963-1969 (1992).
Fan et al., "Detailed Studies on Substrate Structure Requirements of Glycoamidases A and F," *J. Biol. Chem.*, 272(43): 27058-27064 (1997).
Feldman et al., "Engineering N-Linked Protein Glycosylation with Diverse O Antigen Lipopolysaccharide Structures in *Escherichia coli*," *Proc. Natl. Acad. Sci. USA*, 102(8): 3016-3021 (2005).
Felix et al., "Synthesis of Symmetrically and Asymmetrically Branched Pegylating Reagents," *J. Peptide Res.*, 63: 85-90 (2004).
Fibi et al., "N- and O-glycosylation Muteins of Recombinant Human Erythropoietin Secreted From BHK-21 Cells," *Blood*, 85(5): 1229-1236 (1995).
Fischer et al., "Recombinant Coagulation Factor IX: Glycosylation Analysis and In Vitro Conversion into Human-Like Sialylation Pattern," *Thromb. Res.*, 89(3): 147-150 (1998).
Flynn et al., "Campath-1 H Monoclonal Antibody Therapy," *Curr. Opin. Oncol.*, 12(6): 574-581 (2000).
Francis et al.,"PEGylation of Cytokines and other Therapeutic Protiens and Peptides: the Importance of Biological Optimisation of Coupling Techniques," *Intl. J. Hematol.*, 68(1): 1-18 (1998).
Fritz et al., "The Beginnings of Mucin Biosynthesis: the Crystal Structure of UDP-GalNAc:Polypeptide Alpha-N-Acetylgalactosaminyltransferase-T1," *Proc. Natl. Acad. Sci. USA*, 101(43): 15307-15312 (2004).
Fritz et al., "Dynamic Association Between the Catalytic and Lectin Domains of Human UDP-Galnac:Polypeptide Alpha-N-Acetylgalactosaminyltransferase-2," *J. Biol. Chem.*, 281(13): 8613-8619 (2006).
Garnett et al., "Targeted Drug Conjugates: Principles and Progress," *Adv. Drug Deliv. Rev.*, 53(2): 171-216 (2002).
Gatot et al., "Conservative Mutations in the Immunosuppressive Region of the Bovine Leukemia Virus Transmembrane Protein Affect Fusion But Not Infectivity In Vivo," *J. Biol. Chem.*, 273(21): 12870-12880 (1998).
Ge et al., "Cloning and Heterologous Expression of an Alpha1,3-Fucosyltransferase Gene from the Gastric Pathogen *Helicobacter pylori*," *J. Biol. Chem.*, 272(34): 21357-21363 (1997).
Gervais et al., "Glycosylation of Human Recombinant Gonadotrophins: Characterization and Batch-To-Batch Consistency," *Glycobiology*, 13(3): 179-189 (2003).
Gilbert et al., "Effect of Lipids on Insect Cell Growth and Expression of Recombinant Proteins in Serum-Free Medium," *Cytotechnology*, 22(1-3): 211-216 (1996).
Gillis et al., "Production of Recombinant Human Colony Stimulating Factors in Yeast, *Behring Inst. Mitt.*, 83: 1-7 (1988).
Ginns, PEG Glucocerebrosidase, Internet page from www.gaucher.org.uk/peg2.prg, Nov. 1994, printed Jun. 21, 2002.
Gombotz et al., "PEGylation: A Tool for Enhanced Protein Delivery," in *Controlled Drug Delivery*, Park et al. (eds.), Chapter 12, pp. 110-123, ACS Symposium Series, American Chemical Society, Washington D.C. (2000).
Gotschlich, "Genetic Locus for the Biosynthesis of the Variable Portion of *Neisseria gonorrhoeae* Lipooligosaccharide," *J. Exp. Med.*, 180(6): 2181-2190 (1994).
Grabenhorst et al., "Biosynthesis and Secretion of Human Interleukin 2 Glycoprotein Variants From Baculovirus-Infected Sf21 Cells. Characterization of Polypeptides and Posttranslational Modifications," *Eur. J. Biochem.*, 215(1): 189-197 (1993).

(56) References Cited

OTHER PUBLICATIONS

Grabenhorst et al., "The Cytoplasmic, Transmembrane, and Stem Regions of Glycosyltransferases Specify Their In Vivo Functional Sublocalization and Stability in the Golgi," *J. Biol. Chem.*, 274(51): 36107-36116 (1999).

Grodberg et al., "Alanine Scanning Mutagenesis of Human Erythropoietin Identifies Four Amino Acids Which are Critical for Biological Activity," *Eur. J. Biochem.*, 218(2): 597-601 (1993).

Gross et al., "Transfer of Synthetic Sialic Acid Analogues to N- and O-Linked Glycoprotein Glycans Using Four Different Mammalian Sialyltransferases," *Biochemistry*, 28(18): 7386-7392 (1989).

Gross, "Fluorescent CMP-Sialic Acids as a Tool to Study the Specificity of the CMP-Sialic Acid Carrier and the glycoconjugate Sialylation in Permeabilized Cells," *Eur. J. Biochem.*, 203(1-2): 269-275 (1992).

Hagen et al., "Structure-Function Analysis of the UDP-N-acetyl-D-Galactosamine:Polypeptide N-acetylgalactosaminyltransferase. Essential residues Lie in a Predicted Active Site Cleft Resembling a Lactose Repressor Fold," *J. Biol. Chem.*, 274(10): 6797-6803 (1999).

Hagen et al., "Cloning and Characterization of a Ninth Member of the UDP-GalNAc:Polypeptide N-acetylgalactosaminyltransferase Family, ppGaNTase-T9," *J. Biol. Chem.*, 276(20): 17395-17404 (2001).

Hall, "Immunotoxin Treatment of Brain Tumors," *Methods Mol. Biol.*, 166: 139-154 (2001).

Haneda et al., "Transglycosylation of Intact Sialo Complex-Type Oligosaccharides to the N-Acetylglucosamine Moieties of Glycopeptides by Mucor Hiemalis Endo-Beta-N-Acetylglucosaminidase," *Carbohydr. Res.*, 292: 61-70 (1996).

Hang et al., "Ketone Isosteres of 2-N-Acetamidosugars as Substrates for Metabolic Cell Surface Engineering," *J. Am. Chem. Soc.*, 123(6): 1242-1243 (2001).

Hansen et al., "Prediction of O-Glycosylation of Mammalian Proteins: Specificity Patterns of UDP-Galnac:Polypeptide N-Acetylgalactosaminyltransferase," *Biochem J.*, 308: 801-813 (1995).

Haro et al., "Glycosylated Human Growth Hormone (Hgh): Novel 24 Kda Hgh-N Variant," *Biochem. Biophys. Res. Comm.*, 228(2): 549-556 (1996).

Harris et al., "Effect of pegylation on pharmaceuticals," *Nat. Rev. Drug Discov.*, 2(3): 214-221 (2003).

Harris et al., Abstracts of Papers of the American Chemical Society, V 201, APR, P 64-POLY, pp. 154-155 (1991).

Harris, "Laboratory Synthesis of Polyethylene Glycol Derivatives," *J. Macromol. Science, Rev. Macromol. Chem. Phys.*, C25(3): 325-373 (1985).

Harris (ed.), "Poly(Ethylene Glycol) Chemistry: Biotechnical and Biomedical Applications", Plenum Press, New York (1992) (Title Pages only).

Harris et al. (eds.), "Poly(ethylene glycol): Chemistry and Biological Applications," ACS Symposium Series, vol. 680, American Chemical Society (1997) (Title Pages only).

Hassan et al., "The Lectin Domain of UDP-N-Acetyl-D-Galactosamine: Polypeptide N-Acetylgalactosaminyltransferase-T4 Directs its Glycopeptide Specificities," *J. Biol. Chem.*, 275(49): 38197-38205 (2000).

Hassan et al., "Control of Mucin-Type O-Glycosylation: O-Glycan Occupancy is Directed by Substrate Specificities of Polypeptide GalNAc-Transferases," *Carbohydrates in Chemistry and Biology*, Part II, 3: 273-292 (2000).

Hayes et al., "The Biosynthesis of Oligosaccharides in Intact Golgi Preparations from Rat Liver. Analysis of N-linked and O-Linked Glycans Labeled by UDP-[6-3H]N-Acetylgalactosamine," *J. Biol. Chem.*, 268(22): 16170-16178 (1993).

Hellstrom et al., "Development and Activities of the BR96-Doxorubicin Immunoconjugate," *Methods Mol. Biol.*, 166: 3-16 (2001).

Hermanson et al., *Immobilized Affinity Ligand Techniques*, Academic Press (1992) (Table of Contents).

Hermanson, *Bioconjugate Techniques*, Academic Press, San Diego (1996) (Table of Contents).

Hermentin, et al., "The Hypothetical N-Glycan Charge: a Number That Characterizes Protein Glycosylation," *Glycobiology*, 6(2):217-230 (1996).

Herscovics et al., "Glycoprotein Biosynthesis in Yeast," *FASEB J.*, 7(6): 540-550 (1993).

Hills et al., "Control of Therapeutic Monoclonal Antibody Glycosylation Through the Addition of Sugar Media Components and In Vitro Remodling," *Am. Biotechnol. Lab.*, 20(11): 30 (2002).

Hink et al., "Expression of Three Recombinant Proteins Using Baculovirus Vectors in 23 Insect Cell Lines," *Biotechnol. Prog.*, 7(1): 9-14 (1991).

Höglund, "Glycosylated and Non-Glycosylated Recombinant Human Granulocyte Colony-Stimulating Factor (rhG-CSF)—What is the Difference?," *Med. Oncol.*, 15(4): 229-233 (1998).

Hollister et al., "Engineering Lepidopteran Insect Cells for Sialoglycoprotein Production by Genetic Transformation with Mammalian Beta 1,4-Galactosyltransferase and Alpha 2,6-Sialyltransferase Genes," *Glycobiology*, 11(1): 1-9 (2001).

Hounsell et al., "O-Linked Protein Glycosylation Structure and Function," *Glycoconj. J.*, 13(1): 19-26 (1996).

Hu et al., "FGF-18, A Novel Member of the Fibroblast Growth Factor Family, Stimulates Hepatic and Intestinal Proliferation," *Mol. Cell. Biol.*, 18(10): 6063-6074 (1998).

Ichikawa et al., Chemical-Enzymatic Synthesis and Conformational Analysis of Sialyl Lewis x and Derivatives, *J. Am. Chem. Soc.*, 114(24): 9283-9298 (1992).

Ikonomou et al., "Design of an Efficient Medium for Insect Cell Growth and Recombinant Protein Production," *In Vitro Cell. Dev. Biol. Anim.*, 37(9): 549-559 (2001).

Inlow et al., "Insect Cell Culture and Baculovirus Propagation in Protein-Free Medium," *J. Tissue Cult. Methods*, 12(1): 13-16 (1989).

Inoue et al., "The Production of Recombinant Human Erythropoietin," *Biotechnol. Annu. Rev.*, 1: 297-313 (1995).

Ito et al., "Synthesis of Bioactive Sialosides," *Pure Appl. Chem.*, 65(4): 753-762 (1993).

Jackson et al., "Synthesis, Isolation, and Characterization of Conjugates of Ovalbumin with Monomethoxypolyethylene Glycol Using Cyanuric Chloride as the Coupling Agent," *Anal. Biochem.*, 165(1): 114-127 (1987).

Jarvis et al., "Engineering N-Glycosylation Pathways in the Baculovirus-Insect Cell System," *Curr. Opin. Biotechnol.*, 9(5): 528-533 (1998).

Jezek et al., "Solid Phase Synthesis of Glycopeptide Dendrimers with Tn Antigenic Structure and Their Biological Activites. Part 1," *J. Peptide Sci.*, 5: 46-55 (1999).

Joppich et al., "Peptides Flanked by Two Polymer Chains, 1," *Makromol. Chem.*, 180: 1381-1384 (1979).

Josh et al., "ATP Synthase Complex from Bovine Heart Mitochondria. Subunit Arrangement as Revealed by Nearest Neighbor Analysis and Susceptibility to Trypsin," *J. Biol. Chem.*, 265(24): 14518-14525 (1990).

Jung et al., "Crosslinking of Platelet Glycoprotein lb by N-Succinimidyl(4-Azidophenyldithio)Propionate and 3,3'-Dithiobis-(Sulfosuccinimidyl Propionate)," *Biochim. Biophys. Acta*, 761(2): 152-162 (1983).

Kajihara et al., "Enzymatic Synthesis of Kdn Oligosaccharides by a Bacterial Alpha-(2→6)-Sialytransferase," *Carbohydrate Research*, 315: 137-141 (1999).

Kalsner et al., "Insertion into *Aspergillus nidulans* of Functional UDP-GlcNAc: Alpha 3-D-Mannoside Beta-1,2-N-Acetylglucosaminyl-Transferase I, the Enzyme Catalysing the First Committed Step from Oligomannose to Hybrid and Complex N-Glycans," *Glycoconj. J.*, 12(3): 360-370 (1995).

Kaneko et al., "Assignment of the Human Alpha 1,3-fucosyltransferase IX Gene (FUT9) to Chromosome Band 6q16 by In Situ Hybridization," *Cytogenet. Cell Genet.*, 86(3-4): 329-330 (1999).

Kaneko et al., "Alpha1,3-fucosyltransferase IX (Fuc-TIX) is Very Highly Conserved Between Human and Mouse; Molecular Cloning, Characterization and Tissue Distribution of Human Fuc-TIX," *FEBS Lett.*, 452(3): 237-242 (1999).

(56) References Cited

OTHER PUBLICATIONS

Kasina et al., "Simplified Preformed Chelate Protein Radiolabeling with Technetium-99m Mercaptoacetamidoadipoylglycylglycine (N3S-adipate)," *Bioconjug. Chem.*, 9(1): 108-117 (1998).
Katre et al., "Chemical Modification of Recombinant Interleukin 2 by Polyethylene Glycol Increases Its Potency in the Murine Meth a Sarcoma Model," *Proc. Natl. Acad. Sci. USA*, 84(6): 1487-1491 (1987).
Kawasaki et al., "Application of Liquid Chromatography/Mass Spectrometry and Liquid Chromatography With Tandem Mass Spectrometry to the Analysis of the Site-Specific Carbohydrate Heterogeneity in Erythropoietin," *Anal. Biochem.*, 285: 82-91 (2000).
Keana et al., "New Reagents for Photoaffinity Labeling: Synthesis and Photolysis of Functionalized Perfluorophenyl Azides," *J. Org. Chem.*, 55(11): 3640-3647 (1990).
Keene et al., "Expression of Biologically Active Human Follitropin in Chinese Hamster Ovary Cells," *J. Biol. Chem.*, 264(9): 4769-4775 (1989).
Keppler et al., "Biochemical Engineering of the N-Acyl Side Chain of Sialic Acid: Biological Implications," *Glycobiology*, 11(2): 11R-18R (2001).
Kimura et al., "Reconstitution of Functional L-Selectin Ligands on a Cultured Human Endothelial Cell Line by Cotransfection of Alpha1→3 Fucosyltransferase VII and Newly Cloned Glcnacbeta:6-Sulfotransferase Cdna," *Proc. Natl. Acad. Sci. USA*, 96(8): 4530-4535 (1999).
Kisselev, "Polypeptide Release Factors in Prokaryotes and Eukaryotes: Same Function, Different Structure," *Structure*, 10(1): 8-9 (2002).
Kitamura et al., "Polyethylene Glycol Modification of the Monoclonal Antibody A7 Enhances Its Tumor Localization," *Biochem. Biophys. Res. Commun.*, 171(3): 1387-1394 (1990).
Kitamura et al., "Chemical Engineering of the Monoclonal Antibody A7 by Polyethylene Glycol for Targeting Cancer Chemotherapy," *Cancer Res.*, 51(16): 4310-4315 (1991).
Kobayashi et al., "Monoclonal Antibody-Dendrimer Conjugates Enable Radiolabeling of Antibody With Markedly High Specific Activity With Minimal Loss of Immunoreactivity," *Eur. J. Nucl. Med.*, 27(9):1334-1339 (2000).
Kodama et al., "Synthesis of UDP-6-Deoxy- and-6-Fluoro-D-Galactoses and Their Enzymatic Glycosyl Transfer to Mono- and Biantennary Carbohydrate Chains," *Tetrahedron Lett.*, 34(40): 6419-6422 (1993).
Koeller et al., "Emerging Themes in Medicinal Glycoscience," *Nat. Biotechnol.*, 18(8): 835-841 (2000).
Koeller et al., "Enzymes for Chemical Synthesis," *Nature*, 409(6817): 232-240 (2001).
Koide et al., "Modification of Amino Groups in Porcine Pancreatic Elastase With Polyethylene Glycol in Relation to Binding Ability Towards Anti-Serum and to Enzymic Activity," *Biochem. Biophys. Res. Commun.*, 111(2): 659-667 (1983).
Kornfeld et al., "Assembly of Asparagine-Linked Oligosaccharides," *Ann. Rev. Biochem.*, 54: 631-664 (1985).
Kreitman, "Toxin-Labeled Monoclonal Antibodies," *Curr. Pharm. Biotechnol.*, 2(4): 313-325 (2001).
Krystal et al., "Purification of Human Erythropoietin to Homogeneity by a Rapid Five-Step Procedure," *Blood*, 67(1): 71-99 (1986).
Kuhn et al., "Active Site and Oligosaccharide Recognition Residues of Peptide-N4-(N-Acetyl-Beta-D-Glucosaminyl)Asparagine Amidase F," *J. Biol. Chem.*, 270(49): 29493-29497 (1995).
Kukowska-Latallo et al., "A Cloned Human Cdna Determines Expression of a Mouse Stage-Specific Embryonic Antigen and the Lewis Blood Group Alpha(1,3/1,4)Fucosyltransferase," *Genes Dev.*, 4(8): 1288-1303 (1990).
Kukuruzinska et al., "Protein Glycosylation in Yeast: Transcript Heterogeneity of the ALG7 Gene," *Proc. Natl. Acad. Sci. USA*, 84(8): 2145-2149 (1987).
Lai et al, "Structural Characterization of Human Erythropoietin," *J. Biol. Chem.*, 261(7): 3116-3121 (1986).

Langer, "New Methods of Drug Delivery," *Science*, 249(4976): 1527-1533 (1990).
Lau et al., "Quantitative Competitive Reverse Transcription-PCR As a Method to Evaluate Retrovirus Removal During Chromatography Procedures," *J. Biotechnol.*, 75(2-3): 105-115 (1999).
Lee et al., "Efficient Coupling of Glycopeptides to Proteins With a Heterobifunctional Reagent," *Biochemistry*, 28(4): 1856-1861 (1989).
Lee-Huang et al., "Cloning and Expression of Human Erythropoietin Cdna in *Escherichia coli*," *Proc. Natl. Acad. Sci. USA*, 81(9): 2708-2712 (1984).
Legault et al., "Human Alpha(1,3/1,4)-Fucosyltransferases Discriminate Between Different Oligosaccharide Acceptor Substrates Through a Discrete Peptide Fragment," *J. Biol. Chem.*, 270(36): 20987-20996 (1995).
Leist et al., "Derivatives of Erythropoietin That Are Tissue Protective But Not Erythropoietic," *Science*, 305: 239-242 (2004).
Leiter et al., "Purification, Cdna Cloning, and Expression of GDP-L-Fuc:Asn-Linked Glcnac Alpha1,3-Fucosyltransferase From Mung Beans," *J. Biol. Chem.*, 274(31): 21830-21839 (1999).
Leung, "Engineering a Unique Glycosylation Site for Site-Specific Conjugation of Haptens to Antibody Fragments," *J. Immunol.*, 154(11): 5919-5926 (1995).
Lewis et al., "Structure and Properties of Members of the Hgh Family: A Review," *Endocr. J.*, 47(Suppl.): S1-S8 (2000).
Li et al., "The Role of the Transferrin-Transferrin-Receptor System in Drug Delivery and Targeting," *Trends Pharmacol. Sci.*, 23(5): 206-209 (2002).
Li et al., "Transferrin/Transferrin Receptor-Mediated Drug Delivery," *Med. Res. Rev.*, 22(3): 225-250 (2002).
Licari et al., "Modeling the Population Dynamics of Baculovirus-Infected Insect Cells: Optimizing Infection Strategies for Enhanced Recombinant Protein Yields," *Biotechnol. Bioeng.*, 39(4): 432-441 (1992).
Licari et al., "Production of a Discrete, Heterogeneous Population of Beta-Galactosidase Polypeptides Using Baculovirus Expression Vectors," *Biotechnol. Bioeng.*, 39(9): 932-944 (1992).
Lin et al., "Cloning and Expression of the Human Erythropoietin Gene," *Proc. Natl. Acad. Sci. USA*, 82: 7580-7584 (1985).
Liu et al., "A Paradigm Case for the Merging of Glycal and Enzymatic Assembly Methods in Glycoconjugate Synthesis: A Highly Efficient Chemo-Enzymatic Synthesis of $GM_3$," *Chem. Eur. J.*, 2(11): 1359-1362 (1996).
Long et al., "Design of Homogeneous, Monopegylated Erythropoietin Analogs With Preserved In Vitro Bioactivity," *Exp. Hematol.*, 34(6): 697-704 (2006).
Lönnberg, "Solid-Supported Synthesis of Glycoconjugates," *Curr. Org. Synth.*, 6(4): 400-425 (2009).
Lord et al., "Kinetics of Neutrophil Production in Normal and Neutropenic Animals During the Response to Filgrastim (R-Methu G-CSF) or Filgrastim SD/01 (PEG-R-Methu G-CSF)," *Clin. Cancer Res.*, 7(7): 2085-2090 (2001).
Lougheed et al., "Glycosyl Fluorides Can Function As Substrates for Nucleotide Phosphosugar-Dependent Glycosyltransferases," *J. Biol. Chem.*, 274(53): 37717-37722 (1999).
Luckow et al., "Baculovirus Systems for the Expression of Human Gene Products," *Curr. Opin. Biotechnol.*, 4(5): 564-572 (1993).
Lund et al., "Oligosaccharide-Protein Interactions In Igg Can Modulate Recognition by Fc Gamma Receptors," *FASEB J.*, 9(1): 115-119 (1995).
Lund et al., "Multiple Interactions of Igg With Its Core Oligosaccharide Can Modulate Recognition by Complement and Human Fc Gamma Receptor I and Influence the Synthesis of its Oligosaccharide Chains," *J. Immunol.*, 157(11): 4963-4969 (1996).
Mahal et al., "Engineering Chemical Reactivity on Cell Surfaces Through Oligosaccharide Biosynthesis," *Science*, 276(5315): 1125-1128 (1997).
Malissard et al., "Expression of Functional Soluble Forms of Human Beta-1, 4-Galactosyltransferase I, Alpha-2,6-Sialyltransferase, and Alpha-1, 3-Fucosyltransferase VI in the Methylotrophic Yeast *Pichia pastoris*," *Biochem. Biophys. Res. Commun.*, 267(1): 169-173 (2000).

(56) References Cited

OTHER PUBLICATIONS

Maranga et al., "Virus-Like Particle Production At Low Multiplicities of Infection With the Baculovirus Insect Cell System," *Biotechnol. Bioeng.*, 84(2): 245-253 (2003).

Maras et al., "Molecular Cloning and Enzymatic Characterization of a *Trichoderma reesei* 1,2-Alpha-D-Mannosidase," *J. Biotechnol.*, 77(2-3): 255-263 (2000).

Meynial-Salles et al., "In Vitro Glycosylation of Proteins: An Enzymatic Approach," *J. Biotechnol.*, 46(1): 1-14 (1996).

Miller, "Baculoviruses: High-Level Expression in Insect Cells," *Curr. Opin. Genet. Dev.*, 3(1): 97-101 (1993).

Min et al., "Site-Directed Mutagenesis of Recombinant Equine Chorionic Gonadotropin/Luteinizing Hormone: Differential Role of Oligosaccharides in Luteinizing Hormone- and Follicle-Stimulating Hormone-Like Activities," *Endocr. J.*, 43(5): 585-593 (1996).

Mistry et al., "Therapeutic Delivery of Proteins to Macrophages: Implications for Treatment of Gaucher's Disease," *Lancet*, 348(9041): 1555-1559 (1996).

Mollicone et al., "Acceptor Specificity and Tissue Distribution of Three Human Alpha-3-Fucosyltransferases," *Eur. J. Biochem.*, 191(1): 169-176 (1990).

Monaco et al., "Expression of Recombinant Human Granulocyte Colony-Stimulating Factor in CHO Dhfr-Cells: New Insights Into the In Vitro Amplification Expression System," *Gene*, 180: 145-150 (1996).

Morimoto et al., "Biological and Physicochemical Characterization of Recombinant Human Erythropoietins Fractionated by Mono Q Column Chromatography and Their Modification With Sialyltransferase," *Glycoconj. J.*, 13(6): 1013-1020 (1996).

Müller et al., "Localization of O-Glycosylation Sites on Glycopeptide Fragments From Lactation-Associated MUC1. All Putative Sites Within the Tandem Repeat Are Glycosylation Targets In Vivo," *J. Biol. Chem.*, 272(40): 24780-24793 (1997).

Müller et al., "High Density O-Glycosylation on Tandem Repeat Peptide From Secretory MUC1 of T47D Breast Cancer Cells," *J. Biol. Chem.*, 274(26): 18165-18172 (1999).

Nagata et al., "The Chromosomal Gene Structure and Two mRNAs for Human Granulocyte Colony-Stimulating Factor," *EMBO J.*, 5(3): 575-581 (1986).

Natsuka et al., "Molecular Cloning of a cDNA Encoding a Novel Human Leukocyte Alpha-1,3-fucosyltransferase Capable of Synthesizing the Sialyl Lewis X Determinant," *J. Biol. Chem.*, 269(24): 16789-16794 (1994).

NCBI—Accession No. NCAA26095 (2 pgs.) (2006).

NCBI—Accession No. NP_058697 (3 pgs.) (2007).

NCBI—Accession No. NP_999299 (2 pgs.) (2007).

NCBI Database hits for erythropoietin protein sequences (3 pgs.) (2007).

Ngo et al., "The Protein Folding Problem and Tertiary Structure Prediction, Chapter 14: Computational Complexity Protein Structure Prediction, and the Levinthal Paradox," pp. 433-440 and 492-495 (1994).

Nilsson et al., "Immobilization of Ligands with Organic Sulfonyl Chlorides," *Methods Enzymol.*, 104: 56-69 (1984).

Nunez et al., "The Synthesis and Characterization of 60 - and β-L-Fucopyranosyl phosphates and GDP Fucose[1]," *Can. J. Chem.*, 59(14): 2086-2095 (1981).

O'Connell et al., "The Influence of Flanking Sequence on the O-Glycosylation of Threonine In Vitro," *J. Biol. Chem.*, 267(35): 25010-25018 (1992).

Oetke et al., "Versatile Biosynthetic Engineering of Sialic Acid in Living Cells Using Synthetic Sialic Acid Analogues, *J. Biol. Chem.*, 277(8): 6688-6695 (2002).

Oh-Eda et al., "O-Linked Sugar Chain of Human Granulocyte Colony-Stimulating Factor Protects it Against Polymerization and Denaturation Allowing it to Retain its Biological Activity," *J. Biol. Chem.*, 265: 11432-11435 (1990).

Olson et al., "Structural Basis for Recognition of Phosphorylated High Mannose Oligosaccharides by the Cation-Dependent Mannose 6-Phosphate Receptor," *J. Biol. Chem.*, 274(42): 29889-29896 (1999).

Orlean, "vol. III: The Molecular and Cellular Biology of the Yeast *Saccharomyces*: Cell Cycle and Cell Biology", in *Biogenesis of Yeast Wall and Surface Components*, Chapter 3, pp. 229-362, Cold Spring Harbor Laboratory Press (1997).

Orskov et al., "Complete Sequences of Glucagon-Like Peptide-1 from Human and Pig Small Intestine," *J. Biol. Chem.*, 264(22): 12826-12829 (1989).

Palacpac et al., "Stable Expression of Human Beta1,4-Galactosyltransferase in Plant Cells Modifies N-linked Glycosylation Patterns," *Proc. Natl. Acad. Sci. USA*, 96(8): 4692-4697 (1999).

Palcic et al., "Enzymic Synthesis of Oligosaccharides Terminating in the Tumor-Associated Sialyl-Lewis—a Determinant," *Carbohydr. Res.*, 190(1): 1-11 (1989).

Park et al., "Characterization of the Cell Surface Receptor for a Multi-Lineage Colony-Stimulating Factor (CSF-2 alpha).," *J. Biol. Chem.*, 261(1): 205-210 (1986).

Paulson et al., "Reactivation of Asialo-Rabbit Liver Binding Protein by Resialylation with Beta-D-Galactoside Alpha2 Leads to 6 Sialyltransferase," *J. Biol. Chem.*, 252(23): 8624-8628 (1977).

Plummer et al., "Novel, Specific O-Glycosylation of Secreted *Flavobacterium meningosepticum* Proteins. Asp-Ser and Asp—Thr—Thr Consensus Sites," *J. Biol. Chem.*, 270(22): 13192-13196 (1995).

PNGase-F Amidase Sequence from *F. meningosepticum* (RN 128688-70-0) (2007).

PNGase-F Amidase Sequence from *F. meningosepticum* (RN 128688-71-1) (2007).

Prati et al., "Engineering of Coordinated Up- and Down-Regulation of Two Glycosyltransferases of the O-Glycosylation Pathway in Chinese Hamster Ovary (CHO) Cells," *Biotech and Bioeng.*, 79(5): 580-585 (2002).

Prieels et al., "Co-Purification of the Lewis Blood Group N-Acetylglucosaminide Alpha 1 goes to 4 Fucosyltransferase and an N-Acetylglucosaminide Alpha 1 goes to 3 Fucosyltransferase From Human Milk," *J. Biol. Chem.*, 256(20): 10456-10463 (1981).

Pyatak et al., "Preparation of a Polyethylene Glycol: Superoxide Dismutase Adduct, and an Examination of its Blood Circulation Life and Anti-Inflammatory Activity," *Res. Commun. Chem. Pathol. Pharmacol.*, 29(1): 113-127 (1980).

Quelle et al., "High-level Expression and Purification of a Recombinant Human Erythropoietin Produced Using a Baculovirus Vector," *Blood*, 74(2): 652-657 (1989).

Rabouille et al., "The *Drosophila* GMII Gene Encodes a Golgi Alpha-Mannosidase II," *J Cell Sci.*, 112(Pt. 19): 3319-3330 (1999).

Rasko et al., "Cloning and Characterization of the Alpha(1,3/4) Fucosyltransferase of *Helicobacter pylori*," *J. Biol. Chem.*, 275(7): 4988-4994 (2000).

R & D Systems, Fibroblast Growth Factors (FGFs), Internet page from www.rndsystems.com/mini_review_detail_objectname_MR01_FGFs.aspx, 2001, printed Mar. 10, 2011.

Reff et al., "Future of Monoclonal Antibodies in the Treatment of Hematologic Malignancies," *Cancer Control*, 9(2): 152-166 (2002).

Rosenthal et al., "Isolation of Peptidoglycan and Soluble Peptidoglycan Fragments," *Methods Enzymol.*, 235: 253-285 (1994).

Rotondaro et al., "Purification and Characterization of Two Recombinant Human Granulocyte Colony-Stimulating Factor Glycoforms," *Mol. Biotech.*, 11: 117-128 (1999).

Rudikoff et al., "Single Amino Acid Substitution Altering Antigen-Binding Specificity," *Proc. Natl. Acad. Sci. USA*, 79(6):1979-1983 (1982).

Sadler et al., "Purification of Mammalian Glycosyltransferases," *Methods Enzymol.*, 83: 458-514 (1982).

Sandberg et al., "Structural and Functional Characterization of B-Domain Deleted Recombinant Factor VIII," *Semin. Hematol.*, 38(2 Suppl. 4): 4-12 (2001).

Saneyoshi et al., "Equine Follicle-Stimulating Hormone: Molecular Cloning of Beta Subunit and Biological Role of the Asparagine-Linked Oligosaccharide at Asparagine(56) of Alpha Subunit," *Biol. Reprod.*, 65(6): 1686-1690 (2001).

(56) References Cited

OTHER PUBLICATIONS

Sasaki et al., "Carbohydrate Structure of Erythropoietin Expressed in Chinese Hamster Ovary Cells by a Human Erythropoietin CdnA," *J. Biol. Chem.*, 262(25): 12059-12076 (1987).
Sasaki et al., "Expression Cloning of a Novel Alpha 1,3-Fucosyltransferase that is Involved in Biosynthesis of the Sialyl Lewis X Carbohydrate Determinants in Leukocytes," *J.Biol. Chem.*, 269(20): 14730-14737 (1994).
Saxon et al., "Cell Surface Engineering by a Modified Staudinger Reaction," *Science*, 287(5460): 2007-2010 (2000).
Saxon et al., "Investigating Cellular Metabolism of Synthetic Azidosugars with the Staudinger Ligation," *J. Am. Chem. Soc.*, 124(50): 14893-14902 (2002).
Schlaeger, "Medium Design for Insect Cell Culture," *Cytotechnology*, 20(1-3): 57-70 (1996).
Schwientek et al., "Efficient intra- and Extracellular Production of Human Beta-1,4-Galactosyltransferase in *Saccharomyces cerevisiae* is Mediated by Yeast Secretion Leaders," *Gene*, 145(2): 299-303 (1994).
Schwientek et al., "Functional Conservation of Subfamilies of Putative UDP-N-Acetylgalactosamine: Polypeptide N-Acetylgalactosaminyltransferases in *Drosophila, Caenorhabditis elegans*, and Mammals. One Subfamily Composed of I(2)35Aa is Essential in *Drosophila*," *J. Biol. Chem.*, 277(25): 22623-22638 (2002).
Scouten, "A Survey of Enzyme Coupling Techniques," *Methods Enzymol.*, 135: 30-65 (1987).
Seely et al., "Use of Ion-Exchange Chromatography and Hydrophobic Interaction Chromatography in the Preparation and Recovery of Polyethylene Glycol-Linked Proteins," *J. Chromatog.*, 908: 235-241 (2001).
Seffernick et al., "Melamine Deaminase and Atrazine Chlorohydrolase: 98 Percent Identical but Functionally Different," *J. Bacteriol.*, 183(8): 2405-2410 (2001).
Seitz, "Glycopeptide Synthesis and the Effects of Glycosylation on Protein Structure and Activity," *Chembiochem.*, 1(4): 214-246 (2000).
Shah et al., "Transcellular Delivery of an Insulin-Transferrin Conjugate in Enterocyte-Like Caco-2 Cells," *J. Pharm. Sci.*, 85(12): 1306-1311 (1996).
Shapiro et al., "The Safety and Efficacy of Recombinant Human Blood Coagulation Factor IX in Previously Untreated Patients with Severe or Moderately Severe Hemophilia B," *Blood*, 105(2): 518-525 (2005).
Shen et al., "Cis-Aconityl Spacer Between Daunomycin and Macromolecular Carriers: a Model of pH-Sensitive Linkage Releasing Drug from a Lysosomotropic Conjugate," *Biochem. Biophys. Res. Commun.*, 102(3): 1048-1054 (1981).
Shinkai et al., "Protein Expression and Purification," *Prot. Exp. Purif.*, 10: 379-385 (1997).
Sinclair et al., "Glycoengineering: the Effect of Glycosylation on the Properties of Therapeutic Proteins," *J. Pharm. Sci.*, 94: 1626-1635 (2005).
Singh et al., "Glycosidase-catalysed synthesis of oligosaccharides: a two-step synthesis of the core trisaccharide of N-linked glycoproteins using the β-N-Nacetylhexosaminidase and the β-mannosidase from *Aspergillus oryzae*," *Chem. Commun.*, 1996(8): 993-994 (1996).
Sinha et al., "Release of Soluble Peptidoglycan from Growing Conococci: Demonstration of Anhydro-Muramyl-Containing Fragments," *Infect. Immun.*, 29(3): 914-925 (1980).
Skolnick et al., "From Genes to Protein Structure and Function: Novel Applications of Computational Approaches in the Genomic Era," *Trends Biotechnol.*, 18(1): 34-39 (2000).
Smith et al., "The Challenges of Genome Sequence Annotation or "the Devil is in the Details"," *Nat. Biotechnol.*, 15(12): 1222-1223 (1997).
Snider et al., "Characterization of the Heterogeneity of Polyethylene Glycol-Modified Superoxide Dismutase by Chromatographic and Electrophoretic Techniques," *J. Chromatogr.*, A 599(1-2): 141-155 (1992).
Sojar et al., "A Chemical Method for the Deglycosylation of Proteins," *Arch. Biochem. Biophys.*, 259(1): 52-57 (1987).
Song et al., "Reassembled Biosynthetic Pathway for a Large-Scale Synthesis of CMP-Neu5Ac," *Mar. Drugs*, 1: 34-45 (2003).
Srinivasachar et al., "New Protein Cross-Linking Reagents that are Cleaved by Mild Acid," *Biochemistry*, 28(6): 2501-2509 (1989).
Staudacher, "α1,3 Fucosyltransferases," *Trends Glycosci. Glycotechnol.*, 8(44): 391-408 (1996).
Stemmer, "Rapid Evolution of a Protein In Vitro by DNA Shuffling," *Nature*, 370(6488): 389-391 (1994).
Stemmer, "DNA Shuffling by Random Fragmentation and Reassembly: In Vitro Recombination for Molecular Evolution," *Proc. Natl. Acad. Sci. USA*, 91(22): 10747-10751 (1994).
Stephens et al., "The Pyruvate Dehydrogenase Complex of *Escherichia coli* K12. Nucleotide Sequence Encoding the Pyruvate Dehydrogenase Component," *Eur. J. Biochem.*, 133(1): 155-162 (1983).
Stephens et al., "The Pyruvate Dehydrogenase Complex of *Escherichia coli* K12. Nucleotide Sequence Encoding the Dihydrolipoamide Acetyltransferase Component," *Eur. J. Biochem.*, 133(3): 481-489 (1983).
Stephens et al., "Nucleotide Sequence of the Lipoamide Dehydrogenase Gene of *Escherichia coli* K12," *Eur. J. Biochem.*, 135(3): 519-527 (1983).
Strausberg et al., "Generation and Initial Analysis of More Than 15,000 Full-Length Human and Mouse cDNA Sequences," *Proc Natl Acad Sci USA*, 99(26): 16899-16903 (2002).
Takane et al., "Chronopharmacology of Antitumor Effect Induced by Interferon-Beta in Tumor-Bearing Mice," *J Pharmacol Exp Ther.*, 294(2): 746-752 (2000).
Takeda et al., "GPI-Anchor Biosynthesis," *Trends Biochem. Sci.*, 20(9): 367-371 (1995).
Takeuchi et al., "Role of Sugar Chains in the In Vitro Biological Activity of Human Erythropoietin Produced in Recombinant Chinese Hamster Ovary Cells," *J. Biol. Chem.*, 265(21): 12127-12130 (1990).
Taniguchi et al., "A Glycomic Approach to the Identification and Characterization of Glycoprotein Function in Cells Transfected with Glycosyltransferase Genes," *Proteomics*, 1(2): 239-247 (2001).
Tanner et al., "Protein Glycosylation in Yeast," *Biochim. Biophys. Acta*, 906(1): 81-99. (1987).
Taylor et al., Protein Immobilization Fundamentals and Applications, Manual (1991).
Ten Hagen et al., "Characterization of a UDP-GalNAc:Polypeptide N-Acetylgalactosaminyltransferase that Displays Glycopeptide N-Acetylgalactosaminyltransferase Activity," *J. Biol. Chem.*, 274(39): 27867-27874 (1999).
Tenno et al., "The Lectin Domain of UDP-GalNAc:Polypeptide N-Acetylgalactosaminyltransferase 1 is Involved in O-Glycosylation of a Polypeptide With Multiple Acceptor Sites," *J. Biol. Chem.*, 277(49): 47088-47096 (2002).
Thotakura et al., "Enzymatic Deglycosylation of Glycoproteins," *Meth. Enzym.*, 138: 350-9 (1987).
Tom et al., "Reproducible Production of a PEGylated Dual-Acting Peptide for Diabetes," *AAPS Journal*, 9(2): E227-E234 (2007).
Trottein et al., "Molecular Cloning of a Putative Alpha3-Fucosyltransferase from *Schistosoma mansoni*," *Mol. Biochem. Parasitol.*, 107(2): 279-287 (2000).
Tsuboi et al., "Acquisition of P-Selectin Binding Activity by En Bloc Transfer of Sulfo Le(x) Trisaccharide to the Cell Surface: Comparison to a Sialyl Le(x) Tetrasaccharide Transferred on the Cell Surface," *Arch. Biochem. Biophys.*, 374(1): 100-106 (2000).
Tsunoda et al., "Enhanced Antitumor Potency of Polyethylene Glycolylated Tumor Necrosis Factor-α: A Novel Polymer-Conjugation Technique with a Reversible Amino-Protective Reagent[1]," *J. Pharmacol. Exp. Ther.*, 209(1): 368-372 (1999).
Tuddenham"RNA as Drug and Antidote," *Nature*, 419(6902): 23-24 (2002).
Udenfriend et al., "How Glycosylphosphatidylinositol-Anchored Membrane Proteins are Made," *Annu. Rev. Biochem.*, 64: 563-591 (1995).
Ulloa-Aguirre et al., "Role of Glycosylation in Function of Follicle-Stimulating Hormone," *Endocrine*, 11(3): 205-215 (1999).

(56) References Cited

OTHER PUBLICATIONS

Uludag et al., "Targeting Systemically Administered Proteins to Bone by Bisphosphonate Conjugation," *Biotechnol. Prog.*, 18(3): 604-611 (2002).
Urdal et al, "Lymphokine Purification by Reversed-Phase High-Performance Liquid Chromatography," *J. Chromatogr.*, 296: 171-179 (1984).
Van Berkel et al., „Heterogeneity in Utilization of N-Glycosylation Sites Asn624 and Asn138 in Human Lactoferrin: a Study With Glycosylation-Site Mutants, *Biochem. J.*, 319(Pt. 1): 117-122 (1996).
Van Reis et al., "Industrial Scale Harvest of Proteins From Mammalian Cell Culture by Tangential Flow Filtration," *Biotechnol. Bioeng.*, 38(4): 413-422 (1991).
Van Tetering et al., "Characterization of a Core Alpha1→3-Fucosyltransferase from the Snail *Lymnaea stagnalis* that is Involved in the Synthesis of Complex-Type N-Glycans," *FEBS Lett.*, 461(3): 311-314 (1999).
Veronese et al., "Surface Modification of Proteins. Activation of monomethoxy-Polyethylene Glycols by Phenylchloroformates and Modification of ribonuclease and Superoxide Dismutase," *Appl. Biochem. Biotechnol.*, 11(2): 141-152 (1985).
Veronese, „Peptide and Protein PEGylation: a Review of Problems and Solutions, *Biomaterials*, 22(5): 405-417 (2001).
Vitetta et al., "Immunology. Considering Therapeutic Antibodies," *Science*, 313: 308-309 (2006).
Vocadlo et al., "Glycosidase-Catalysed Oligosaccharide Synthesis" in *Carbohydrate Chemistry and Biology*, vol. 2, Chapter 29, pp. 723-844 (2000).
Vyas et al., "Ligand-Receptor-Mediated Drug Delivery: An Emerging Paradigm in Cellular Drug Targeting," *Crit. Rev. Ther. Drug Carrier Syst.*, 18(1): 1-76 (2001).
Wang et al., "Identification of a GDP-L-Fucose:Polypeptide Fucosyltransferase and Enzymatic Addition of O-Linked Fucose to EGF Domains," *Glycobiology*, 6(8): 837-842 (1996).
Wang et al., "Chemoenzymatic Synthesis of a High-Mannose-Type N-Glycopeptide Analog With C-Glycosidic Linkage," *Tetrahedron Lett.*, 37(12): 1975-1978 (1996).
Wang et al., "Single-Chain Fv With Manifold N-Glycans As Bifunctional Scaffolds for Immunomolecules," *Protein Eng.*, 11(12): 1277-1283 (1998).
Wang et al., "Novel *Helicobacter pylori* Alpha1,2-Fucosyltransferase, A Key Enzyme in the Synthesis of Lewis Antigens," *Microbiol.*, 145(Pt. 11): 3245-3253 (1999).
Wellhöner et al., "Uptake and Concentration of Bioactive Macromolecules by K562 Cells Via the Transferrin Cycle Utilizing an Acid-Labile Transferrin Conjugate," *J. Biol. Chem.*, 266(7): 4309-4314 (1991).
Wells, "Additivity of Mutational Effects in Proteins," *Biochemistry*, 29(37): 8509-8517 (1990).
Weston et al., "Isolation of a Novel Human Alpha (1,3) Fucosyltransferase Gene and Molecular Comparison to the Human Lewis Blood Group Alpha (1,3/1,4) Fucosyltransferase Gene. Syntenic, Homologous, Nonallelic Genes Encoding Enzymes With Distinct Acceptor Substrate Specificities," *J. Biol. Chem.*, 267(6): 4152-4160 (1992).
Weston et al., "Molecular Cloning of a Fourth Member of a Human Alpha (1,3)Fucosyltransferase Gene Family," *J. Biol. Chem.*, 267(34): 24575-24584 (1992).
White et al., "Purification and Cdna Cloning of a Human UDP-N-Acetyl-Alpha-D-Galactosamine:Polypeptide N-Acetylgalactosaminyltransferase," *J. Biol. Chem.*, 270(41): 24156-24165 (1995).
Wishart et al., "A Single Mutation Converts a Novel Phosphotyrosine Binding Domain Into a Dual-Specificity Phosphatase," *J. Biol. Chem.*, 270(45): 26782-26785 (1995).
Witkowski et al., "Conversion of a Beta-Ketoacyl Synthase to a Malonyl Decarboxylase by Replacement of the Active-Site Cysteine With Glutamine," *Biochemistry*, 38(36): 11643-11650 (1999).
Witte et al., "Enzymatic Glycoprotein Synthesis: Preparation of Ribonuclease Glycoforms Via Enzymatic Glycopeptide Condensation and Glycosylation," *J. Am. Chem. Soc.*, 119(9): 2114-2118 (1997).
Witte et al., "Monoclonal Antibodies Targeting the VEGF Receptor-2 (Flk1/KDR) As an Anti-Angiogenic Therapeutic Strategy," *Cancer and Metastasis Rev.*, 17: 155-161 (1998).
Woghiren et al., "Protected Thiol-Polyethylene Glycol: A New Activated Polymer for Reversible Protein Modification," *Bioconjug. Chem.*, 4(5): 314-318 (1993).
Wong et al., "Enzyme-Catalyzed Synthesis of *N*-Acetyllactosamine With In Situ Regeneration of Uridine 5'-Diphosphate Glucose and Uridine 5'-Diphosphate Galactose," *J. Org. Chem.*, 47(27): 5416-5418 (1982).
Wong et al., "Chemical Crosslinking and the Stabilization of Proteins and Enzymes," *Enzyme Microb Technol.*, 14(11): 866-874 (1992).
Wong et al., "Low Multiplicity of Infection of Insect Cells With a Recombinant Baculovirus: The Cell Yield Concept," *Biotechnol. Bioeng.*, 49(6): 659-666 (1996).
Woods et al., "Transferrin Receptors and Cation-Independent Mannose-6-Phosphate Receptors Deliver Their Ligands to Two Distinct Subpopulations of Multivesicular Endosomes," *Eur. J. Cell Biol.*, 50(1): 132-143 (1989).
Wright et al., "Effect of C2-Associated Carbohydrate Structure on Ig Effector Function: Studies With Chimeric Mouse-Human Igg1 Antibodies in Glycosylation Mutants of Chinese Hamster Ovary Cells," *J. Immunol.*, 160(7): 3393-3402 (1998).
Wu et al., "Pharmacokinetics and Brain Uptake of Biotinylated Basic Fibroblast Growth Factor Conjugated to a Blood-Brain Barrier Drug Delivery System," *J. Drug Target.*, 10(3): 239-245 (2002).
Xing et al., "Design of a Transferrin-Proteinase Inhibitor Conjugate to Probe for Active Cysteine Proteinases in Endosomes," *Biochem. J.*, 336(Pt. 3): 667-673 (1998).
Yamada et al., "Selective Modification of Aspartic Acid-101 in Lysozyme by Carbodiimide Reaction," *Biochemistry*, 20(17): 4836-4842 (1981).
Yamamoto et al., "Chemoenzymatic Synthesis of a Novel Glycopeptide Using a Microbial Endoglycosidase," *Carbohydr. Res.*, 305(3-4): 415-422 (1998).
Yarema et al., "Metabolic Delivery of Ketone Groups to Sialic Acid Residues. Application to Cell Surface Glycoform Engineering," *J. Biol. Chem.*, 273(47): 31168-31179 (1998).
Yoshida et al., "Expression and Characterization of Rat UDP-N-Acetylglucosamine: Alpha-3-D-Mannoside Beta-1,2-N-Acetylglucosaminyltransferase I in *Saccharomyces cerevisiae*," *Glycobiology*, 9(1): 53-58 (1999).
Yoshitake et al., "Nucleotide Sequence of the Gene for Human Factor IX (Antihemophilic Factor B)," *Biochemistry*, 24(14): 3736-3750 (1985).
Younes et al., "Morphological Study of Biodegradable PEO/PLA Block Copolymers," *J. Biomed. Mater. Res.*, 21(11): 1301-1316 (1987).
Zalipsky et al., "Use of Functionalized Poly(Ethylene Glycol)s for Modification of Polypeptides" in *Poly(Ethylene Glycol) Chemistry: Biotechnical and Biomedical Applications*, Harris (ed.), Chapter 21, pp. 347-370 (Plenum Press, New York, 1992).
Zalipsky, "Functionalized Poly(Ethylene Glycol) for Preparation of Biologically Relevant Conjugates," *Bioconjug. Chem.*, 6(2): 150-165 (1995).
Zarling et al., "Mapping of Lymphocyte Surface Polypeptide Antigens by Chemical Cross-Linking With BSOCOES," *J. Immunol.*, 124(2): 913-920 (1980).
Zhang et al., "Stable Expression of Human Alpha-2,6-Sialyltransferase in Chinese Hamster Ovary Cells: Functional Consequences for Human Erythropoietin Expression and Bioactivity," *Biochim. Biophys. Acta*, 1425: 441-452 (1998).
Zheng et al., "Optimized Production of Recombinant Bluetongue Core-Like Particles Produced by The Baculovirus Expression System," *Biotechnol. Bioeng.*, 65(5): 600-604 (1999).
Zhou et al., "Lipooligosaccharide Biosynthesis in *Neisseria gonorrhoeae*: Cloning, Identification and Characterization of the Alpha 1,5 Heptosyltransferase I Gene (Rfac)," *Mol. Microbiol.*, 14(4): 609-618 (1994).

(56) References Cited

OTHER PUBLICATIONS

Drucker et al., *J. Biol. Chem.*, 263(27): 13475-13478 (1988).
Office Action dated Mar. 13, 2013 in U.S. Appl. No. 12/811,963.
Office Action dated Mar. 14, 2013 in U.S. Appl. No. 12/784,323.
Office Action dated Mar. 21, 2013 in U.S. Appl. No. 13/541,185.
Office Action dated May 9, 2013 in U.S. Appl. No. 12/594,326.
Office Action dated May 21, 2013 in U.S. Appl. No. 12/811,963.
Office Action dated Jun. 6, 2013 in U.S. Appl. No. 11/701,949.
Office Action dated Oct. 6, 2011 in U.S. Appl. No. 12/663,748.
Office Action dated Nov. 2, 2011 in U.S. Appl. No. 12/201,705.
Office Action dated Nov. 17, 2011 in U.S. Appl. No. 12/443,428.
Office Action dated Dec. 1, 2011 in U.S. Appl. No. 11/794,560.
Office Action dated Dec. 22, 2011 in U.S. Appl. No. 12/858,247.
Office Action dated Jan. 3, 2012 in U.S. Appl. No. 11/632,005.
Office Action dated Feb. 29, 2012 in U.S. Appl. No. 12/858,247.
Office Action dated Mar. 21, 2012 in U.S. Appl. No. 11/794,560.
Office Action dated Mar. 29, 2012 in U.S. Appl. No. 12/594,326.
Office Action dated Apr. 18, 2012 in U.S. Appl. No. 12/663,748.
Office Action dated Apr. 19, 2012 in U.S. Appl. No. 13/215,439.
Office Action dated Aug. 8, 2012 in U.S. Appl. No. 13/157,575.
Office Action dated Aug. 17, 2012 in U.S. Appl. No. 12/594,326.
Office Action dated Sep. 21, 2012 in U.S. Appl. No. 12/663,748.
Office Action dated Sep. 24, 2012 in U.S. Appl. No. 12/784,323.
Office Action dated Sep. 25, 2012 in U.S. Appl. No. 13/186,726.
Office Action dated Oct. 23, 2012 in U.S. Appl. No. 12/811,963.
Office Action dated Nov. 9, 2012 in U.S. Appl. No. 12/663,056.
Office Action dated Nov. 26, 2012 in U.S. Appl. No. 13/215,439.
Office Action dated Dec. 21, 2012 in U.S. Appl. No. 13/246,512.
Office Action dated Jan. 17, 2013 in U.S. Appl. No. 13/541,185.
Office Action dated Mar. 6, 2013 in U.S. Appl. No. 13/157,575.
Monfardini et al., "A Branched Monomethoxypoly (ethylene glycol) for Protein Modification," *Bioconjug. Chem.*, 6(1): 62-69 (1995).
Moscatelli et al., "Enzymatic Properties of a β-Glucanase from *Bacillus subtilis*," *J. Biol. Chem.*, 236(11): 2858-2862 (1961).
Rabina et al., "Analysis of Nucleotide Sugars from Cell Lysates by Ion-Pair Solid-Phase Extraction and Reversed-Phase High-Performance Liquid Chromatography," *Glycoconj. J.*, 18(10): 799-805 (2001).
Office Action dated Jul. 11, 2013 in U.S. Appl. No. 11/652,467.
Office Action dated Jul. 17, 2013 in U.S. Appl. No. 13/215,439.
Office Action dated Jul. 30, 2013 in U.S. Appl. No. 13/246,512.
Office Action dated Aug. 12, 2013 in U.S. Appl. No. 13/541,185.
Office Action dated Sep. 6, 2013 in U.S. Appl. No. 12/784,323.
Office Action dated Sep. 16, 2013 in U.S. Appl. No. 11/781,885.
Office Action dated Sep. 17, 2013 in U.S. Appl. No. 11/781,888.
Office Action dated Sep. 25, 2013 in U.S. Appl. No. 12/663,748.
Office Action dated Oct. 10, 2013 in U.S. Appl. No. 10/581,538.
Office Action dated Oct. 16, 2013 in U.S. Appl. No. 11/597,258.
Office Action dated Nov. 7, 2013 in U.S. Appl. No. 12/811,963.
Office Action dated Dec. 5, 2013 in U.S. Appl. No. 10/565,331.
Ajisaka et al., *Biosci. Biotechnol. Biochem.*, 65(5): 1240-1243 (2001).
Andree et al., *Biochim. Biophys. Acta*, 544(3): 489-495 (1978).
Apicella et al., *Infect. Immun.*, 55(8): 1755-1761 (1987).
Arsequell et al., *Tetrahedron: Asymmetry*, 10(16): 3045-3094 (1999).
ATCC Catalog of Bacteria and Bacteriophages, 17th ed., p. 150-151 (1989).
Auge et al., *Carbohydr. Res.*, 151: 147-156 (1986).
Auge et al., *Carbohydr. Res.*, 200: 257-268 (1990).
Avigad et al., *J. Biol. Chem.*, 237(9): 2736-2743 (1962).
Barker et al., *J. Biol. Chem.*, 247(22): 7135-7147 (1972).
Bayer et al., *Glycobiology*, 13(11): 890-891 (2003).
Bertozzi et al., *J. Am. Chem. Soc.*, 114(26): 10639-10641 (1992).
Biemann et al., *Science*, 237(4818): 992-998 (1987).
Binder et al., *Tetrahedron*, 50(35): 10407-10418 (1994).
Bishop et al., *Endocrinology*, 136(6): 2635-2640 (1995).
Bocci, *Adv. Drug Deliv. Rev.*, 4(2): 149-169 (1989).
Borman, *Chem. Eng. News*, 84(36): 13-22 (2006).
Breton et al., *Curr. Opin. Struct. Biol.*, 9(5): 563-571 (1999).
Breton et al., *Biochimie*, 83(8): 713-718 (2001).

Brinkman-Van Der Linden et al., *J. Biol. Chem.*, 271(24): 14492-14495 (1996).
Broquet et al., *Eur. J. Biochem.* 123(1): 9-13 (1982).
Burczak et al., *Biochim. Biophys. Acta*, 804(4): 442-449 (1984).
Burns et al., *J. Org. Chem.*, 56(8): 2648-2650 (1991).
Calvet, *Pediatr. Nephrol.*, 5(6): 751-757 (1991).
Carlson et al., *J. Biol. Chem.*, 248(16): 5742-5750 (1973).
Chang et al, *Biotechnol. Bioprocess Eng.*, 3(1): 40-43 (1998).
Chang et al., *Biochemistry*, 38(34): 10940-10948 (1999).
Clogston et al., *J. Chromatogr. A*, 637(1): 55-62 (1993).
Corfield, "Analysis of Sugar Sequences in Glycoproteins by Glycosidase Digestion and Gel Filtration," *Methods in Molecular Biology*, 19: 269-286 (1993).
Dabkowski et al., *Transplant Proc.*, 25(5): 2921 (1993).
Danaher et al., *J. Bacteriol.*, 177(24): 7275-7279 (1995).
Datta et al., *J. Biol. Chem.*, 270(4): 1497-1500 (1995).
David et al., *Pure Appl. Chem.*, 59(11): 1501-1508 (1987).
Davis et al., *Synlett* 1999, (9): 1495-1507 (1999).
De Rosa et al., *Phytochemistry*, 42(4): 1031-1034 (1996).
Deangelis et al., *Biochemistry*, 33(31): 9033-9039 (1994).
Deluca et al., *J. Am. Chem. Soc.*, 117(21): 5869-5870 (1995).
Dennis et al., *J. Biol. Chem.*, 277(38): 35035-35043 (2002).
Dickinson et al., *Proc. Natl. Acad. Sci. USA*, 93(25): 14379-14384 (1996).
Dreyfus et al., *Anal. Biochem.*, 249(1): 67-78 (1997).
Dudas et al., *Infect. Immun.*, 56(2): 499-504 (1988).
Dudziak et al., *Tetrahedron*, 56(32): 5865-5869 (2000).
Edano et al., *Biol. Pharm. Bull.*, 21(4): 382-385 (1998).
Ellis, "Vaccines" Plotkin et al. (eds.), Chapter 29, W.B. Saunders Co., Philadelphia, pp. 568-575 (1988).
EMBL Accession No. M80599 and M86935 (Jan. 23, 1992).
EMBL Accession No. S56361 (May 4, 1993).
EMBL Accession No. U00039 (Jun. 2, 1994).
Ernst et al., *Glycoconj. J.*, 16(2): 161-170 (1999).
Fu et al., *Bioconjug. Chem.*, 12(2): 271-279 (2001).
Fujita et al., *Biochim. Biophys. Acta*, 1528(1): 9-14 (2001).
GE Healthcare, Instructions 28-9064-05 AA (2006).
GE Healthcare, Instructions 28-9064-05 AC (2006).
Genbank Accession No. AAA98726, "Factor IX," pp. 1-3 (Apr. 14, 2009).
Genbank Accession No. CAA01607, "Factor IX of *Homo sapiens*," pp. 1-2 (Apr. 14, 2009).
Genbank Accession No. D49915 (Sep. 1, 1995).
Genbank Accession No. U02304 (Mar. 8, 1994).
Genbank Accession No. U18918 (Oct. 1, 1995).
Gibson et al., *J. Bacteriol.*, 175(9): 2702-2712 (1993).
Gilbert et al., "The Synthesis of Sialylated Oligosaccharides Using a CMP-Neu5Ac Synthetase/Sialyltransferase Fusion," *Nature Biotechnology*, 16: 769-772 (1998).
Gilbert, "Methods in Enzymology" Packer (ed.), 2(251): 8-28, Biothiols Part A, Elsevier (1995).
Gillespie et al., *FASEB Journal*, 4(7): A2068 [Abstract No. 2173] (1990).
Gillespie et al., *J. Biol. Chem.*, 267(29): 21004-21010 (1992).
Goodson et al., *Biotechnology* (N.Y.), 8(4): 343-346 (1990).
Greenwell et al., *Blood Group A Synthesising Activity of the Blood Group B Gene Specified α-3-D-Galactosyl Transferase*, p. 268-269 (1979).
Greenwell et al., *Carbohydr. Res.*, 149(1): 149-170 (1986).
Gross et al., *Eur. J. Biochem.*, 168(3): 595-602 (1987).
Grundmann et al., *Nucleic Acids Res.*, 18(3): 667 (1990).
Gu et al., *FEBS Lett.*, 275(1-2): 83-86 (1990).
Guivisdalsky et al., *J. Med. Chem.*, 33(9): 2614-2621 (1990).
Hakomori et al., "Methods in Enzymology," Fleischer et al. (eds.), 33(32): 345-367, Biomembranes Part B, Elsevier USA (1974).
Hedner et al., "Recombinant Activated Factor VII in the Treatment of Bleeding Episodes in Patients With Inherited and Acquired Bleeding Disorders," *Transfusion Medicine Reviews*, VII(2): 78-83 (1993).
Heimgartner et al., "Reversible and Irreversible Cross-Linking of Immunoglobulin Heavy Chains Through Their Carbohydrate Residues," *Biochem. J.*, 267: 585-591 (1990).
Helling et al., *Cancer Res.*, 54(1): 197-203 (1994).
Higa et al., *J. Biol. Chem.*, 260(15): 8838-8849 (1985).

(56) References Cited

OTHER PUBLICATIONS

Higashi et al., *J. Biol. Chem.*, 272(41): 25724-25730 (1997).
High et al., *Mol. Microbiol.*, 9(6): 1275-1282 (1993).
Hoffman et al., *Thromb. Haemost.*, 85(6): 958-965 (2001).
Ichikawa et al., *J. Am. Chem. Soc.*, 113(12): 4698-4700 (1991).
Ichikawa et al., *J. Am. Chem. Soc.*, 113(16): 6300-6302 (1991).
Ito et al., *J. Am. Chem. Soc.*, 115(4): 1603-1605 (1993).
Japanese Biochemical Society, "New Course in Biochemistry Experiments 3, Sugars I, Glycoproteins (top)," Tokyo Kagaku Dojin K.K., First Edition, p. 340 (1990).
Jennemann et al., *J. Biochem.*, 115(6): 1047-1052 (1994).
Jennings et al., *Mol. Microbiol.*, 10(2): 361-369 (1993).
John et al., *J. Biol. Chem.*, 266(29): 19303-19311 (1991).
Jonsson et al., *EMBO J.*, 10(2): 477-488 (1991).
Joziasse et al., *J. Biol. Chem.*, 260(8): 4941-4951 (1985).
Joziasse et al., *J. Biol. Chem.*, 264(24): 14290-14297 (1989).
Kawai et al., *J. Lipid Res.*, 26(3): 338-343 (1985).
Kerwood et al., *Biochemistry*, 31(51): 12760-12768 (1992).
Khidekel et al., *J. Am. Chem. Soc.*, 125(52): 16162-16163 (2003).
Kitagawa et al., *Biochem. Biophys. Res. Commun.*, 194(1): 375-382 (1993).
Kitagawa et al., *J. Biol. Chem.*, 269(27): 17872-17878 (1994).
Knight et al., *Mol. Microbiol.*, 6(11): 1565-1573 (1992).
Koeller et al., "Complex Carbohydrate Synthesis Tools for Glycobiologists: Enzyme-Based Approach and Programmable One-Pot Strategies," *Glycobiology*, 10(11): 1157-1169 (2000).
Kogan, *Synth. Commun.*, 22(16): 2417-2424 (1992).
Koike et al., *Carbohydr. Res.*, 162(2): 237-246 (1987).
Kurosawa et al., *Eur. J. Biochem.*, 219(1-2): 375-381 (1994).
Larsen et al, *Proc. Natl. Acad. Sci. USA*, 86(21): 8227-8231 (1989).
Lee et al., *Science*, 239(4845): 1288-1291 (1988).
Lidholt et al, *Biochem. J.*, 261(3): 999-1007 (1989).
Livingston et al., *J. Biol. Chem.*, 268(16): 11504-11507 (1993).
Lundstrom-Ljung et al., *J. Biol. Chem.*, 270(14): 7822-7828 (1995).
Luo et al., "Spontaneous Calcification of Arteries and Cartilage in Mice Lacking Matrix GLA Protein," *Nature*, 386: 78-81 (1997).
Maccioni et al., *Biochim Biophys Acta*, 1437(2): 101-118 (1999).
Mackenzie et al., *J. Am. Chem. Soc.*, 120(22): 5583-5584 (1998).
Madnick et al., *Arch. Biochem. Biophys.*, 212(2): 432-442 (1981).
Mandrell et al., *J. Exp. Med.*, 168(1): 107-126 (1988).
Mandrell et al., *J. Exp. Med.*, 171(5): 1649-1664 (1990).
Mandrell et al., *J. Bacteriol.*, 173(9): 2823-2832 (1991).
Mandrell, *Infect. Immun.*, 60(7): 3017-3020 (1992).
Manfioletti et al., "The Protein Encoded by a Growth Arrest-Specific Gene (gas6) Is a New Member of the Vitamin K-Dependent Proteins Related to Protein S, a Negative Coregulator in the Blood Coagulation Cascade," *Mol. Cell. Bio.*, 13(8): 4976-4985 (1993).
Marinier et al., *J. Med. Chem.*, 40(20): 3234-3247 (1997).
Mathews et al., *J. Biol. Chem.*, 262(16): 7537-7545 (1987).
Mizuguchi et al., *Thromb. Haemost.*, Abstract 1474: 466, Suppl. (Aug. 1999).
Muramatsu et al., *Comprehensive Research on Clinical Organ Xenotransplantation by Genetic Regulation*, p. 10-12. (1997).
Nelsestuen et al., "Vitamin K-Dependent Proteins," *Vitamins and Hormones*, 58: 355-389 (2000).
Nemansky et al., *FEBS Lett.*, 312(1): 31-36 (1992).
Nilsson, *Trends Biotechnol.*, 6(10): 256-264 (1988).
Nucci et al., *Adv. Drug Deliv. Rev.*, 6(2): 133-151 (1991).
Nunez et al., *Biochemistry*, 15(17): 3843-3847 (1976).
Palcic et al., *Glycobiology*, 1(2): 205-209 (1991).
Parsons et al., *Microb. Pathog.*, 7(1): 63-72 (1989).
Patra et al., *Protein Expr. Purif.*, 18(2): 182-192 (2000).
Paulson et al., *Chemical Abstracts*, 86(25): 213 [Abstract No. 185016b] (1977).
Paulson et al., *J. Biol. Chem.*, 252(7): 2356-2362 (1977).
Paulson et al., *J. Biol. Chem.*, 264(19):10931-10934 (1989).
Pfaffli et al., *Carbohydr. Res.*, 23(2): 195-206 (1972).
Pradel et al., *J. Bacteriol.*, 174(14): 4736-4745 (1992).
Preuss et al., *J. Biol. Chem.*, 268(35): 26273-26278 (1993).
Probert et al., *Tetrahedron Lett.*, 38(33): 5861-5864 (1997).

Raju et al., "Glycoengineering of Therapeutic Glycoproteins: In Vitro Galactosylation and Sialylation of Glycoproteins with Terminal N-Acetylglucosamine and Galactose Residues," *Biochemistry*, 40(30): 8868-8876 (2001).
Rao et al., *Protein Sci.*, 8(11): 2338-2346 (1999).
Rearick et al., *J. Biol. Chem.*, 254(11): 4444-4451 (1979).
Rice et al., *J. Biol. Chem.*, 265(30): 18423-18428 (1990).
Robertson et al., *Mol. Microbiol.*, 8(5): 891-901 (1993).
Rosevear et al., *Biochemistry*, 21(6): 1421-1431 (1982).
Sadler et al., *J. Biol. Chem.*, 254(11): 4434-4442 (1979).
Sadler et al., *J. Biol. Chem.*, 254(13): 5934-5941 (1979).
Saenko et al., *Haemophilia*, 12(suppl. 3): 42-51 (2006).
Sambrook et al., "Molecular Cloning: A Laboratory Manual" 2nd ed., Cold Spring Harbor Laboratory Press, Cold Spring Harbor, New York, pp. 9.50-9.51 (1989).
Sandlin et al., *J. Bacteriol.*, 176(10): 2930-2937 (1994).
Schmidt et al., *Trends Cardiovasc. Med.*, 13(1): 39-45 (2003).
Schneider et al., *Infect. Immun.*, 56(4): 942-946 (1988).
Schneider et al., *J. Exp. Med.*, 174(6): 1601-1605 (1991).
Schram et al., *Biochim. Biophys. Acta*, 482(1): 138-144 (1977).
Sears et al., *Science*, 291(5512): 2344-2350 (2001).
Shames et al., *Glycobiology*, 1(2): 187-191 (1991).
Shao et al., *Glycobiology*, 12(11): 763-770 (2002).
Simon et al., *J. Am. Chem. Soc.*, 110(21): 7159-7163 (1988).
Sogin et al., *Biochemistry* 19(23): 5417-5420 (1980).
Sorensen et al., "Incorporation of an Active Site Inhibitor in Factor VIIa Alters the Affinity for Tissue Factor," *J. Biol. Chem.*, 272(18): 11863-11868 (1997).
Stamenkovic et al., *J. Exp. Med.*, 172(2): 641-643 (1990).
Stennicke et al., *Anal. Biochem.*, 248(1): 141-148 (1997).
Stephens et al., *Infect Immun.*, 62(7): 2947-2952 (1994).
Stoolmiller et al., *J. Biol. Chem.*, 244(2): 236-246 (1969).
Suzuki et al., *J. Biol. Chem.*, 260(3): 1362-1365 (1985).
Swiss-Prot Accession No. P19817 (Feb. 1, 1991).
Swiss-Prot Accession No. P25740 (May 1, 1992).
Swiss-Prot Accession No. P27129 (Aug. 1, 1992).
Takegawa et al., *J. Biol. Chem.*, 270(7): 3094-3099 (1995).
Takeya et al., *J. Biol. Chem.*, 263(29): 14868-14877 (1988).
Takeya et al., *Jpn. J. Med. Sci. Biol.*, 46(1): 1-15 (1993).
Tarui et al., *J. Biosci. Bioeng.*, 90(5): 508-514 (2000).
Toone et al., *Tetrahedron*, 45(17): 5365-5422 (1989).
Tsai et al., *Infect. Immun.*, 59(10): 3604-3609 (1991).
Tsuboi et al., "6'-Sulfo Sialyl Le$^x$ but Not 6-Sulfo Sialyl Le$^x$ Expressed on the Cell Surface Supports L-selectin-mediated Adhesion," *J. Biol. Chem.*, 271(44): 27213-27216 (1996).
Tsuji, "Molecular Cloning and Functional Analysis of Sialyltransferases," *J. Biochemistry*, 120: 1-13 (1996).
Tsujihara et al., *Chem. Pharm. Bull.*, (Tokyo) 29(11): 3262-3273 (1981).
Van Den Eijnden et al., *J. Biol. Chem.*, 256(7): 3159-3162 (1981).
Van Den Eijnden et al., *J. Biol. Chem.*, 258(6): 3435-3437 (1983).
Van Putten et al., *EMBO J.*, 12(11): 4043-4051 (1993).
Van Roey et al., *Biochemistry*, 33(47): 13989-13996 (1994).
Vann et al., *J Biol Chem.*, 262(36): 17556-17562 (1987).
Verheul et al., *Microbiol. Rev.*, 57(1): 34-49 (1993).
Vijay et al., *J. Biol. Chem.*, 250(1): 164-170 (1975).
Waddling et al., *Biochemistry*, 39(27): 7878-7885 (2000).
Wakarchuk et al., *J. Biol. Chem.*, 271(32): 19166-19173 (1996).
Wang et al., *Protein Eng.*, 10(4): 405-411 (1997).
Webster et al., *J. Biol. Chem.*, 258(17): 10637-10641 (1983).
Weinstein et al., *J. Biol. Chem.*, 257(22): 13835-13844 (1982).
Weinstein et al., *J. Biol. Chem.*, 257(22): 13845-13853 (1982).
Wen et al., *FASEB Journal*, 6(1): A231 [abstract No. 1329] (1992).
Wen et al., *J. Biol. Chem.*, 267(29): 21011-21019 (1992).
Whisstock et al., *Q. Rev. Biophys.*, 36(3): 307-340 (2003).
Wikipedia, Image:Ceramide.svg, http://en.wikipedia.org/wiki/Ceramide, pp. 1-2 (2007).
Wong et al., *J. Org. Chem.*, 57(16): 4343-4344 (1992).
Xiao et al., *J. Biol. Chem.*, 280(22): 21099-21106 (2005).
Yamamoto et al., *J. Biol. Chem.*, 265(31): 19257-19262 (1990).
Yamamoto et al., *Nature*, 345(6272): 229-233 (1990).
Yamasaki et al., *J. Bacteriol.*, 175(14): 4565-4568 (1993).
Yoshikawa et al., *Phytochemistry*, 34(5): 1431-1433 (1993).

(56) References Cited

OTHER PUBLICATIONS

Zalipsky et al., *Polymer Prepr.*, 27(1): 1-2 (1986).
Zalipsky et al., *Int. J. Pept. Protein Res.*, 30(6): 740-783 (1987).
Zapata et al., *J. Biol. Chem.*, 264(25): 14769-14774 (1989).
Zhou et al., *J. Biol. Chem.*, 269(15): 11162-11169 (1994).
Weerapana et al., "Investigating Bacterial N-Linked Glycosylation: Synthesis and Glycosyl Acceptor Activity of the Undecaprenyl Pyrophosphate-Linked Bacillosamine," *J. Am. Chem. Soc.*, 127(40): 13766-13767 (2005).

Peptides which can be utilized as substrates in this invention:

- AcuTec
- angiomax
- Antagon
- atosiban
- calcitonin
- carperitide
- cargutocin
- Cerebrolysin
- Cetrotide
- ceruletide
- daptomycin
- desirudin
- desmopressin
- eledoisin
- Fuzeon
- glucagon
- GRH (Gcref)
- Integrelin
- lepirudin
- Lupron
- Natrecor
- Neospect
- pranlukast
- prezatide
- romurtide
- saralasin
- secretin
- somatostatin
- sulglicotide
- teicoplanin
- thymalfasin
- thymopentin
- Thyrel (TRH)
- Virulizin
- Vueffe

- A6
- ABT-510
- AC-162352
- AIPs
- AnergiX
- betatropin
- BIM-23190
- BAM-205
- cilengitide
- D-22212
- GLP-1
- INGAP peptide
- INT
- HTI-286
- LU-223651
- nepadutant
- netamiftide
- PSP-94
- semparatide
- teduglutide
- ThGRF 1-44
- TX14(A)
- 131-I-TM-601
- Xerecept

BRANCHED PEG REMODELING AND GLYCOSYLATION OF GLUCAGON-LIKE PEPTIDE-1 [GLP-1]

CROSS-REFERENCE TO RELATED APPLICATIONS

The present application is a continuation of copending U.S. patent application Ser. No. 11/632,005, filed on Jan. 9, 2007, which is the U.S. national phase of International Patent Application PCT/US2005/024781 filed on Jul. 13, 2005, which claims the benefit of U.S. Provisional Patent Application No. 60/587,738, filed Jul. 13, 2004, and U.S. Provisional Patent Application No. 60/608,723 filed Sep. 10, 2004, the disclosures of which are incorporated herein by reference in their entireties for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 74,229 bytes ASCII (Text) file named "ReplacementSequenceListing" created Nov. 9, 2012.

FIELD OF THE INVENTION

The present invention relates to O-linked glycosylated glycopeptides, particularly glucagon-like peptide-1 (GLP-1) and GLP-1 peptide mutants that include O-linked glycosylation sites not present in the wild-type peptide.

BACKGROUND OF THE INVENTION

Glucagon-like peptide-1 (GLP-1) is an important glucoincretin hormone secreted from intestinal L cells in response to nutrient ingestion. GLP-1 functions to regulate plasma glucose levels via various independent mechanisms, making it an ideal candidate for treatment of diabetes, and possibly useful in the pharmacotherapy of obesity.

The biologically active forms of GLP-1 possess multiple functions in vivo, including enhancement of glucose-dependent insulin secretion, stimulation of proinsulin gene expression, and suppression of glucagon secretion and gastric emptying. GLP-1 also enhances insulin sensitivity, induces β cell differentiation and proliferation, decreases caloric intake, and increases satiety.

The mature, active form of GLP-1 is a 30 amino acid derivative of proglucagon, a 160 amino acid prohormone. GLP-1 is synthesized by post translational processing of proglucagon in intestinal L cells. Posttranslational processing of proglucagon gives rise to glucagon, GLP-1, GLP-2 and other peptide sequences, IP-1 and IP-2, of unknown function. The initial GLP-1 cleaved from proglucagon is further processed first by N-terminal cleavage to form a biologically active peptide (GLP-1$_{(7-37)}$). GLP-1$_{(7-37)}$ is then C-terminally truncated and amidated to form the predominant biologically active species, GLP-1$_{(7-36)amide}$.

GLP-1$_{(7-36)amide}$ has a very short half life in vivo. The plasma half life of GLP-1 is about 5 minutes, and the metabolic clearance rate is about 12-13 minutes. In circulation, the predominant form of GLP-1 is rapidly inactivated as a result of degradation by dipeptidyl-peptidase IV (see e.g., Deacon et al. (1995) *Endocrinol. Metab.* 80:952-957, and Hansen et al. (1999) *Endocrinology* 140:5356). GLP-1$_{(7-36)amide}$ is also susceptible to degradation by neutral endopeptidases, including NEP 24.11 (Sodman et al. (1995) *Reg. Peptides* 58:149-156).

The unique ability of GLP-1 to lower postprandial hyperglycemia via three independent and complementary mechanisms of action (increased insulin secretion, inhibition of glucagon release, and inhibition of gastrointestinal motility) are what make this peptide hormone an ideal candidate for the treatment of diabetes. Indeed, GLP-1 provides unprecedented advantages over any other pharmacological agent currently available. Unfortunately, despite its potential, there are serious limitations to the possible therapeutic use of GLP-1 in humans. The most serious limitation is the very short half life of GLP-1 in vivo. Even when administered subcutaneously, peak concentrations return to baseline within 90 minutes.

The therapeutic potential of GLP-1 and its very short half life have prompted the search for and discovery of analogs that may provide an extended GLP-1-like biological activity. Several analogs have been isolated from other species (Fehmann, H. C., et al. (1995) *Endocrine Reviews* 16:390-410, and Thorens B. et al. (1993) *Diabetes* 42:1678-1682), and mutant GLP-1 peptides resistant to degradation have been created (Xiao et al. (2001) *Biochemistry* 40:2860-2869).

Some GLP-1 analogs may show some promise as therapeutics. However, since GLP-1 peptide is a highly multifunctional protein, mutants and interspecies homologs may have unpredictable plieotropic effects. Indeed, Xiao et al. showed that some mutants exhibit altered biological activity independent of any changes in receptor binding activity. Thus, the biological activities of GLP-1 can be uncoupled from one another.

Diabetes, obesity and other disorders of sugar metabolism and glycemic control carry a very high price for the individual, as well as the society in terms of health, lost productivity and the loss of wages and financial output. Thus, there is clearly a need in the art for effective medications that facilitate glycemic control in the individual. A stabilized GLP-1 with increased half life in vivo could meet this need. Preferably a stabilized GLP-1 peptide would be very similar to the wild type protein, such that changes to biological activity, and hence possible side effects of therapy can be minimized. The present invention answers the need for stabilized GLP-1 molecules, thereby providing therapeutically effective GLP-1 peptides. Other objects and advantages will become apparent from the detailed description that follows.

BRIEF SUMMARY OF THE INVENTION

Diabetes and disorders of glycemic control are serious conditions which, if unchecked can have dire consequences for the individual and society at large. Although type 1 diabetes can be controlled more or less effectively with insulin injections, there are multiple pathways of glycemic control. If some of those pathway could also be recruited into therapeutic methods, glycemic control for diabetics would be improved. Further, enhanced glycemic control for type 2 diabetics and individuals struggling with obesity, could provide enhanced health benefits for these groups of individuals as well.

As noted above, Glucagon-Like Peptide-1 (GLP-1) facilitates glycemic control in the individual by multiple mechanisms. Thus, GLP-1 is an ideal candidate for the pharmacotherapy of glycemic disorders. Unfortunately, the potential therapeutic uses of GLP-1 are limited by the short in vivo half life of the protein. Fortunately, methods that improve in vivo half life of the protein have now been discovered. These methods have the added advantage that they introduce minimal alterations to the protein and therefore the risks of side effects are minimized.

Indeed, it has now been discovered that enzymatic glycoconjugation reactions can be specifically targeted to O-linked glycosylation sites and to glycosyl residues that are attached to O-linked glycosylation sites. The targeted O-linked glycosylation sites can be sites native to a wild-type peptide or, alternatively, they can be introduced into a peptide by mutation. Thus, a method for prolonging the in vivo half life of GLP-1 (and other proteins) is provided by the methods of the invention.

In addition to the discovery that O-linked glycosylation sites, and glycosyl residues linked thereto, are useful targets for glycoconjugation reactions, the present invention provides mutant polypeptides in which the amino acid sequence is manipulated by mutation to insert, remove or relocate one or more O-linked glycosylation site in the peptide. When a site is added or relocated, it is not present or not present in a selected location in the wild type peptide. The mutant O-linked glycosylation site is a point of attachment for a modified glycosyl residue that is enzymatically conjugated to the O-linked glycosylation site. Using the methods of the invention, the glycosylation site can be shifted to any efficacious position on the peptide. For example, if the native glycosylation site is sufficiently proximate the active site of the peptide that conjugation of a large water-soluble polymer interferes with the biological activity of the peptide, it is within the scope of the invention to engineer a mutant peptide that includes an O-linked glycosylation site as removed from the active site as necessary to provide a biologically active peptide conjugate.

Post-expression in vitro modification of peptides is an attractive strategy to remedy the deficiencies of methods that rely on controlling glycosylation by engineering expression systems; including both modification of glycan structures or introduction of glycans at novel sites. A comprehensive toolbox of recombinant eukaryotic glycosyltransferases is becoming available, making in vitro enzymatic synthesis of mammalian glycoconjugates with custom designed glycosylation patterns and glycosyl structures possible. See, for example, U.S. Pat. Nos. 5,876,980; 6,030,815; 5,728,554; 5,922,577; and WO/9831826; US2003180835; and WO 03/031464.

In vitro glycosylation offers a number of advantages compared to recombinant expression of glycoproteins of which custom design and higher degree of homogeneity of the glycosyl moiety are examples. Moreover, combining bacterial expression of glycotherapeutics with in vitro modification (or placement) of the glycosyl residue offers numerous advantages over traditional recombinant expression technology including reduced potential exposure to adventitious agents, increased homogeneity of product, and cost reduction.

In addition to methods of O-linked glycosylation, inserting O-linked glycosylation sites into peptides and methods of glycosylating the inserted sites, the present invention provides methods of improving pharmacological parameters of glycopeptide therapeutics, e.g., altering pharmacokinetics, pharmacodynamics and bioavailability of therapeutic (glyco) proteins, e.g., hormones, and enzymes. In particular, the invention provides a method for lengthening the in vivo half-lives of glycopeptide therapeutics by conjugating a water-soluble polymer to the peptide through an intact glycosyl linking group. In an exemplary embodiment, covalent attachment of polymers, such as polyethylene glycol (PEG), e.g., m-PEG, to such peptides affords conjugates having in vivo residence times, and pharmacokinetic and pharmacodynamic properties, enhanced relative to the unconjugated peptide.

Art-recognized methods of covalent PEGylation rely on chemical conjugation through reactive groups on amino acids or carbohydrates. A major shortcoming of chemical conjugation of PEG to proteins or glycoproteins is lack of selectivity, which often results in attachment of PEG at sites implicated in protein or glycoprotein bioactivity. Several strategies have been developed to address site selective conjugation chemistries, however, one universal method suitable for a variety of recombinant proteins has yet to be developed.

In contrast to art-recognized methods, the present invention provides a novel strategy for highly selective site directed O-linked glycoconjugation, e.g., glyco-PEGylation. In an exemplary embodiment of the invention, site directed attachment sites for PEGylation are provided by in vitro enzymatic GalNAc O-linked glycosylation of specific peptide sequences, e.g., mutant sequences, containing serine and threonine residues. The recombinant proteins are preferably expressed in bacteria, e.g., E. coli, to avoid host cell glycosylation. Glyco-PEGylation is subsequently performed enzymatically utilizing a glycosyltransferase, e.g., a sialyltransferase, capable of transferring the species PEG-glycosyl, e.g., PEG-sialic acid, to an O-linked glycosylation site ("glyco-PEGylation"). O-linked glycosylation sites may be introduced into any peptide sequence by providing a mutant peptide with simple short sequence motifs.

Additional aspects, advantages and objects of the present invention will be apparent from the detailed description that follows.

BRIEF DESCRIPTION OF THE FIGURES

FIG. 1 provides a list of peptides which can be used as substrates for this invention.

DETAILED DESCRIPTION OF THE INVENTION

Abbreviations

PEG, poly(ethyleneglycol); m-PEG, methoxy-poly(ethylene glycol); PPG, poly(propyleneglycol); m-PPG, methoxy-poly(propylene glycol); Fuc, fucosyl; Gal, galactosyl; GalNAc, N-acetylgalactosaminyl; Glc, glucosyl; GlcNAc, N-acetylglucosaminyl; Man, mannosyl; ManAc, mannosaminyl acetate; Sia, sialic acid; and NeuAc, N-acetylneuraminyl.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

"Peptide" refers to a polymer in which the monomers are amino acids and are joined together through amide bonds, alternatively referred to as a polypeptide. Additionally, unnatural amino acids, for example, β-alanine, phenylglycine and homoarginine are also included. Amino acids that are not gene-encoded may also be used in the present invention.

Furthermore, amino acids that have been modified to include reactive groups, glycosylation sites, polymers, therapeutic moieties, biomolecules and the like may also be used in the invention. All of the amino acids used in the present invention may be either the D- or L-isomer. The L-isomer is generally preferred. In addition, other peptidomimetics are also useful in the present invention. As used herein, "peptide" refers to both glycosylated and unglycosylated peptides. Also included are peptides that are incompletely glycosylated by a system that expresses the peptide. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

In the present application, amino acid residues are numbered according to their relative positions from the left most residue, which is numbered 1, in a peptide sequence.

"Proximate a proline residue," as used herein refers to an amino acid that is less than about 10 amino acids removed from a proline residue, preferably, less than about 9, 8, 7, 6 or 5 amino acids removed from a proline residue, more preferably, less than about 4, 3, 2 or 1 residues removed from a proline residue. The amino acid "proximate a proline residue" may be on the C- or N-terminal side of the proline residue.

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

As used herein, the term "modified sugar," refers to a naturally- or non-naturally-occurring carbohydrate that is enzymatically added onto an amino acid or a glycosyl residue of a peptide in a process of the invention. The modified sugar is selected from a number of enzyme substrates including, but not limited to sugar nucleotides (mono-, di-, and tri-phosphates), activated sugars (e.g., glycosyl halides, glycosyl mesylates) and sugars that are neither activated nor nucleotides. The "modified sugar" is covalently functionalized with a "modifying group." Useful modifying groups include, but are not limited to, water-soluble polymers, therapeutic moieties, diagnostic moieties, biomolecules and the like. The modifying group is preferably not a naturally occurring, or an unmodified carbohydrate. The locus of functionalization with the modifying group is selected such that it does not prevent the "modified sugar" from being added enzymatically to a peptide.

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like. Peptides can have mixed sequences of be composed of a single amino acid, e.g., poly(lysine). An exemplary polysaccharide is poly(sialic acid). An exemplary poly(ether) is poly(ethylene glycol), e.g., m-PEG. Poly(ethylene imine) is an exemplary polyamine, and poly(acrylic) acid is a representative poly(carboxylic acid).

The polymer backbone of the water-soluble polymer can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly (ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as R(—PEG-OH).sub.m in which R represents the core moiety, such as glycerol or pentaerythritol, and m represents the number of arms. Multi-armed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of from about 100 Da to about 100,000 Da, often from about 6,000 Da to about 80,000 Da.

The term "glycoconjugation," as used herein, refers to the enzymatically mediated conjugation of a modified sugar species to an amino acid or glycosyl residue of a polypeptide, e.g., a mutant human growth hormone of the present invention. A subgenus of "glycoconjugation" is "glycol-PEGylation," in which the modifying group of the modified sugar is poly(ethylene glycol), and alkyl derivative (e.g., m-PEG) or reactive derivative (e.g., H2N-PEG, HOOC-PEG) thereof.

The terms "large-scale" and "industrial-scale" are used interchangeably and refer to a reaction cycle that produces at least about 250 mg, preferably at least about 500 mg, and more preferably at least about 1 gram of glycoconjugate at the completion of a single reaction cycle.

The term, "glycosyl linking group," as used herein refers to a glycosyl residue to which a modifying group (e.g., PEG moiety, therapeutic moiety, biomolecule) is covalently attached; the glycosyl linking group joins the modifying group to the remainder of the conjugate. In the methods of the invention, the "glycosyl linking group" becomes covalently attached to a glycosylated or unglycosylated peptide, thereby linking the agent to an amino acid and/or glycosyl residue on the peptide. A "glycosyl linking group" is generally derived from a "modified sugar" by the enzymatic attachment of the "modified sugar" to an amino acid and/or glycosyl residue of the peptide. The glycosyl linking group can be a saccharide-derived structure that is degraded during formation of modifying group-modified sugar cassette (e.g., oxidation→Schiff base formation→reduction), or the glycosyl linking group may be intact. An "intact glycosyl linking group" refers to a linking group that is derived from a glycosyl moiety in which the saccharide monomer that links the modifying group and to the remainder of the conjugate is not degraded, e.g., oxidized, e.g., by sodium metaperiodate. "Intact glycosyl linking groups" of the invention may be derived from a naturally occurring oligosaccharide by addition of glycosyl unit(s) or removal of one or more glycosyl unit from a parent saccharide structure.

The term "targeting moiety," as used herein, refers to species that will selectively localize in a particular tissue or region of the body. The localization is mediated by specific recognition of molecular determinants, molecular size of the targeting agent or conjugate, ionic interactions, hydrophobic interactions and the like. Other mechanisms of targeting an agent to a particular tissue or region are known to those of skill in the art. Exemplary targeting moieties include antibodies, antibody fragments, transferrin, HS-glycoprotein, coagulation factors, serum proteins, β-glycoprotein, G-CSF, GM-CSF, M-CSF, EPO and the like.

As used herein, "therapeutic moiety" means any agent useful for therapy including, but not limited to, antibiotics, anti-inflammatory agents, anti-tumor drugs, cytotoxins, and radioactive agents. "Therapeutic moiety" includes prodrugs of bioactive agents, constructs in which more than one therapeutic moiety is bound to a carrier, e.g., multivalent agents. Therapeutic moiety also includes proteins and constructs that include proteins. Exemplary proteins include, but are not limited to, Glucagon like protein-1 (GLP-1), Erythropoietin (EPO), Granulocyte Colony Stimulating Factor (GCSF), Granulocyte Macrophage Colony Stimulating Factor (GMCSF), Interferon (e.g., Interferon-α, -β, -γ), Interleukin (e.g., Interleukin II), serum proteins (e.g., Factors VII, VIIa, VIII, IX, and X), Human Chorionic Gonadotropin (HCG), Follicle Stimulating Hormone (FSH) and Lutenizing Hormone (LH) and antibody fusion proteins (e.g. Tumor Necrosis Factor Receptor ((TNFR)/Fc domain fusion protein)).

As used herein, "anti-tumor drug" means any agent useful to combat cancer including, but not limited to, cytotoxins and agents such as antimetabolites, alkylating agents, anthracyclines, antibiotics, antimitotic agents, procarbazine, hydroxyurea, asparaginase, corticosteroids, interferons and radioactive agents. Also encompassed within the scope of the term "anti-tumor drug," are conjugates of peptides with anti-tumor activity, e.g. TNF-α. Conjugates include, but are not limited to those formed between a therapeutic protein and a glycoprotein of the invention. A representative conjugate is that formed between PSGL-1 and TNF-α.

As used herein, "a cytotoxin or cytotoxic agent" means any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracinedione, mitoxantrone, mithramycin, actinomycin D, 1-dehydrotestosterone, glucocorticoids, procaine, tetracaine, lidocaine, propranolol, and puromycin and analogs or homologs thereof. Other toxins include, for example, ricin, CC-1065 and analogues, the duocarmycins. Still other toxins include diptheria toxin, and snake venom (e.g., cobra venom).

As used herein, "a radioactive agent" includes any radioisotope that is effective in diagnosing or destroying a tumor. Examples include, but are not limited to, indium-111, cobalt-60. Additionally, naturally occurring radioactive elements such as uranium, radium, and thorium, which typically represent mixtures of radioisotopes, are suitable examples of a radioactive agent. The metal ions are typically chelated with an organic chelating moiety.

Many useful chelating groups, crown ethers, cryptands and the like are known in the art and can be incorporated into the compounds of the invention (e.g., EDTA, DTPA, DOTA, NTA, HDTA, etc. and their phosphonate analogs such as DTPP, EDTP, HDTP, NTP, etc). See, for example, Pitt et al., "The Design of Chelating Agents for the Treatment of Iron Overload," In, INORGANIC CHEMISTRY IN BIOLOGY AND MEDICINE; Martell, Ed.; American Chemical Society, Washington, D.C., 1980, pp. 279-312; Lindoy, THE CHEMISTRY OF MACROCYCLIC LIGAND COMPLEXES; Cambridge University Press, Cambridge, 1989; Dugas, BIOORGANIC CHEMISTRY; Springer-Verlag, New York, 1989, and references contained therein.

Additionally, a manifold of routes allowing the attachment of chelating agents, crown ethers and cyclodextrins to other molecules is available to those of skill in the art. See, for example, Meares et al., "Properties of In Vivo Chelate-Tagged Proteins and Polypeptides." In, MODIFICATION OF PROTEINS: FOOD, NUTRITIONAL, AND PHARMACOLOGICAL ASPECTS;" Feeney, et al., Eds., American Chemical Society, Washington, D.C., 1982, pp. 370-387; Kasina et al., *Bioconjugate Chem.*, 9: 108-117 (1998); Song et al., *Bioconjugate Chem.*, 8: 249-255 (1997).

As used herein, "pharmaceutically acceptable carrier" includes any material, which when combined with the conjugate retains the conjugates' activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

As used herein, "administering" means oral administration, administration as a suppository, topical contact, intravenous, intraperitoneal, intramuscular, intralesional, or subcutaneous administration, administration by inhalation, or the implantation of a slow-release device, e.g., a mini-osmotic pump, to the subject. Administration is by any route including parenteral and transmucosal (e.g., oral, nasal, vaginal, rectal, or transdermal), particularly by inhalation. Parenteral administration includes, e.g., intravenous, intramuscular, intra-arteriole, intradermal, subcutaneous, intraperitoneal, intraventricular, and intracranial. Moreover, where injection is to treat a tumor, e.g., induce apoptosis, administration may be directly to the tumor and/or into tissues surrounding the tumor. Other modes of delivery include, but are not limited to, the use of liposomal formulations, intravenous infusion, transdermal patches, etc.

The term "isolated" refers to a material that is substantially or essentially free from components, which are used to produce the material. For peptide conjugates of the invention, the term "isolated" refers to material that is substantially or essentially free from components, which normally accompany the material in the mixture used to prepare the peptide conjugate. "Isolated" and "pure" are used interchangeably. Typically, isolated peptide conjugates of the invention have a level of purity preferably expressed as a range. The lower end of the range of purity for the peptide conjugates is about 60%, about 70% or about 80% and the upper end of the range of purity is about 70%, about 80%, about 90% or more than about 90%.

When the peptide conjugates are more than about 90% pure, their purities are also preferably expressed as a range. The lower end of the range of purity is about 90%, about 92%, about 94%, about 96% or about 98%. The upper end of the range of purity is about 92%, about 94%, about 96%, about 98% or about 100% purity.

Purity is determined by any art-recognized method of analysis (e.g., band intensity on a silver stained gel, polyacrylamide gel electrophoresis, HPLC, or a similar means).

"Essentially each member of the population," as used herein, describes a characteristic of a population of peptide conjugates of the invention in which a selected percentage of the modified sugars added to a peptide are added to multiple, identical acceptor sites on the peptide. "Essentially each member of the population" speaks to the "homogeneity" of the sites on the peptide conjugated to a modified sugar and refers to conjugates of the invention, which are at least about 80%, preferably at least about 90% and more preferably at least about 95% homogenous.

"Homogeneity," refers to the structural consistency across a population of acceptor moieties to which the modified sugars are conjugated. Thus, in a peptide conjugate of the invention in which each modified sugar moiety is conjugated to an acceptor site having the same structure as the acceptor site to which every other modified sugar is conjugated, the peptide conjugate is said to be about 100% homogeneous. Homogeneity is typically expressed as a range. The lower end of the range of homogeneity for the peptide conjugates is about 60%, about 70% or about 80% and the upper end of the range of purity is about 70%, about 80%, about 90% or more than about 90%.

When the peptide conjugates are more than or equal to about 90% homogeneous, their homogeneity is also preferably expressed as a range. The lower end of the range of homogeneity is about 90%, about 92%, about 94%, about 96% or about 98%. The upper end of the range of purity is about 92%, about 94%, about 96%, about 98% or about 100% homogeneity. The purity of the peptide conjugates is typically determined by one or more methods known to those of skill in the art, e.g., liquid chromatography-mass spectrometry (LC-MS), matrix assisted laser desorption mass time of flight spectrometry (MALDITOF), capillary electrophoresis, and the like.

"Substantially uniform glycoform" or a "substantially uniform glycosylation pattern," when referring to a glycopeptide species, refers to the percentage of acceptor moieties that are glycosylated by the glycosyltransferase of interest (e.g., fucosyltransferase). For example, in the case of a α1,2 fucosyltransferase, a substantially uniform fucosylation pattern exists if substantially all (as defined below) of the Galβ1,4-GlcNAc-R and sialylated analogues thereof are fucosylated in a peptide conjugate of the invention. It will be understood by one of skill in the art, that the starting material may contain glycosylated acceptor moieties (e.g., fucosylated Galβ1,4-GlcNAc-R moieties). Thus, the calculated percent glycosylation will include acceptor moieties that are glycosylated by the methods of the invention, as well as those acceptor moieties already glycosylated in the starting material.

The term "substantially" in the above definitions of "substantially uniform" generally means at least about 40%, at least about 70%, at least about 80%, or more preferably at least about 90%, and still more preferably at least about 95% of the acceptor moieties for a particular glycosyltransferase are glycosylated.

Introduction

The present invention provides stabilized peptides for therapeutic use. In one embodiment the invention provides conjugates of glycopeptides in which a modified sugar moiety is attached either directly or indirectly (e.g., through and intervening glycosyl residue) to an O-linked glycosylation site on the peptide. Also provided are methods for producing the conjugates of the invention.

The O-linked glycosylation site is generally the hydroxy side chain of a natural (e.g., serine, threonine) or unnatural (e.g., 5-hydroxyproline or 5-hydroxylysine) amino acid. Exemplary O-linked saccharyl residues include N-acetylgalactosamine, galactose, mannose, GlcNAc, glucose, fucose or xylose.

The methods of the invention can be practiced on any peptide having an O-linked glycosylation site. For example, in some embodiments the methods are of use to produce O-linked glycoconjugates in which the glycosyl moiety is attached to an O-linked glycosylation site that is present in the wild type peptide.

In other embodiments the invention provides novel mutant peptides that include one or more O-linked glycosylation site(s) that is/are not present in the wild-type peptide. Also provided are O-linked glycosylated versions of the mutant peptides, and methods of preparing O-linked glycosylated mutant peptides. Additional methods include the elaboration, trimming back and/or modification of the O-linked glycosyl residue and glycosyl residues that are N-, rather than O-linked.

In an exemplary aspect, the invention provides a mutant peptide having the formula:

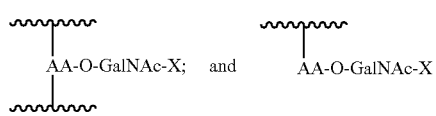

in which AA is an amino acid with a side chain that includes a hydroxyl moiety. Exemplary hydroxyamino acids are threonine and serine. The GalNAc moiety is linked to AA through the oxygen atom of the hydroxyl moiety. AA may be present in the wild type peptide or, alternatively, it is added or relocated by mutating the sequence of the wild type peptide. X is a modifying group or it is a saccharyl moiety, e.g., sialyl, galactosyl and Gal-Sia groups. In an exemplary embodiment, in which X is a saccharyl moiety, it includes a modifying group, as discussed herein.

As shown in the formulae above, the glycosylated amino acid can be at the N- or C-peptide terminus or internal to the peptide sequence.

In another exemplary embodiment, the invention provides a peptide conjugate having the formula:

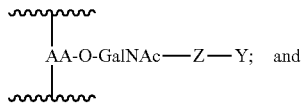

-continued

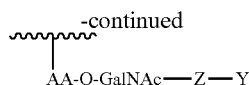

AA-O-GalNAc—Z—Y in which Z is a bond or a saccharyl residue selected from Gal, Sia and Gal-Sia. Y is a modifying group. The saccharyl residue bearing the modifying group ("glycosyl linking group") is enzymatically attached to the peptide-tethered glycosyl residue, e.g., forming an intact glycosyl linking group between the modified sugar and the remainder of the peptide-tethered glycosyl residue.

In yet another exemplary embodiment, AA is located within a proline-rich segment of the mutant peptide and/or it is proximate a proline residue. Appropriate sequences forming O-linked glycosylation sites are readily determined by interrogating the enzymatic O-linked glycosylation of short peptides containing one or more putative O-linked glycosylation sites. In another exemplary embodiment, O-linked glycosylation sites can be created at any position in a molecule, using techniques well known in the art. Peptides with introduced O-linked glycosylation sites can be tested for biological activity according to the methods of the invention.

The conjugates of the invention are formed between peptides and diverse species such as water-soluble polymers, therapeutic moieties, diagnostic moieties, targeting moieties and the like. Also provided are conjugates that include two or more peptides linked together through a linker arm, i.e., multifunctional conjugates; at least one peptide being O-glycosylated or including a mutant O-linked glycosylation site. The multi-functional conjugates of the invention can include two or more copies of the same peptide or a collection of diverse peptides with different structures, and/or properties. In exemplary conjugates according to this embodiment, the linker between the two peptides is attached to at least one of the peptides through an O-linked glycosyl residue, such as an O-linked glycosyl intact glycosyl linking group.

The conjugates of the invention are formed by the enzymatic attachment of a modified sugar to the glycosylated or unglycosylated peptide. The modified sugar is directly added to an O-linked glycosylation site, or to a glycosyl residue attached either directly or indirectly (e.g., through one or more glycosyl residue) to an O-linked glycosylation site. The invention also provides a conjugate of an O-linked glycosylated peptide in which a modified sugar is directly attached to an N-linked site, or to a glycosyl residue attached either directly or indirectly to an N-linked glycosylation site.

The modified sugar, when interposed between the peptide (or glycosyl residue) and the modifying group on the sugar becomes what is referred to herein as "an intact glycosyl linking group." Using the exquisite selectivity of enzymes, such as glycosyltransferases, the present method provides peptides that bear a desired group at one or more specific locations. Thus, according to the present invention, a modified sugar is attached directly to a selected locus on the peptide chain or, alternatively, the modified sugar is appended onto a carbohydrate moiety of a glycopeptide. Peptides in which modified sugars are bound to both a glycopeptide carbohydrate and directly to an amino acid residue of the peptide backbone are also within the scope of the present invention.

In contrast to known chemical and enzymatic peptide elaboration strategies, the methods of the invention, make it possible to assemble peptides and glycopeptides that have a substantially homogeneous derivatization pattern; the enzymes used in the invention are generally selective for a particular amino acid residue or combination of amino acid residues of the peptide. The methods are also practical for large-scale production of modified peptides and glycopeptides. Thus, the methods of the invention provide a practical means for large-scale preparation of glycopeptides having preselected uniform derivatization patterns. The methods are particularly well suited for modification of therapeutic peptides may be used to modify glycopeptides that are incompletely glycosylated during production in cell culture cells (e.g., mammalian cells, insect cells, plant cells, fungal cells, yeast cells, or prokaryotic cells) or transgenic plants or animals. In other embodiments, the invention may be used to glycosylate peptides, such as GLP-1, that are not glycosylated in the wild type state. In still further embodiments, glycosylation sites can be introduced by mutation at any position along the peptide backbone. The invention further provides method for testing the biological activity of mutants with introduced glycosylation sites.

The methods of the invention also provide conjugates of glycosylated and unglycosylated peptides with increased therapeutic half-life due to, for example, reduced clearance rate, or reduced rate of uptake by the immune or reticuloendothelial system (RES). Moreover, the methods of the invention provide a means for masking antigenic determinants on peptides, thus reducing or eliminating a host immune response against the peptide. Selective attachment of targeting agents to a peptide using an appropriate modified sugar can also be used to target a peptide to a particular tissue or cell surface receptor that is specific for the particular targeting agent. Moreover, there is provided a class of peptides that are specifically modified with a therapeutic moiety conjugated through a glycosyl linking group.

O-Glycosylation

The present invention provides O-linked glycosylated peptides, conjugates of these species and methods for forming O-linked glycosylated peptides that include a selected amino acid sequence ("an O-linked glycosylation site"). Of particular interest are mutant peptides that include an O-linked glycosylation site that is not present in the wild type peptide. The O-linked glycosylation site is a locus for attachment of a glycosyl residue that bears a modifying group.

Mucin-type O-linked glycosylation, one of the most abundant forms of protein glycosylation, is found on secreted and cell surface associated glycoproteins of all eukaryotic cells. There is great diversity in the structures created by O-linked glycosylation (hundreds of potential structures), which are produced by the catalytic activity of hundreds of glycosyltransferase enzymes that are resident in the Golgi complex. Diversity exists at the level of the glycan structure and in positions of attachment of O-glycans to protein backbones. Despite the high degree of potential diversity, it is clear that O-linked glycosylation is a highly regulated process that shows a high degree of conservation among multicellular organisms.

The first step in mucin-type O-linked glycosylation is catalysed by one or more members of a large family of UDP-GalNAc: polypeptide N-acetylgalactosaminyltransferases (GalNAc-transferases) (EC 2.4.1.41), which transfer GalNAc to serine and threonine acceptor sites (Hassan et al., *J. Biol. Chem.* 275: 38197-38205 (2000)). To date twelve members of the mammalian GalNAc-transferase family have been identified and characterized (Schwientek et al., J. Biol. Chem. 277: 22623-22638 (2002)), and several additional putative members of this gene family have been predicted from analysis of genome databases. The GalNAc-transferase isoforms have different kinetic properties and show differential expression patterns temporally and spatially, suggesting that they have distinct biological functions (Hassan et al., *J. Biol.*

Chem. 275: 38197-38205 (2000)). Sequence analysis of GalNAc-transferases have led to the hypothesis that these enzymes contain two distinct subunits: a central catalytic unit, and a C-terminal unit with sequence similarity to the plant lectin ricin, designated the "lectin domain" (Hagen et al., J. Biol. Chem. 274: 6797-6803 (1999); Hazes, *Protein Eng.* 10: 1353-1356 (1997); Breton et al., *Curr. Opin. Struct. Biol.* 9: 563-571 (1999)). Previous experiments involving site-specific mutagenesis of selected conserved residues confirmed that mutations in the catalytic domain eliminated catalytic activity. In contrast, mutations in the "lectin domain" had no significant effects on catalytic activity of the GalNAc-transferase isoform, GalNAc-T1 (Tenno et al., *J. Biol. Chem.* 277(49): 47088-96 (2002)). Thus, the C-terminal "lectin domain" was believed not to be functional and not to play roles for the enzymatic functions of GalNAc-transferases (Hagen et al., J. Biol. Chem. 274: 6797-6803 (1999)).

However, recent evidence demonstrates that some GalNAc-transferases exhibit unique activities with partially GalNAc-glycosylated glycopeptides. The catalytic actions of at least three GalNAc-transferase isoforms, GalNAc-T4, -T7, and -T10, selectively act on glycopeptides corresponding to mucin tandem repeat domains where only some of the clustered potential glycosylation sites have been GalNAc glycosylated by other GalNAc-transferases (Bennett et al., *FEBS Letters* 460: 226-230 (1999); Ten Hagen et al., *J. Biol. Chem.* 276: 17395-17404 (2001); Bennett et al., *J. Biol. Chem.* 273: 30472-30481 (1998); Ten Hagen et al., *J. Biol. Chem.* 274: 27867-27874 (1999)). GalNAc-T4 and -T7 recognize different GalNAc-glycosylated peptides and catalyse transfer of GalNAc to acceptor substrate sites in addition to those that were previously utilized. One of the functions of such GalNAc-transferase activities is predicted to represent a control step of the density of O-glycan occupancy in mucins and mucin-like glycoproteins with high density of O-linked glycosylation.

One example of this is the glycosylation of the cancer-associated mucin MUC1. MUC1 contains a tandem repeat O-linked glycosylated region of 20 residues (HGVTSAPDTRPAPGSTAPPA) (SEQ ID NO: 1) with five potential O-linked glycosylation sites. GalNAc-T1, -T2, and -T3 can initiate glycosylation of the MUC1 tandem repeat and incorporate at only three sites (HGVTSAPDTRPAPGSTAPPA (SEQ ID NO: 1), GalNAc attachment sites underlined). GalNAc-T4 is unique in that it is the only GalNAc-transferase isoform identified so far that can complete the O-linked glycan attachment to all five acceptor sites in the 20 amino acid tandem repeat sequence of the breast cancer associated mucin, MUC1. GalNAc-T4 transfers GalNAc to at least two sites not used by other GalNAc-transferase isoforms on the GalNAc₄TAP24 glycopeptide (TAPPAHGVTSAPDTRPAPGSTAPP (SEQ ID NO: 2), unique GalNAc-T4 attachment sites are in bold) (Bennett et al., *J. Biol. Chem.* 273: 30472-30481 (1998). An activity such as that exhibited by GalNAc-T4 appears to be required for production of the glycoform of MUC1 expressed by cancer cells where all potential sites are glycosylated (Muller et al., *J. Biol. Chem.* 274: 18165-18172 (1999)). Normal MUC1 from lactating mammary glands has approximately 2.6 O-linked glycans per repeat (Muller et al., *J. Biol. Chem.* 272: 24780-24793 (1997) and MUC1 derived from the cancer cell line T47D has 4.8 O-linked glycans per repeat (Muller et al., *J. Biol. Chem.* 274: 18165-18172 (1999)). The cancer-associated form of MUC1 is therefore associated with higher density of O-linked glycan occupancy and this is accomplished by a GalNAc-transferase activity identical to or similar to that of GalNAc-T4.

Polypeptide GalNAc-transferases, which have not displayed apparent GalNAc-glycopeptide specificities, also appear to be modulated by their putative lectin domains (PCT WO 01/85215 A2). Recently, it was found that mutations in the GalNAc-T1 putative lectin domain, similarly to those previously analysed in GalNAc-T4 (Hassan et al., *J. Biol. Chem.* 275: 38197-38205 (2000)), modified the activity of the enzyme in a similar fashion as GalNAc-T4. Thus, while wild type GalNAc-T1 added multiple consecutive GalNAc residues to a peptide substrate with multiple acceptor sites, mutated GalNAc-T1 failed to add more than one GalNAc residue to the same substrate (Tenno et al., *J. Biol. Chem.* 277(49): 47088-96 (2002)).

Since it has been demonstrated that mutations of GalNAc transferases can be utilized to produce glycosylation patterns that are distinct from those produced by the wild-type enzymes, it is within the scope of the present invention to utilize one or more mutant GalNAc transferase in preparing the O-linked glycosylated peptides of the invention.

Mutant GLP-1 Peptides with O-Linked Glycosylation Sites

The peptides provided by the present invention include an amino acid sequence that is recognized as a GalNAc acceptor by one or more wild-type or mutant GalNAc transferases. The amino acid sequence of the peptide is either the wild-type, for those peptides that include an O-linked glycosylation site, or may be a mutant sequence in which a non-naturally occurring O-linked glycosylation site is introduced. An exemplary peptide with which the present invention is practiced includes Glucagon-Like Peptide-1 (GLP-1). The emphasis of the following discussion on GLP-1 is for clarity of illustration. Those of skill will understand that the strategy set forth herein for preparing O-linked glycoconjugated analogues of wild-type and mutant peptides is applicable to any peptide.

In an exemplary embodiment, the peptide is a biologically active GLP-1 mutant that includes one or more mutations at one or more sites distributed along the peptide backbone. Representative wild type and mutant GLP-1 polypeptides of the invention have sequences that are selected from:

GLP-1 Glycopeptides

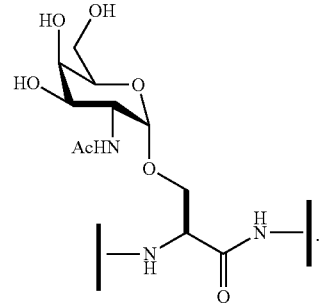

(SEQ ID NO: 3)
Ac-X-HAEGTFTSDVSSYLEGQAAKEFIAWLVKGR-NH₂, (SEQ ID NO: 4)
H-X-EGTFTSDVSSYLEGQAAKEFIAWLVKGR-NH₂, (SEQ ID NO: 5)
HA-X-GTFTSDVSSYLEGQAAKEFIAWLVKGR-NH₂, (SEQ ID NO: 6)
HAE-X-TFTSDVSSYLEGQAAKEFIAWLVKGR-NH₂,

HAEG-X-FTSDVSSYLEGQAAKEFIAWLVKGR-NH₂, (SEQ ID NO: 7)

HAEGT-X-TSDVSSYLEGQAAKEFIAWLVKGR-NH₂, (SEQ ID NO: 8)

HAEGTF-X-SDVSSYLEGQAAKEFIAWLVKGR-NH₂, (SEQ ID NO: 9)

HAEGTFT-X-DVSSYLEGQAAKEFIAWLVKGR-NH₂, (SEQ ID NO: 10)

HAEGTFTS-X-VSSYLEGQAAKEFIAWLVKGR-NH₂, (SEQ ID NO: 11)

HAEGTFTSD-X-SSYLEGQAAKEFIAWLVKGR-NH₂, (SEQ ID NO: 12)

HAEGTFTSDV-X-SYLEGQAAKEFIAWLVKGR-NH₂, (SEQ ID NO: 13)

HAEGTFTSDVS-X-YLEGQAAKEFIAWLVKGR-NH₂, (SEQ ID NO: 14)

HAEGTFTSDVSS-X-LEGQAAKEFIAWLVKGR-NH₂, (SEQ ID NO: 15)

HAEGTFTSDVSSY-X-EGQAAKEFIAWLVKGR-NH₂, (SEQ ID NO: 16)

HAEGTFTSDVSSYL-X-GQAAKEFIAWLVKGR-NH₂, (SEQ ID NO: 17)

HAEGTFTSDVSSYLE-X-QAAKEFIAWLVKGR-NH₂, (SEQ ID NO: 18)

HAEGTFTSDVSSYLEG-X-AAKEFIAWLVKGR-NH₂, (SEQ ID NO: 19)

HAEGTFTSDVSSYLEGQ-X-AKEFIAWLVKGR-NH₂, (SEQ ID NO: 20)

HAEGTFTSDVSSYLEGQA-X-KEFIAWLVKGR-NH₂, (SEQ ID NO: 21)

HAEGTFTSDVSSYLEGQAA-X-EFIAWLVKGR-NH₂, (SEQ ID NO: 22)

HAEGTFTSDVSSYLEGQAAK-X-FIAWLVKGR-NH₂, (SEQ ID NO: 23)

HAEGTFTSDVSSYLEGQAAKE-X-IAWLVKGR-NH₂, (SEQ ID NO: 24)

HAEGTFTSDVSSYLEGQAAKEF-X-AWLVKGR-NH₂, (SEQ ID NO: 25)

HAEGTFTSDVSSYLEGQAAKEFI-X-WLVKGR-NH₂, (SEQ ID NO: 26)

HAEGTFTSDVSSYLEGQAAKEFIA-X-LVKGR-NH₂, (SEQ ID NO: 27)

HAEGTFTSDVSSYLEGQAAKEFIAW-X-VKGR-NH₂, (SEQ ID NO: 28)

HAEGTFTSDVSSYLEGQAAKEFIAWL-X-KGR-NH₂, (SEQ ID NO: 29)

HAEGTFTSDVSSYLEGQAAKEFIAWLV-X-GR-NH₂, (SEQ ID NO: 30)

HAEGTFTSDVSSYLEGQAAKEFIAWLVK-X-R-NH₂, (SEQ ID NO: 31)

HAEGTFTSDVSSYLEGQAAKEFIAWLVKG-X-NH₂, (SEQ ID NO: 32)
and

HAEGTFTSDVSSYLEGQAAKEFIAWLVKGR-X-NH₂. (SEQ ID NO: 33)

In another exemplary embodiment, the peptide is a fusion of one or more peptides. In another exemplary embodiment, the components of the peptide are members selected from a GLP-1, GLP-1 analogs and/or GLP-1 mutants. In another exemplary embodiment, the components of the peptide are one or more non-GLP-1 peptides and GLP-1, GLP-1 analog and/or GLP-1 mutant. In another exemplary embodiment, the peptide is an Oxyntomodulin-GLP-1 fusion. This peptide has the following sequence.

HSQGTFTSDY SKYLDSRRAQ DFVQWLMNTK RNRNNIAKRH DEFERHAEGT FTSDVSSYLE GQAAKEFIAW LVKGRG (SEQ ID NO: 34).

In another exemplary embodiment, the peptide is an oxyntomodulin/GLP-1 mutant fusion. In another exemplary embodiment, oxyntomodulin/GLP-1 mutant fusions have the following "natural" sequence -----T$^{29}$KRNRNNIAKRHDEFERHAE (SEQ ID NO: 35)-----, natural sequence; replaced with sequences that are selected from:

T$^{29}$BJJ'RN(Z')$_a$NIAOUXX'O'FEZHAE (SEQ ID NO: 36) wherein all substitutions are independently selected from:
B=N (natural human variant), K, A, G, S, T, L
J=R, G, A, S, T, L
O=K, P
U=T, S, K
X=H, A, Q, N, G, or any uncharged amino acid
X'=D, G, A, N, E, or any uncharged amino acid
Z=R, A, G, S, T, V, I, L or any uncharged amino acid
Z'=G, A
J'=N, S, T
O'=E, A, G, M, any uncharged amino acid
a=0 or 1

Representative examples of oxyntomodulin/GLP-1 mutant fusions have the following natural sequence -----T$^{29}$KRNRNNIAKRHDEFERHAE (SEQ ID NO: 35)-----, natural sequence; replaced with sequences that are selected from:
--T$^{29}$NANRNNIAPTHDEFEAHAE (SEQ ID NO: 37)--,
--T$^{29}$NANRNNIAPTQDEFEAHAE (SEQ ID NO: 38)--,
--T$^{29}$NANRNNIAPTTDEFEAHAE (SEQ ID NO: 39)--,
--T$^{29}$NANRNNIAPTQGEFEAHAE (SEQ ID NO: 40)--,
--T$^{29}$NANRNNIAPTQGAFEAHAE (SEQ ID NO: 41)--,
--T$^{29}$NANRNNIAPTQGAMPAHAE (SEQ ID NO: 42)--,
--T$^{29}$ARNRNNIAPTQGAMEAHAE (SEQ ID NO: 43)--,
--T$^{29}$NANRNNIAPTINTFEAHAE (SEQ ID NO: 44)--,
--T$^{29}$NANRNNIAPTQAYSEGHAE (SEQ ID NO: 45)--,
--T$^{29}$NANRNNIAPTQAYFEGHAE (SEQ ID NO: 46)--,
--T$^{29}$NANRNNIAPTTASFEGHAE (SEQ ID NO: 47)--,
--T$^{29}$NANRNNIAPTTLYVEGHAE (SEQ ID NO: 48)--,
--T$^{29}$ARNRNNIAPTINTFEGHAE (SEQ ID NO: 49)--,
--T$^{29}$NANRNNIAPTINTFEGHAE (SEQ ID NO: 50)--,
and
--T$^{29}$NANRSGDIPTINTFEGHAE (SEQ ID NO: 51)-.

These sequences are based on human sequences in an attempt to minimize immunogenicity while creating a site for glycosylation and preventing proteolysis.

In another exemplary embodiment, one of the non-GLP-1 peptides is a member selected from a GLP-2, GLP-2 analog and/or GLP-2 mutant. In another exemplary embodiment, the peptide is a GLP-1/GLP-2 fusion. This peptide has the following sequence.

HAE GTFTSDVSSY LEGQAAKEFI AWLVKGRGRR DFPEEVAIVE ELGRRHADGS FSDEMNTILD NLAARDFINW LIQTKITDRK (SEQ ID NO: 52).

In another exemplary embodiment, the peptide is a GLP-1/GLP-2 mutant fusion. In another exemplary embodiment, GLP-1/GLP-2 mutant fusions have the following "natural" sequence HA--R$^{30}$GRRDFPEEVAIVEELGRRHADG—(SEQ ID NO: 52), natural sequence;

replaced with sequences that are selected from:

HX"--R$^{30}$GBB'DFPOU(O')$_a$JJ'VEELGZEHADG—(SEQ ID NO: 53)

wherein all substitutions are independently selected from:
B and B' (independently selected)=R, A, G, V, I, L, Q, P
J=P, A, I, V, G
O=T, S, E
U=E, S, T, Q, I, V, L, and uncharged amino acid
X"=A, G, S, T
Z and Z' (independently selected)=R, A, G, S, T, V, I, L or any uncharged amino acid
J'=E, Y, I, N, A, F, G, or any uncharged amino acid
O'=SLP, NT, Y, V, Y
a=0 or 1

Representative examples of GLP-1/GLP-2 mutant fusions have the following natural sequence HA--R$^{30}$GRRDFPEEVAIVEELGRRHADG—(SEQ ID NO: 52), natural sequence;

replaced with sequences that are selected from:

HS--R$^{30}$GQPDFPEGSLPVAIVEELGRGHADG—(SEQ ID NO: 54),
HS--R$^{30}$GQPDFPTGSLPVAIVEELGRGHADG—(SEQ ID NO: 55),
HS--R$^{30}$GQPDFPTTSEPVAIVEELGRGHADG—(SEQ ID NO: 56),
HS--R$^{30}$GQPDFPTAVIPVAIVEELGRGHADG—(SEQ ID NO: 57),
HS--R$^{30}$GQPDFPGSTAPVAIVEELGRGHADG—(SEQ ID NO: 58),
HS--R$^{30}$GQPDFPLTLEPVAIVEELGRGHADG—(SEQ ID NO: 59),
HS--R$^{30}$GQPDFPTSGEPVAIVEELGRGHADG—(SEQ ID NO: 60),
HS--R$^{30}$GQPDFPTINTPVAIVEELGRGHADG—(SEQ ID NO: 61),
HS--R$^{30}$GQPDFPTTLYPVAIVEELGRGHADG—(SEQ ID NO: 62),
HS--R$^{30}$GQPDFPEGSLPTAIVEELGRGHADG—(SEQ ID NO: 63),
HS--R$^{30}$GQPDFPEGSLPTINTEELGRGHADG—(SEQ ID NO: 64),
HS--R$^{30}$GQPDFPEGSLPTQAVEELGRGHADG—(SEQ ID NO: 65),
HS--R$^{30}$GQADFPEEVPTVEELGRGHADG—(SEQ ID NO: 66),
HS--R$^{30}$GQADFPEEVPTINTLGRGHADG—(SEQ ID NO: 67),
HS--R$^{30}$GQADFPEEVPTQGALGRGHADG—(SEQ ID NO: 68),
HS--R$^{30}$GQADFPEEVPTTLYLGRGHADG—(SEQ ID NO: 69),
HS--R$^{30}$GQADFPTVLPIVEELGRGHADG—(SEQ ID NO: 70),
HS--R$^{30}$GQADFPTEIPIVEELGRGHADG—(SEQ ID NO: 71),
HS--R$^{30}$GQADFPSDGPIVEELGRGHADG—(SEQ ID NO: 72), and
HS--R$^{30}$GQADFPTEVPIVEELGRGHADG—(SEQ ID NO: 73).

These sequences are based on human sequences in an attempt to minimize immunogenicity while creating a site for glycosylation and preventing proteolysis.

In another exemplary embodiment, the peptide is a fusion of three peptides, thus forming a triple fusion. The three peptides can be arranged in any order. In another exemplary embodiment, the three peptides are oxyntomodulin, GLP-1 and GLP-2. This peptide has the following sequence.

HSQGTFTS DYSKYLDSRR AQDFVQWLMN TKRN-RNNIAK RHDEFERHAE GTFTSDVSSY LEGQAAKEFI AWLVKGRGRR DFPEEVAIVE ELGRRHADGS FSDEMNTILD NLAARDFINW LIQTKITDRK (SEQ ID NO: 74)

In another exemplary embodiment, the peptide is an oxyntomodulin/GLP-1/GLP-2 mutant fusion. In another exemplary embodiment, an oxyntomodulin/GLP-1/GLP-2 mutant fusion has the following "natural" sequence HS-----T$^{29}$KRNRNNIAKRHDEFERHAE---R$^{75}$ GRRDFPEEVAIVEELGRRHADG-- (SEQ ID NO: 74), natural sequence;

replaced with sequences that are selected from:

HS--T$^{29}$BJJ'RN(Z')$_a$NIAOUXX'O'FEZHAE--R$^{76}$GB'B"DFPO"U' (O''')$_a$J"J'''VEELGX'''Z"HADG-- (SEQ ID NO: 75)

wherein all substitutions are independently selected from:
B=N (natural human variant), K, A, G, S, T, L
J=R, G, A, S, T, L
O=K, P
U=T, S
X=H, A, Q, N, G, or any uncharged amino acid
X'=D, G, A, N, E, or any uncharged amino acid
Z=R, A, G, S, T, V, I, L or any uncharged amino acid
Z'=G, A
J'=N, S, T
O'=E, A, G, M, any uncharged amino acid
a=0 or 1
B" and B' (independently selected)=R, A, G, V, I, L, Q, P
J"=P, A, I, V, G
O"=T, S, E
U'=E, S, T, Q, I, V, L, and uncharged amino acid
X''' and Z" (independently selected)=R, A, G, S, T, V, I, L or any uncharged amino acid
J'''=E, Y, I, N, A, F, G, or any uncharged amino acid
O'''=SLP, NT, Y, V, Y Representative examples of an oxyntomodulin/GLP-1/GLP-2 mutant fusion have the following "natural" sequence HS-----T$^{29}$KRNRNNIAKRHDEFERHAE---R$^{75}$ GRRDFPEEVAIVEELGRRHADG-- (SEQ ID NO: 74), natural sequence;

replaced with sequences that are selected from:

HS--T$^{29}$NANRSGDIPKAHDEFEAHAE--R$^{76}$ GQPDFPEGSLPVAIVEELGRGHADG—(SEQ ID NO: 76),
HS--T$^{29}$NANRSDIPKAHDEFEAHAE--R$^{75}$ GQPDFPEGSLPVAIVEELGRGHADG—(SEQ ID NO: 77),
HS--T$^{29}$NANANNIAKAHDEFEAHAE--R$^{75}$ GQPDFPTGSLPVAIVEELGRGHADG—(SEQ ID NO: 78),
HS--T$^{29}$NANANNIAKAHDEFEAHAE--R$^{75}$ GQPDFPTTSEPVAIVEELGRGHADG—(SEQ ID NO: 79),
HS--T$^{29}$NANANNIAKAHDEFEAHAE--

R$^{75}$ GQPDFPTAVIPVAIVEELGRGHADG—(SEQ ID NO: 80),
HS--T$^{29}$NANANNIAKAHDEFEAHAE--R$^{75}$ GQPDFPGSTAPVAIVEELGRGHADG—(SEQ ID NO: 81),
HS--T$^{29}$NANANNIAKAHDEFEAHAE--R$^{75}$ GQPDFPLTLEPVAIVEELGRGHADG—(SEQ ID NO: 82),
HS--T$^{29}$NANANNIAKAHDEFEAHAE--R$^{75}$ GQPDFPTSGEPVAIVEELGRGHADG—(SEQ ID NO: 83),
HS--T$^{29}$NANANNIAKAHDEFEAHAE--R$^{75}$ GQPDFPTINTPVAIVEELGRGHADG—(SEQ ID NO: 84),
HS--T$^{29}$NANANNIAKAHDEFEAHAE--R$^{75}$ GQPDFPTTLYPVAIVEELGRGHADG—(SEQ ID NO: 85),
HS--T$^{29}$NANANNIAKAHDEFEAHAE--R$^{75}$ GQPDFPEGSLPTAIVEELGRGHADG—(SEQ ID NO: 86),
HS--T$^{29}$NANANNIAKAHDEFEAHAE--R$^{75}$ GQPDFPEGSLPTINTEELGRGHADG—(SEQ ID NO: 87),
HS--T$^{29}$NANANNIAKAHDEFEAHAE--R$^{75}$ GQPDFPEGSLPTQAVEELGRGHADG—(SEQ ID NO: 88),
HS--T$^{29}$NANANNIAKAHDEFEAHAE--R$^{75}$ GQADFPEEVPTVEELGRGHADG—(SEQ ID NO: 89),
HS--T$^{29}$NANANNIAKAHDEFEAHAE--R$^{75}$ GQADFPEEVPTINTLGRGHADG—(SEQ ID NO: 90),
HS--T$^{29}$NANANNIAKAHDEFEAHAE--R$^{75}$ GQADFPEEVPTQGALGRGHADG—(SEQ ID NO: 91),
HS--T$^{29}$NANANNIAKAHDEFEAHAE--R$^{75}$ GQADFPEEVPTTLYLGRGHADG—(SEQ ID NO: 92),
HS--T$^{29}$NANANNIAKAHDEFEAHAE--R$^{75}$ GQADFPTVLPIVEELGRGHADG—(SEQ ID NO: 93),
HS--T$^{29}$NANANNIAKAHDEFEAHAE--R$^{75}$ GQADFPTEIPIVEELGRGHADG—(SEQ ID NO: 94),
HS--T$^{29}$NANANNIAKAHDEFEAHAE--R$^{75}$ GQADFPSDGPIVEELGRGHADG—(SEQ ID NO: 95), and
HS--T$^{29}$NANANNIAKAHDEFEAHAE--R$^{75}$ GQADFPTEVPIVEELGRGHADG—(SEQ ID NO: 96).

These sequences are based on human sequences in an attempt to minimize immunogenicity while creating a site for glycosylation and preventing proteolysis.

Appropriate O-linked glycosylation sequences for GLP-1 and peptides other than GLP-1 can be determined by preparing a polypeptide incorporating a putative O-linked glycosylation site and submitting that polypeptide to suitable O-linked glycosylation conditions, thereby confirming its ability to serve as an acceptor for a GalNAc transferase.

Moreover, as will be apparent to one of skill in the art, peptides that include one or more mutations are within the scope of the present invention. The mutations are designed to allow the adjustment of desirable properties of the peptides, e.g., activity and number and position of O- and/or N-linked glycosylation sites on the peptide.

Acquisition of Peptide Coding Sequences
General Recombinant Technology

This invention relies on routine techniques in the field of recombinant genetics. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Entire genes can also be chemically synthesized. Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of the cloned wild-type peptide genes, polynucleotide encoding mutant peptides, and synthetic oligonucleotides can be verified after cloning using, e.g., the chain termination method for sequencing double-stranded templates of Wallace et al., *Gene* 16: 21-26 (1981).

Cloning and Subcloning of a Wild-Type Peptide Coding Sequence

Numerous polynucleotide sequences encoding wild-type peptides have been determined and are available from a commercial supplier, e.g., human growth hormone, e.g., GenBank Accession Nos. NM 000515, NM 002059, NM 022556, NM 022557, NM 022558, NM 022559, NM 022560, NM 022561, and NM 022562.

The rapid progress in the studies of human genome has made possible a cloning approach where a human DNA sequence database can be searched for any gene segment that has a certain percentage of sequence homology to a known nucleotide sequence, such as one encoding a previously identified peptide. Any DNA sequence so identified can be subsequently obtained by chemical synthesis and/or a polymerase chain reaction (PCR) technique such as overlap extension method. For a short sequence, completely de novo synthesis may be sufficient; whereas further isolation of full length coding sequence from a human cDNA or genomic library using a synthetic probe may be necessary to obtain a larger gene.

Alternatively, a nucleic acid sequence encoding a peptide can be isolated from a human cDNA or genomic DNA library using standard cloning techniques such as polymerase chain reaction (PCR), where homology-based primers can often be derived from a known nucleic acid sequence encoding a peptide. Most commonly used techniques for this purpose are described in standard texts, e.g., Sambrook and Russell, supra.

cDNA libraries suitable for obtaining a coding sequence for a wild-type peptide may be commercially available or can be constructed. The general methods of isolating mRNA, making cDNA by reverse transcription, ligating cDNA into a recombinant vector, transfecting into a recombinant host for propagation, screening, and cloning are well known (see, e.g., Gubler and Hoffman, *Gene*, 25: 263-269 (1983); Ausubel et al., supra). Upon obtaining an amplified segment of nucleotide sequence by PCR, the segment can be further used as a probe to isolate the full-length polynucleotide sequence encoding the wild-type peptide from the cDNA library. A general description of appropriate procedures can be found in Sambrook and Russell, supra.

A similar procedure can be followed to obtain a full length sequence encoding a wild-type peptide, e.g., any one of the GenBank Accession Nos mentioned above, from a human genomic library. Human genomic libraries are commercially available or can be constructed according to various art-recognized methods. In general, to construct a genomic library, the DNA is first extracted from an tissue where a peptide is likely found. The DNA is then either mechanically sheared or enzymatically digested to yield fragments of about 12-20 kb in length. The fragments are subsequently separated by gradient centrifugation from polynucleotide fragments of undesired sizes and are inserted in bacteriophage λ vectors. These vectors and phages are packaged in vitro. Recombinant phages are analyzed by plaque hybridization as described in Benton and Davis, *Science*, 196: 180-182 (1977). Colony hybridization is carried out as described by Grunstein et al., *Proc. Natl. Acad. Sci. USA*, 72: 3961-3965 (1975).

Based on sequence homology, degenerate oligonucleotides can be designed as primer sets and PCR can be performed under suitable conditions (see, e.g., White et al., *PCR Protocols: Current Methods and Applications*, 1993; Griffin and Griffin, *PCR Technology*, CRC Press Inc. 1994) to amplify a segment of nucleotide sequence from a cDNA or genomic library. Using the amplified segment as a probe, the full-length nucleic acid encoding a wild-type peptide is obtained.

Upon acquiring a nucleic acid sequence encoding a wild-type peptide, the coding sequence can be subcloned into a vector, for instance, an expression vector, so that a recombinant wild-type peptide can be produced from the resulting construct. Further modifications to the wild-type peptide coding sequence, e.g., nucleotide substitutions, may be subsequently made to alter the characteristics of the molecule.

Introducing Mutations into a Peptide Sequence

From an encoding polynucleotide sequence, the amino acid sequence of a wild-type peptide can be determined. Subsequently, this amino acid sequence may be modified to alter the protein's glycosylation pattern, by introducing additional glycosylation site(s) at various locations in the amino acid sequence.

Several types of protein glycosylation sites are well known in the art. For instance, in eukaryotes, N-linked glycosylation occurs on the asparagine of the consensus sequence Asn-$X_{aa}$-Ser/Thr, in which $X_{aa}$ is any amino acid except proline (Kornfeld et al., *Ann Rev Biochem* 54:631-664 (1985); Kukuruzinska et al., *Proc. Natl. Acad. Sci. USA* 84:2145-2149 (1987); Herscovics et al., *FASEB J* 7:540-550 (1993); and Orlean, *Saccharomyces* Vol. 3 (1996)). O-linked glycosylation takes place at serine or threonine residues (Tanner et al., *Biochim. Biophys. Acta.* 906:81-91 (1987); and Hounsell et al., *Glycoconj. J.* 13:19-26 (1996)). Other glycosylation patterns are formed by linking glycosylphosphatidylinositol to the carboxyl-terminal carboxyl group of the protein (Takeda et al., *Trends Biochem. Sci.* 20:367-371 (1995); and Udenfriend et al., *Ann. Rev. Biochem.* 64:593-591 (1995). Based on this knowledge, suitable mutations can thus be introduced into a wild-type peptide sequence to form new glycosylation sites.

Although direct modification of an amino acid residue within a peptide polypeptide sequence may be suitable to introduce a new N-linked or O-linked glycosylation site, more frequently, introduction of a new glycosylation site is accomplished by mutating the polynucleotide sequence encoding a peptide. This can be achieved by using any of known mutagenesis methods, some of which are discussed below. Exemplary modifications to a GLP-1 peptide include those illustrated in SEQ ID NO: ________.

A variety of mutation-generating protocols are established and described in the art. See, e.g., Zhang et al., *Proc. Natl. Acad. Sci. USA,* 94: 4504-4509 (1997); and Stemmer, *Nature,* 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortle, *Science,* 229: 1193-1201 (1985)), mutagenesis using uracil-containing templates (Kunkel, *Proc. Natl. Acad. Sci. USA,* 82: 488-492 (1985)), oligonucleotide-directed mutagenesis (Zoller and Smith, *Nucl. Acids Res.,* 10: 6487-6500 (1982)), phosphorothioate-modified DNA mutagenesis (Taylor et al., *Nucl. Acids Res.,* 13: 8749-8764 and 8765-8787 (1985)), and mutagenesis using gapped duplex DNA (Kramer et al., *Nucl. Acids Res.,* 12: 9441-9456 (1984)).

Other methods for generating mutations include point mismatch repair (Kramer et al., *Cell,* 38: 879-887 (1984)), mutagenesis using repair-deficient host strains (Carter et al., *Nucl. Acids Res.,* 13: 4431-4443 (1985)), deletion mutagenesis (Eghtedarzadeh and Henikoff, *Nucl. Acids Res.,* 14: 5115 (1986)), restriction-selection and restriction-purification (Wells et al., *Phil. Trans. R. Soc. Lond. A,* 317: 415-423 (1986)), mutagenesis by total gene synthesis (Nambiar et al., *Science,* 223: 1299-1301 (1984)), double-strand break repair (Mandecki, *Proc. Natl. Acad. Sci. USA,* 83: 7177-7181 (1986)), mutagenesis by polynucleotide chain termination methods (U.S. Pat. No. 5,965,408), and error-prone PCR (Leung et al., *Biotechniques,* 1: 11-15 (1989)).

Modification of Nucleic Acids for Preferred Codon Usage in a Host Organism

The polynucleotide sequence encoding a mutant peptide can be further altered to coincide with the preferred codon usage of a particular host. For example, the preferred codon usage of one strain of bacterial cells can be used to derive a polynucleotide that encodes a mutant peptide of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell. U.S. Pat. No. 5,824,864, for example, provides the frequency of codon usage by highly expressed genes exhibited by dicotyledonous plants and monocotyledonous plants.

At the completion of modification, the mutant peptide coding sequences are verified by sequencing and are then subcloned into an appropriate expression vector for recombinant production in the same manner as the wild-type peptides.

Expression and Purification of the Mutant Peptide

Following sequence verification, the mutant peptide of the present invention can be produced using routine techniques in the field of recombinant genetics, relying on the polynucleotide sequences encoding the polypeptide disclosed herein.

Expression Systems

To obtain high-level expression of a nucleic acid encoding a mutant peptide of the present invention, one typically subclones a polynucleotide encoding the mutant peptide into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the wild-type or mutant peptide are available in, e.g., *E. coli, Bacillus* sp., *Salmonella*, and Caulobacter. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the mutant peptide in host cells. A typical expression cassette thus contains a promoter operably linked to the nucleic acid sequence encoding the mutant peptide and signals required for efficient polyadenylation of the transcript, ribosome binding sites, and translation termination. The nucleic acid sequence encoding the peptide is typically linked to a cleavable signal peptide sequence to promote secretion of the peptide by the transformed cell. Such signal peptides include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322-based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A⁺, pMTO10/A⁺, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the mutant peptide under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

When periplasmic expression of a recombinant protein (e.g., a hgh mutant of the present invention) is desired, the expression vector further comprises a sequence encoding a secretion signal, such as the *E. coli* OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., *Gene* 39: 247-254 (1985), U.S. Pat. Nos. 6,160,089 and 6,436,674.

As discussed above, a person skilled in the art will recognize that various conservative substitutions can be made to any wild-type or mutant peptide or its coding sequence while still retaining the biological activity of the peptide. Moreover, modifications of a polynucleotide coding sequence may also be made to accommodate preferred codon usage in a particular expression host without altering the resulting amino acid sequence.

Transfection Methods

Standard transfection methods are used to produce bacterial, mammalian, yeast or insect cell lines that express large quantities of the mutant peptide, which are then purified using standard techniques (see, e.g., Colley et al., J. Biol. Chem. 264: 17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132: 349-351 (1977); Clark-Curtiss & Curtiss, Methods in Enzymology 101: 347-362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the mutant peptide.

Detection of Expression of Mutant Peptide in Host Cells

After the expression vector is introduced into appropriate host cells, the transfected cells are cultured under conditions favoring expression of the mutant peptide. The cells are then screened for the expression of the recombinant polypeptide, which is subsequently recovered from the culture using standard techniques (see, e.g., Scopes, *Protein Purification: Principles and Practice* (1982); U.S. Pat. No. 4,673,641; Ausubel et al., supra; and Sambrook and Russell, supra).

Several general methods for screening gene expression are well known among those skilled in the art. First, gene expression can be detected at the nucleic acid level. A variety of methods of specific DNA and RNA measurement using nucleic acid hybridization techniques are commonly used (e.g., Sambrook and Russell, supra). Some methods involve an electrophoretic separation (e.g., Southern blot for detecting DNA and Northern blot for detecting RNA), but detection of DNA or RNA can be carried out without electrophoresis as well (such as by dot blot). The presence of nucleic acid encoding a mutant peptide in transfected cells can also be detected by PCR or RT-PCR using sequence-specific primers.

Second, gene expression can be detected at the polypeptide level. Various immunological assays are routinely used by those skilled in the art to measure the level of a gene product, particularly using polyclonal or monoclonal antibodies that react specifically with a mutant peptide of the present invention, such as a polypeptide having the amino acid sequence of SEQ ID NO:1-7, (e.g., Harlow and Lane, *Antibodies, A Laboratory Manual, Chapter* 14, Cold Spring Harbor, 1988; Kohler and Milstein, *Nature,* 256: 495-497 (1975)). Such techniques require antibody preparation by selecting antibodies with high specificity against the mutant peptide or an antigenic portion thereof. The methods of raising polyclonal and monoclonal antibodies are well established and their descriptions can be found in the literature, see, e.g., Harlow and Lane, supra; Kohler and Milstein, *Eur. J. Immunol.,* 6: 511-519 (1976). More detailed descriptions of preparing antibody against the mutant peptide of the present invention and conducting immunological assays detecting the mutant peptide are provided in a later section.

Purification of Recombinantly Produced Mutant Peptide

Once the expression of a recombinant mutant peptide in transfected host cells is confirmed, the host cells are then cultured in an appropriate scale for the purpose of purifying the recombinant polypeptide.

1. Purification of Recombinantly Produced Mutant Peptide from Bacteria

When the mutant peptides of the present invention are produced recombinantly by transformed bacteria in large amounts, typically after promoter induction, although expression can be constitutive, the proteins may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 μg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing reformation of the immunologically and/or biologically active protein of interest. After solubilization, the protein can be separated from other bacterial proteins by standard separation techniques. For further description of purifying recombinant peptide from bacterial inclusion body, see, e.g., Patra et al., Protein Expression and Purification 18: 182-190 (2000).

Alternatively, it is possible to purify recombinant polypeptides, e.g., a mutant peptide, from bacterial periplasm. Where the recombinant protein is exported into the periplasm of the bacteria, the periplasmic fraction of the bacteria can be isolated by cold osmotic shock in addition to other methods known to those of skill in the art (see e.g., Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

2. Standard Protein Separation Techniques for Purification

When a recombinant polypeptide, e.g., the mutant peptide of the present invention, is expressed in host cells in a soluble form, its purification can follow the standard protein purification procedure described below.

i. Solubility Fractionation

Often as an initial step, and if the protein mixture is complex, an initial salt fractionation can separate many of the unwanted host cell proteins (or proteins derived from the cell culture media) from the recombinant protein of interest, e.g., a mutant peptide of the present invention. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

ii. Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., a mutant peptide. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

iii. Column Chromatography

The proteins of interest (such as the mutant peptide of the present invention) can also be separated from other proteins on the basis of their size, net surface charge, hydrophobicity, or affinity for ligands. In addition, antibodies raised against peptide can be conjugated to column matrices and the peptide immunopurified. All of these methods are well known in the art.

It will be apparent to one of skill that chromatographic techniques can be performed at any scale and using equipment from many different manufacturers (e.g., Pharmacia Biotech).

Immunoassays for Detection of Mutant Peptide Expression

To confirm the production of a recombinant mutant peptide, immunological assays may be useful to detect in a sample the expression of the polypeptide. Immunological assays are also useful for quantifying the expression level of the recombinant hormone. Antibodies against a mutant peptide are necessary for carrying out these immunological assays.

Production of Antibodies Against Mutant Peptide

Methods for producing polyclonal and monoclonal antibodies that react specifically with an immunogen of interest are known to those of skill in the art (see, e.g., Coligan, Current Protocols in Immunology Wiley/Greene, N.Y., 1991; Harlow and Lane, Antibodies: A Laboratory Manual Cold Spring Harbor Press, NY, 1989; Stites et al. (eds.) Basic and Clinical Immunology (4th ed.) Lange Medical Publications, Los Altos, Calif., and references cited therein; Goding, Monoclonal Antibodies: Principles and Practice (2d ed.) Academic Press, New York, N.Y., 1986; and Kohler and Milstein Nature 256: 495-497, 1975). Such techniques include antibody preparation by selection of antibodies from libraries of recombinant antibodies in phage or similar vectors (see, Huse et al., Science 246: 1275-1281, 1989; and Ward et al., Nature 341: 544-546, 1989).

In order to produce antisera containing antibodies with desired specificity, the polypeptide of interest (e.g., a mutant peptide of the present invention) or an antigenic fragment thereof can be used to immunize suitable animals, e.g., mice, rabbits, or primates. A standard adjuvant, such as Freund's adjuvant, can be used in accordance with a standard immunization protocol. Alternatively, a synthetic antigenic peptide derived from that particular polypeptide can be conjugated to a carrier protein and subsequently used as an immunogen.

The animal's immune response to the immunogen preparation is monitored by taking test bleeds and determining the titer of reactivity to the antigen of interest. When appropriately high titers of antibody to the antigen are obtained, blood is collected from the animal and antisera are prepared. Further fractionation of the antisera to enrich antibodies specifically reactive to the antigen and purification of the antibodies can be performed subsequently, see, Harlow and Lane, supra, and the general descriptions of protein purification provided above.

Monoclonal antibodies are obtained using various techniques familiar to those of skill in the art. Typically, spleen cells from an animal immunized with a desired antigen are immortalized, commonly by fusion with a myeloma cell (see, Kohler and Milstein, Eur. J. Immunol. 6:511-519, 1976). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and the yield of the monoclonal antibodies produced by such cells may be enhanced by various techniques, including injection into the peritoneal cavity of a vertebrate host.

Additionally, monoclonal antibodies may also be recombinantly produced upon identification of nucleic acid sequences encoding an antibody with desired specificity or a binding fragment of such antibody by screening a human B cell cDNA library according to the general protocol outlined by Huse et al., supra. The general principles and methods of recombinant polypeptide production discussed above are applicable for antibody production by recombinant methods.

When desired, antibodies capable of specifically recognizing a mutant peptide of the present invention can be tested for their cross-reactivity against the wild-type peptide and thus distinguished from the antibodies against the wild-type protein. For instance, antisera obtained from an animal immunized with a mutant peptide can be run through a column on which a wild-type peptide is immobilized. The portion of the antisera that passes through the column recognizes only the mutant peptide and not the wild-type peptide. Similarly, monoclonal antibodies against a mutant peptide can also be screened for their exclusivity in recognizing only the mutant but not the wild-type peptide.

Polyclonal or monoclonal antibodies that specifically recognize only the mutant peptide of the present invention but not the wild-type peptide are useful for isolating the mutant protein from the wild-type protein, for example, by incubating a sample with a mutant peptide-specific polyclonal or monoclonal antibody immobilized on a solid support.

Immunoassays for Detecting Mutant Peptide Expression

Once antibodies specific for a mutant peptide of the present invention are available, the amount of the polypeptide in a sample, e.g., a cell lysate, can be measured by a variety of immunoassay methods providing qualitative and quantitative results to a skilled artisan. For a review of immunological and immunoassay procedures in general see, e.g., Stites, supra; U.S. Pat. Nos. 4,366,241; 4,376,110; 4,517,288; and 4,837,168.

Labeling in Immunoassays

Immunoassays often utilize a labeling agent to specifically bind to and label the binding complex formed by the antibody and the target protein. The labeling agent may itself be one of the moieties comprising the antibody/target protein complex, or may be a third moiety, such as another antibody, that specifically binds to the antibody/target protein complex. A label may be detectable by spectroscopic, photochemical, biochemical, immunochemical, electrical, optical or chemical means. Examples include, but are not limited to, magnetic beads (e.g., Dynabeads™), fluorescent dyes (e.g., fluorescein isothiocyanate, Texas red, rhodamine, and the like), radiolabels (e.g., $^{3}H$, $^{125}I$, $^{135}S$, $^{14}C$, or $^{32}P$), enzymes (e.g., horse radish peroxidase, alkaline phosphatase, and others commonly used in an ELISA), and colorimetric labels such as colloidal gold or colored glass or plastic (e.g., polystyrene, polypropylene, latex, etc.) beads.

In some cases, the labeling agent is a second antibody bearing a detectable label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as protein A or protein G, can also be used as the label agents. These proteins are normal constituents of the cell walls of streptococcal bacteria. They exhibit a strong non-immunogenic reactivity with immunoglobulin constant regions from a variety of species (see, generally, Kronval, et al. *J. Immunol.*, 111: 1401-1406 (1973); and Akerstrom, et al., *J. Immunol.*, 135: 2589-2542 (1985)).

Immunoassay Formats

Immunoassays for detecting a target protein of interest (e.g., a mutant human growth hormone) from samples may be either competitive or noncompetitive. Noncompetitive immunoassays are assays in which the amount of captured target protein is directly measured. In one preferred "sandwich" assay, for example, the antibody specific for the target protein can be bound directly to a solid substrate where the antibody is immobilized. It then captures the target protein in test samples. The antibody/target protein complex thus immobilized is then bound by a labeling agent, such as a second or third antibody bearing a label, as described above.

In competitive assays, the amount of target protein in a sample is measured indirectly by measuring the amount of an added (exogenous) target protein displaced (or competed away) from an antibody specific for the target protein by the target protein present in the sample. In a typical example of such an assay, the antibody is immobilized and the exogenous target protein is labeled. Since the amount of the exogenous target protein bound to the antibody is inversely proportional to the concentration of the target protein present in the sample, the target protein level in the sample can thus be determined based on the amount of exogenous target protein bound to the antibody and thus immobilized.

In some cases, western blot (immunoblot) analysis is used to detect and quantify the presence of a mutant peptide in the samples. The technique generally comprises separating sample proteins by gel electrophoresis on the basis of molecular weight, transferring the separated proteins to a suitable solid support (such as a nitrocellulose filter, a nylon filter, or a derivatized nylon filter) and incubating the samples with the antibodies that specifically bind the target protein. These antibodies may be directly labeled or alternatively may be subsequently detected using labeled antibodies (e.g., labeled sheep anti-mouse antibodies) that specifically bind to the antibodies against a mutant peptide.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.*, 5: 34-41 (1986)).

The Conjugates

In a representative aspect, the present invention provides a glycoconjugate between a peptide and a selected modifying group, in which the modifying group is conjugated to the peptide through a glycosyl linking group, e.g., an intact glycosyl linking group. The glycosyl linking group is directly bound to an O-linked glycosylation site on the peptide or, alternatively, it is bound to an O-linked glycosylation site through one or more additional glycosyl residues. Methods of preparing the conjugates are set forth herein and in U.S. Pat. Nos. 5,876,980; 6,030,815; 5,728,554; 5,922,577; WO 98/31826; US2003180835; and WO 03/031464.

Exemplary peptides include an O-linked GalNAc residue that is bound to the O-linked glycosylation site through the action of a GalNAc transferase. The GalNAc itself may be the intact glycosyl linking group. The GalNAc may also be further elaborated by, for example, a Gal or Sia residue, either of which can act as the intact glycosyl linking group. In representative embodiments, the O-linked saccharyl residue is GalNAc-X, GalNAc-Gal-Sia-X, or GalNAc-Gal-Gal-Sia-X, in which X is a modifying group.

In an exemplary embodiment, the peptide is a mutant peptide that includes an O-linked glycosylation site not present in the wild-type peptide. The peptide is preferably O-glycosylated at the mutated site with a GalNAc residue. The discussion immediately preceding regarding the structure of the saccharyl moiety is relevant here as well.

The link between the peptide and the selected moiety includes an intact glycosyl linking group interposed between the peptide and the modifying moiety. As discussed herein, the selected moiety is essentially any species that can be attached to a saccharide unit, resulting in a "modified sugar" that is recognized by an appropriate transferase enzyme, which appends the modified sugar onto the peptide. The saccharide component of the modified sugar, when interposed between the peptide and a selected moiety, becomes an "intact glycosyl linking group." The glycosyl linking group is formed from any mono- or oligo-saccharide that, after modification with a selected moiety, is a substrate for an appropriate transferase.

The conjugates of the invention will typically correspond to the general structure:

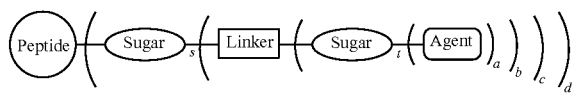

in which the symbols a, b, c, d and s represent a positive, non-zero integer; and t is either 0 or a positive integer. The "agent" is a therapeutic agent, a bioactive agent, a detectable label, water-soluble moiety or the like. The "agent" can be a peptide, e.g., enzyme, antibody, antigen, etc. The linker can be any of a wide array of linking groups, infra. Alternatively, the linker may be a single bond or a "zero order linker." The identity of the peptide is without limitation.

In an exemplary embodiment, the selected moiety is a water-soluble polymer, e.g., PEG, m-PEG, PPG, m-PPG, etc. The water-soluble polymer is covalently attached to the peptide via a glycosyl linking group. The glycosyl linking group is covalently attached to either an amino acid residue or a glycosyl residue of the peptide. Alternatively, the glycosyl linking group is attached to one or more glycosyl units of a glycopeptide. The invention also provides conjugates in which the glycosyl linking group (e.g., GalNAc) is attached to an amino acid residue (e.g., Thr or Ser).

In an exemplary embodiment, the protein is an interferon. The interferons are antiviral glycoproteins that, in humans, are secreted by human primary fibroblasts after induction with virus or double-stranded RNA. Interferons are of interest as therapeutics, e.g., antiviral agents (e.g., hepatitis B and C), antitumor agents (e.g., hepatocellular carcinoma) and in the treatment of multiple sclerosis. For references relevant to interferon-α, see, Asano, et al., *Eur. J. Cancer*, 27(Suppl 4):S21-S25 (1991); Nagy, et al., *Anticancer Research*, 8(3): 467-470 (1988); Dron, et al., *J. Biol. Regul. Homeost. Agents*, 3(1):13-19 (1989); Habib, et al., *Am. Surg.*, 67(3):257-260

(March 2001); and Sugyiama, et al., *Eur. J. Biochem.*, 217: 921-927 (1993). For references discussing interferon-β, see, e.g., Yu, et al., *J. Neuroimmunol.*, 64(1):91-100 (1996); Schmidt, J., *J. Neurosci. Res.*, 65(1):59-67 (2001); Wender, et al., *Folia Neuropathol.*, 39(2):91-93 (2001); Martin, et al., *Springer Semin. Immunopathol.*, 18(1):1-24 (1996); Takane, et al., *J. Pharmacol. Exp. Ther.*, 294(2):746-752 (2000); Sburlati, et al., *Biotechnol. Prog.*, 14:189-192 (1998); Dodd, et al., *Biochimica et Biophysica Acta*, 787:183-187 (1984); Edelbaum, et al., *J. Interferon Res.*, 12:449-453 (1992); Conradt, et al., *J. Biol. Chem.*, 262(30):14600-14605 (1987); Civas, et al., *Eur. J. Biochem.*, 173:311-316 (1988); Demolder, et al., *J. Biotechnol.*, 32:179-189 (1994); Sedmak, et al., *J. Interferon Res.*, 9(Suppl 1):S61-S65 (1989); Kagawa, et al., *J. Biol. Chem.*, 263(33):17508-17515 (1988); Hershenson, et al., U.S. Pat. No. 4,894,330; Jayaram, et al., *J. Interferon Res.*, 3(2):177-180 (1983); Menge, et al., *Develop. Biol. Standard.*, 66:391-401 (1987); Vonk, et al., *J. Interferon Res.*, 3(2):169-175 (1983); and Adolf, et al., *J. Interferon Res.*, 10:255-267 (1990).

In an exemplary interferon conjugate, interferon alpha, e.g., interferon alpha 2β, is conjugated to a water soluble polymer through an intact glycosyl linker.

In a further exemplary embodiment, the invention provides a conjugate of human Glucagon-like peptide-1 (GLP-1). GLP-1 is protein that has pleiotropic effects in the maintenance of glyceic control of the organism. GLP-1 is released in response to the oral ingestion of food. GLP-1 appears to regulate plasma glucose levels by a variety of mechanisms including the enhancement of glucose dependent insulin secretion, stimulation of proinsulin gene expression, suppression of glucagon release and gastric emptying, enhancement of insulin sensitivity, and increase of satiety (see e.g., Xiao et al. (2001 Biochemisrty 40:2860, and Perfetti, R. and Merkel, P. (2000) European J. of Endocrinology 143:717). GLP-1 is rapidly cleared from the body. The half life of GLP-1 in vivo is about minutes, with clearance completed within about 12-13 minutes. Even when administered subcutaneously, GLP-1 is cleared from the circulation within 90 minutes (Perfetti, R. and Merkel, P. supra)

In addition to providing conjugates that are formed through an enzymatically added intact glycosyl linking group, the present invention provides conjugates that are highly homogenous in their substitution patterns. Using the methods of the invention, it is possible to form peptide conjugates in which essentially all of the modified sugar moieties across a population of conjugates of the invention are attached to a structurally identical amino acid or glycosyl residue. Thus, in a second aspect, the invention provides a peptide conjugate having a population of water-soluble polymer moieties, which are covalently bound to the peptide through an intact glycosyl linking group. In a preferred conjugate of the invention, essentially each member of the population is bound via the glycosyl linking group to a glycosyl residue of the peptide, and each glycosyl residue of the peptide to which the glycosyl linking group is attached has the same structure.

Also provided is a peptide conjugate having a population of water-soluble polymer moieties covalently bound thereto through a glycosyl linking group. In a preferred embodiment, essentially every member of the population of water soluble polymer moieties is bound to an amino acid residue of the peptide via an intact glycosyl linking group, and each amino acid residue having an intact glycosyl linking group attached thereto has the same structure.

The present invention also provides conjugates analogous to those described above in which the peptide is conjugated to a therapeutic moiety, diagnostic moiety, targeting moiety, toxin moiety or the like via a glycosyl linking group. Each of the above-recited moieties can be a small molecule, natural polymer (e.g., polypeptide) or synthetic polymer.

The conjugates of the invention can include glycosyl linking groups that are mono- or multi-valent (e.g., antennary structures). Thus, conjugates of the invention include both species in which a selected moiety is attached to a peptide via a monovalent glycosyl linking group. Also included within the invention are conjugates in which more than one selected moiety is attached to a peptide via a multivalent linking group.

The Methods

In addition to the conjugates discussed above, the present invention provides methods for preparing these and other conjugates. Moreover, the invention provides methods of preventing, curing or ameliorating a disease state by administering a conjugate of the invention to a subject at risk of developing a disease or condition, (e.g., diabetes or obesity) or a subject that has the disease or condition.

Thus, the invention provides a method of forming a covalent conjugate between a selected moiety and a peptide. In exemplary embodiments, the conjugate is formed between a water-soluble polymer, a therapeutic moiety, targeting moiety or a biomolecule, and a glycosylated or non-glycosylated peptide. The polymer, therapeutic moiety or biomolecule is conjugated to the peptide via a glycosyl linking group, which is interposed between, and covalently linked to both the peptide and the modifying group (e.g. water-soluble polymer). The method includes contacting the peptide with a mixture containing a modified sugar and a glycosyltransferase for which the modified sugar is a substrate. The reaction is conducted under conditions appropriate to form a covalent bond between the modified sugar and the peptide. The sugar moiety of the modified sugar is preferably selected from nucleotide sugars, activated sugars and sugars, which are neither nucleotides nor activated.

The acceptor peptide (O-glycosylated or non-glycosylated) is typically synthesized de novo, or recombinantly expressed in a prokaryotic cell (e.g., bacterial cell, such as *E. coli*) or in a eukaryotic cell such as a mammalian, yeast, insect, fungal or plant cell. The peptide can be either a full-length protein or a fragment. Moreover, the peptide can be a wild type or mutated peptide. In an exemplary embodiment, the peptide includes a mutation that adds one or more N- or O-linked glycosylation sites to the peptide sequence.

The method of the invention also provides for modification of incompletely glycosylated peptides that are produced recombinantly. Many recombinantly produced glycoproteins are incompletely glycosylated, exposing carbohydrate residues that may have undesirable properties, e.g., immunogenicity, recognition by the RES. Employing a modified sugar in a method of the invention, the peptide can be simultaneously further glycosylated and derivatized with, e.g., a water-soluble polymer, therapeutic agent, or the like. The sugar moiety of the modified sugar can be the residue that would properly be conjugated to the acceptor in a fully glycosylated peptide, or another sugar moiety with desirable properties.

Any peptides modified by the methods of the invention. However, the peptides are typically mutated peptides, produced by methods known in the art, such as site-directed mutagenesis. Glycosylation of peptides is typically either N-linked or O-linked. An exemplary N-linkage is the attachment of the modified sugar to the side chain of an asparagine residue. The tripeptide sequences asparagine-X-serine and asparagine-X-threonine, where X is any amino acid except proline, are the recognition sequences for enzymatic attachment of a carbohydrate moiety to the asparagine side chain. Thus, the presence of either of these tripeptide sequences in a polypeptide creates a potential glycosylation site. O-linked glycosylation refers to the attachment of one sugar (e.g., N-acetylgalactosamine, galactose, mannose, GlcNAc, glucose, fucose or xylose) to the hydroxy side chain of a hydroxyamino acid, preferably serine or threonine, although unusual or non-natural amino acids, e.g., 5-hydroxyproline or 5-hydroxylysine may also be used.

Moreover, in addition to peptides, the methods of the present invention can be practiced with other biological structures (e.g., glycolipids, lipids, sphingoids, ceramides, whole cells, and the like, containing an O-linked glycosylation site).

Addition of glycosylation sites to a peptide or other structure is conveniently accomplished by altering the amino acid sequence such that it contains one or more glycosylation sites. The addition may also be made by the incorporation of one or more species presenting an —OH group, preferably serine or threonine residues, within the sequence of the peptide (for O-linked glycosylation sites). The addition may be made by mutation or by full chemical synthesis of the peptide. The peptide amino acid sequence is preferably altered through changes at the DNA level, particularly by mutating the DNA encoding the peptide at preselected bases such that codons are generated that will translate into the desired amino acids. The DNA mutation(s) are preferably made using methods known in the art.

In an exemplary embodiment, the glycosylation site is added by shuffling polynucleotides. Polynucleotides encoding a candidate peptide can be modulated with DNA shuffling protocols. DNA shuffling is a process of recursive recombination and mutation, performed by random fragmentation of a pool of related genes, followed by reassembly of the fragments by a polymerase chain reaction-like process. See, e.g., Stemmer, *Proc. Natl. Acad. Sci. USA* 91:10747-10751 (1994); Stemmer, *Nature* 370:389-391 (1994); and U.S. Pat. Nos. 5,605,793, 5,837,458, 5,830,721 and 5,811,238.

The present invention also provides means of adding (or removing) one or more selected glycosyl residues to a peptide, after which a modified sugar is conjugated to at least one of the selected glycosyl residues of the peptide. The present embodiment is useful, for example, when it is desired to conjugate the modified sugar to a selected glycosyl residue that is either not present on a peptide or is not present in a desired amount. Thus, prior to coupling a modified sugar to a peptide, the selected glycosyl residue is conjugated to the peptide by enzymatic or chemical coupling. In another embodiment, the glycosylation pattern of a glycopeptide is altered prior to the conjugation of the modified sugar by the removal of a carbohydrate residue from the glycopeptide. See, for example WO 98/31826.

Addition or removal of any carbohydrate moieties present on the glycopeptide is accomplished either chemically or enzymatically. Chemical deglycosylation is preferably brought about by exposure of the polypeptide variant to the compound trifluoromethanesulfonic acid, or an equivalent compound. This treatment results in the cleavage of most or all sugars except the linking sugar (N-acetylglucosamine or N-acetylgalactosamine), while leaving the peptide intact. Chemical deglycosylation is described by Hakimuddin et al., *Arch. Biochem. Biophys.* 259: 52 (1987) and by Edge et al., *Anal. Biochem.* 118: 131 (1981). Enzymatic cleavage of carbohydrate moieties on polypeptide variants can be achieved by the use of a variety of endo- and exo-glycosidases as described by Thotakura et al., *Meth. Enzymol.* 138: 350 (1987).

Chemical addition of glycosyl moieties is carried out by any art-recognized method. Enzymatic addition of sugar moieties is preferably achieved using a modification of the methods set forth herein, substituting native glycosyl units for the modified sugars used in the invention. Other methods of adding sugar moieties are disclosed in U.S. Pat. Nos. 5,876,980, 6,030,815, 5,728,554, and 5,922,577.

Exemplary attachment points for selected glycosyl residue include, but are not limited to: (a) consensus sites for N-linked glycosylation, and sites for O-linked glycosylation; (b) terminal glycosyl moieties that are acceptors for a glycosyltransferase; (c) arginine, asparagine and histidine; (d) free carboxyl groups; (e) free sulfhydryl groups such as those of cysteine; (f) free hydroxyl groups such as those of serine, threonine, or hydroxyproline; (g) aromatic residues such as those of phenylalanine, tyrosine, or tryptophan; or (h) the amide group of glutamine. Exemplary methods of use in the present invention are described in WO 87/05330 published Sep. 11, 1987, and in Aplin and Wriston, CRC Crit. Rev. Biochem., pp. 259-306 (1981).

In one embodiment, the invention provides a method for linking two or more peptides through a linking group. The linking group is of any useful structure and may be selected from straight- and branched-chain structures. Preferably, each terminus of the linker, which is attached to a peptide, includes a modified sugar (i.e., a nascent intact glycosyl linking group).

In an exemplary method of the invention, two peptides are linked together via a linker moiety that includes a PEG linker. The construct conforms to the general structure set forth in the cartoon above. As described herein, the construct of the invention includes two intact glycosyl linking groups (i.e., s+t=1). The focus on a PEG linker that includes two glycosyl groups is for purposes of clarity and should not be interpreted as limiting the identity of linker arms of use in this embodiment of the invention.

Thus, a PEG moiety is functionalized at a first terminus with a first glycosyl unit and at a second terminus with a second glycosyl unit. The first and second glycosyl units are preferably substrates for different transferases, allowing orthogonal attachment of the first and second peptides to the first and second glycosyl units, respectively. In practice, the (glycosyl)$^1$-PEG-(glycosyl)$^2$ linker is contacted with the first peptide and a first transferase for which the first glycosyl unit is a substrate, thereby forming (peptide)$^1$-(glycosyl)$^1$-PEG-(glycosyl)$^2$. Transferase and/or unreacted peptide is then optionally removed from the reaction mixture. The second peptide and a second transferase for which the second glycosyl unit is a substrate are added to the (peptide)$^1$-(glycosyl)$^1$-PEG-(glycosyl)$^2$ conjugate, forming (peptide)$^1$-(glycosyl)$^1$-PEG-(glycosyl)$^2$-(peptide)$^2$; at least one of the glycosyl residues is either directly or indirectly O-linked. Those of skill in the art will appreciate that the method outlined above is also applicable to forming conjugates between more than two peptides by, for example, the use of a branched PEG, dendrimer, poly(amino acid), polysaccharide or the like.

The use of reactive derivatives of PEG (or other linkers) to attach one or more peptide moieties to a linker is within the scope of the present invention. The invention is not limited by the identity of the reactive PEG analogue. Many activated derivatives of poly(ethyleneglycol) are available commercially and in the literature. It is well within the abilities of one of skill to choose, and synthesize if necessary, an appropriate activated PEG derivative with which to prepare a substrate useful in the present invention. See, Abuchowski et al. *Cancer Biochem. Biophys.*, 7: 175-186 (1984); Abuchowski et al., *J. Biol. Chem.*, 252: 3582-3586 (1977); Jackson et al., *Anal. Biochem.*, 165: 114-127 (1987); Koide et al., *Biochem Biophys. Res. Commun.*, 111: 659-667 (1983)), tresylate (Nilsson et al., *Methods Enzymol.*, 104: 56-69 (1984); Delgado et al., *Biotechnol. Appl. Biochem.*, 12: 119-128 (1990)); N-hydroxysuccinimide derived active esters (Buckmann et al., *Makromol. Chem.*, 182: 1379-1384 (1981); Joppich et al., *Makromol. Chem.*, 180: 1381-1384 (1979); Abuchowski et al., *Cancer Biochem. Biophys.*, 7: 175-186 (1984); Katre et al. *Proc. Natl. Acad. Sci. U.S.A.*, 84: 1487-1491 (1987); Kitamura et al., *Cancer Res.*, 51: 4310-4315 (1991); Boccu et al., *Z. Naturforsch.*, 38C: 94-99 (1983), carbonates (Zalipsky et al., Poly(ethylene glycol) Chemistry: Biotechnical and Biomedical Applications, Harris, Ed., Plenum Press, New York, 1992, pp. 347-370; Zalipsky et al., *Biotechnol. Appl. Biochem.*, 15: 100-114 (1992); Veronese et al., *Appl. Biochem. Biotech.*, 11: 141-152 (1985)), imidazolyl formates (Beauchamp et al., *Anal. Biochem.*, 131: 25-33 (1983); Berger et al., *Blood,* 71: 1641-1647 (1988)), 4-dithiopyridines (Woghiren et al., *Bioconjugate Chem.*, 4: 314-318 (1993)), isocyanates (Byun et al., *ASAIO Journal*, M649-M-653 (1992)) and epoxides (U.S. Pat. No. 4,806,595, issued to Noishiki et al., (1989). Other linking groups include the urethane linkage between amino groups and activated PEG. See, Veronese, et al., *Appl. Biochem. Biotechnol.*, 11: 141-152 (1985).

In another exemplary embodiment in which a reactive PEG derivative is utilized, the invention provides a method for extending the blood-circulation half-life of a selected peptide, in essence targeting the peptide to the blood pool, by conjugating the peptide to a synthetic or natural polymer of a size sufficient to retard the filtration of the protein by the glomerulus (e.g., albumin). For example, GLP-1 can be conjugated to albumin via a PEG linker using a combination of chemical and enzymatic modification.

Modified Sugars

Modified glycosyl donor species ("modified sugars") are preferably selected from modified sugar nucleotides, activated modified sugars and modified sugars that are simple saccharides that are neither nucleotides nor activated. Any desired carbohydrate structure can be added to a peptide using the methods of the invention. Typically, the structure will be a monosaccharide, but the present invention is not limited to the use of modified monosaccharide sugars; oligosaccharides and polysaccharides are useful as well.

The modifying group is attached to a sugar moiety by enzymatic means, chemical means or a combination thereof, thereby producing a modified sugar. The sugars are substituted at any position that allows for the attachment of the modifying moiety, yet which still allows the sugar to function as a substrate for the enzyme used to ligate the modified sugar to the peptide. In a preferred embodiment, when sialic acid is the sugar, the sialic acid is substituted with the modifying group at either the 9-position on the pyruvyl side chain or at the 5-position on the amine moiety that is normally acetylated in sialic acid.

In certain embodiments of the present invention, a modified sugar nucleotide is utilized to add the modified sugar to the peptide. Exemplary sugar nucleotides that are used in the present invention in their modified form include nucleotide mono-, di- or triphosphates or analogs thereof. In a preferred embodiment, the modified sugar nucleotide is selected from a UDP-glycoside, CMP-glycoside, or a GDP-glycoside. Even more preferably, the modified sugar nucleotide is selected from an UDP-galactose, UDP-galactosamine, UDP-glucose, UDP-glucosamine, GDP-mannose, GDP-fucose, CMP-sialic acid, or CMP-NeuAc. N-acetylamine derivatives of the sugar nucleotides are also of use in the method of the invention.

The invention also provides methods for synthesizing a modified peptide using a modified sugar, e.g., modified-galactose, -fucose, -GalNAc and -sialic acid. When a modified sialic acid is used, either a sialyltransferase or a trans-sialidase (for α2,3-linked sialic acid only) can be used in these methods.

In other embodiments, the modified sugar is an activated sugar. Activated modified sugars, which are useful in the present invention are typically glycosides which have been synthetically altered to include an activated leaving group. As used herein, the term "activated leaving group" refers to those moieties, which are easily displaced in enzyme-regulated nucleophilic substitution reactions. Many activated sugars are known in the art. See, for example, Vocadlo et al., In CARBOHYDRATE CHEMISTRY AND BIOLOGY, Vol. 2, Ernst et al. Ed., Wiley-VCH Verlag: Weinheim, Germany, 2000; Kodama et al., *Tetrahedron Lett.* 34: 6419 (1993); Lougheed, et al., *J. Biol. Chem.* 274: 37717 (1999)).

Examples of activating groups (leaving groups) include fluoro, chloro, bromo, tosylate ester, mesylate ester, triflate ester and the like. Preferred activated leaving groups, for use in the present invention, are those that do not significantly sterically encumber the enzymatic transfer of the glycoside to the acceptor. Accordingly, preferred embodiments of activated glycoside derivatives include glycosyl fluorides and glycosyl mesylates, with glycosyl fluorides being particularly preferred. Among the glycosyl fluorides, α-galactosyl fluoride, α-mannosyl fluoride, α-glucosyl fluoride, α-fucosyl fluoride, α-xylosyl fluoride, α-sialyl fluoride, α-N-acetylglucosaminyl fluoride, α-N-acetylgalactosaminyl fluoride, β-galactosyl fluoride, β-mannosyl fluoride, β-glucosyl fluoride, β-fucosyl fluoride, β-xylosyl fluoride, β-sialyl fluoride, β-N-acetylglucosaminyl fluoride and β-N-acetylgalactosaminyl fluoride are most preferred.

By way of illustration, glycosyl fluorides can be prepared from the free sugar by first acetylating the sugar and then treating it with HF/pyridine. This generates the thermodynamically most stable anomer of the protected (acetylated) glycosyl fluoride (i.e., the α-glycosyl fluoride). If the less stable anomer (i.e., the β-glycosyl fluoride) is desired, it can be prepared by converting the peracetylated sugar with HBr/HOAc or with HCl to generate the anomeric bromide or chloride. This intermediate is reacted with a fluoride salt such as silver fluoride to generate the glycosyl fluoride. Acetylated glycosyl fluorides may be deprotected by reaction with mild (catalytic) base in methanol (e.g. NaOMe/MeOH). In addition, many glycosyl fluorides are commercially available.

Other activated glycosyl derivatives can be prepared using conventional methods known to those of skill in the art. For example, glycosyl mesylates can be prepared by treatment of the fully benzylated hemiacetal form of the sugar with mesyl chloride, followed by catalytic hydrogenation to remove the benzyl groups.

In a further exemplary embodiment, the modified sugar is an oligosaccharide having an antennary structure. In a preferred embodiment, one or more of the termini of the antennae bear the modifying moiety. When more than one modifying moiety is attached to an oligosaccharide having an antennary structure, the oligosaccharide is useful to "amplify" the modifying moiety; each oligosaccharide unit conjugated to the peptide attaches multiple copies of the modifying group to the peptide. The general structure of a typical conjugate of the invention as set forth in the drawing above, encompasses multivalent species resulting from preparing a conjugate of the invention utilizing an antennary structure. Many antennary saccharide structures are known in the art, and the present method can be practiced with them without limitation.

Exemplary modifying groups are discussed below. The modifying groups can be selected for their ability to impart to a peptide one or more desirable property. Exemplary properties include, but are not limited to, enhanced pharmacokinetics, enhanced pharmacodynamics, improved biodistribution, providing a polyvalent species, improved water solubility, enhanced or diminished lipophilicity, and tissue targeting.

Water-Soluble Polymers

The hydrophilicity of a selected peptide is enhanced by conjugation with polar molecules such as amine-, ester-, hydroxyl- and polyhydroxyl-containing molecules. Representative examples include, but are not limited to, polylysine, polyethyleneimine, and polyethers, e.g., poly(ethyleneglycol), m-poly(ethylene glycol), poly(propyleneglycol), m-poly(ethylene glycol), and other O-alkyl poly(alkylene glycol) moieties. Preferred water-soluble polymers are essentially non-fluorescent, or emit such a minimal amount of fluorescence that they are inappropriate for use as a fluorescent marker in an assay. Moreover, it is generally preferred to use polymers that are not naturally occurring sugars. An exception to this preference is the use of an otherwise naturally occurring sugar that is modified by covalent attachment of another entity (e.g., poly(ethylene glycol), poly(propylene glycol), biomolecule, therapeutic moiety, diagnostic moiety, etc.). In another exemplary embodiment, a therapeutic sugar moiety is conjugated to a linker arm and the sugar-linker arm cassette is subsequently conjugated to a peptide via a method of the invention.

Methods and chemistry for activation of water-soluble polymers and saccharides as well as methods for conjugating saccharides and polymers to various species are described in the literature. Commonly used methods for activation of polymers include activation of functional groups with cyanogen bromide, periodate, glutaraldehyde, biepoxides, epichlorohydrin, divinylsulfone, carbodiimide, sulfonyl halides, trichlorotriazine, etc. (see, R. F. Taylor, (1991), PROTEIN IMMOBILISATION. FUNDAMENTALS AND APPLICATIONS, Marcel Dekker, N.Y.; S. S. Wong, (1992), CHEMISTRY OF PROTEIN CONJUGATION AND CROSSLINKING, CRC Press, Boca Raton; G. T. Hermanson et al., (1993), IMMOBILIZED AFFINITY LIGAND TECHNIQUES, Academic Press, N.Y.; Dunn, R. L., et al., Eds. POLYMERIC DRUGS AND DRUG DELIVERY SYSTEMS, ACS Symposium Series Vol. 469, American Chemical Society, Washington, D.C. 1991).

Many water-soluble polymers are known to those of skill in the art and are useful in practicing the present invention. The term water-soluble polymer encompasses species such as saccharides (e.g., dextran, amylose, hyalouronic acid, poly (sialic acid), heparans, heparins, etc.); poly(amino acids); nucleic acids; synthetic polymers (e.g., poly(acrylic acid), poly(ethers), e.g., poly(ethylene glycol); peptides, proteins, and the like. The present invention may be practiced with any water-soluble polymer with the sole limitation that the polymer must include a point at which the remainder of the conjugate can be attached.

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and more WO 93/15189, and for conjugation between activated polymers and peptides, e.g. Coagulation Factor VIII (WO 94/15625), haemoglobin (WO 94/09027), oxygen carrying molecule (U.S. Pat. No. 4,412,989), ribonuclease and superoxide dismutase (Veronese at al., App. Biochem. Biotech. 11: 141-45 (1985)).

Preferred water-soluble polymers are those in which a substantial proportion of the polymer molecules in a sample of the polymer are of approximately the same molecular weight; such polymers are "homodisperse."

The present invention is further illustrated by reference to a poly(ethylene glycol) or monomethoxy-poly(ethylene glycol) (m-PEG) conjugate. Several reviews and monographs on the functionalization and conjugation of PEG are available. See, for example, Harris, Macronol. Chem. Phys. C25: 325-373 (1985); Scouten, Methods in Enzymology 135: 30-65 (1987); Wong et al., Enzyme Microb. Technol. 14: 866-874 (1992); Delgado et al., Critical Reviews in Therapeutic Drug Carrier Systems 9: 249-304 (1992); Zalipsky, Bioconjugate Chem. 6: 150-165 (1995); and Bhadra, et al., Pharmazie, 57:5-29 (2002).

The poly(ethylene glycol) useful in forming the conjugate of the invention is either linear or branched.

The in vivo half-life of therapeutic glycopeptides can also be enhanced with water-soluble polymers such as polyethylene glycol (PEG, m-PEG) and polypropylene glycol (PPG). For example, chemical modification of proteins with PEG (PEG-ylation, m-PEG-ylation) increases their molecular size and decreases their surface- and functional group-accessibility, each of which are dependent on the size of the PEG attached to the protein. This results in an improvement of plasma half-lives and in proteolytic-stability, and a decrease in immunogenicity and hepatic uptake (Chaffee et al. J. Clin. Invest. 89: 1643-1651 (1992); Pyatak et al. Res. Commun. Chem. Pathol Pharmacol. 29: 113-127 (1980)). PEGylation of interleukin-2 has been reported to increase its antitumor potency in vivo (Katre et al. Proc. Natl. Acad. Sci. USA. 84: 1487-1491 (1987)) and PEG-ylation of a F(ab')2 derived from the monoclonal antibody A7 has improved its tumor localization (Kitamura et al. Biochem. Biophys. Res. Commun. 28: 1387-1394 (1990)). Thus, in another preferred embodiment, the in vivo half-life of a peptide such as e.g., Glucagon-like peptide-1, derivatized with a water-soluble polymer by a method of the invention is increased relevant to the in vivo half-life of the non-derivatized peptide.

The increase in peptide in vivo half-life is best expressed as a range of percent increase in this quantity. The lower end of the range of percent increase is about 40%, about 60%, about 80%, about 100%, about 150% or about 200%. The upper end of the range is about 60%, about 80%, about 100%, about 150%, or more than about 250%.

In selected glyco-PEG-ylated peptides of the invention, the PEG-intact glycosyl linker cassette has the structure:

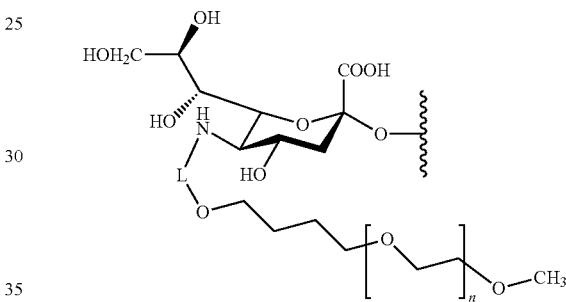

in which L is a substituted or unsubstituted alkyl or substituted or unsubstituted heteroalkyl linker moiety joining the sialic acid moiety and the PEG moiety. The index n is selected from the integers from 0 to about 2500, more preferably from about 50 to about 1500, and more preferable still from about 100 to about 600. An example of this structure has the formula:

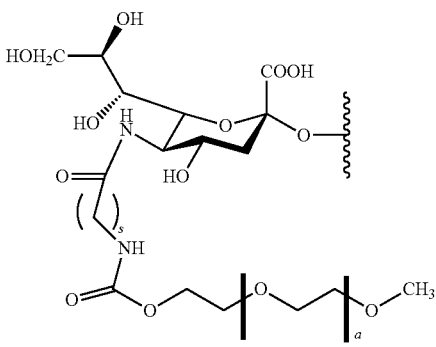

in which the index "s" represents an integer from 0 to 20.

PEG moieties of any molecular weight, e.g., 5 Kd, 10 Kd, 20 Kd, 30 kD, 40 kD, 60 kD and 100 kD are of use in the present invention.

Exemplary activated modified sugars of use in preparing water-soluble polymer-peptide conjugates of the invention include; an linear PEG species (A) and a branched PEG species (B):

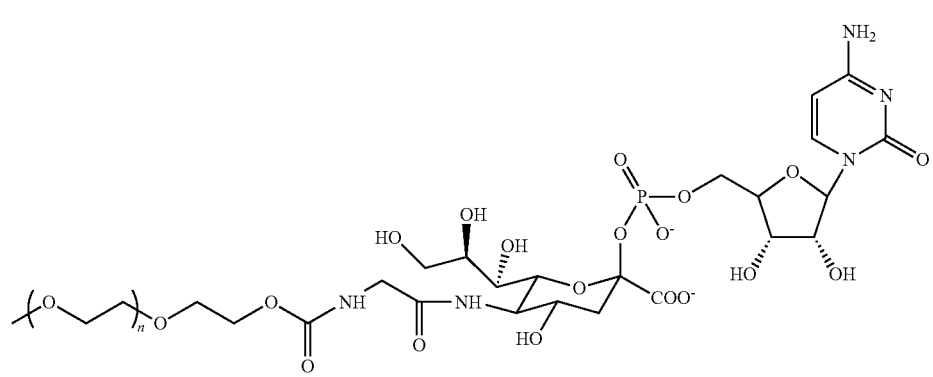
A
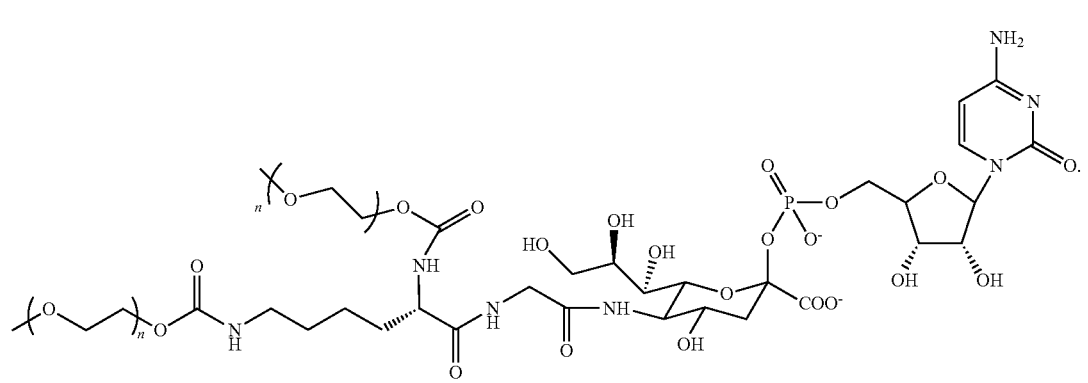
B
Following their conjugation to an O-linked site, exemplary PEG-sialic acid-glycosyl moieties can have one or more of the following structures:
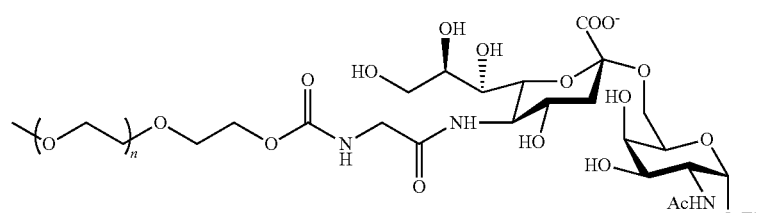
GalNAc-SA-PEG-20 KDa
n = 440-510
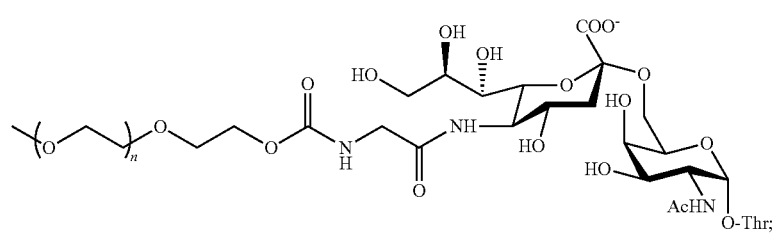
GalNAc-SA-PEG-30 KDa
n = 680-775

-continued

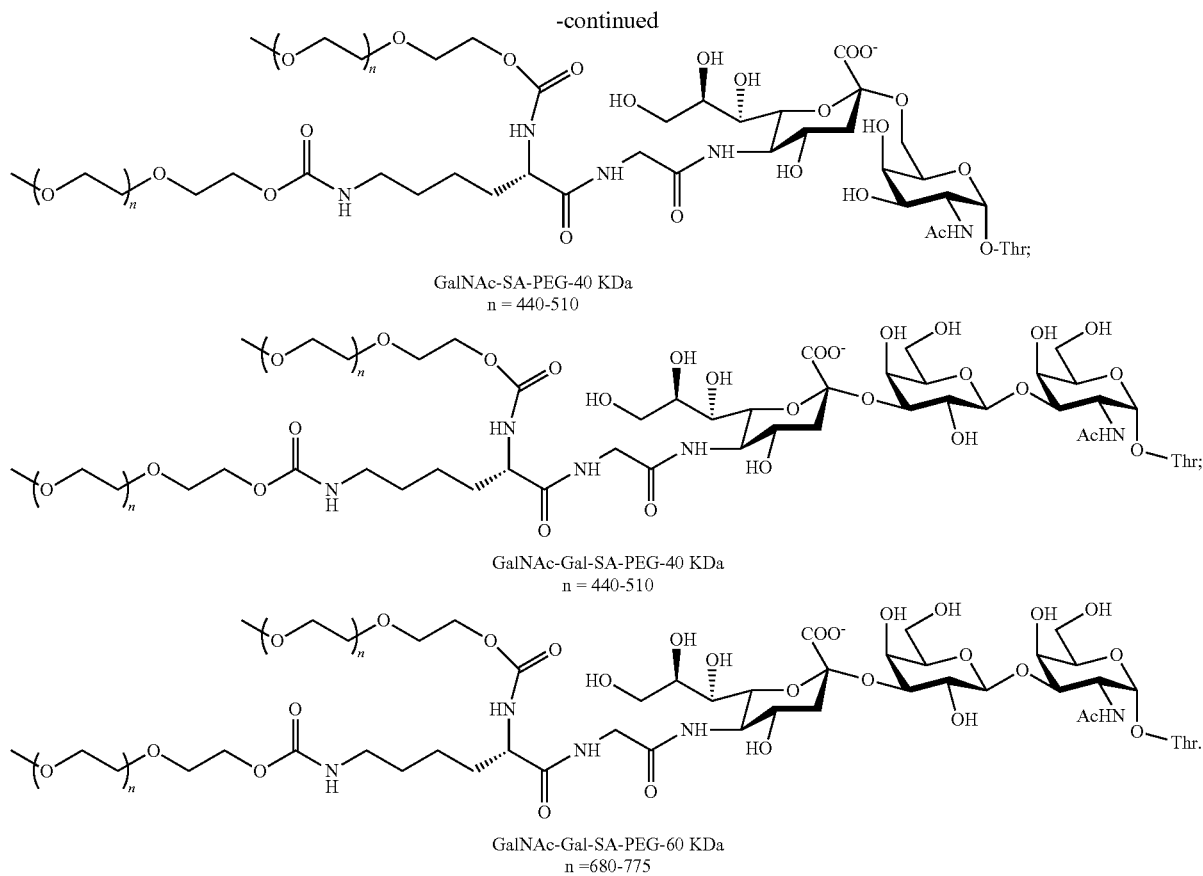

GalNAc-SA-PEG-40 KDa
n = 440-510

GalNAc-Gal-SA-PEG-40 KDa
n = 440-510

GalNAc-Gal-SA-PEG-60 KDa
n = 680-775

In an exemplary embodiment, the Thr shown in the structures above is Thr[106] of interferon alpha 2b.

In another exemplary embodiment, poly(ethylene glycol) molecules of use in the invention include, but are not limited to, those species set forth below.

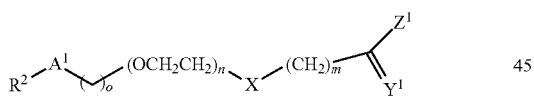

in which $R^2$ is H, substituted or unsubstituted alkyl, substituted or unsubstituted aryl, substituted or unsubstituted heteroaryl, substituted or unsubstituted heterocycloalkyl, substituted or unsubstituted heteroalkyl, e.g., acetal, OHC—, $H_2N-(CH_2)_q-$, $HS-(CH_2)_q$, and $-(CH_2)_qC(Y^1)Z^2$; -sugar-nucleotide, or protein. The index "n" represents an integer from 1 to 2500. The indeces m, o, and q independently represent integers from 0 to 20. The symbols $Z^1$ and $Z^2$ independently represent OH, $NH_2$, halogen, $S-R^3$, the alcohol portion of activated esters, $-(CH_2)_pC(Y^2)V$, $-(CH_2)_pU(CH_2)_sC(Y^2)_v$, sugar-nucleotide, protein, and leaving groups, e.g., imidazole, p-nitrophenyl, HOBT, tetrazole, halide. The symbols X, $Y^1$, $Y^2$, $A^1$, and U independently represent the moieties O, S, $N-R^4$. The symbol V represents OH, $NH_2$, halogen, $S-R^5$, the alcohol component of activated esters, the amine component of activated amides, sugar-nucleotides, and proteins. The indeces p, q, s and v are members independently selected from the integers from 0 to 20. The symbols $R^3$, $R^4$ and $R^5$ independently represent H, substituted or unsubstituted alkyl, substituted or unsubstituted heteroalkyl, substituted or unsubstituted aryl, substituted or unsubstituted heterocycloalkyl and substituted or unsubstituted heteroaryl.

In other exemplary embodiments, the poly(ethylene glycol) molecule is selected from the following:

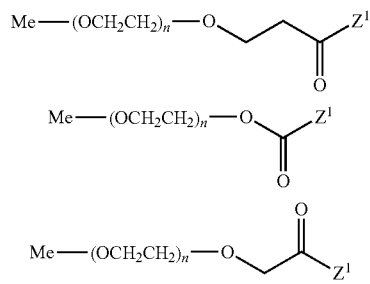

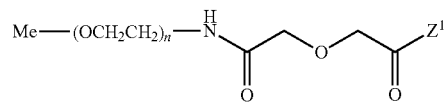

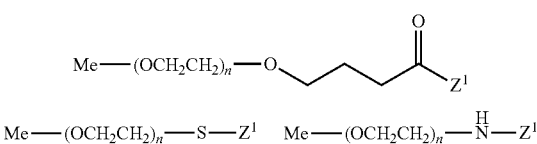

-continued

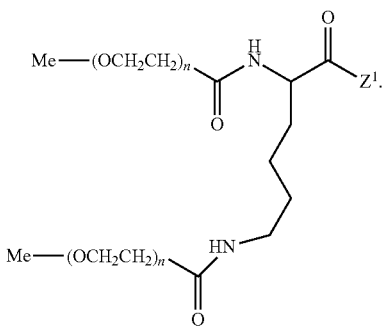

In an exemplary embodiment, the invention provides a glycopeptide that is conjugated to a polymeric modifying moiety through an intact glycosyl linking group having a formula that is selected from:

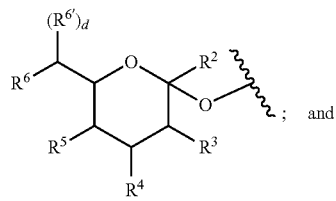

I

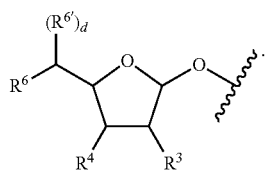

II

In Formulae I $R^2$ is H, $CH_2OR^7$, $COOR^7$ or $OR^7$, in which $R^7$ represents H, substituted or unsubstituted alkyl or substituted or unsubstituted heteroalkyl. When $COOR^7$ is a carboxylic acid or carboxylate, both forms are represented by the designation of the single structure $COO^-$ or COOH. In Formulae I and II, the symbols $R^3$, $R^4$, $R^5$, $R^6$ and $R^{6'}$ independently represent H, substituted or unsubstituted alkyl, $OR^8$, NHC(O)$R^9$. The index d is 0 or 1. $R^8$ and $R^9$ are independently selected from H, substituted or unsubstituted alkyl, substituted or unsubstituted heteroalkyl, sialic acid or polysialic acid. At least one of $R^3$, $R^4$, $R^5$, $R^6$ or $R^{6'}$ includes the polymeric modifying moiety e.g., PEG, linked through a bond or a linking group. In an exemplary embodiment, $R^6$ and $R^{6'}$, together with the carbon to which they are attached are components of the pyruvyl side chain of sialic acid. In a further exemplary embodiment, this side chain is functionalized with the polymeric modifying moiety. In another exemplary embodiment, $R^6$ and $R^{6'}$, together with the carbon to which they are attached are components of the side chain of sialic acid and the polymeric modifying moiety is a component of $R^5$.

In a further exemplary embodiment, the polymeric modifying moiety is bound to the sugar core, generally through a heteroatom, e.g., nitrogen, on the core through a linker, L, as shown below:

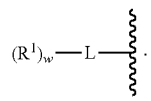

$R^1$ is the polymeric moiety and L is selected from a bond and a linking group. The index w represents an integer selected from 1-6, preferably 1-3 and more preferably 1-2. Exemplary linking groups include substituted or unsubstituted alkyl, substituted or unsubstituted heteroalkyl moieties and sialic acid. An exemplary component of the linker is an acyl moiety.

An exemplary compound according to the invention has a structure according to Formulae I or II, in which at least one of $R^2$, $R^3$, $R^4$, $R^5$, $R^6$ or $R^{6'}$ has the formula:

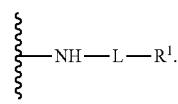

In another example according to this embodiment at least one of $R^2$, $R^3$, $R^4$, $R^5$, $R^6$ or $R^{6'}$ has the formula:

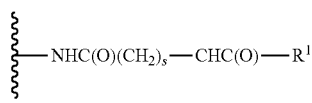

in which s is an integer from 0 to 20 and $R^1$ is a linear polymeric modifying moiety.

In an exemplary embodiment, the polymeric modifying moiety-linker construct is a branched structure that includes two or more polymeric chains attached to the central moiety. In this embodiment, the construct has the formula:

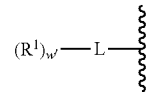

in which $R^1$ and L are as discussed above and w' is an integer from 2 to 6, preferably from 2 to 4 and more preferably from 2 to 3.

When L is a bond it is formed between a reactive functional group on a precursor of $R^1$ and a reactive functional group of complementary reactivity on the saccharyl core. When L is a non-zero order linker, a precursor of L can be in place on the glycosyl moiety prior to reaction with the $R^1$ precursor. Alternatively, the precursors of $R^1$ and L can be incorporated into a preformed cassette that is subsequently attached to the glycosyl moiety. As set forth herein, the selection and preparation of precursors with appropriate reactive functional groups is within the ability of those skilled in the art. Moreover, coupling the precursors proceeds by chemistry that is well understood in the art.

In an exemplary embodiment, L is a linking group that is formed from an amino acid, or small peptide (e.g., 1-4 amino acid residues) providing a modified sugar in which the polymeric modifying moiety is attached through a substituted alkyl linker. Exemplary linkers include glycine, lysine, serine and cysteine. The PEG moiety can be attached to the amine moiety of the linker through an amide or urethane bond. The PEG is linked to the sulfur or oxygen atoms of cysteine and serine through thioether or ether bonds, respectively.

In an exemplary embodiment, $R^5$ includes the polymeric modifying moiety. In another exemplary embodiment, $R^5$ includes both the polymeric modifying moiety and a linker, L, joining the modifying moiety to the remainder of the molecule. As discussed above, L can be a linear or branched structure. Similarly, the polymeric modifying can be branched or linear.

In one embodiment, the present invention provides an GLP-1 peptide comprising the moiety:

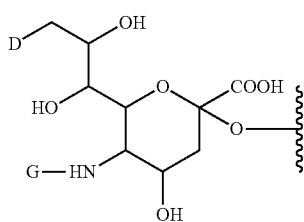

wherein D is a member selected from —OH and $R^1$-L-HN—; G is a member selected from H and $R^1$-L- and —C(O)(C$_1$-C$_6$)alkyl; $R^1$ is a moiety comprising a straight-chain or branched poly(ethylene glycol) residue; and L is a linker, e.g., a bond ("zero order"), substituted or unsubstituted alkyl and substituted or unsubstituted heteroalkyl. In exemplary embodiments, when D is OH, G is $R^1$-L-, and when G is —C(O)(C$_1$-C$_6$)alkyl, D is $R^1$-L-NH—.

In another exemplary embodiment, the invention provides a conjugate formed between a modified sugar of the invention and a substrate GLP-1 peptide. In this embodiment, the sugar moiety of the modified sugar becomes a glycosyl linking group interposed between the peptide substrate and the modifying group. An exemplary glycosyl linking group is an intact glycosyl linking group, in which the glycosyl moiety or moieties forming the linking group are not degraded by chemical (e.g., sodium metaperiodate) or enzymatic (e.g., oxidase) processes. Selected conjugates of the invention include a modifying group that is attached to the amine moiety of an amino-saccharide, e.g., mannosamine, glucosamine, galactosamine, sialic acid etc. Exemplary modifying group-intact glycosyl linking group cassettes according to this motif are based on a sialic acid structure, such as those having the formulae:

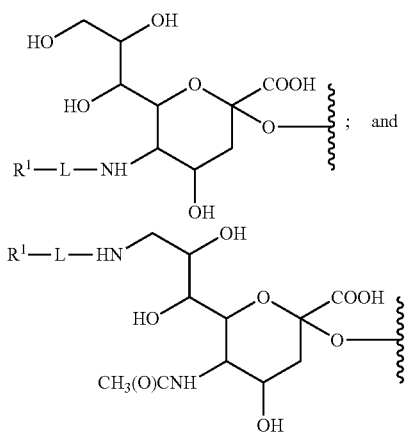

In the formulae above, $R^1$ and L are as described above. Further detail about the structure of exemplary $R^1$ groups is provided below.

In still a further exemplary embodiment, the conjugate is formed between a substrate GLP-1 and a saccharyl moiety in which the modifying group is attached through a linker at the 6-carbon position of the saccharyl moiety. Thus, illustrative conjugates according to this embodiment have the formula:

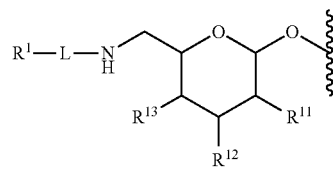

in which the radicals are as discussed above. Such saccharyl moieties include, without limitation, glucose, glucosamine, N-acetyl-glucosamine, galactose, galactosamine, N-acetyl-galactosamine, mannose, mannosamine, N-acetyl-mannosamine, and the like.

Due to the versatility of the methods available for modifying glycosyl residues on a therapeutic peptide such as GLP-1, the glycosyl structures on the peptide conjugates of the invention can have substantially any structure. Moreover, the glycans can be O-linked or N-linked. As exemplified in the discussion below, each of the pyranose and furanose derivatives discussed above can be a component of a glycosyl moiety of a peptide.

The invention provides a modified GLP-1 peptide that includes a glycosyl group having the formula:

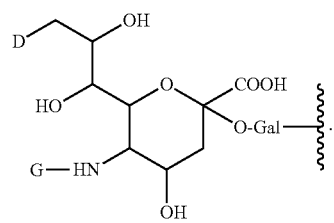

In other embodiments, the group has the formula:

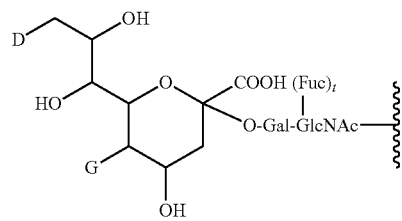

in which the index t is 0 or 1.

In a still further exemplary embodiment, the group has the formula:

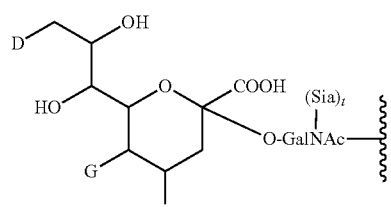

in which the index t is 0 or 1.

In yet another embodiment, the group has the formula:

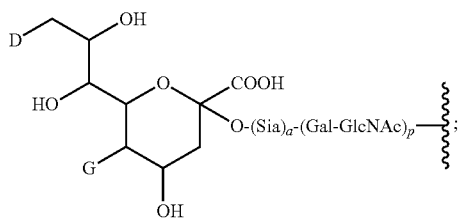

in which the index p represents and integer from 1 to 10; and a is either 0 or 1.

In an exemplary embodiment, a glycoPEGylated GLP-1 peptide of the invention includes at least one N-linked glycosyl residue selected from the glycosyl residues set forth below:

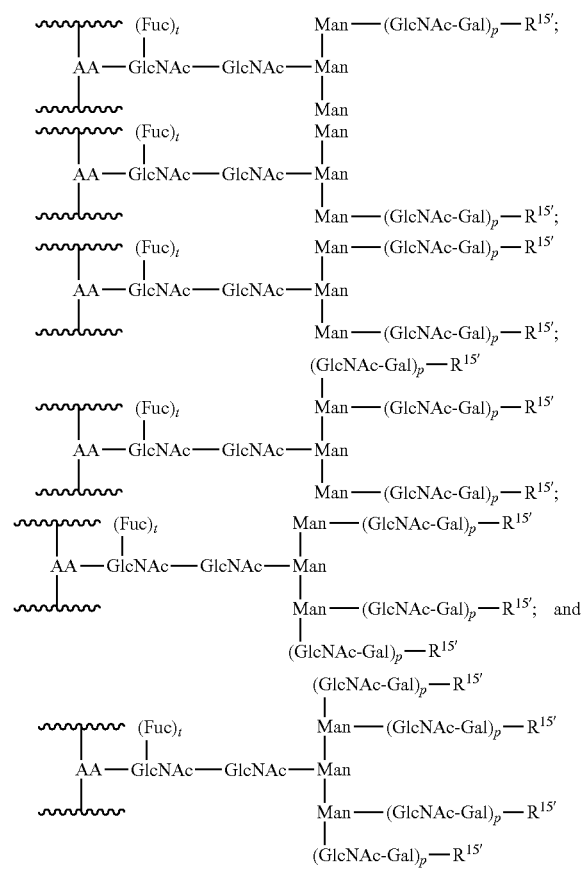

In the formulae above, the index t is 0 or 1 and the index p is an integer from 1 to 10. The symbol $R^{15'}$ represents H, OH (e.g., Gal-OH), a sialyl moiety, a polymer modified sialyl moiety (i.e., glycosyl linking group-polymeric modifying moiety (Sia-L-$R^1$)) or a sialyl moiety to which is bound a polymer modified sialyl moiety (e.g., Sia-Sia-L-$R^1$) ("Sia-Sia$^p$"). Exemplary polymer modified saccharyl moieties have a structure according to Formulae I and II. An exemplary GLP-1 peptide of the invention will include at least one glycan having a $R^{15'}$ that includes a structure according to Formulae I or II. The oxygen, with the open valence, of Formulae I and II is preferably attached through a glycosidic linkage to a carbon of a Gal or GalNAc moiety. In a further exemplary embodiment, the oxygen is attached to the carbon at position 3 of a galactose residue. In an exemplary embodiment, the modified sialic acid is linked α2,3- to the galactose residue. In another exemplary embodiment, the sialic acid is linked α2,6- to the galactose residue.

In another exemplary embodiment, the invention provides a GLP-1 peptide conjugate that includes a glycosyl linking group, such as those set forth above, that is covalently attached to an amino acid residue of the peptide. In one embodiment according to this motif, the glycosyl linking moiety is linked to a galactose residue through a Sia residue:

An exemplary species according to this motif is prepared by conjugating Sia-L-$R^1$ to a terminal sialic acid of a glycan using an enzyme that forms Sia-Sia bonds, e.g., CST-II, ST8Sia-II, ST8Sia-III and ST8Sia-IV.

In another exemplary embodiment, the glycans have a formula that is selected from the group:

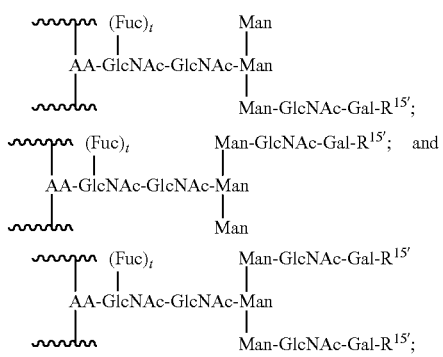

and combinations thereof.

The glycans of this group generally correspond to those found on a GLP-1 peptide that is produced by insect (e.g., Sf-9) cells, following remodeling according to the methods set forth herein. For example insect-derived GLP-1 that is expressed with a tri-mannosyl core is subsequently contacted with a GlcNAc donor and a GlcNAc transferase and a Gal donor and a Gal transferase. Appending GlcNAc and Gal to the tri-mannosyl core is accomplished in either two steps or a single step. A modified sialic acid is added to at least one branch of the glycosyl moiety as discussed herein. Those Gal moieties that are not functionalized with the modified sialic acid are optionally "capped" by reaction with a sialic acid donor in the presence of a sialyl transferase.

In an exemplary embodiment, at least 60% of terminal Gal moieties in a population of peptides is capped with sialic acid, preferably at least 70%, more preferably, at least 80%, still more preferably at least 90% and even more preferably at least 95%, 96%, 97%, 98% or 99% are capped with sialic acid.

In each of the formulae above, $R^{15'}$ is as discussed above. Moreover, an exemplary modified GLP-1 peptide of the invention will include at least one glycan with an $R^{15}$ moiety having a structure according to Formulae I or II.

In an exemplary embodiment, the glycosyl linking moiety has the formula:

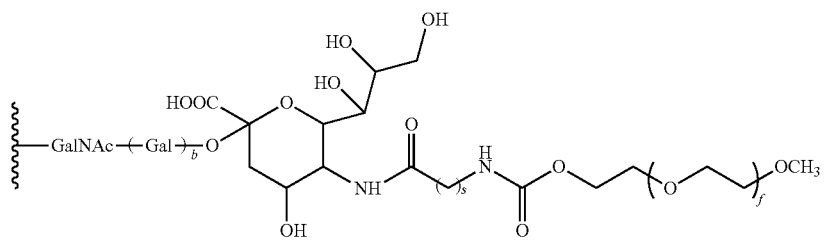

in which b is 0 or 1. The index s represents and integer from 1 to 10; and f represents and integer from 1 to 2500. Generally preferred is the use of a PEG moiety that has a molecular weight of about 20 kDa.

In another exemplary embodiment, the GLP-1 is derived from insect cells, remodeled by adding GlcNAc and Gal to the mannose core and glycopegylated using a sialic acid bearing a linear PEG moiety, affording a GLP-1 peptide that comprises at least one moiety having the formula:

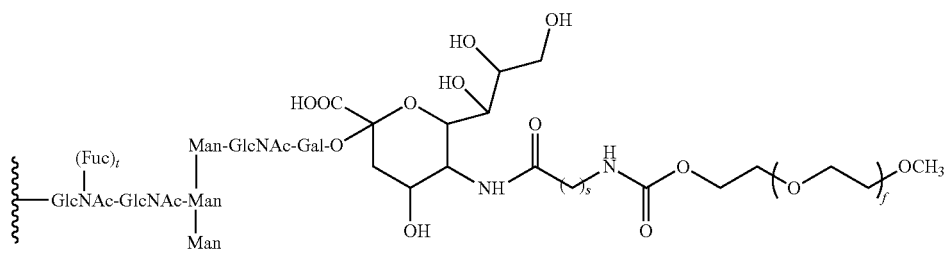

in which s represents and integer from 1 to 10; and f represents and integer from 1 to 2500.

As discussed herein, the PEG of use in the conjugates of the invention can be linear or branched. An exemplary precursor of use to form the branched conjugates according to this embodiment of the invention has the formula:

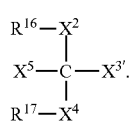

(III)

The branched polymer species according to this formula are essentially pure water-soluble polymers. $X^{3'}$ is a moiety that includes an ionizable, e.g., OH, COOH, $H_2PO_4$, $HSO_3$, $HPO_3$, and salts thereof, etc.) or other reactive functional group, e.g., infra. C is carbon. $X^5$ is preferably a non-reactive group (e.g., H, unsubstituted alkyl, unsubstituted heteroalkyl), and can be a polymeric arm. $R^{16}$ and $R^{17}$ are independently selected polymeric arms, e.g., nonpeptidic, nonreactive polymeric arms (e.g., PEG)). $X^2$ and $X^4$ are linkage fragments that are preferably essentially non-reactive under physiological conditions, which may be the same or different. An exemplary linker includes neither aromatic nor ester moieties. Alternatively, these linkages can include one or more moiety that is designed to degrade under physiologically relevant conditions, e.g., esters, disulfides, etc. $X^2$ and $X^4$ join polymeric arms $R^{16}$ and $R^{17}$ to C. When $X^{3'}$ is reacted with a reactive functional group of complementary reactivity on a linker, sugar or linker-sugar cassette, $X^{3'}$ is converted to a component of linkage fragment $X^3$.

Exemplary linkage fragments for $X^2$, $X^3$ and $X^4$ are independently selected and include S, SC(O)NH, HNC(O)S, SC(O)O, O, NH, NHC(O), (O)CNH and NHC(O)O, and OC(O)NH, $CH_2S$, $CH_2O$, $CH_2CH_2O$, $CH_2CH_2S$, $(CH_2)_oO$, $(CH_2)_oS$ or $(CH_2)_oY'$-PEG wherein, Y' is S, NH, NHC(O), C(O)NH, NHC(O)O, OC(O)NH, or O and o is an integer from 1 to 50. In an exemplary embodiment, the linkage fragments $X^2$ and $X^4$ are different linkage fragments.

In an exemplary embodiment, the precursor (III), or an activated derivative thereof, is reacted with, and thereby bound to a sugar, an activated sugar or a sugar nucleotide through a reaction between $X^{3'}$ and a group of complementary reactivity on the sugar moiety, e.g., an amine. Alternatively, $X^{3'}$ reacts with a reactive functional group on a precursor to linker, L. One or more of $R^2$, $R^3$, $R^4$, $R^5R^6$ or $R^{6'}$ of Formulae I and II can include the branched polymeric modifying moiety, or this moiety bound through L.

In an exemplary embodiment, the moiety:

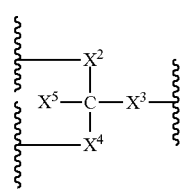

is the linker arm, L. In this embodiment, an exemplary linker is derived from a natural or unnatural amino acid, amino acid analogue or amino acid mimetic, or a small peptide formed from one or more such species. For example, certain branched polymers found in the compounds of the invention have the formula:

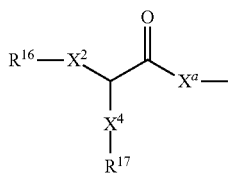

(IV)

$X^a$ is a linkage fragment that is formed by the reaction of a reactive functional group, e.g., $X^{3'}$, on a precursor of the branched polymeric modifying moiety and a reactive functional group on the sugar moiety, or a precursor to a linker. For example, when $X^{3'}$ is a carboxylic acid, it can be activated and bound directly to an amine group pendent from an aminosaccharide (e.g., Sia, GalNH$_2$, GlcNH$_2$, ManNH$_2$, etc.), forming an $X^a$ that is an amide. Additional exemplary reactive functional groups and activated precursors are described hereinbelow. The index c represents an integer from 1 to 10. The other symbols have the same identity as those discussed above.

In another exemplary embodiment, $X^a$ is a linking moiety formed with another linker:

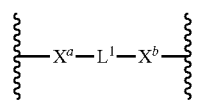

in which $X^b$ is a second linkage fragment and is independently selected from those groups set forth for $X^a$, and, similar to L, $L^1$ is a bond, substituted or unsubstituted alkyl or substituted or unsubstituted heteroalkyl.

Exemplary species for $X^a$ and $X^b$ include S, SC(O)NH, HNC(O)S, SC(O)O, O, NH, NHC(O), C(O)NH and NHC(O)O, and OC(O)NH.

In another exemplary embodiment, $X^4$ is a peptide bond to $R^{17}$, which is an amino acid, di-peptide (e.g., Lys-Lys) or tri-peptide (E.G., Lys-Lys-Lys) in which the alpha-amine moiety(ies) and/or side chain heteroatom(s) are modified with a polymeric modifying moiety.

In a further exemplary embodiment, the conjugates of the invention include a moiety, e.g., an $R^{15}$ moiety that has a formula that is selected from:

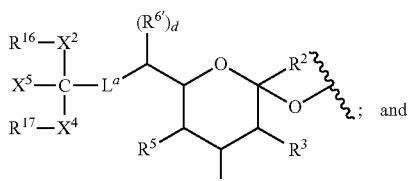

V

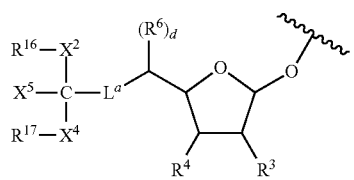

VI in which the identity of the radicals represented by the various symbols is the same as that discussed hereinabove. $L^a$ is a bond or a linker as discussed above for L and $L^1$, e.g., substituted or unsubstituted alkyl or substituted or unsubstituted heteroalkyl moiety. In an exemplary embodiment, $L^a$ is a moiety of the side chain of sialic acid that is functionalized with the polymeric modifying moiety as shown. Exemplary $L^a$ moieties include substituted or unsubstituted alkyl chains that include one or more OH or NH$_2$.

In yet another exemplary embodiment, the invention provides conjugates having a moiety, e.g., an $R^{15}$ moiety with formula:

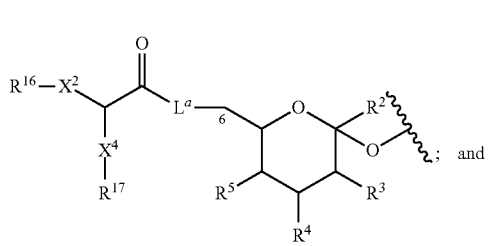

VI

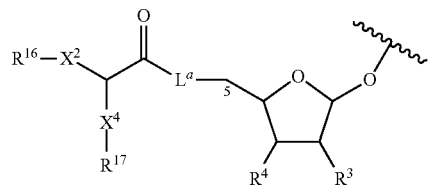

VII

The identity of the radicals represented by the various symbols is the same as that discussed hereinabove. As those of skill will appreciate, the linker arm in Formulae VI and VII is equally applicable to other modified sugars set forth herein. In exemplary embodiment, the species of Formulae VI and VII are the $R^{15}$ moieties attached to the glycan structures set forth herein.

In yet another exemplary embodiment, the GLP-1 peptide includes an $R^{15}$ moiety with the formula:

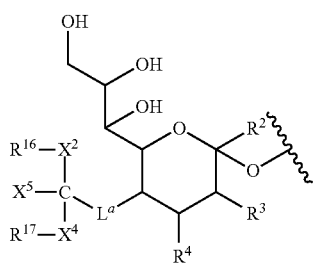

in which the identities of the radicals are as discussed above. An exemplary species for $L^a$ is —(CH$_2$)$_j$C(O)NH(CH$_2$)$_h$C(O)NH—, in which h and j are independently selected integers from 0 to 10. A further exemplary species is —C(O)NH—.

The embodiments of the invention set forth above are further exemplified by reference to species in which the polymer is a water-soluble polymer, particularly poly(ethylene glycol) ("PEG"), e.g., methoxy-poly(ethylene glycol). Those of skill will appreciate that the focus in the sections that follow is for clarity of illustration and the various motifs set forth using PEG as an exemplary polymer are equally applicable to species in which a polymer other than PEG is utilized.

PEG of any molecular weight, e.g., 1 kDa, 2 kDa, 5 kDa, 10 kDa, 15 kDa, 20 kDa, kDa and 40 kDa is of use in the present invention.

In an exemplary embodiment, the $R^{15}$ moiety has a formula that is a member selected from the group:
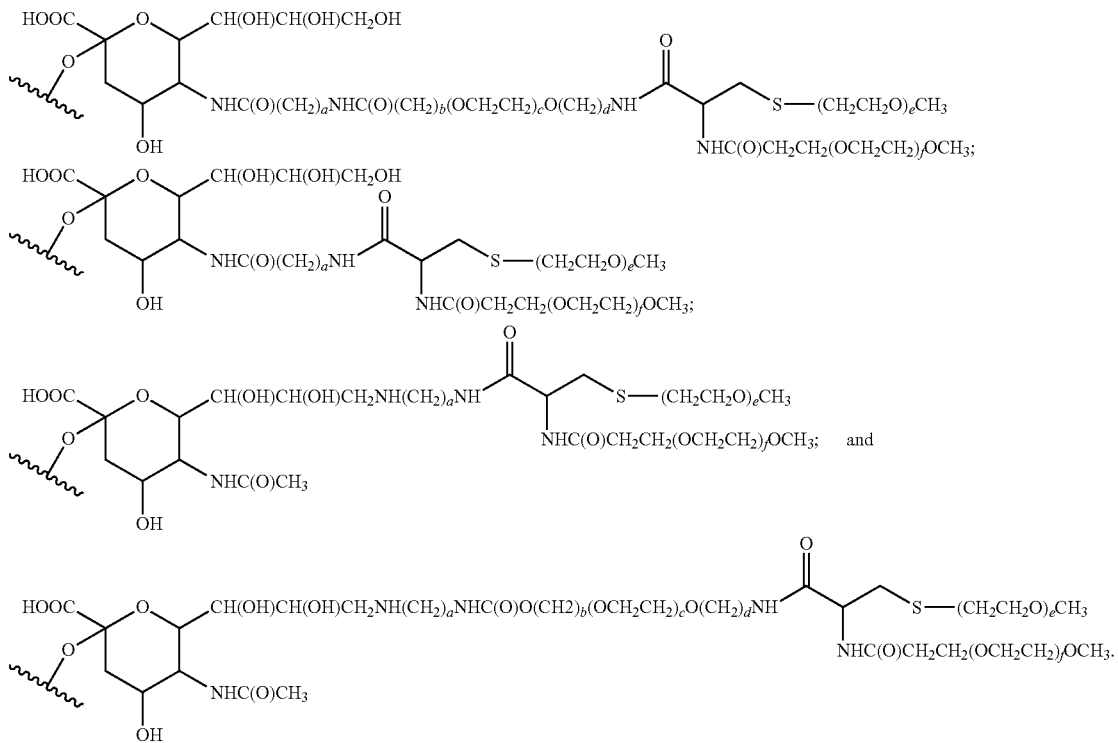
In each of the structures above, the linker fragment —NH$(CH_2)_a$— can be present or absent.
In other exemplary embodiments, the conjugate includes an $R^{15}$ moiety selected from the group:
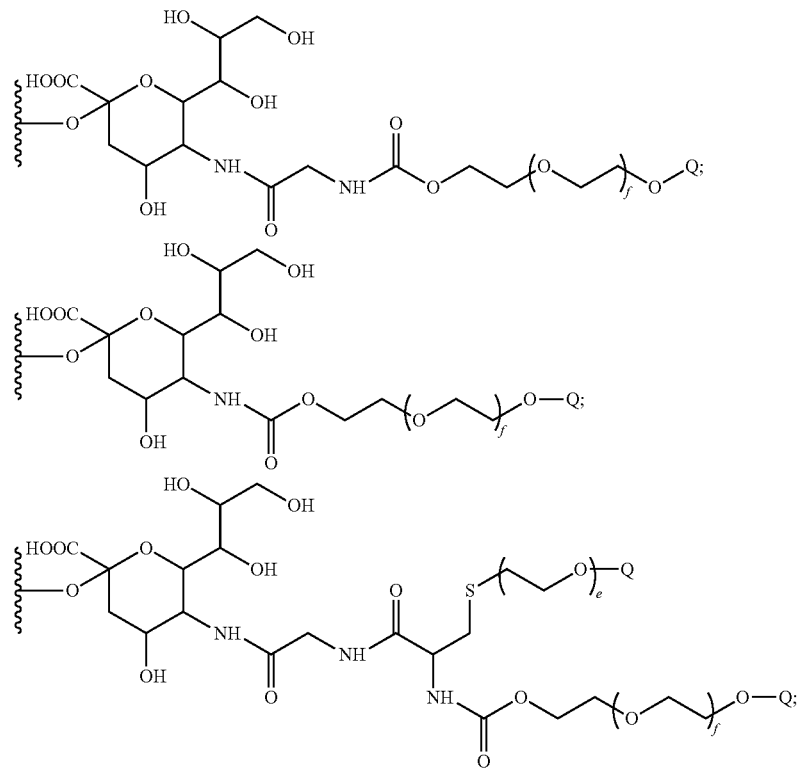

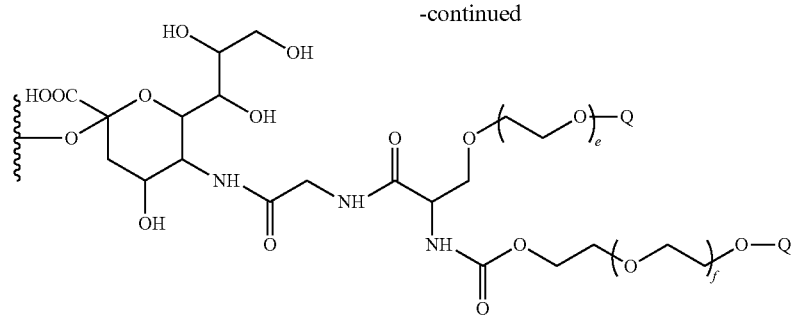

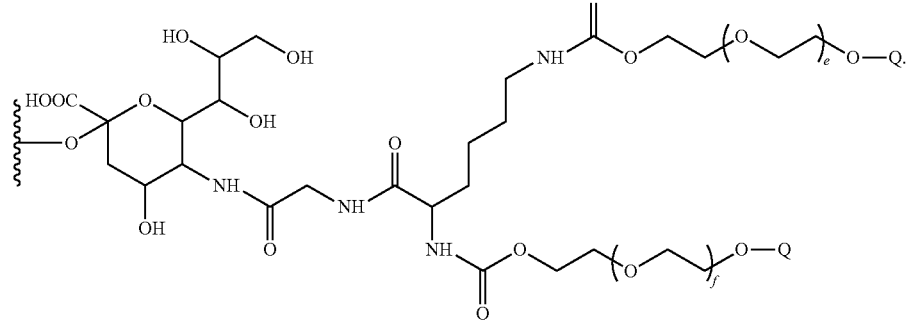

In each of the formulae above, the indices e and f are independently selected from the integers from 1 to 2500. In further exemplary embodiments, e and f are selected to provide a PEG moiety that is about 1 kD, 2 kD, 10 kD, 15 kD, 20 kD, 30 kD or 40 kD. The symbol Q represents substituted or unsubstituted alkyl (e.g., $C_1$-$C_6$ alkyl, e.g., methyl), substituted or unsubstituted heteroalkyl or H.

Other branched polymers have structures based on di-lysine (Lys-Lys) peptides, e.g.:

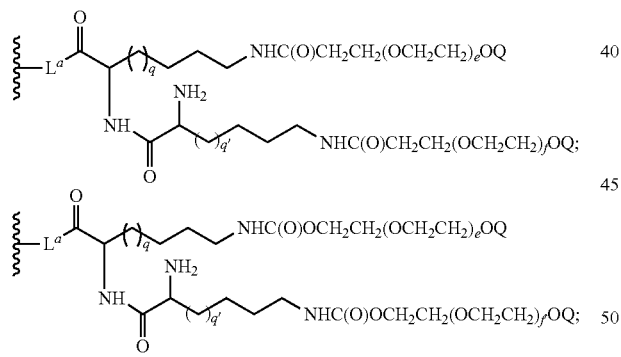

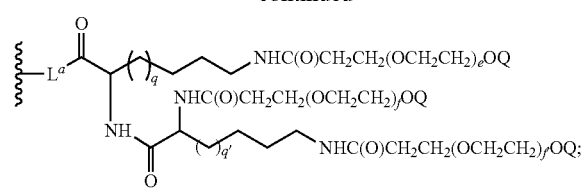

and

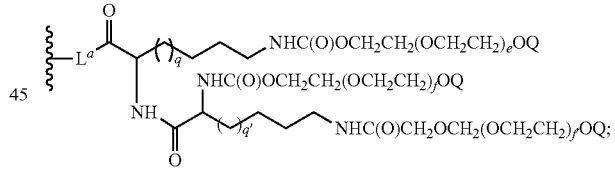

and tri-lysine peptides (Lys-Lys-Lys), e.g.:

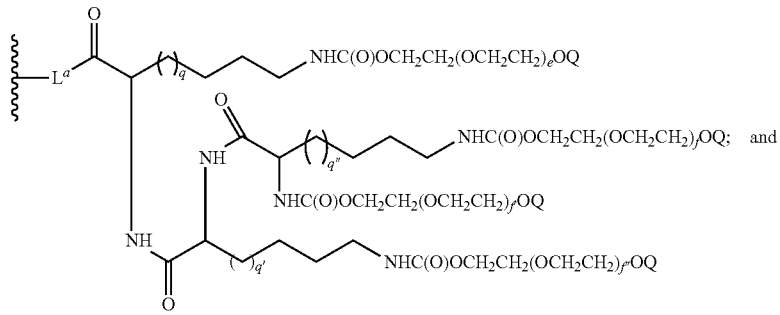

-continued

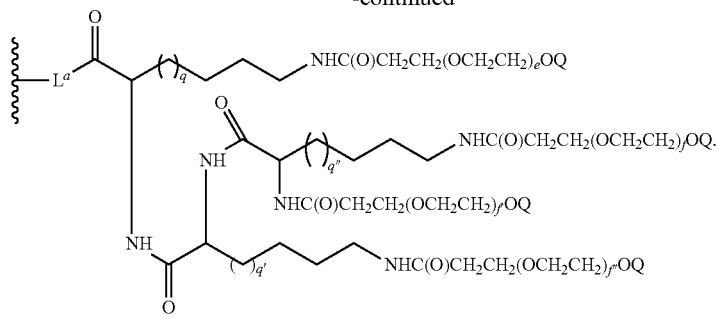

In each of the figures above, e, f, f' and f" represent integers independently selected from 1 to 2500. The indices q, q' and q" represent integers independently selected from 1 to 20.

In another exemplary embodiment, the GLP-1 peptide comprises a glycosyl moiety selected from the formulae:

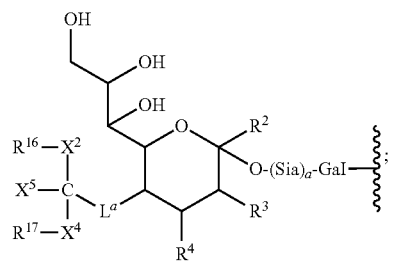

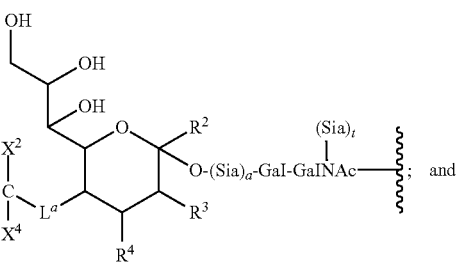

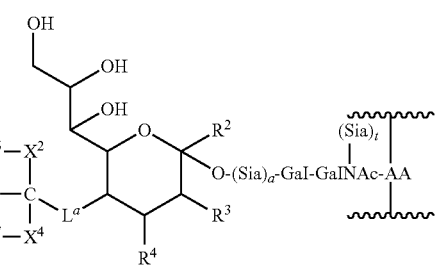

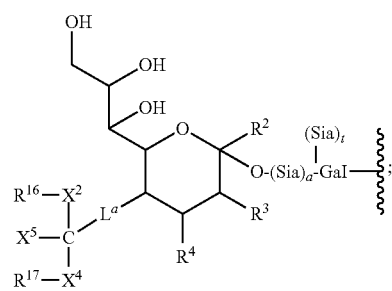

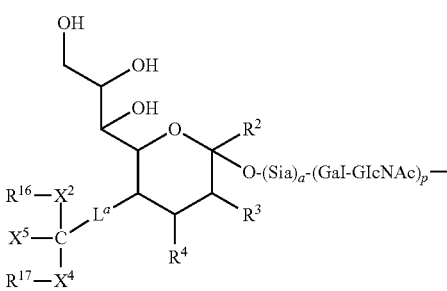

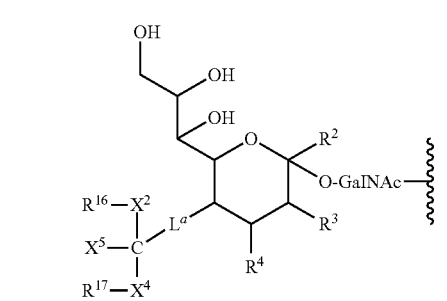

in which $L^a$ is a bond or a linker as described herein; the index t represents 0 or 1; and the index a represents 0 or 1. Each of these groups can be included as components of the mono-, bi-, tri- and tetra-antennary saccharide structures set forth above.

In yet another embodiment, the conjugates of the invention include a modified glycosyl residue that includes the substructure selected from:

in which the index a and the linker $L^a$ are as discussed above. The index p is an integer from 1 to 10. The indices t and a are independently selected from 0 or 1. Each of these groups can be included as components of the mono-, bi-, tri- and tetra-antennary saccharide structures set forth above.

In a further exemplary embodiment, the invention utilizes modified sugars in which the 6-hydroxyl position is converted to the corresponding amine moiety, which bears a linker-modifying group cassette such as those set forth above. Exemplary saccharyl groups that can be used as the core of these modified sugars include Gal, GalNAc, Glc, GlcNAc, Fuc, Xyl, Man, and the like. A representative modified sugar according to this embodiment has the formula:

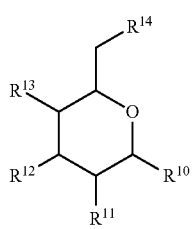

in which $R^{11}$-$R^{14}$ are members independently selected from H, OH, C(O)CH$_3$, NH, and NH C(O)CH$_3$. $R^{10}$ is a link to another glycosyl residue (—O-glycosyl) or to an amino acid of the GLP-1 peptide (—NH-(GLP-1)). $R^{14}$ is OR$^1$, NHR$^1$ or NH-L-R$^1$. R$^1$ and NH-L-R$^1$ are as described above.

Selected conjugates according to this motif are based on mannose, galactose or glucose, or on species having the stereochemistry of mannose, galactose or glucose. The general formulae of these conjugates are:

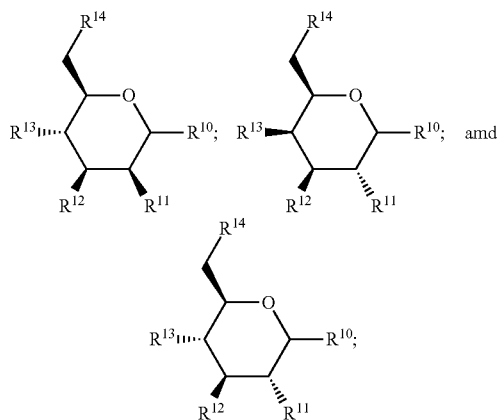

As discussed above, the invention provides saccharides bearing a modifying group, activated analogues of these species and conjugates formed between species such as peptides and lipids and a modified saccharide of the invention.

Biomolecules

In another preferred embodiment, the modified sugar bears a biomolecule. In still further preferred embodiments, the biomolecule is a functional protein, enzyme, antigen, antibody, peptide, nucleic acid (e.g., single nucleotides or nucleosides, oligonucleotides, polynucleotides and single- and higher-stranded nucleic acids), lectin, receptor or a combination thereof.

Preferred biomolecules are essentially non-fluorescent, or emit such a minimal amount of fluorescence that they are inappropriate for use as a fluorescent marker in an assay. Moreover, it is generally preferred to use biomolecules that are not sugars. An exception to this preference is the use of an otherwise naturally occurring sugar that is modified by covalent attachment of another entity (e.g., PEG, biomolecule, therapeutic moiety, diagnostic moiety, etc.). In an exemplary embodiment, a sugar moiety, which is a biomolecule, is conjugated to a linker arm and the sugar-linker arm cassette is subsequently conjugated to a peptide via a method of the invention.

Biomolecules useful in practicing the present invention can be derived from any source. The biomolecules can be isolated from natural sources or they can be produced by synthetic methods. Peptides can be natural peptides or mutated peptides. Mutations can be effected by chemical mutagenesis, site-directed mutagenesis or other means of inducing mutations known to those of skill in the art. Peptides useful in practicing the instant invention include, for example, enzymes, antigens, antibodies and receptors. Antibodies can be either polyclonal or monoclonal; either intact or fragments. The peptides are optionally the products of a program of directed evolution Both naturally derived and synthetic peptides and nucleic acids are of use in conjunction with the present invention; these molecules can be attached to a sugar residue component or a crosslinking agent by any available reactive group. For example, peptides can be attached through a reactive amine, carboxyl, sulfhydryl, or hydroxyl group. The reactive group can reside at a peptide terminus or at a site internal to the peptide chain. Nucleic acids can be attached through a reactive group on a base (e.g., exocyclic amine) or an available hydroxyl group on a sugar moiety (e.g., 3'- or 5'-hydroxyl). The peptide and nucleic acid chains can be further derivatized at one or more sites to allow for the attachment of appropriate reactive groups onto the chain. See, Chrisey et al. *Nucleic Acids Res.* 24: 3031-3039 (1996).

In a further preferred embodiment, the biomolecule is selected to direct the peptide modified by the methods of the invention to a specific tissue, thereby enhancing the delivery of the peptide to that tissue relative to the amount of underivatized peptide that is delivered to the tissue. In a still further preferred embodiment, the amount of derivatized peptide delivered to a specific tissue within a selected time period is enhanced by derivatization by at least about 20%, more preferably, at least about 40%, and more preferably still, at least about 100%. Presently, preferred biomolecules for targeting applications include antibodies, hormones and ligands for cell-surface receptors.

In still a further exemplary embodiment, there is provided as conjugate with biotin. Thus, for example, a selectively biotinylated peptide is elaborated by the attachment of an avidin or streptavidin moiety bearing one or more modifying groups.

Therapeutic Moieties

In another preferred embodiment, the modified sugar includes a therapeutic moiety. Those of skill in the art will appreciate that there is overlap between the category of therapeutic moieties and biomolecules; many biomolecules have therapeutic properties or potential.

The therapeutic moieties can be agents already accepted for clinical use or they can be drugs whose use is experimental, or whose activity or mechanism of action is under investigation. The therapeutic moieties can have a proven action in a given disease state or can be only hypothesized to show desirable action in a given disease state. In a preferred embodiment, the therapeutic moieties are compounds, which are being screened for their ability to interact with a tissue of choice. Therapeutic moieties, which are useful in practicing the instant invention include drugs from a broad range of drug classes having a variety of pharmacological activities. Preferred therapeutic moieties are essentially non-fluorescent, or emit such a minimal amount of fluorescence that they are inappropriate for use as a fluorescent marker in an assay. Moreover, it is generally preferred to use therapeutic moieties that are not sugars. An exception to this preference is the use of a sugar that is modified by covalent attachment of another entity, such as a PEG, biomolecule, therapeutic moiety, diagnostic moiety and the like. In another exemplary embodiment, a therapeutic sugar moiety is conjugated to a linker arm and the sugar-linker arm cassette is subsequently conjugated to a peptide via a method of the invention.

Methods of conjugating therapeutic and diagnostic agents to various other species are well known to those of skill in the art. See, for example Hermanson, BIOCONJUGATE TECHNIQUES, Academic Press, San Diego, 1996; and Dunn et al., Eds. POLYMERIC DRUGS AND DRUG DELIVERY SYSTEMS, ACS Symposium Series Vol. 469, American Chemical Society, Washington, D.C. 1991.

In an exemplary embodiment, the therapeutic moiety is attached to the modified sugar via a linkage that is cleaved under selected conditions. Exemplary conditions include, but are not limited to, a selected pH (e.g., stomach, intestine, endocytotic vacuole), the presence of an active enzyme (e.g., esterase, reductase, oxidase), light, heat and the like. Many cleavable groups are known in the art. See, for example, Jung et al., *Biochem. Biophys. Acta*, 761: 152-162 (1983); Joshi et al., *J. Biol. Chem.*, 265: 14518-14525 (1990); Zarling et al., *J. Immunol.*, 124: 913-920 (1980); Bouizar et al., *Eur. J. Biochem.*, 155: 141-147 (1986); Park et al., *J. Biol. Chem.*, 261: 205-210 (1986); Browning et al., *J. Immunol.*, 143: 1859-1867 (1989).

Preparation of Modified Sugars

In general, the sugar moiety and the modifying group are linked together through the use of reactive groups, which are typically transformed by the linking process into a new organic functional group or unreactive species. The sugar reactive functional group(s), is located at any position on the sugar moiety. Reactive groups and classes of reactions useful in practicing the present invention are generally those that are well known in the art of bioconjugate chemistry. Currently favored classes of reactions available with reactive sugar moieties are those, which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups pendent from a sugar nucleus or modifying group include, but are not limited to:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups, which can be converted to, e.g., esters, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc; and (j) epoxides, which can react with, for example, amines and hydroxyl compounds.

The reactive functional groups can be chosen such that they do not participate in, or interfere with, the reactions necessary to assemble the reactive sugar nucleus or modifying group. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In the discussion that follows, a number of specific examples of modified sugars that are useful in practicing the present invention are set forth. In the exemplary embodiments, a sialic acid derivative is utilized as the sugar nucleus to which the modifying group is attached. The focus of the discussion on sialic acid derivatives is for clarity of illustration only and should not be construed to limit the scope of the invention. Those of skill in the art will appreciate that a variety of other sugar moieties can be activated and derivatized in a manner analogous to that set forth using sialic acid as an example. For example, numerous methods are available for modifying galactose, glucose, N-acetylgalactosamine and fucose to name a few sugar substrates, which are readily modified by art recognized methods. See, for example, Elhalabi et al., *Curr. Med. Chem.* 6: 93 (1999); and Schafer et al., *J. Org. Chem.* 65: 24 (2000)).

In an exemplary embodiment, the peptide that is modified by a method of the invention is a GLP-1 peptide that has had one or more mutations introduced according to the methods of the invention. The oligosaccharide chains of the glycopeptide lacking a sialic acid and containing a terminal galactose residue can be glyco-PEG-ylated, glyco-PPG-ylated or otherwise modified with a modified sialic acid.

In Scheme 1, the amino glycoside 1, is treated with the active ester of a protected amino acid (e.g., glycine) derivative, converting the sugar amine residue into the corresponding protected amino acid amide adduct. The adduct is treated with an aldolase to form α-hydroxy carboxylate 2. Compound 2 is converted to the corresponding CMP derivative by the action of CMP-SA synthetase, followed by catalytic hydrogenation of the CMP derivative to produce compound 3. The amine introduced via formation of the glycine adduct is utilized as a locus of PEG or PPG attachment by reacting compound 3 with an activated (m-) PEG or (m-) PPG derivative (e.g., PEG-C(O)NHS, PPG-C(O)NHS), producing 4 or 5, respectively.

Scheme 1

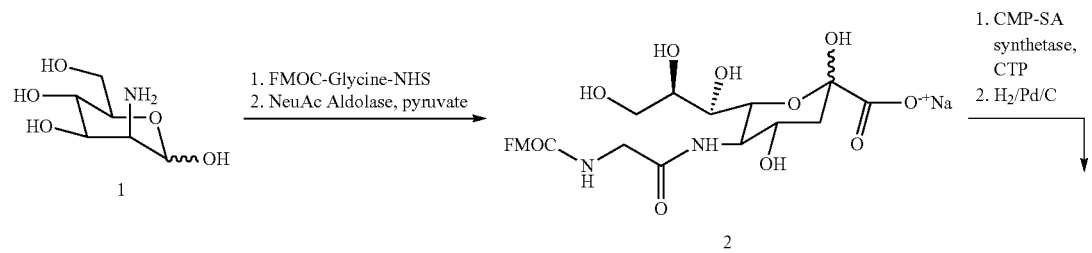

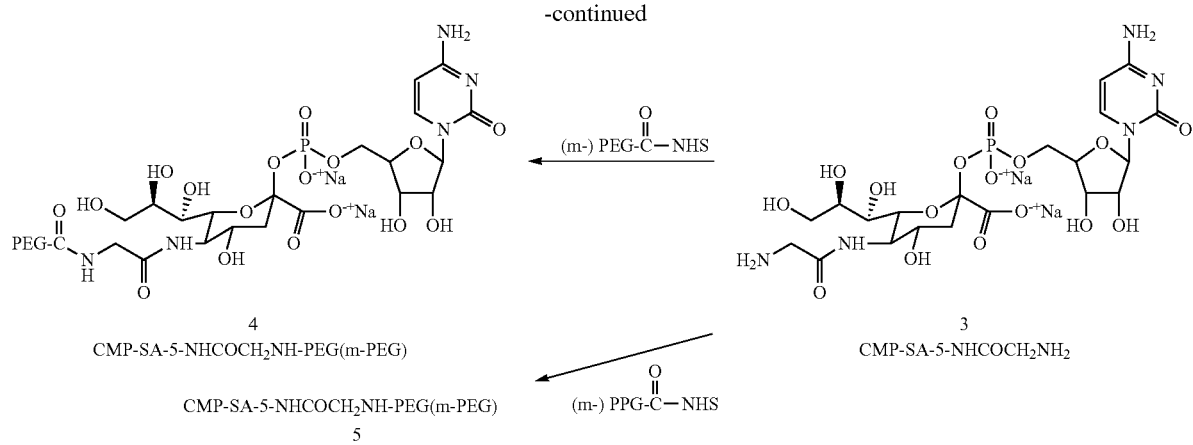

Table 1 sets forth representative examples of sugar monophosphates that are derivatized with a PEG or PPG moiety. Certain of the compounds of Table 1 are prepared by the method of Scheme 1. Other derivatives are prepared by art-recognized methods. See, for example, Keppler et al., *Glycobiology* 11: 11R (2001); and Charter et al., *Glycobiology* 10: 1049 (2000)). Other amine reactive PEG and PPG analogues are commercially available, or they can be prepared by methods readily accessible to those of skill in the art.

TABLE 1

TABLE 1-continued

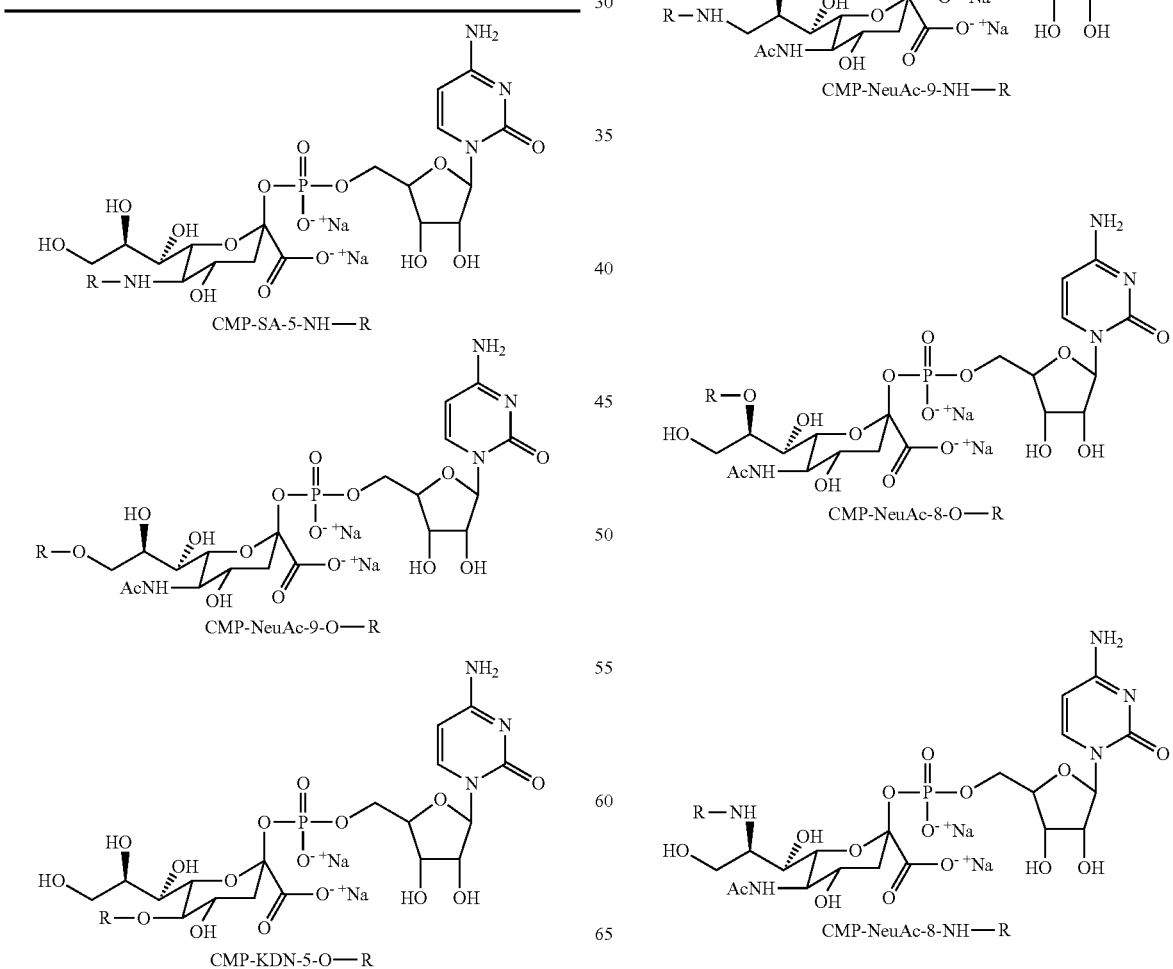

TABLE 1-continued

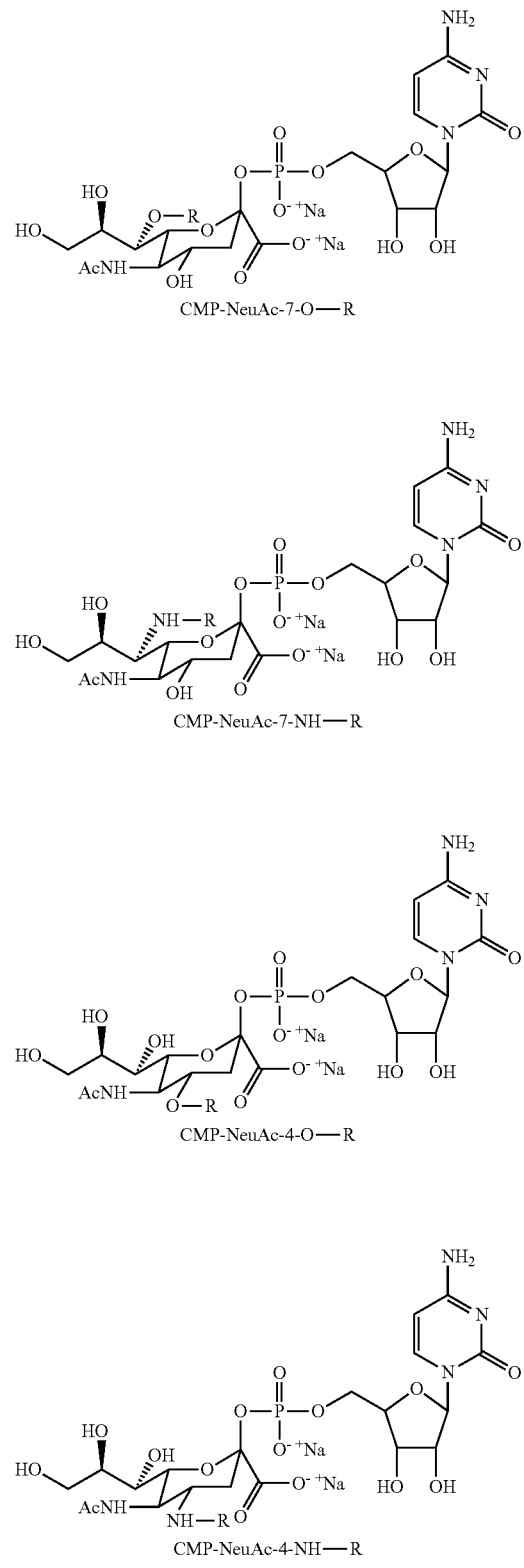

The modified sugar phosphates of use in practicing the present invention can be substituted in other positions as well as those set forth above. Presently preferred substitutions of sialic acid are set forth in Formula I:

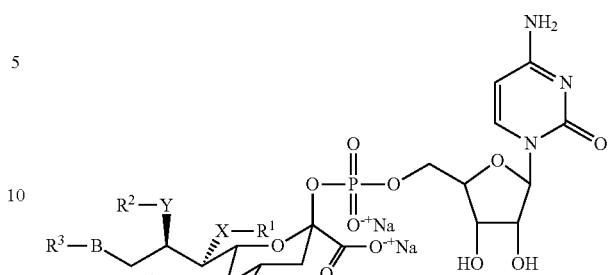

in which X is a linking group, which is preferably selected from —O—, —N(H)—, —S, $CH_2$—, and —N(R)$_2$, in which each R is a member independently selected from $R^1$-$R^5$. The symbols Y, Z, A and B each represent a group that is selected from the group set forth above for the identity of X. X, Y, Z, A and B are each independently selected and, therefore, they can be the same or different. The symbols $R^1$, $R^2$, $R^3$, $R^4$ and $R^5$ represent H, a water-soluble polymer, therapeutic moiety, biomolecule or other moiety. Alternatively, these symbols represent a linker that is bound to a water-soluble polymer, therapeutic moiety, biomolecule or other moiety.

Exemplary moieties attached to the conjugates disclosed herein include, but are not limited to, PEG derivatives (e.g., alkyl-PEG, acyl-PEG, acyl-alkyl-PEG, alkyl-acyl-PEG carbamoyl-PEG, aryl-PEG), PPG derivatives (e.g., alkyl-PPG, acyl-PPG, acyl-alkyl-PPG, alkyl-acyl-PPG carbamoyl-PPG, aryl-PPG), therapeutic moieties, diagnostic moieties, mannose-6-phosphate, heparin, heparan, SLe$_x$, mannose, mannose-6-phosphate, Sialyl Lewis X, FGF, VFGF, proteins, chondroitin, keratan, dermatan, albumin, integrins, antennary oligosaccharides, peptides and the like. Methods of conjugating the various modifying groups to a saccharide moiety are readily accessible to those of skill in the art (POLY (ETHYLENE GLYCOL CHEMISTRY: BIOTECHNICAL AND BIOMEDICAL APPLICATIONS, J. Milton Harris, Ed., Plenum Pub. Corp., 1992; POLY (ETHYLENE GLYCOL) CHEMICAL AND BIOLOGICAL APPLICATIONS, J. Milton Harris, Ed., ACS Symposium Series No. 680, American Chemical Society, 1997; Hermanson, BIOCONJUGATE TECHNIQUES, Academic Press, San Diego, 1996; and Dunn et al., Eds. POLYMERIC DRUGS AND DRUG DELIVERY SYSTEMS, ACS Symposium Series Vol. 469, American Chemical Society, Washington, D.C. 1991).

Cross-Linking Groups

Preparation of the modified sugar for use in the methods of the present invention includes attachment of a modifying group to a sugar residue and forming a stable adduct, which is a substrate for a glycosyltransferase. The sugar and modifying group can be coupled by a zero- or higher-order cross-linking agent. Exemplary bifunctional compounds which can be used for attaching modifying groups to carbohydrate moieties include, but are not limited to, bifunctional poly(ethyleneglycols), polyamides, polyethers, polyesters and the like. General approaches for linking carbohydrates to other molecules are known in the literature. See, for example, Lee et al., Biochemistry 28: 1856 (1989); Bhatia et al., Anal. Biochem. 178: 408 (1989); Janda et al., J. Am. Chem. Soc. 112: 8886 (1990) and Bednarski et al., WO 92/18135. In the discussion that follows, the reactive groups are treated as benign on the sugar moiety of the nascent modified sugar. The focus of the discussion is for clarity of illustration. Those of skill in the art will appreciate that the discussion is relevant to reactive groups on the modifying group as well.

An exemplary strategy involves incorporation of a protected sulfhydryl onto the sugar using the heterobifunctional crosslinker SPDP (n-succinimidyl-3-(2-pyridyldithio)propionate and then deprotecting the sulfhydryl for formation of a disulfide bond with another sulfhydryl on the modifying group.

If SPDP detrimentally affects the ability of the modified sugar to act as a glycosyltransferase substrate, one of an array of other crosslinkers such as 2-iminothiolane or N-succinimidyl S-acetylthioacetate (SATA) is used to form a disulfide bond. 2-iminothiolane reacts with primary amines, instantly incorporating an unprotected sulfhydryl onto the amine-containing molecule. SATA also reacts with primary amines, but incorporates a protected sulfhydryl, which is later deacetaylated using hydroxylamine to produce a free sulfhydryl. In each case, the incorporated sulfhydryl is free to react with other sulfhydryls or protected sulfhydryl, like SPDP, forming the required disulfide bond.

The above-described strategy is exemplary, and not limiting, of linkers of use in the invention. Other crosslinkers are available that can be used in different strategies for crosslinking the modifying group to the peptide. For example, TPCH (S-(2-thiopyridyl)-L-cysteine hydrazide and TPMPH ((S-(2-thiopyridyl) mercapto-propionohydrazide) react with carbohydrate moieties that have been previously oxidized by mild periodate treatment, thus forming a hydrazone bond between the hydrazide portion of the crosslinker and the periodate generated aldehydes. TPCH and TPMPH introduce a 2-pyridylthione protected sulfhydryl group onto the sugar, which can be deprotected with DTT and then subsequently used for conjugation, such as forming disulfide bonds between components.

If disulfide bonding is found unsuitable for producing stable modified sugars, other crosslinkers may be used that incorporate more stable bonds between components. The heterobifunctional crosslinkers GMBS (N-gama-malimidobutyryloxy)succinimide) and SMCC (succinimidyl 4-(N-maleimido-methyl)cyclohexane) react with primary amines, thus introducing a maleimide group onto the component. The maleimide group can subsequently react with sulfhydryls on the other component, which can be introduced by previously mentioned crosslinkers, thus forming a stable thioether bond between the components. If steric hindrance between components interferes with either component's activity or the ability of the modified sugar to act as a glycosyltransferase substrate, crosslinkers can be used which introduce long spacer arms between components and include derivatives of some of the previously mentioned crosslinkers (i.e., SPDP). Thus, there is an abundance of suitable crosslinkers, which are useful; each of which is selected depending on the effects it has on optimal peptide conjugate and modified sugar production.

A variety of reagents are used to modify the components of the modified sugar with intramolecular chemical crosslinks (for reviews of crosslinking reagents and crosslinking procedures see: Wold, F., *Meth. Enzymol.* 25: 623-651, 1972; Weetall, H. H., and Cooney, D. A., In: ENZYMES AS DRUGS. (Holcenberg, and Roberts, eds.) pp. 395-442, Wiley, New York, 1981; Ji, T. H., Meth. Enzymol. 91: 580-609, 1983; Mattson et al., *Mol. Biol. Rep.* 17: 167-183, 1993, all of which are incorporated herein by reference). Preferred crosslinking reagents are derived from various zero-length, homo-bifunctional, and hetero-bifunctional crosslinking reagents. Zero-length crosslinking reagents include direct conjugation of two intrinsic chemical groups with no introduction of extrinsic material. Agents that catalyze formation of a disulfide bond belong to this category. Another example is reagents that induce condensation of a carboxyl and a primary amino group to form an amide bond such as carbodiimides, ethylchloroformate, Woodward's reagent K (2-ethyl-5-phenylisoxazolium-3'-sulfonate), and carbonyldiimidazole. In addition to these chemical reagents, the enzyme transglutaminase (glutamyl-peptide γ-glutamyltransferase; EC 2.3.2.13) may be used as zero-length crosslinking reagent. This enzyme catalyzes acyl transfer reactions at carboxamide groups of protein-bound glutaminyl residues, usually with a primary amino group as substrate. Preferred homo- and hetero-bifunctional reagents contain two identical or two dissimilar sites, respectively, which may be reactive for amino, sulfhydryl, guanidino, indole, or nonspecific groups.

i. Preferred Specific Sites in Crosslinking Reagents

1. Amino-Reactive Groups

In one preferred embodiment, the sites on the cross-linker are amino-reactive groups. Useful non-limiting examples of amino-reactive groups include N-hydroxysuccinimide (NHS) esters, imidoesters, isocyanates, acylhalides, arylazides, p-nitrophenyl esters, aldehydes, and sulfonyl chlorides.

NHS esters react preferentially with the primary (including aromatic) amino groups of a modified sugar component. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide. Thus, the positive charge of the original amino group is lost.

Imidoesters are the most specific acylating reagents for reaction with the amine groups of the modified sugar components. At a pH between 7 and 10, imidoesters react only with primary amines. Primary amines attack imidates nucleophilically to produce an intermediate that breaks down to amidine at high pH or to a new imidate at low pH. The new imidate can react with another primary amine, thus crosslinking two amino groups, a case of a putatively monofunctional imidate reacting bifunctionally. The principal product of reaction with primary amines is an amidine that is a stronger base than the original amine. The positive charge of the original amino group is therefore retained.

Isocyanates (and isothiocyanates) react with the primary amines of the modified sugar components to form stable bonds. Their reactions with sulfhydryl, imidazole, and tyrosyl groups give relatively unstable products.

Acylazides are also used as amino-specific reagents in which nucleophilic amines of the affinity component attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of modified sugar components, but also with sulfhydryl and imidazole groups.

p-Nitrophenyl esters of mono- and dicarboxylic acids are also useful amino-reactive groups. Although the reagent specificity is not very high, α- and ε-amino groups appear to react most rapidly.

Aldehydes such as glutaraldehyde react with primary amines of modified sugar. Although unstable Schiff bases are formed upon reaction of the amino groups with the aldehydes of the aldehydes, glutaraldehyde is capable of modifying the modified sugar with stable crosslinks. At pH 6-8, the pH of typical crosslinking conditions, the cyclic polymers undergo a dehydration to form α-β unsaturated aldehyde polymers. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product.

Aromatic sulfonyl chlorides react with a variety of sites of the modified sugar components, but reaction with the amino groups is the most important, resulting in a stable sulfonamide linkage.

2. Sulfhydryl-Reactive Groups

In another preferred embodiment, the sites are sulfhydryl-reactive groups. Useful, non-limiting examples of sulfhydryl-reactive groups include maleimides, alkyl halides, pyridyl disulfides, and thiophthalimides.

Maleimides react preferentially with the sulfhydryl group of the modified sugar components to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryls via disulfide exchange to give mixed disulfides. As a result, pyridyl disulfides are the most specific sulfhydryl-reactive groups.

Thiophthalimides react with free sulfhydryl groups to form disulfides.

3. Carboxyl-Reactive Residue

In another embodiment, carbodiimides soluble in both water and organic solvent, are used as carboxyl-reactive reagents. These compounds react with free carboxyl groups forming a pseudourea that can then couple to available amines yielding an amide linkage teach how to modify a carboxyl group with carbodiimde (Yamada et al., *Biochemistry* 20: 4836-4842, 1981).

ii. Preferred Nonspecific Sites in Crosslinking Reagents

In addition to the use of site-specific reactive moieties, the present invention contemplates the use of non-specific reactive groups to link the sugar to the modifying group.

Exemplary non-specific cross-linkers include photoactivatable groups, completely inert in the dark, which are converted to reactive species upon absorption of a photon of appropriate energy. In one preferred embodiment, photoactivatable groups are selected from precursors of nitrenes generated upon heating or photolysis of azides. Electron-deficient nitrenes are extremely reactive and can react with a variety of chemical bonds including N—H, O—H, C—H, and C=C. Although three types of azides (aryl, alkyl, and acyl derivatives) may be employed, arylazides are presently preferred. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wavelength. Unsubstituted arylazides have an absorption maximum in the range of 260-280 nm, while hydroxy and nitroarylazides absorb significant light beyond 305 nm. Therefore, hydroxy and nitroarylazides are most preferable since they allow to employ less harmful photolysis conditions for the affinity component than unsubstituted arylazides.

In another preferred embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al., *J. Org. Chem.* 55: 3640-3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming crosslinks.

iii. Homobifunctional Reagents

1. Homobifunctional Crosslinkers Reactive with Primary Amines

Synthesis, properties, and applications of amine-reactive cross-linkers are commercially described in the literature (for reviews of crosslinking procedures and reagents, see above). Many reagents are available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional NHS esters include disuccinimidyl glutarate (DSG), disuccinimidyl suberate (DSS), bis(sulfosuccinimidyl) suberate (BS), disuccinimidyl tartarate (DST), disulfosuccinimidyl tartarate (sulfo-DST), bis-2-(succinimidooxycarbonyloxy) ethylsulfone (BSOCOES), bis-2-(sulfosuccinimidooxy-carbonyloxy)ethylsulfone (sulfo-BSOCOES), ethylene glycol-bis(succinimidylsuccinate) (EGS), ethylene glycolbis(sulfosuccinimidylsuccinate) (sulfo-EGS), dithiobis(succinimidyl-propionate) (DSP), and dithiobis(sulfosuccinimidylpropionate) (sulfo-DSP). Preferred, non-limiting examples of homobifunctional imidoesters include dimethyl malonimidate (DMM), dimethyl succinimidate (DMSC), dimethyl adipimidate (DMA), dimethyl pimelimidate (DMP), dimethyl suberimidate (DMS), dimethyl-3,3'-oxydipropionimidate (DODP), dimethyl-3,3'-(methylenedioxy)dipropionimidate (DMDP), dimethyl-,3'-(dimethylenedioxy)dipropionimidate (DDDP), dimethyl-3,3'-(tetramethylenedioxy)-dipropionimidate (DTDP), and dimethyl-3,3'-dithiobispropionimidate (DTBP).

Preferred, non-limiting examples of homobifunctional isothiocyanates include: p-phenylenediisothiocyanate (DITC), and 4,4'-diisothiocyano-2,2'-disulfonic acid stilbene (DIDS).

Preferred, non-limiting examples of homobifunctional isocyanates include xylene-diisocyanate, toluene-2,4-diisocyanate, toluene-2-isocyanate-4-isothiocyanate, 3-methoxy-diphenylmethane-4,4'-diisocyanate, 2,2'-dicarboxy-4,4'-azophenyldiisocyanate, and hexamethylenediisocyanate.

Preferred, non-limiting examples of homobifunctional arylhalides include 1,5-difluoro-2,4-dinitrobenzene (DFDNB), and 4,4'-difluoro-3,3'-dinitrophenyl-sulfone.

Preferred, non-limiting examples of homobifunctional aliphatic aldehyde reagents include glyoxal, malondialdehyde, and glutaraldehyde.

Preferred, non-limiting examples of homobifunctional acylating reagents include nitrophenyl esters of dicarboxylic acids.

Preferred, non-limiting examples of homobifunctional aromatic sulfonyl chlorides include phenol-2,4-disulfonyl chloride, and α-naphthol-2,4-disulfonyl chloride.

Preferred, non-limiting examples of additional amino-reactive homobifunctional reagents include erythritolbiscarbonate which reacts with amines to give biscarbamates.

2. Homobifunctional Crosslinkers Reactive with Free Sulfhydryl Groups

Synthesis, properties, and applications of such reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional maleimides include bismaleimidohexane (BMH), N,N'-(1,3-phenylene)bismaleimide, N,N'-(1,2-phenylene)bismaleimide, azophenyldimaleimide, and bis(N-maleimidomethyl) ether.

Preferred, non-limiting examples of homobifunctional pyridyl disulfides include 1,4-di-3'-(2'-pyridyldithio)propionamidobutane (DPDPB).

Preferred, non-limiting examples of homobifunctional alkyl halides include 2,2'-dicarboxy-4,4'-diiodoacetamidoazobenzene, α,α'-diiodo-p-xylenesulfonic acid, α,α'-dibromo-p-xylenesulfonic acid, N,N'-bis(b-bromoethyl)benzylamine, N,N'-di(bromoacetyl)phenylthydrazine, and 1,2-di(bromoacetyl)amino-3-phenylpropane.

3. Homobifunctional Photoactivatable Crosslinkers

Synthesis, properties, and applications of such reagents are described in the literature (for reviews of crosslinking procedures and reagents, see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional photoactivatable crosslinker include bis-β-(4-azidosalicylamido)ethyldisulfide (BASED), di-N-(2-nitro-4-azidophenyl)-cystamine-S,S-dioxide (DNCO), and 4,4'-dithiobisphenylazide.

iv. HeteroBifunctional Reagents

1. Amino-Reactive HeteroBifunctional Reagents with a Pyridyl Disulfide Moiety

Synthesis, properties, and applications of such reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of hetero-bifunctional reagents with a pyridyl disulfide moiety and an amino-reactive NHS ester include N-succinimidyl-3-(2-pyridyldithio) propionate (SPDP), succinimidyl 6-3-(2-pyridyldithio)propionamidohexanoate (LC-SPDP), sulfosuccinimidyl 6-3-(2-pyridyldithio)propionamidohexanoate (sulfo-LCSPDP), 4-succinimidyloxycarbonyl-α-methyl-α-(2-pyridyldithio) toluene (SMPT), and sulfosuccinimidyl 6-α-methyl-α-(2-pyridyldithio)toluamidohexanoate (sulfo-LC-SMPT).

2. Amino-Reactive HeteroBifunctional Reagents with a Maleimide Moiety

Synthesis, properties, and applications of such reagents are described in the literature. Preferred, non-limiting examples of hetero-bifunctional reagents with a maleimide moiety and an amino-reactive NHS ester include succinimidyl maleimidylacetate (AMAS), succinimidyl 3-maleimidylpropionate (BMPS), N-γ-maleimidobutyryloxysuccinimide ester (GMBS)N-γ-maleimidobutyryloxysulfo succinimide ester (sulfo-GMBS) succinimidyl 6-maleimidylhexanoate (EMCS), succinimidyl 3-maleimidylbenzoate (SMB), m-maleimidobenzoyl-N-hydroxysuccinimide ester (MBS), m-maleimidobenzoyl-N-hydroxysulfosuccinimide ester (sulfo-MBS), succinimidyl 4-(N-maleimidomethyl)-cyclohexane-1-carboxylate (SMCC), sulfosuccinimidyl 4-(N-maleimidomethyl)cyclohexane-1-carboxylate (sulfo-SMCC), succinimidyl 4-(p-maleimidophenyl)butyrate (SMPB), and sulfosuccinimidyl 4-(p-maleimidophenyl)butyrate (sulfo-SMPB).

3. Amino-Reactive HeteroBifunctional Reagents with an Alkyl Halide Moiety

Synthesis, properties, and applications of such reagents are described in the literature Preferred, non-limiting examples of hetero-bifunctional reagents with an alkyl halide moiety and an amino-reactive NHS ester include N-succinimidyl-(4-iodoacetyl)aminobenzoate (SIAB), sulfosuccinimidyl-(4-iodoacetyl)aminobenzoate (sulfo-SIAB), succinimidyl-6-(iodoacetyl)aminohexanoate (SIAX), succinimidyl-6-(6-((iodoacetyl)-amino)hexanoylamino)hexanoate (SIAXX), succinimidyl-6-(((4-(iodoacetyl)-amino)-methyl)-cyclohexane-1-carbonyl)aminohexanoate (SIACX), and succinimidyl-4-((iodoacetyl)-amino)methylcyclohexane-1-carboxylate (SIAC).

A preferred example of a hetero-bifunctional reagent with an amino-reactive NHS ester and an alkyl dihalide moiety is N-hydroxysuccinimidyl 2,3-dibromopropionate (SDBP). SDBP introduces intramolecular crosslinks to the affinity component by conjugating its amino groups. The reactivity of the dibromopropionyl moiety towards primary amine groups is controlled by the reaction temperature (McKenzie et al., *Protein Chem.* 7: 581-592 (1988)).

Preferred, non-limiting examples of hetero-bifunctional reagents with an alkyl halide moiety and an amino-reactive p-nitrophenyl ester moiety include p-nitrophenyl iodoacetate (NPIA).

Other cross-linking agents are known to those of skill in the art. See, for example, Pomato et al., U.S. Pat. No. 5,965,106. It is within the abilities of one of skill in the art to choose an appropriate cross-linking agent for a particular application.

v. Cleavable Linker Groups

In yet a further embodiment, the linker group is provided with a group that can be cleaved to release the modifying group from the sugar residue. Many cleaveable groups are known in the art. See, for example, Jung et al., *Biochem. Biophys. Acta* 761: 152-162 (1983); Joshi et al., *J. Biol. Chem.* 265: 14518-14525 (1990); Zarling et al., *J. Immunol.* 124: 913-920 (1980); Bouizar et al., *Eur. J. Biochem.* 155: 141-147 (1986); Park et al., *J. Biol. Chem.* 261: 205-210 (1986); Browning et al., *J. Immunol.* 143: 1859-1867 (1989). Moreover a broad range of cleavable, bifunctional (both homo- and hetero-bifunctional) linker groups is commercially available from suppliers such as Pierce.

Exemplary cleaveable moieties can be cleaved using light, heat or reagents such as thiols, hydroxylamine, bases, periodate and the like. Moreover, certain preferred groups are cleaved in vivo in response to being endocytized (e.g., cis-aconityl; see, Shen et al., *Biochem. Biophys. Res. Commun.* 102: 1048 (1991)). Preferred cleaveable groups comprise a cleaveable moiety which is a member selected from the group consisting of disulfide, ester, imide, carbonate, nitrobenzyl, phenacyl and benzoin groups.

Conjugation of Modified Sugars to Peptides

The modified sugars are conjugated to a glycosylated or non-glycosylated peptide using an appropriate enzyme to mediate the conjugation. Preferably, the concentrations of the modified donor sugar(s), enzyme(s) and acceptor peptide(s) are selected such that glycosylation proceeds until the acceptor is consumed. The considerations discussed below, while set forth in the context of a sialyltransferase, are generally applicable to other glycosyltransferase reactions.

A number of methods of using glycosyltransferases to synthesize desired oligosaccharide structures are known and are generally applicable to the instant invention. Exemplary methods are described, for instance, WO 96/32491, Ito et al., *Pure Appl. Chem.* 65: 753 (1993), and U.S. Pat. Nos. 5,352, 670, 5,374,541, and 5,545,553.

The present invention is practiced using a single glycosyltransferase or a combination of glycosyltransferases. For example, one can use a combination of a sialyltransferase and a galactosyltransferase. In those embodiments using more than one enzyme, the enzymes and substrates are preferably combined in an initial reaction mixture, or the enzymes and reagents for a second enzymatic reaction are added to the reaction medium once the first enzymatic reaction is complete or nearly complete. By conducting two enzymatic reactions in sequence in a single vessel, overall yields are improved over procedures in which an intermediate species is isolated. Moreover, cleanup and disposal of extra solvents and by-products is reduced.

In a preferred embodiment, each of the first and second enzyme is a glycosyltransferase. In another preferred embodiment, one enzyme is an endoglycosidase. In an additional preferred embodiment, more than two enzymes are used to assemble the modified glycoprotein of the invention. The enzymes are used to alter a saccharide structure on the peptide at any point either before or after the addition of the modified sugar to the peptide.

The O-linked glycosyl moieties of the conjugates of the invention are generally originate with a GalNAc moiety that is attached to the peptide. Any member of the family of GalNAc transferases can be used to bind a GalNAc moiety to the peptide (Hassan H, Bennett E P, Mandel U, Hollingsworth M A, and Clausen H (2000). Control of Mucin-Type O-Glycosylation: O-Glycan Occupancy is Directed by Substrate Specificities of Polypeptide GalNAc-Transferases. (Eds. Ernst, Hart, and Sinay). Wiley-VCH chapter "Carbohydrates in Chemistry and Biology—a Comprehensive Handbook", 273-292). The GalNAc moiety itself can be the intact glycosyl linker. Alternatively, the saccharyl residue is built out using one more enzyme and one or more appropriate glycosyl substrate for the enzyme, the modified sugar being added to the built out glycosyl moiety.

In another embodiment, the method makes use of one or more exo- or endoglycosidase. The glycosidase is typically a mutant, which is engineered to form glycosyl bonds rather than cleave them. The mutant glycanase typically includes a substitution of an amino acid residue for an active site acidic amino acid residue. For example, when the endoglycanase is endo-H, the substituted active site residues will typically be Asp at position 130, Glu at position 132 or a combination thereof. The amino acids are generally replaced with serine, alanine, asparagine, or glutamine.

The mutant enzyme catalyzes the reaction, usually by a synthesis step that is analogous to the reverse reaction of the endoglycanase hydrolysis step. In these embodiments, the glycosyl donor molecule (e.g., a desired oligo- or monosaccharide structure) contains a leaving group and the reaction proceeds with the addition of the donor molecule to a GlcNAc residue on the protein. For example, the leaving group can be a halogen, such as fluoride. In other embodiments, the leaving group is a Asn, or a Asn-peptide moiety. In yet further embodiments, the GlcNAc residue on the glycosyl donor molecule is modified. For example, the GlcNAc residue may comprise a 1,2 oxazoline moiety.

In a preferred embodiment, each of the enzymes utilized to produce a conjugate of the invention are present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

The temperature at which an above process is carried out can range from just above freezing to the temperature at which the most sensitive enzyme denatures. Preferred temperature ranges are about 0° C. to about 55° C., and more preferably about 20° C. to about 30° C. In another exemplary embodiment, one or more components of the present method are conducted at an elevated temperature using a thermophilic enzyme.

The reaction mixture is maintained for a period of time sufficient for the acceptor to be glycosylated, thereby forming the desired conjugate. Some of the conjugate can often be detected after a few hours, with recoverable amounts usually being obtained within 24 hours or less. Those of skill in the art understand that the rate of reaction is dependent on a number of variable factors (e.g., enzyme concentration, donor concentration, acceptor concentration, temperature, solvent volume), which are optimized for a selected system.

The present invention also provides for the industrial-scale production of modified peptides. As used herein, an industrial scale generally produces at least about 250 mg, preferably at least about 500 mg, and more preferably at least about 1 gram of finished, purified conjugate, preferably after a single reaction cycle, i.e., the conjugate is not a combination the reaction products from identical, consecutively iterated synthesis cycles.

In the discussion that follows, the invention is exemplified by the conjugation of modified sialic acid moieties to a glycosylated peptide. The exemplary modified sialic acid is labeled with (m-) PEG. The focus of the following discussion on the use of PEG-modified sialic acid and glycosylated peptides is for clarity of illustration and is not intended to imply that the invention is limited to the conjugation of these two partners. One of skill understands that the discussion is generally applicable to the additions of modified glycosyl moieties other than sialic acid. Moreover, the discussion is equally applicable to the modification of a glycosyl unit with agents other than PEG including other water-soluble polymers, therapeutic moieties, and biomolecules.

An enzymatic approach can be used for the selective introduction of (m-) PEG-ylated or (m-) PPG-ylated carbohydrates onto a peptide or glycopeptide. The method utilizes modified sugars containing PEG, PPG, or a masked reactive functional group, and is combined with the appropriate glycosyltransferase or glycosynthase. By selecting the glycosyltransferase that will make the desired carbohydrate linkage and utilizing the modified sugar as the donor substrate, the PEG or PPG can be introduced directly onto the peptide backbone, onto existing sugar residues of a glycopeptide or onto sugar residues that have been added to a peptide.

An acceptor for the sialyltransferase is present on the peptide to be modified by the methods of the present invention either as a naturally occurring structure or one placed there recombinantly, enzymatically or chemically. Suitable acceptors, include, for example, galactosyl acceptors such as GalNAc, Galβ1,4GlcNAc, Galβ1,4GalNAc, Galβ1,3GalNAc, lacto-N-tetraose, Galβ1,3GlcNAc, Galβ1,3Ara, Galβ1, 6GlcNAc, Galβ1,4Glc (lactose), and other acceptors known to those of skill in the art (see, e.g., Paulson et al., *J. Biol. Chem.* 253: 5617-5624 (1978)).

In one embodiment, an acceptor for the sialyltransferase is present on the glycopeptide to be modified upon in vivo synthesis of the glycopeptide. Such glycopeptides can be sialylated using the claimed methods without prior modification of the glycosylation pattern of the glycopeptide. Alternatively, the methods of the invention can be used to sialylate a peptide that does not include a suitable acceptor; one first modifies the peptide to include an acceptor by methods known to those of skill in the art. In an exemplary embodiment, a GalNAc residue is added to an O-linked glycosylation site by the action of a GalNAc transferase. Hassan H, Bennett E P, Mandel U, Hollingsworth M A, and Clausen H (2000). Control of Mucin-Type O-Glycosylation: O-Glycan Occupancy is Directed by Substrate Specificities of Polypeptide GalNAc-Transferases. (Eds. Ernst, Hart, and Sinay). Wiley- VCH chapter "Carbohydrates in Chemistry and Biology—a Comprehension Handbook", 273-292.

In an exemplary embodiment, the galactosyl acceptor is assembled by attaching a galactose residue to an appropriate acceptor linked to the peptide, e.g., a GalNAc. The method includes incubating the peptide to be modified with a reaction mixture that contains a suitable amount of a galactosyltransferase (e.g., Galβ1,3 or Galβ1,4), and a suitable galactosyl donor (e.g., UDP-galactose). The reaction is allowed to proceed substantially to completion or, alternatively, the reaction is terminated when a preselected amount of the galactose residue is added. Other methods of assembling a selected saccharide acceptor will be apparent to those of skill in the art.

In yet another embodiment, glycopeptide-linked oligosaccharides are first "trimmed," either in whole or in part, to expose either an acceptor for the sialyltransferase or a moiety to which one or more appropriate residues can be added to obtain a suitable acceptor. Enzymes such as glycosyltransferases and endoglycosidases (see, for example U.S. Pat. No. 5,716,812) are useful for the attaching and trimming reactions.

In the discussion that follows, the method of the invention is exemplified by the use of modified sugars having a water-soluble polymer attached thereto. The focus of the discussion is for clarity of illustration. Those of skill will appreciate that the discussion is equally relevant to those embodiments in which the modified sugar bears a therapeutic moiety, biomolecule or the like.

In an exemplary embodiment, an O-linked carbohydrate residue is "trimmed" prior to the addition of the modified sugar. For example a GalNAc-Gal residue is trimmed back to GalNAc. A modified sugar bearing a water-soluble polymer is conjugated to one or more of the sugar residues exposed by the "trimming." In one example, a glycopeptide is "trimmed" and a water-soluble polymer is added to the resulting O-side chain amino acid or glycopeptide glycan via a saccharyl moiety, e.g., Sia, Gal or GalNAc moiety conjugated to the water-soluble polymer. The modified saccharyl moiety is attached to an acceptor site on the "trimmed" glycopeptide.

Alternatively, an unmodified saccharyl moiety, e.g., Gal can be added the terminus of the O-linked glycan.

In another exemplary embodiment, a water-soluble polymer is added to a GalNAc residue via a modified sugar having a galactose residue. Alternatively, an unmodified Gal can be added to the terminal GalNAc residue.

In yet a further example, a water-soluble polymer is added onto a Gal residue using a modified sialic acid.

In another exemplary embodiment, an O-linked glycosyl residue is "trimmed back" to the GalNAc attached to the amino acid. In one example, a water-soluble polymer is added via a Gal modified with the polymer. Alternatively, an unmodified Gal is added to the GalNAc, followed by a Gal with an attached water-soluble polymer. In yet another embodiment, one or more unmodified Gal residue is added to the GalNAc, followed by a sialic acid moiety modified with a water-soluble polymer.

The exemplary embodiments discussed above provide an illustration of the power of the methods set forth herein. Using the methods of the invention, it is possible to "trim back" and build up a carbohydrate residue of substantially any desired structure. The modified sugar can be added to the termini of the carbohydrate moiety as set forth above, or it can be intermediate between the peptide core and the terminus of the carbohydrate.

In an exemplary embodiment, the water-soluble polymer is added to a terminal Gal residue using a polymer modified sialic acid. An appropriate sialyltransferase is used to add a modified sialic acid. The approach is summarized in Scheme 2.

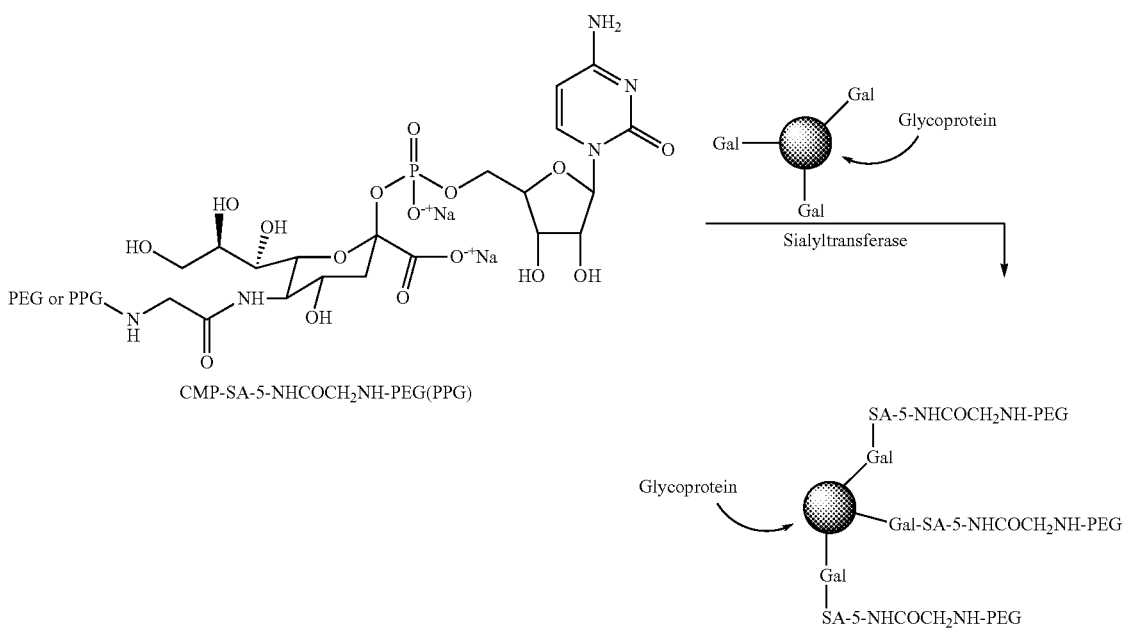

Scheme 2

In yet a further approach, summarized in Scheme 3, a masked reactive functionality is present on the sialic acid. The masked reactive group is preferably unaffected by the conditions used to attach the modified sialic acid to the peptide. After the covalent attachment of the modified sialic acid to the peptide, the mask is removed and the peptide is conjugated with an agent such as PEG, PPG, a therapeutic moiety, biomolecule or other agent. The agent is conjugated to the peptide in a specific manner by its reaction with the unmasked reactive group on the modified sugar residue.

Scheme 3

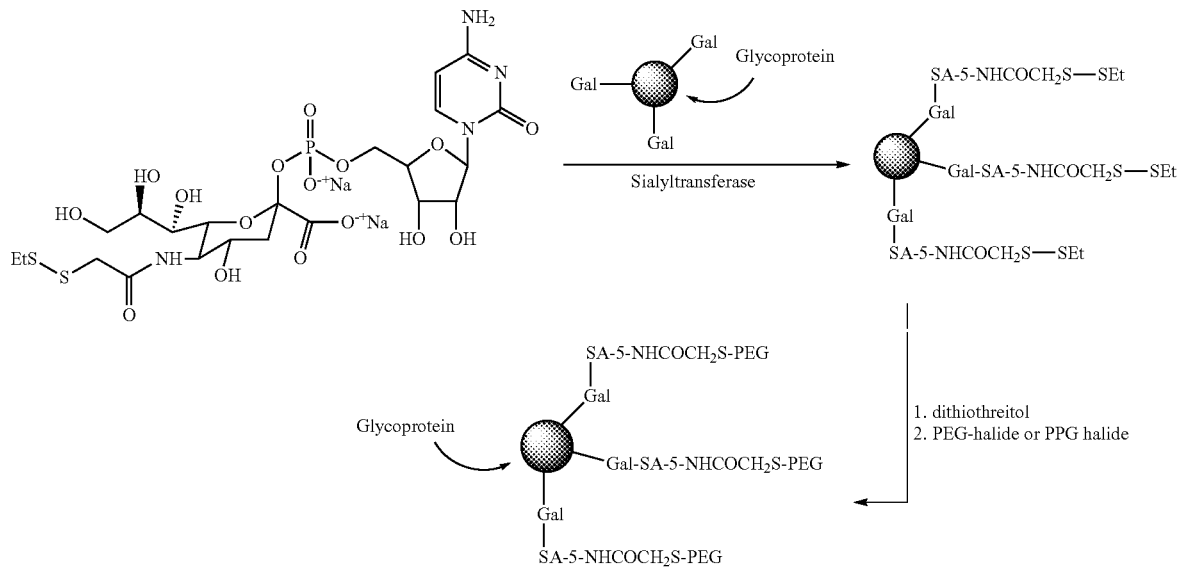

Any modified sugar can be used with its appropriate glycosyltransferase, depending on the terminal sugars of the oligosaccharide side chains of the glycopeptide (Table 2). As discussed above, the terminal sugar of the glycopeptide required for introduction of the PEG-ylated or PPGylated structure can be introduced naturally during expression or it can be produced post expression using the appropriate glycosidase(s), glycosyltransferase(s) or mix of glycosidase(s) and glycosyltransferase(s).

TABLE 2

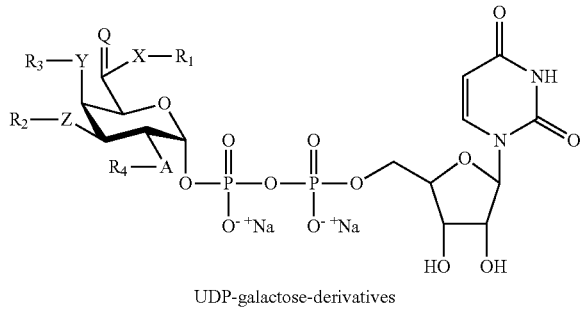

UDP-galactose-derivatives

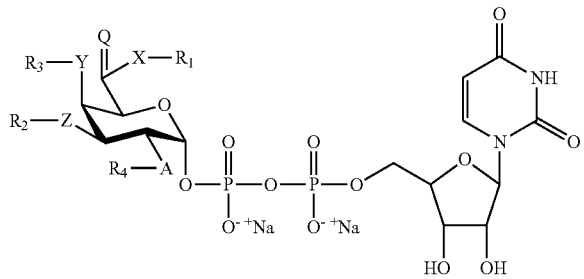

UDP-galactosamine-derivatives
(when A = NH, $R_4$ may be acetyl)

TABLE 2-continued

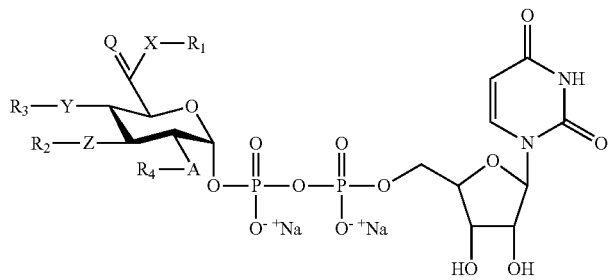

UDP-Glucose-derivatives

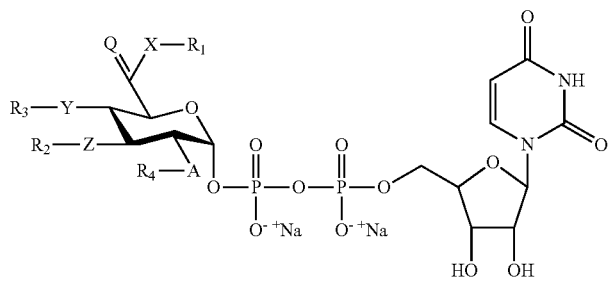

UDP-Glucosamine-derivatives
(when A = NH, R₄ may be acetyl)

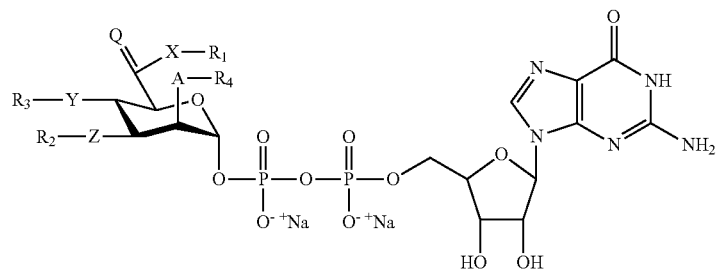

GDP-Mannose-derivatives

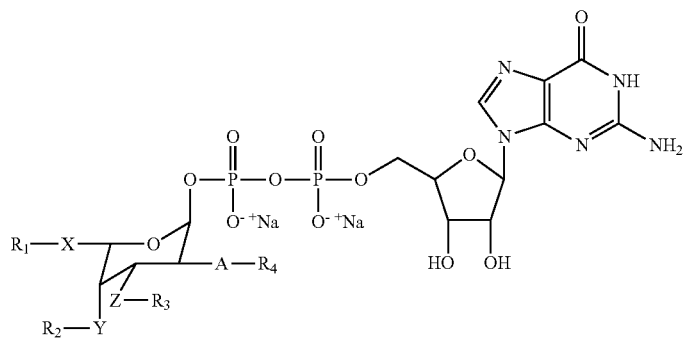

GDP-fucose-derivatives

X = O, NH, S, CH$_2$, N—(R$_{1-5}$)$_2$.

Y = X; Z = X; A = X; B = X.

Q = H$_2$, O, S, NH, N—R.

R, R$_{1-4}$ = H, Linker-M, M.

M = Ligand of interest

Ligand of interest = acyl-PEG, acyl-PPG, alkyl-PEG, acyl-alkyl-PEG, acyl-alkyl-PEG, carbamoyl-PEG, carbamoyl-PPG, PEG, PPG, acyl-aryl-PEG, acyl-aryl-PPG, aryl-PEG, aryl-PPG, Mannose-$_6$-phosphate, heparin, heparan, SLex, Mannose, FGF, VFGF, protein, chondroitin, keratan, dermatan, albumin, integrins, peptides, etc.

In an alternative embodiment, the modified sugar is added directly to the peptide backbone using a glycosyltransferase known to transfer sugar residues to the O-linked glycosylation site on the peptide backbone. This exemplary embodiment is set forth in Scheme 4. Exemplary glycosyltransferases useful in practicing the present invention include, but are not limited to, GalNAc transferases (GalNAc T1-20), GlcNAc transferases, fucosyltransferases, glucosyltransferases, xylosyltransferases, mannosyltransferases and the like. Use of this approach allows the direct addition of modified sugars onto peptides that lack any carbohydrates or, alternatively, onto existing glycopeptides. In both cases, the addition of the modified sugar occurs at specific positions on the peptide backbone as defined by the substrate specificity of the glycosyltransferase and not in a random manner as occurs during modification of a protein's peptide backbone using chemical methods. An array of agents can be introduced into proteins or glycopeptides that lack the glycosyltransferase substrate peptide sequence by engineering the appropriate amino acid sequence into the polypeptide chain.

Other agents useful for targeting are apparent to those of skill in the art. For example, glucose, glutamine and IGF are also useful to target muscle.

The targeting moiety and therapeutic peptide are conjugated by any method discussed herein or otherwise known in the art. Those of skill will appreciate that peptides in addition to those set forth above can also be derivatized as set forth herein. Exemplary peptides are set forth in the Appendix attached to copending, commonly owned U.S. Provisional Patent Application No. 60/328,523 filed Oct. 10, 2001.

In an exemplary embodiment, the targeting agent and the therapeutic peptide are coupled via a linker moiety. In this embodiment, at least one of the therapeutic peptide or the targeting agent is coupled to the linker moiety via an intact glycosyl linking group according to a method of the invention. In an exemplary embodiment, the linker moiety includes a poly(ether) such as poly(ethylene glycol). In another exemplary embodiment, the linker moiety includes at least one bond that is degraded in vivo, releasing the therapeutic peptide from the targeting agent, following delivery of the conjugate to the targeted tissue or region of the body.

Scheme 4

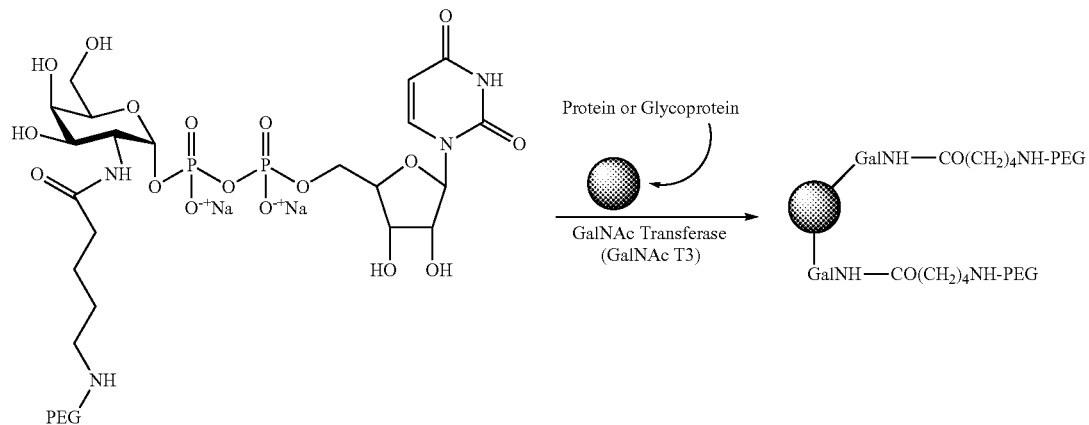

In each of the exemplary embodiments set forth above, one or more additional chemical or enzymatic modification steps can be utilized following the conjugation of the modified sugar to the peptide. In an exemplary embodiment, an enzyme (e.g., fucosyltransferase) is used to append a glycosyl unit (e.g., fucose) onto the terminal modified sugar attached to the peptide. In another example, an enzymatic reaction is utilized to "cap" (e.g., sialylate) sites to which the modified sugar failed to conjugate. Alternatively, a chemical reaction is utilized to alter the structure of the conjugated modified sugar. For example, the conjugated modified sugar is reacted with agents that stabilize or destabilize its linkage with the peptide component to which the modified sugar is attached. In another example, a component of the modified sugar is deprotected following its conjugation to the peptide. One of skill will appreciate that there is an array of enzymatic and chemical procedures that are useful in the methods of the invention at a stage after the modified sugar is conjugated to the peptide. Further elaboration of the modified sugar-peptide conjugate is within the scope of the invention.

In another exemplary embodiment, the glycopeptide is conjugated to a targeting agent, e.g., transferrin (to deliver the peptide across the blood-brain barrier, and to endosomes), carnitine (to deliver the peptide to muscle cells; see, for example, LeBorgne et al., *Biochem. Pharmacol.* 59: 1357-63 (2000), and phosphonates, e.g., bisphosphonate (to target the peptide to bone and other calciferous tissues; see, for example, Modern Drug Discovery, August 2002, page 10).

In yet another exemplary embodiment, the in vivo distribution of the therapeutic moiety is altered via altering a glycoform on the therapeutic moiety without conjugating the therapeutic peptide to a targeting moiety. For example, the therapeutic peptide can be shunted away from uptake by the reticuloendothelial system by capping a terminal galactose moiety of a glycosyl group with sialic acid (or a derivative thereof).

i. Enzymes

1. Glycosyltransferases

Glycosyltransferases catalyze the addition of activated sugars (donor NDP-sugars), in a step-wise fashion, to a protein, glycopeptide, lipid or glycolipid or to the non-reducing end of a growing oligosaccharide. N-linked glycopeptides are synthesized via a transferase and a lipid-linked oligosaccharide donor Dol-PP-NAG$_2$Glc$_3$Man$_9$ in an en block transfer followed by trimming of the core. In this case the nature of the "core" saccharide is somewhat different from subsequent attachments. A very large number of glycosyltransferases are known in the art.

The glycosyltransferase to be used in the present invention may be any as long as it can utilize the modified sugar as a sugar donor. Examples of such enzymes include Leloir pathway glycosyltransferase, such as galactosyltransferase, N-acetylglucosaminyltransferase, N-acetylgalactosaminyltransferase, fucosyltransferase, sialyltransferase, mannosyltransferase, xylosyltransferase, glucurononyltransferase and the like.

For enzymatic saccharide syntheses that involve glycosyltransferase reactions, glycosyltransferase can be cloned, or isolated from any source. Many cloned glycosyltransferases are known, as are their polynucleotide sequences. See, e.g., "The WWW Guide To Cloned Glycosyltransferases," (http://www.vei.co.uk/TGN/gt_guide.htm). Glycosyltransferase amino acid sequences and nucleotide sequences encoding glycosyltransferases from which the amino acid sequences can be deduced are also found in various publicly available databases, including GenBank, Swiss-Prot, EMBL, and others.

Glycosyltransferases that can be employed in the methods of the invention include, but are not limited to, galactosyltransferases, fucosyltransferases, glucosyltransferases, N-acetylgalactosaminyltransferases, N-acetylglucosaminyltransferases, glucuronyltransferases, sialyltransferases, mannosyltransferases, glucuronic acid transferases, galacturonic acid transferases, and oligosaccharyltransferases. Suitable glycosyltransferases include those obtained from eukaryotes, as well as from prokaryotes.

DNA encoding glycosyltransferases may be obtained by chemical synthesis, by screening reverse transcripts of mRNA from appropriate cells or cell line cultures, by screening genomic libraries from appropriate cells, or by combinations of these procedures. Screening of mRNA or genomic DNA may be carried out with oligonucleotide probes generated from the glycosyltransferases gene sequence. Probes may be labeled with a detectable group such as a fluorescent group, a radioactive atom or a chemiluminescent group in accordance with known procedures and used in conventional hybridization assays. In the alternative, glycosyltransferases gene sequences may be obtained by use of the polymerase chain reaction (PCR) procedure, with the PCR oligonucleotide primers being produced from the glycosyltransferases gene sequence. See, U.S. Pat. No. 4,683,195 to Mullis et al. and U.S. Pat. No. 4,683,202 to Mullis.

The glycosyltransferase may be synthesized in host cells transformed with vectors containing DNA encoding the glycosyltransferases enzyme. Vectors are used either to amplify DNA encoding the glycosyltransferases enzyme and/or to express DNA which encodes the glycosyltransferases enzyme. An expression vector is a replicable DNA construct in which a DNA sequence encoding the glycosyltransferases enzyme is operably linked to suitable control sequences capable of effecting the expression of the glycosyltransferases enzyme in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

In an exemplary embodiment, the invention utilizes a prokaryotic enzyme. Such glycosyltransferases include enzymes involved in synthesis of lipooligosaccharides (LOS), which are produced by many gram negative bacteria (Preston et al., *Critical Reviews in Microbiology* 23(3): 139-180 (1996)). Such enzymes include, but are not limited to, the proteins of the rfa operons of species such as *E. coli* and *Salmonella typhimurium*, which include a β1,6 galactosyltransferase and a β1,3 galactosyltransferase (see, e.g., EMBL Accession Nos. M80599 and M86935 (*E. coli*); EMBL Accession No. S56361 (*S. typhimurium*)), a glucosyltransferase (Swiss-Prot Accession No. P25740 (*E. coli*), an (β1,2-glucosyltransferase (rfaJ) (Swiss-Prot Accession No. P27129 (*E. coli*) and Swiss-Prot Accession No. P19817 (*S. typhimurium*)), and an β1,2-N-acetylglucosaminyltransferase (rfaK) (EMBL Accession No. U00039 (*E. coli*). Other glycosyltransferases for which amino acid sequences are known include those that are encoded by operons such as rfaB, which have been characterized in organisms such as *Klebsiella pneumoniae, E. coli, Salmonella typhimurium, Salmonella enterica, Yersinia enterocolitica, Mycobacterium leprosum*, and the rh1 operon of *Pseudomonas aeruginosa*.

Also suitable for use in the present invention are glycosyltransferases that are involved in producing structures containing lacto-N-neotetraose, D-galactosyl-β-1,4-N-acetyl-D-glucosaminyl-β-1,3-D-galactosyl-β-1,4-D-glucose, and the $P^k$ blood group trisaccharide sequence, D-galactosyl-α-1,4-D-galactosyl-β-1,4-D-glucose, which have been identified in the LOS of the mucosal pathogens *Neisseria gonnorhoeae* and *N. meningitidis* (Scholten et al., *J. Med. Microbiol.* 41: 236-243 (1994)). The genes from *N. meningitidis* and *N. gonorrhoeae* that encode the glycosyltransferases involved in the biosynthesis of these structures have been identified from *N. meningitidis* immunotypes L3 and L1 (Jennings et al., *Mol. Microbiol.* 18: 729-740 (1995)) and the *N. gonorrhoeae* mutant F62 (Gotshlich, *J. Exp. Med.* 180: 2181-2190 (1994)). In *N. meningitidis*, a locus consisting of three genes, lgtA, lgtB and lg E, encodes the glycosyltransferase enzymes required for addition of the last three of the sugars in the lacto-N-neotetraose chain (Wakarchuk et al., *J. Biol. Chem.* 271: 19166-73 (1996)). Recently the enzymatic activity of the lgtB and lgtA gene product was demonstrated, providing the first direct evidence for their proposed glycosyltransferase function (Wakarchuk et al., *J. Biol. Chem.* 271(45): 28271-276 (1996)). In *N. gonorrhoeae*, there are two additional genes, lgtD which adds β-D-GalNAc to the 3 position of the terminal galactose of the lacto-N-neotetraose structure and lgtC which adds a terminal α-D-Gal to the lactose element of a truncated LOS, thus creating the $P^k$ blood group antigen structure (Gotshlich (1994), supra.). In *N. meningitidis*, a separate immunotype L1 also expresses the $P^k$ blood group antigen and has been shown to carry an lgtC gene (Jennings et al., (1995), supra.). Neisseria glycosyltransferases and associated genes are also described in U.S. Pat. No. 5,545,553 (Gotshlich). Genes for α1,2-fucosyltransferase and α1,3-fucosyltransferase from *Helicobacter pylori* has also been characterized (Martin et al., *J. Biol. Chem.* 272: 21349-21356 (1997)). Also of use in the present invention are the glycosyltransferases of *Campylobacter jejuni* (see, for example, http://afmb.cnrs-mrs.fr/~pedro/CAZY/gtf_42.html).

a) Fucosyltransferases

In some embodiments, a glycosyltransferase used in the method of the invention is a fucosyltransferase. Fucosyltransferases are known to those of skill in the art. Exemplary fucosyltransferases include enzymes, which transfer L-fucose from GDP-fucose to a hydroxy position of an acceptor sugar. Fucosyltransferases that transfer non-nucleotide sugars to an acceptor are also of use in the present invention.

In some embodiments, the acceptor sugar is, for example, the GlcNAc in a Galβ(1→3,4)GlcNAcβ- group in an oligosaccharide glycoside. Suitable fucosyltransferases for this reaction include the Galβ(1→3,4)GlcNAcβ1-α(1→3,4)fucosyltransferase (FTIII E.C. No. 2.4.1.65), which was first characterized from human milk (see, Palcic, et al., *Carbohydrate Res.* 190:1-11 (1989); Prieels, et al., *J. Biol. Chem.* 256: 10456-10463 (1981); and Nunez, et al., *Can. J. Chem.* 59: 2086-2095 (1981)) and the Galβ(1→4)GlcNAcβ-αfucosyltransferases (FTIV, FTV, FTVI) which are found in human serum. FTVII (E.C. No. 2.4.1.65), a sialyl α(2→3)Galβ ((1→3)GlcNAcβ fucosyltransferase, has also been characterized. A recombinant form of the Galβ(1→3,4) GlcNAcβ-α (1→3,4)fucosyltransferase has also been characterized (see, Dumas, et al., *Bioorg. Med. Letters* 1: 425-428 (1991) and Kukowska-Latallo, et al., *Genes and Development* 4: 1288-

1303 (1990)). Other exemplary fucosyltransferases include, for example, α1,2 fucosyltransferase (E.C. No. 2.4.1.69). Enzymatic fucosylation can be carried out by the methods described in Mollicone, et al., *Eur. J. Biochem.* 191: 169-176 (1990) or U.S. Pat. No. 5,374,655. Cells that are used to produce a fucosyltransferase will also include an enzymatic system for synthesizing GDP-fucose.

b) Galactosyltransferases

In another group of embodiments, the glycosyltransferase is a galactosyltransferase. Exemplary galactosyltransferases include α(1,3) galactosyltransferases (E.C. No. 2.4.1.151, see, e.g., Dabkowski et al., *Transplant Proc.* 25:2921 (1993) and Yamamoto et al. *Nature* 345: 229-233 (1990), bovine (GenBank j04989, Joziasse et al., *J. Biol. Chem.* 264: 14290-14297 (1989)), murine (GenBank m26925; Larsen et al., *Proc. Nat'l. Acad. Sci. USA* 86: 8227-8231 (1989)), porcine (GenBank L36152; Strahan et al., *Immunogenetics* 41: 101-105 (1995)). Another suitable α1,3 galactosyltransferase is that which is involved in synthesis of the blood group B antigen (EC 2.4.1.37, Yamamoto et al., *J. Biol. Chem.* 265: 1146-1151 (1990) (human)). Yet a further exemplary galactosyltransferase is core Gal-T1.

Also suitable for use in the methods of the invention are β(1,4) galactosyltransferases, which include, for example, EC 2.4.1.90 (LacNAc synthetase) and EC 2.4.1.22 (lactose synthetase) (bovine (D'Agostaro et al., *Eur. J. Biochem.* 183: 211-217 (1989)), human (Masri et al., *Biochem. Biophys. Res. Commun.* 157: 657-663 (1988)), murine (Nakazawa et al., J. Biochem. 104: 165-168 (1988)), as well as E.C. 2.4.1.38 and the ceramide galactosyltransferase (EC 2.4.1.45, Stahl et al., *J. Neurosci. Res.* 38: 234-242 (1994)). Other suitable galactosyltransferases include, for example, α1,2 galactosyltransferases (from e.g., *Schizosaccharomyces pombe*, Chapell et al., *Mol. Biol. Cell* 5: 519-528 (1994)).

c) Sialyltransferases

Sialyltransferases are another type of glycosyltransferase that is useful in the recombinant cells and reaction mixtures of the invention. Cells that produce recombinant sialyltransferases will also produce CMP-sialic acid, which is a sialic acid donor for sialyltransferases. Examples of sialyltransferases that are suitable for use in the present invention include ST3Gal III (e.g., a rat or human ST3Gal III), ST3Gal IV, ST3Gal I, ST6Gal I, ST3Gal V, ST6Gal II, ST6GalNAc I, ST6GalNAc II, and ST6GalNAc III (the sialyltransferase nomenclature used herein is as described in Tsuji et al., *Glycobiology* 6: v-xiv (1996)). An exemplary α(2,3)sialyltransferase referred to as α(2,3)sialyltransferase (EC 2.4.99.6) transfers sialic acid to the non-reducing terminal Gal of a Galβ1→3Glc disaccharide or glycoside. See, Van den Eijnden et al., J. Biol. Chem. 256: 3159 (1981), Weinstein et al., J. Biol. Chem. 257: 13845 (1982) and Wen et al., J. Biol. Chem. 267: 21011 (1992). Another exemplary α2,3-sialyltransferase (EC 2.4.99.4) transfers sialic acid to the non-reducing terminal Gal of the disaccharide or glycoside. see, Rearick et al., J. Biol. Chem. 254: 4444 (1979) and Gillespie et al., J. Biol. Chem. 267: 21004 (1992). Further exemplary enzymes include Gal-β-1,4-GlcNAc α-2,6 sialyltransferase (See, Kurosawa et al. Eur. J. Biochem. 219: 375-381 (1994)).

Preferably, for glycosylation of carbohydrates of glycopeptides the sialyltransferase will be able to transfer sialic acid to the sequence Galβ1,4GlcNAc-, the most common penultimate sequence underlying the terminal sialic acid on fully sialylated carbohydrate structures (see, Table 5).

TABLE 5

Sialyltransferases which use the Galβ1, 4GlcNAc sequence as an acceptor substrate

| Sialyl-transferase | Source | Sequence(s) formed | Ref. |
|---|---|---|---|
| ST6Gal I | Mammalian | NeuAc2, 6Galβ1, 4GlCNAc— | 1 |
| ST3Gal III | Mammalian | NeuAc2, 3Galβ1, 4GlCNAc— | 1 |
|  |  | NeuAc2, 3Galβ1, 3GlCNAc— |  |
| ST3Gal IV | Mammalian | NeuAc2, 3Galβ1, 4GlCNAc— | 1 |
|  |  | NeuAc2, 3Galβ1, 3GlCNAc— |  |
| ST6Gal II | Mammalian | NeuAc2, 6Galβ1, 4GlCNA |  |
| ST6Gal II | photobacterium | NeuAc2, 6Galβ1, 4GlCNAc— | 2 |
| ST3Gal V | N. meningitides N. gonorrhoeae | NeuAc2, 3Galβ1, 4GlCNAc— | 3 |

1) Goochee et al., *Bio/Technology* 9: 1347-1355 (1991)
2) Yamamoto et al., *J. Biochem.* 120: 104-110 (1996)
3) Gilbert et al., *J. Biol. Chem.* 271: 28271-28276 (1996)

An example of a sialyltransferase that is useful in the claimed methods is ST3Gal III, which is also referred to as α(2,3)sialyltransferase (EC 2.4.99.6). This enzyme catalyzes the transfer of sialic acid to the Gal of a Galβ1,3GlcNAc or Galβ1,4GlcNAc glycoside (see, e.g., Wen et al., *J. Biol. Chem.* 267: 21011 (1992); Van den Eijnden et al., *J. Biol. Chem.* 256: 3159 (1991)) and is responsible for sialylation of asparagine-linked oligosaccharides in glycopeptides. The sialic acid is linked to a Gal with the formation of an α-linkage between the two saccharides. Bonding (linkage) between the saccharides is between the 2-position of NeuAc and the 3-position of Gal. This particular enzyme can be isolated from rat liver (Weinstein et al., *J. Biol. Chem.* 257: 13845 (1982)); the human cDNA (Sasaki et al. (1993) *J. Biol. Chem.* 268: 22782-22787; Kitagawa & Paulson (1994) *J. Biol. Chem.* 269: 1394-1401) and genomic (Kitagawa et al. (1996) *J. Biol. Chem.* 271: 931-938) DNA sequences are known, facilitating production of this enzyme by recombinant expression. In a preferred embodiment, the claimed sialylation methods use a rat ST3Gal III.

Other exemplary sialyltransferases of use in the present invention include those isolated from *Campylobacter jejuni*, including the α(2,3). See, e.g., WO99/49051.

Sialyltransferases other those listed in Table 5, are also useful in an economic and efficient large-scale process for sialylation of commercially important glycopeptides. As a simple test to find out the utility of these other enzymes, various amounts of each enzyme (1-100 mU/mg protein) are reacted with asialo-α$_1$ AGP (at 1-10 mg/ml) to compare the ability of the sialyltransferase of interest to sialylate glycopeptides relative to either bovine ST6Gal I, ST3Gal III or both sialyltransferases. Alternatively, other glycopeptides, or N-linked oligosaccharides enzymatically released from the peptide backbone can be used in place of asialo-α$_1$ AGP for this evaluation. Sialyltransferases with the ability to sialylate N-linked oligosaccharides of glycopeptides more efficiently than ST6Gal I are useful in a practical large-scale process for peptide sialylation (as illustrated for ST3Gal III in this disclosure).

d) GalNAc Transferases

N-acetylgalactosaminyltransferases are of use in practicing the present invention, particularly for binding a GalNAc moiety to an amino acid of the O-linked glycosylation site of the peptide. Suitable N-acetylgalactosaminyltransferases include, but are not limited to, α(1,3) N-acetylgalactosaminyltransferase, β(1,4) N-acetylgalactosaminyltransferases (Nagata et al., *J. Biol. Chem.* 267: 12082-12089 (1992) and Smith et al., J. Biol. Chem. 269: 15162 (1994)) and polypeptide N-acetylgalactosaminyltransferase (Homa et al., J. Biol. Chem. 268: 12609 (1993)).

Production of proteins such as the enzyme GalNAc $T_{I-XX}$ from cloned genes by genetic engineering is well known. See, eg., U.S. Pat. No. 4,761,371. One method involves collection of sufficient samples, then the amino acid sequence of the enzyme is determined by N-terminal sequencing. This information is then used to isolate a cDNA clone encoding a full-length (membrane bound) transferase which upon expression in the insect cell line Sf9 resulted in the synthesis of a fully active enzyme. The acceptor specificity of the enzyme is then determined using a semiquantitative analysis of the amino acids surrounding known glycosylation sites in 16 different proteins followed by in vitro glycosylation studies of synthetic peptides. This work has demonstrated that certain amino acid residues are overrepresented in glycosylated peptide segments and that residues in specific positions surrounding glycosylated serine and threonine residues may have a more marked influence on acceptor efficiency than other amino acid moieties.

2. Sulfotransferases

The invention also provides methods for producing peptides that include sulfated molecules, including, for example sulfated polysaccharides such as heparin, heparan sulfate, carragenen, and related compounds. Suitable sulfotransferases include, for example, chondroitin-6-sulphotransferase (chicken cDNA described by Fukuta et al., J. Biol. Chem. 270: 18575-18580 (1995); GenBank Accession No. D49915), glycosaminoglycan N-acetylglucosamine N-deacetylase/N-sulphotransferase 1 (Dixon et al., Genomics 26: 239-241 (1995); UL18918), and glycosaminoglycan N-acetylglucosamine N-deacetylase/N-sulphotransferase 2 (murine cDNA described in Orellana et al., J. Biol. Chem. 269: 2270-2276 (1994) and Eriksson et al., J. Biol. Chem. 269: 10438-10443 (1994); human cDNA described in GenBank Accession No. U2304).

3. Cell-Bound Glycosyltransferases

In another embodiment, the enzymes utilized in the method of the invention are cell-bound glycosyltransferases. Although many soluble glycosyltransferases are known (see, for example, U.S. Pat. No. 5,032,519), glycosyltransferases are generally in membrane-bound form when associated with cells. Many of the membrane-bound enzymes studied thus far are considered to be intrinsic proteins; that is, they are not released from the membranes by sonication and require detergents for solubilization. Surface glycosyltransferases have been identified on the surfaces of vertebrate and invertebrate cells, and it has also been recognized that these surface transferases maintain catalytic activity under physiological conditions. However, the more recognized function of cell surface glycosyltransferases is for intercellular recognition (Roth, MOLECULAR APPROACHES to SUPRACELLULAR PHENOMENA, 1990).

Methods have been developed to alter the glycosyltransferases expressed by cells. For example, Larsen et al., Proc. Natl. Acad. Sci. USA 86: 8227-8231 (1989), report a genetic approach to isolate cloned cDNA sequences that determine expression of cell surface oligosaccharide structures and their cognate glycosyltransferases. A cDNA library generated from mRNA isolated from a murine cell line known to express UDP-galactose:.β.-D-galactosyl-1,4-N-acetyl-D-glucosaminide α-1,3-galactosyltransferase was transfected into COS-1 cells. The transfected cells were then cultured and assayed for α 1-3 galactosyltransferase activity.

Francisco et al., Proc. Natl. Acad. Sci. USA 89: 2713-2717 (1992), disclose a method of anchoring β-lactamase to the external surface of Escherichia coli. A tripartite fusion consisting of (i) a signal sequence of an outer membrane protein, (ii) a membrane-spanning section of an outer membrane protein, and (iii) a complete mature β-lactamase sequence is produced resulting in an active surface bound β-lactamase molecule. However, the Francisco method is limited only to procaryotic cell systems and as recognized by the authors, requires the complete tripartite fusion for proper functioning.

4. Fusion Proteins

In other exemplary embodiments, the methods of the invention utilize fusion proteins that have more than one enzymatic activity that is involved in synthesis of a desired glycopeptide conjugate. The fusion polypeptides can be composed of, for example, a catalytically active domain of a glycosyltransferase that is joined to a catalytically active domain of an accessory enzyme. The accessory enzyme catalytic domain can, for example, catalyze a step in the formation of a nucleotide sugar that is a donor for the glycosyltransferase, or catalyze a reaction involved in a glycosyltransferase cycle. For example, a polynucleotide that encodes a glycosyltransferase can be joined, in-frame, to a polynucleotide that encodes an enzyme involved in nucleotide sugar synthesis. The resulting fusion protein can then catalyze not only the synthesis of the nucleotide sugar, but also the transfer of the sugar moiety to the acceptor molecule. The fusion protein can be two or more cycle enzymes linked into one expressible nucleotide sequence. In other embodiments the fusion protein includes the catalytically active domains of two or more glycosyltransferases. See, for example, U.S. Pat. No. 5,641,668. The modified glycopeptides of the present invention can be readily designed and manufactured utilizing various suitable fusion proteins (see, for example, PCT Patent Application PCT/CA98/01180, which was published as WO 99/31224 on Jun. 24, 1999.)

5. Immobilized Enzymes

In addition to cell-bound enzymes, the present invention also provides for the use of enzymes that are immobilized on a solid and/or soluble support. In an exemplary embodiment, there is provided a glycosyltransferase that is conjugated to a PEG via an intact glycosyl linker according to the methods of the invention. The PEG-linker-enzyme conjugate is optionally attached to solid support. The use of solid supported enzymes in the methods of the invention simplifies the work up of the reaction mixture and purification of the reaction product, and also enables the facile recovery of the enzyme. The glycosyltransferase conjugate is utilized in the methods of the invention. Other combinations of enzymes and supports will be apparent to those of skill in the art.

Purification of Peptide Conjugates

The products produced by the above processes can be used without purification. However, it is usually preferred to recover the product. Standard, well-known techniques for recovery of glycosylated saccharides such as thin or thick layer chromatography, column chromatography, ion exchange chromatography, or membrane filtration can be used. It is preferred to use membrane filtration, more preferably utilizing a reverse osmotic membrane, or one or more column chromatographic techniques for the recovery as is discussed hereinafter and in the literature cited herein. For instance, membrane filtration wherein the membranes have molecular weight cutoff of about 3000 to about 10,000 can be used to remove proteins such as glycosyl transferases. Nanofiltration or reverse osmosis can then be used to remove salts and/or purify the product saccharides (see, e.g., WO 98/15581). Nanofilter membranes are a class of reverse osmosis membranes that pass monovalent salts but retain polyvalent salts and uncharged solutes larger than about 100 to about 2,000 Daltons, depending upon the membrane used. Thus, in a typical application, saccharides prepared by the methods of the present invention will be retained in the membrane and contaminating salts will pass through.

If the modified glycoprotein is produced intracellularly, as a first step, the particulate debris, either host cells or lysed fragments, is removed, for example, by centrifugation or ultrafiltration; optionally, the protein may be concentrated with a commercially available protein concentration filter, followed by separating the polypeptide variant from other impurities by one or more steps selected from immunoaffinity chromatography, ion-exchange column fractionation (e.g., on diethylaminoethyl (DEAE) or matrices containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, SP-Sepharose, or protein A Sepharose, SDS-PAGE chromatography, silica chromatography, chromatofocusing, reverse phase HPLC (e.g., silica gel with appended aliphatic groups), gel filtration using, e.g., Sephadex molecular sieve or size-exclusion chromatography, chromatography on columns that selectively bind the polypeptide, and ethanol or ammonium sulfate precipitation.

Modified glycopeptides produced in culture are usually isolated by initial extraction from cells, enzymes, etc., followed by one or more concentration, salting-out, aqueous ion-exchange, or size-exclusion chromatography steps, e.g., SP Sepharose. Additionally, the modified glycoprotein may be purified by affinity chromatography. HPLC may also be employed for one or more purification steps.

A protease inhibitor, e.g., methylsulfonylfluoride (PMSF) may be included in any of the foregoing steps to inhibit proteolysis and antibiotics may be included to prevent the growth of adventitious contaminants.

Within another embodiment, supernatants from systems which produce the modified glycopeptide of the invention are first concentrated using a commercially available protein concentration filter, for example, an Amicon or Millipore Pellicon ultrafiltration unit. Following the concentration step, the concentrate may be applied to a suitable purification matrix. For example, a suitable affinity matrix may comprise a ligand for the peptide, a lectin or antibody molecule bound to a suitable support. Alternatively, an anion-exchange resin may be employed, for example, a matrix or substrate having pendant DEAE groups. Suitable matrices include acrylamide, agarose, dextran, cellulose, or other types commonly employed in protein purification. Alternatively, a cation-exchange step may be employed. Suitable cation exchangers include various insoluble matrices comprising sulfopropyl or carboxymethyl groups. Sulfopropyl groups are particularly preferred.

Finally, one or more RP-HPLC steps employing hydrophobic RP-HPLC media, e.g., silica gel having pendant methyl or other aliphatic groups, may be employed to further purify a polypeptide variant composition. Some or all of the foregoing purification steps, in various combinations, can also be employed to provide a homogeneous modified glycoprotein.

The modified glycopeptide of the invention resulting from a large-scale fermentation may be purified by methods analogous to those disclosed by Urdal et al., *J. Chromatog.* 296: 171 (1984). This reference describes two sequential, RP-HPLC steps for purification of recombinant human IL-2 on a preparative HPLC column. Alternatively, techniques such as affinity chromatography may be utilized to purify the modified glycoprotein.

Pharmaceutical Compositions

Polypeptides modified at various O-linked glycosylation site according to the method of the present invention have a broad range of pharmaceutical applications. For example, GLP-1 may be used for the treatment or prevention of diabetes or obesity.

An additional example, human growth hormone (hGH) modified according to the methods of the present invention may be used to treat growth-related conditions such as dwarfism, short-stature in children and adults, cachexia/muscle wasting, general muscular atrophy, and sex chromosome abnormality (e.g., Turner's Syndrome). Other conditions may be treated using modified hGH include: short-bowel syndrome, lipodystrophy, osteoporosis, uraemaia, burns, female infertility, bone regeneration, general diabetes, type II diabetes, osteo-arthritis, chronic obstructive pulmonary disease (COPD), and insomnia. Moreover, modified hGH may also be used to promote various processes, e.g., general tissue regeneration, bone regeneration, and wound healing, or as a vaccine adjunct.

Thus, in one aspect, the invention provides a pharmaceutical composition. The pharmaceutical composition includes a pharmaceutically acceptable diluent and a covalent conjugate between a non-naturally-occurring, water-soluble polymer, therapeutic moiety or biomolecule and a glycosylated or non-glycosylated peptide. The polymer, therapeutic moiety or biomolecule is conjugated to the peptide via an intact glycosyl linking group interposed between and covalently linked to both the peptide and the polymer, therapeutic moiety or biomolecule.

Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985). For a brief review of methods for drug delivery, see, Langer, *Science* 249:1527-1533 (1990).

The pharmaceutical compositions may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable matrises, such as microspheres (e.g., polylactate polyglycolate), may also be employed as carriers for the pharmaceutical compositions of this invention. Suitable biodegradable microspheres are disclosed, for example, in U.S. Pat. Nos. 4,897,268 and 5,075,109.

Commonly, the pharmaceutical compositions are administered subcutaneously or parenterally, e.g., intravenously. Thus, the invention provides compositions for parenteral administration which comprise the compound dissolved or suspended in an acceptable carrier, preferably an aqueous carrier, e.g., water, buffered water, saline, PBS and the like. The compositions may also contain detergents such as Tween 20 and Tween 80; stabilizers such as mannitol, sorbitol, sucrose, and trehalose; and preservatives such as EDTA and m-cresol. The compositions may contain pharmaceutically acceptable auxiliary substances as required to approximate physiological conditions, such as pH adjusting and buffering agents, tonicity adjusting agents, wetting agents, detergents and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9 and most preferably from 7 and 8.

In some embodiments the glycopeptides of the invention can be incorporated into liposomes formed from standard vesicle-forming lipids. A variety of methods are available for preparing liposomes, as described in, e.g., Szoka et al., *Ann. Rev. Biophys. Bioeng.* 9: 467 (1980), U.S. Pat. Nos. 4,235, 871, 4,501,728 and 4,837,028. The targeting of liposomes using a variety of targeting agents (e.g., the sialyl galactosides of the invention) is well known in the art (see, e.g., U.S. Pat. Nos. 4,957,773 and 4,603,044).

Standard methods for coupling targeting agents to liposomes can be used. These methods generally involve incorporation into liposomes of lipid components, such as phosphatidylethanolamine, which can be activated for attachment of targeting agents, or derivatized lipophilic compounds, such as lipid-derivatized glycopeptides of the invention.

Targeting mechanisms generally require that the targeting agents be positioned on the surface of the liposome in such a manner that the target moieties are available for interaction with the target, for example, a cell surface receptor. The carbohydrates of the invention may be attached to a lipid molecule before the liposome is formed using methods known to those of skill in the art (e.g., alkylation or acylation of a hydroxyl group present on the carbohydrate with a long chain alkyl halide or with a fatty acid, respectively). Alternatively, the liposome may be fashioned in such a way that a connector portion is first incorporated into the membrane at the time of forming the membrane. The connector portion must have a lipophilic portion, which is firmly embedded and anchored in the membrane. It must also have a reactive portion, which is chemically available on the aqueous surface of the liposome. The reactive portion is selected so that it will be chemically suitable to form a stable chemical bond with the targeting agent or carbohydrate, which is added later. In some cases it is possible to attach the target agent to the connector molecule directly, but in most instances it is more suitable to use a third molecule to act as a chemical bridge, thus linking the connector molecule which is in the membrane with the target agent or carbohydrate which is extended, three dimensionally, off of the vesicle surface.

The following examples are provided to illustrate the conjugates, and methods and of the present invention, but not to limit the claimed invention.

EXAMPLES

Example 1

1.1 Preparation of Glucagon-Like Peptide Mutants Comprising Artificial Glycosylation Sites Mutations in the amino acid sequence of Glucagon-Like Peptide-1 (GLP-1) will be made in order to introduce sites for O-linked glycosylation, such that the protein may be modified at these sites using the method of the present invention. Mutants can be created using well known methods for solid state synthesis. Alternatively, mutations will be introduced into a nucleic acid the sequence encoding GLP-1 such that O-linked glycosylation sites will be introduced at each position along the peptide back bone.

The following are some exemplary GLP-1 mutants.

GLP-1 Glycopeptides

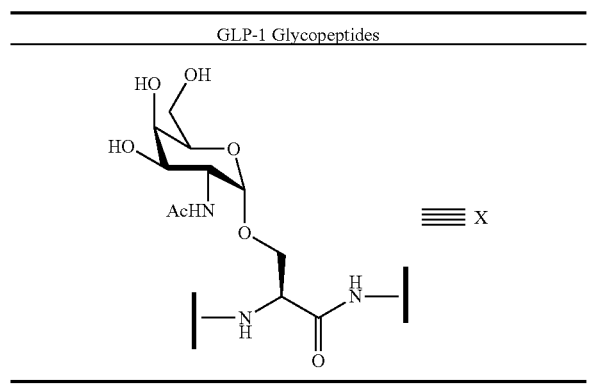

Ac-X-  HAEGTFTSDVSSYLEGQAAKEFIAWLVKGR-NH$_2$
H-X-EGTFTSDVSSYLEGQAAKEFIAWLVKGR-NH$_2$
HA-X-GTFTSDVSSYLEGQAAKEFIAWLVKGR-NH$_2$
HAE-X-TFTSDVSSYLEGQAAKEFIAWLVKGR-NH$_2$
HAEG-X-FTSDVSSYLEGQAAKEFIAWLVKGR-NH$_2$

-continued

GLP-1 Glycopeptides

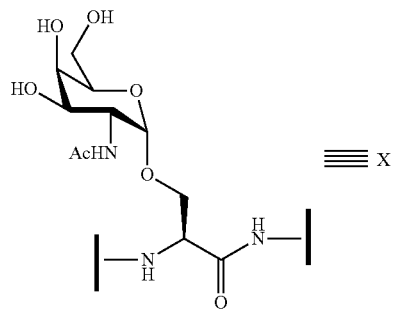

HAEGT-X-TSDVSSYLEGQAAKEFIAWLVKGR-NH$_2$
HAEGTF-X-SDVSSYLEGQAAKEFIAWLVKGR-NH$_2$
HAEGTFT-X-DVSSYLEGQAAKEFIAWLVKGR-NH$_2$
HAEGTFTS-X-VSSYLEGQAAKEFIAWLVKGR-NH$_2$
HAEGTFTSD-X-SSYLEGQAAKEFIAWLVKGR-NH$_2$
HAEGTFTSDV-X-SYLEGQAAKEFIAWLVKGR-NH$_2$
HAEGTFTSDVS-X-YLEGQAAKEFIAWLVKGR-NH$_2$
HAEGTFTSDVSS-X-LEGQAAKEFIAWLVKGR-NH$_2$
HAEGTFTSDVSSY-X-EGQAAKEFIAWLVKGR-NH$_2$
HAEGTFTSDVSSYL-X-GQAAKEFIAWLVKGR-NH$_2$
HAEGTFTSDVSSYLE-X-QAAKEFIAWLVKGR-NH$_2$
HAEGTFTSDVSSYLEG-X-AAKEFIAWLVKGR-NH$_2$
HAEGTFTSDVSSYLEGQ-X-AKEFIAWLVKGR-NH$_2$
HAEGTFTSDVSSYLEGQA-X-KEFIAWLVKGR-NH$_2$
HAEGTFTSDVSSYLEGQAA-X-EFIAWLVKGR-NH$_2$
HAEGTFTSDVSSYLEGQAAK-X-FIAWLVKGR-NH$_2$
HAEGTFTSDVSSYLEGQAAKE-X-IAWLVKGR-NH$_2$
HAEGTFTSDVSSYLEGQAAKEF-X-AWLVKGR-NH$_2$
HAEGTFTSDVSSYLEGQAAKEFI-X-WLVKGR-NH$_2$
HAEGTFTSDVSSYLEGQAAKEFIA-X-LVKGR-NH$_2$
HAEGTFTSDVSSYLEGQAAKEFIAW-X-VKGR-NH$_2$
HAEGTFTSDVSSYLEGQAAKEFIAWL-X-KGR-NH$_2$
HAEGTFTSDVSSYLEGQAAKEFIAWLV-X-GR-NH$_2$
HAEGTFTSDVSSYLEGQAAKEFIAWLVK-X-R-NH$_2$
HAEGTFTSDVSSYLEGQAAKEFIAWLVKG-X-NH$_2$
HAEGTFTSDVSSYLEGQAAKEFIAWLVKGR-X-NH$_2$

1.2 Preparation of GLP-1-GalNAc (pH 6.2)

GLP-1 (960 µg) in 3.2 mL of buffer will be concentrated by ultrafiltration using an UF filter (5 KDa) and then reconstituted with 1 mL of 25 mM MES buffer (pH 6.2, 0.005% NaN$_3$). The UDP-GalNAc (6 mg, 9.24 mM), GalNAc-T2 (40 µL, 0.04 U), and 100 mM MnCl$_2$ (40 µL, 4 mM) will then be added and the resulting solution will be incubated at room temperature. After 48 h, the MALDI should the reaction was complete (shift of the mass ion from 18800 to 19023 mass units). The reaction mixture will be purified by HPLC using SEC (Superdex 75 and Superdex 200). The column will be eluted using phosphate buffered saline, pH 4.9 and 0.005% tween 80. The peak corresponding to GLP-1-GalNAc will be collected and concentrated to about 150 µL using a Centricon 5 KDa filter and the volume will be adjusted to 1 mL using PBS (phosphate buffered saline, pH 4.9 and 0.005% tween 80); protein concentration 1 mg/mL A$_{280}$).

1.3 Preparation of GLP-1-GalNAc-Gal (pH 6.0)

GLP-1-GalNAc (100 µg) will be added to a 100 µL of a solution containing 25 mM MES buffer, pH 6.0, 1.5 mM UDP-GalNAc, 10 mM MgCl$_2$ and 80 mU GalNAc-T2. The CMP-SA-PEG-20 KDa (0.5 mg, 0.025 µmole), UDP-galactose 75 µg (0.125 µmole), core-1-Gal-T 20 µL (10 mU) will then be added and the solution slowly rocked at 32° C. for 24 h. MALDI should indicate complete conversion of GLP-1-GalNAc into GLP-1-GalNAc-Gal.

1.4 Preparation of GLP-1-F-GalNAc-SA-PEG-20 KDa (C).

1.3a Sequential Process (pH 6.2).

A GLP-1-GalNAc solution containing 1 mg of protein will be buffer exchanged into 25 mM MES buffer (pH 6.2, 0.005% $NaN_3$) and CMP-SA-PEG (20 KDa) (5 mg, 0.25 µmole). $MnCl_2$ (100 µL, 100 mM solution) and ST6GalNAc-I (100 µL) will be added and the reaction mixture will be rocked slowly at 32° C. Aliquots will be taken at time points (24, 48 and 72 h) and analyzed by SDS-PAGE. After 24 h, no further reaction should be observed. The reaction mixture will be concentrated by spin filtration (5 KDa), buffer exchanged with 25 mM NaOAc (pH 4.9) and concentrated to 1 mL. The product will be purified using ion exchange (SP-Sepharose, 25 mM NaOAc, pH 4.9) and SEC (Superdex 75; PBS-pH 7.2, 0.005% tween 80, 1 ml/min). The desired fraction will be collected, concentrated to 0.5 mL and stored at 4° C.

1.4b One Pot Process Using ST6GalNAc-I (pH 6.0)

GLP-1 (960 g of protein dissolved in 3.2 mL of product formulation buffer) will be concentrated by spin filtration (5 KDa) to 0.5 mL and reconstituted in 25 mM MES buffer (pH 6.0, 0.005% $NaN_3$) to a total volume of about 1 mL, or a protein concentration of 1 mg/mL. UDP-GalNAc (6 mg, 9.21 µmol), GalNAc-T2 (80 µL, 80 mU), CMP-SA-PEG (20 KDa) (6 mg, 0.3 µmol) and mouse enzyme ST6GalNAc-I (120 µL will be added). The solution will be rocked at 32° C. for 48 h and purified using standard chromatography conditions on SP-Sepharose and SEC as described above. A total of 0.5 mg of protein ($A_{280}$) should be obtained, or about a 50% overall yield. The product structure will be confirmed by analysis with both MALDI and SDS-PAGE.

1.5 Preparation of GLP-1-GalNAc-Gal-SA-PEG-20 KDa (D)

1.5a Starting from GLP-1-GalNAc

UDP-galactose (4 mg, 6.5 mmole), core-1-Gal-$T_1$ (320 µL, 160 mU), CMP-SA-PEG-20 KDa (8 mg, 0.4 µmole), ST3Gal2 (80 µL, 0.07 mU) and 100 mM $MnCl_2$ (80 µL) will be directly added to the crude reaction mixture of the GLP-1-GalNAc (1.5 mg) in 25 mM MES buffer (pH 6.0), 1.5 mL, as described above. The resulting mixture will be incubated at 32° C. for 60 h, however, the reaction should be complete after 24 h. The reaction mixture will be centrifuged and the solution was concentrated to 0.2 mL using ultrafiltration (5 KDa) and then redissolved in 25 mM NaOAc (pH 4.5) to a final volume of 1 mL. The product will be purified using SP-Sepharose, the peak fractions were concentrated using a spin filter (5 KDa), and the residue purified further using SEC (Superdex 75). After concentration using a spin filter (5 KDa), the protein will be diluted to 1 mL using formulation buffer (PBS, 2.5% mannitol, 0.005% polysorbate, pH 6.5) and formulated at a protein concentration of 850 µg protein per mL ($A_{280}$). The overall yield should be around 55%.

1.5b Starting from GLP-1

GLP-1 (960 µg, 3.2 mL) will be concentrated by spin filter (5 KDa) and reconstituted with 25 mM MES buffer (pH 6.0, 0.005% $NaN_3$). The total volume of the GLP-1 solution will be adjusted to about 1 mg/mL and UDP-GalNAc (6 mg), GalNAc-T2 (80 µL), UDP-galactose (6 mg), core-1-Gal-$T_1$ (160 µL, 80 µU), CMP-SA-PEG (20 KDa) (6 mg), ST3Gal-2 (160 µL, 120 µU) and $MnCl_2$ (40 µL of a 100 mM solution) will be added. The resulting mixture will be incubated at 32° C. for 48 h.

1.6 SP Sepharose HPLC Chromatography.

The SP Sepharose column (HiTrap HP, FF, 1 mL, Amersham) can be used with a Varian HPLC system to separate individual GLP-1 peptides from crude extracts. Absorbance at 280 nm will be monitored. The column will be washed with 20 mL of 2 M NaCl in 25 mM sodium acetate (pH 4.5) contained 0.005% polysorbate 80 and was equilibrated with 20 mL of 25 mM sodium acetate (pH 4.5) contained 0.005% polysorbate 80 at a flow rate of 1.0 mL/min. The sample (about 0.5 mg/200 µL) will be injected onto the column and the product will be eluted using the gradient: 0-10 min, 25 mM NaAc, pH 4.5, 0.005% Polysorbate 80; 10-20 min, a gradient of 0-0.5 M NaCl in 25 mM NaAc, pH 4.5, 0.005% Polysorbate 80; 20-25 min, a gradient of 0.5 M-0.0 M NaCl in 25 mM NaAc, pH 4.5, 0.005% Polysorbate 80; and 25-30 min, 25 mM NaAc, pH 4.5, 0.005% Polysorbate 80). Fractions will be collected and concentrated to about 1 mL by using 5 KDa filter for analysis and further purification. Samples will be stored at 4° C.

1.6 Size Exclusion Chromatography

A Varian HPLC system containing a Superdex 75 column (HR 10/30, 10×300 mm, Amersham) will be used at a flow rate of 1.0 mL/min, while monitoring absorbance at 280 nm. The sample will be injected (about 0.2 mg/200 µL) and eluted with PBS, pH 7.4, 0.005% Polysorbate 80. Fractions will be collected and concentrated to about 1 mL by using a 5 KDa filter. Samples will be stored at 4° C.

1.7 SDS PAGE Analysis 4-20% acrylamide gradient slab gels will be used. Samples will be mixed with SDS Sample Buffer contained 1 mM DTT, and heated at 85° C. for 6 min. Samples will be run in gel under a consistent voltage at 125 mV for 1 h 50 min. After electrophoresis, the proteins will be stained with colloidal stain solution at room temperature for 2-24 hours depended on the protein concentration. The standard proteins shown on Tris-Glycine gel will be myosin (250 KDa), phosphorylase (148 KDa), BSA (98 KDa, glutamic dehydrogenase (64 KDa), alcohol dehydrogenase (50 KDa), carbonic anhydrase (36 KDa), lysozyme (22 KDa), aprotinin (6 KDa), and insulin β-chain (4 KDa). The protein bands in wet gel will be visualized using an HP Scanjet 7400C, and the picture of gel will be optimized using the HP Precision Scan Program.

1.8 MALDI Analysis

Samples will be dialyzed for 45 min using an MF-Millipore membrane filter (0.025 µm pore, 47 mm dia), floating on water. The dialyzed aliquots will be dried on a speedvac, re-dissolved in a small amount of water, and mixed with a solution of 2,5-dihydroxybenzoic acid (9 g/L) and 5-methoxysalicylic acid (1 g/L) dissolved in water/acetonitrile (50:50). The mixtures will be dried onto the MALDI target and analyzed using an Applied Biosystems DE-Pro mass spectrometer operated in the linear/negative-ion mode (Analytic lab, Neose Tech., Horsham, Pa.).

1.9 Peptide Mapping Analysis

Protein sample will be digested by trypsin overnight at 37° C. and loaded on a LC-MS system equipped with a Finnigan LCQ-classic ion trap mass spectrometer system with a electrospray ion source interfaced to a 15 cm×300 um id LC Packings PepMap reverse-phase capillary chromatography column. 1 µL volume of the extract will be injected and the peptides will be eluted from the column using a $CH_3CN$/0.1% formic acid gradient at a flow rate of 3 µL/min. The electrospray ion source will be operated at 4.0 kV. The digest will be analyzed using the data dependent multitask capability of the instrument acquiring full scan mass spectra to determine peptide molecular weights and product ion spectra to determine amino acid sequence in successive instrument scans. This mode of analysis produced approximately 100 collisionally induced dissociation (CID) spectra of ions ranging in abundance over several orders of magnitude.

The data will be analyzed by locating the ten to fifteen most abundant ions in a base peak presentation of the full scan data and interpreting the CID spectra of those ions to produce the tabulated results for each digest.

1.10 Protein Concentration Assay

Protein concentration will be determined by spectrophotometer at a fixed absorbance of 280 nm with 1 cm path length of cell. Triplicate readings will be measured for a tested sample with water and buffer as controls. Protein concentration will be determined using extinction coefficient at 0.799 mL/mg protein.

1.11 Formulation of Final Product

The formulation buffer contained pyrogen-free PBS, pH 6.5, 2.5% mannitol, and 0.05% Polysorbate 80 that will be degassed by vacuum and sterile filtered (0.2 µm).

Any endotoxin will be removed using a Detoxi-Gel™ equilibrated with 5 column beds of the formulation buffer (PBS, pH 6.5, 2.5% mannitol, and 0.05% Polysorbate 80). The flow rate was controlled by gravity at ~0.3 mL/min. Product samples will be applied onto the gel, and the product eluted using the formulation buffer. The volume of the collected product will be adjusted with additional formulation buffer to provide a protein concentration of about 100 µg/mL.

The peptide formulations will be sterile filtered (0.2µ) and the effluent will be dispensed as 1 mL aliquots into 2.0 mL pyrogen-free vials. In addition, aliquots will be taken for endotoxin and protein analysis. All products will be stored at 4° C.

1.12 Endotoxin Determination

Endotoxin contamination will be determined using *Limulus* Amebocyte Lysate (LAL) assay (BioWhittaker, Kinetic-QCL Kit, Cat#: 50-650U).

Example 2

Determination of Biological Activity of GLP-1 Peptides

Methods for measuring biological activity of GLP-1 are known in the art. In particular, GLP-1 activity will be measured in vivo and in vitro as disclosed in Xiao Q., et al. (2001) Biochemistry 40:2860-2869, which is incorporated herein by reference in its entirety.

While this invention has been disclosed with reference to specific embodiments, it is apparent that other embodiments and variations of this invention may be devised by others skilled in the art without departing from the true spirit and scope of the invention.

All patents, patent applications, and other publications cited in this application are incorporated by reference in the entirety.

SEQUENCE LISTING

```
<160> NUMBER OF SEQ ID NOS: 96

<210> SEQ ID NO 1
<211> LENGTH: 20
<212> TYPE: PRT
<213> ORGANISM: Artificial Sequence
<220> FEATURE:
<223> OTHER INFORMATION: MUC1 tandem repeat

<400> SEQUENCE: 1

His Gly Val Thr Ser Ala Pro Asp Thr Arg Pro Ala Pro Gly Ser Thr
1               5                   10                  15

Ala Pro Pro Ala
            20

<210> SEQ ID NO 2
<211> LENGTH: 24
<212> TYPE: PRT
<213> ORGANISM: Artificial Sequence
<220> FEATURE:
<223> OTHER INFORMATION: GalNAc4TAP24 glycopeptide

<400> SEQUENCE: 2

Thr Ala Pro Pro Ala His Gly Val Thr Ser Ala Pro Asp Thr Arg Pro
1               5                   10                  15

Ala Pro Gly Ser Thr Ala Pro Pro
            20

<210> SEQ ID NO 3
<211> LENGTH: 31
<212> TYPE: PRT
<213> ORGANISM: Artificial Sequence
<220> FEATURE:
<223> OTHER INFORMATION: GLP-1 mutant 1
<220> FEATURE:
<221> NAME/KEY: MISC_FEATURE
<222> LOCATION: (1)..(1)
<223> OTHER INFORMATION: Xaa is an O-glycosylated amino acid
<220> FEATURE:
<221> NAME/KEY: MOD_RES
<222> LOCATION: (31)..(31)
<223> OTHER INFORMATION: AMIDATION

<400> SEQUENCE: 3
```

```
Xaa His Ala Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg
            20                  25                  30
```

<210> SEQ ID NO 4
<211> LENGTH: 30
<212> TYPE: PRT
<213> ORGANISM: Artificial Sequence
<220> FEATURE:
<223> OTHER INFORMATION: GLP-1 mutant 2
<220> FEATURE:
<221> NAME/KEY: MISC_FEATURE
<222> LOCATION: (2)..(2)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 4

```
His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

<210> SEQ ID NO 5
<211> LENGTH: 30
<212> TYPE: PRT
<213> ORGANISM: Artificial Sequence
<220> FEATURE:
<223> OTHER INFORMATION: GLP-1 mutant 3
<220> FEATURE:
<221> NAME/KEY: MISC_FEATURE
<222> LOCATION: (3)..(3)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 5

```
His Ala Xaa Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

<210> SEQ ID NO 6
<211> LENGTH: 30
<212> TYPE: PRT
<213> ORGANISM: Artificial Sequence
<220> FEATURE:
<223> OTHER INFORMATION: GLP-1 mutant 4
<220> FEATURE:
<221> NAME/KEY: MISC_FEATURE
<222> LOCATION: (4)..(4)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 6

```
His Ala Glu Xaa Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

-continued

```
<210> SEQ ID NO 7
<211> LENGTH: 30
<212> TYPE: PRT
<213> ORGANISM: Artificial Sequence
<220> FEATURE:
<223> OTHER INFORMATION: GLP-1 mutant 5
<220> FEATURE:
<221> NAME/KEY: MISC_FEATURE
<222> LOCATION: (5)..(5)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 7

His Ala Glu Gly Xaa Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: GLP-1 mutant 6
<220> FEATURE:
<221> NAME/KEY: MISC_FEATURE
<222> LOCATION: (6)..(6)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 8

His Ala Glu Gly Thr Xaa Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: GLP-1 mutant 7
<220> FEATURE:
<221> NAME/KEY: MISC_FEATURE
<222> LOCATION: (7)..(7)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 9

His Ala Glu Gly Thr Phe Xaa Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: GLP-1 mutant 8
<220> FEATURE:
```

<221> NAME/KEY: MISC_FEATURE
<222> LOCATION: (8)..(8)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 10

His Ala Glu Gly Thr Phe Thr Xaa Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: GLP-1 mutant 9
<220> FEATURE:
<221> NAME/KEY: MISC_FEATURE
<222> LOCATION: (9)..(9)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 11

His Ala Glu Gly Thr Phe Thr Ser Xaa Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: GLP-1 mutant 10
<220> FEATURE:
<221> NAME/KEY: MISC_FEATURE
<222> LOCATION: (10)..(10)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 12

His Ala Glu Gly Thr Phe Thr Ser Asp Xaa Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: GLP-1 mutant 11
<220> FEATURE:
<221> NAME/KEY: MISC_FEATURE
<222> LOCATION: (11)..(11)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 13

His Ala Glu Gly Thr Phe Thr Ser Asp Val Xaa Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: GLP-1 mutant 12
<220> FEATURE:
<221> NAME/KEY: MISC_FEATURE
<222> LOCATION: (12)..(12)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 14

His Ala Glu Gly Thr Phe Thr Ser Asp Val Ser Xaa Tyr Leu Glu Gly
1               5                   10                  15

Gln Ala Ala Lys Glu Phe Ile Ala Trp Leu Val Lys Gly Arg
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: GLP-1 mutant 13
<220> FEATURE:
<221> NAME/KEY: MISC_FEATURE
<222> LOCATION: (13)..(13)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 15

His Ala Glu Gly Thr Phe Thr Ser Asp Val Ser Ser Xaa Leu Glu Gly
1               5                   10                  15

Gln Ala Ala Lys Glu Phe Ile Ala Trp Leu Val Lys Gly Arg
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: GLP-1 mutant 14
<220> FEATURE:
<221> NAME/KEY: MISC_FEATURE
<222> LOCATION: (14)..(14)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 16

His Ala Glu Gly Thr Phe Thr Ser Asp Val Ser Ser Tyr Xaa Glu Gly
1               5                   10                  15

Gln Ala Ala Lys Glu Phe Ile Ala Trp Leu Val Lys Gly Arg

```
                20                  25                  30

<210> SEQ ID NO 17
<211> LENGTH: 30
<212> TYPE: PRT
<213> ORGANISM: Artificial Sequence
<220> FEATURE:
<223> OTHER INFORMATION: GLP-1 mutant 15
<220> FEATURE:
<221> NAME/KEY: MISC_FEATURE
<222> LOCATION: (15)..(15)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 17

His Ala Glu Gly Thr Phe Thr Ser Asp Val Ser Ser Tyr Leu Xaa Gly
1               5                   10                  15

Gln Ala Ala Lys Glu Phe Ile Ala Trp Leu Val Lys Gly Arg
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: GLP-1 mutant 16
<220> FEATURE:
<221> NAME/KEY: MISC_FEATURE
<222> LOCATION: (16)..(16)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 18

His Ala Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: GLP-1 mutant 17
<220> FEATURE:
<221> NAME/KEY: MISC_FEATURE
<222> LOCATION: (17)..(17)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 19

His Ala Glu Gly Thr Phe Thr Ser Asp Val Ser Ser Tyr Leu Glu Gly
1               5                   10                  15

Xaa Ala Ala Lys Glu Phe Ile Ala Trp Leu Val Lys Gly Arg
            20                  25                  30

<210> SEQ ID NO 20
<211> LENGTH: 30
<212> TYPE: PRT
<213> ORGANISM: Artificial Sequence
```

```
<220> FEATURE:
<223> OTHER INFORMATION: GLP-1 mutant 18
<220> FEATURE:
<221> NAME/KEY: MISC_FEATURE
<222> LOCATION: (18)..(18)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 20

His Ala Glu Gly Thr Phe Thr Ser Asp Val Ser Ser Tyr Leu Glu Gly
1               5                   10                  15

Gln Xaa Ala Lys Glu Phe Ile Ala Trp Leu Val Lys Gly Arg
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: GLP-1 mutant 19
<220> FEATURE:
<221> NAME/KEY: MISC_FEATURE
<222> LOCATION: (19)..(19)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 21

His Ala Glu Gly Thr Phe Thr Ser Asp Val Ser Ser Tyr Leu Glu Gly
1               5                   10                  15

Gln Ala Xaa Lys Glu Phe Ile Ala Trp Leu Val Lys Gly Arg
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: GLP-1 mutant 20
<220> FEATURE:
<221> NAME/KEY: MISC_FEATURE
<222> LOCATION: (20)..(20)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 22

His Ala Glu Gly Thr Phe Thr Ser Asp Val Ser Ser Tyr Leu Glu Gly
1               5                   10                  15

Gln Ala Ala Xaa Glu Phe Ile Ala Trp Leu Val Lys Gly Arg
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: GLP-1 mutant 21
<220> FEATURE:
<221> NAME/KEY: MISC_FEATURE
<222> LOCATION: (21)..(21)
<223> OTHER INFORMATION: Xaa is an O-glycosylated amino acid
<220> FEATURE:
```

```
<221> NAME/KEY: MOD_RES
<222> LOCATION: (30)..(30)
<223> OTHER INFORMATION: AMIDATION

<400> SEQUENCE: 23

His Ala Glu Gly Thr Phe Thr Ser Asp Val Ser Ser Tyr Leu Glu Gly
1               5                   10                  15

Gln Ala Ala Lys Xaa Phe Ile Ala Trp Leu Val Lys Gly Arg
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: GLP-1 mutant 22
<220> FEATURE:
<221> NAME/KEY: MISC_FEATURE
<222> LOCATION: (22)..(22)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 24

His Ala Glu Gly Thr Phe Thr Ser Asp Val Ser Ser Tyr Leu Glu Gly
1               5                   10                  15

Gln Ala Ala Lys Glu Xaa Ile Ala Trp Leu Val Lys Gly Arg
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: GLP-1 mutant 23
<220> FEATURE:
<221> NAME/KEY: MISC_FEATURE
<222> LOCATION: (23)..(23)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 25

His Ala Glu Gly Thr Phe Thr Ser Asp Val Ser Ser Tyr Leu Glu Gly
1               5                   10                  15

Gln Ala Ala Lys Glu Phe Xaa Ala Trp Leu Val Lys Gly Arg
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: GLP-1 mutant 24
<220> FEATURE:
<221> NAME/KEY: MISC_FEATURE
<222> LOCATION: (24)..(24)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 26

His Ala Glu Gly Thr Phe Thr Ser Asp Val Ser Ser Tyr Leu Glu Gly
```

```
                1               5                   10                  15
Gln Ala Ala Lys Glu Phe Ile Xaa Trp Leu Val Lys Gly Arg
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: GLP-1 mutant 25
<220> FEATURE:
<221> NAME/KEY: MISC_FEATURE
<222> LOCATION: (25)..(25)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 27

His Ala Glu Gly Thr Phe Thr Ser Asp Val Ser Ser Tyr Leu Glu Gly
1               5                   10                  15

Gln Ala Ala Lys Glu Phe Ile Ala Xaa Leu Val Lys Gly Arg
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: GLP-1 mutant 26
<220> FEATURE:
<221> NAME/KEY: MISC_FEATURE
<222> LOCATION: (26)..(26)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 28

His Ala Glu Gly Thr Phe Thr Ser Asp Val Ser Ser Tyr Leu Glu Gly
1               5                   10                  15

Gln Ala Ala Lys Glu Phe Ile Ala Trp Xaa Val Lys Gly Arg
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: GLP-1 mutant 27
<220> FEATURE:
<221> NAME/KEY: MISC_FEATURE
<222> LOCATION: (27)..(27)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 29

His Ala Glu Gly Thr Phe Thr Ser Asp Val Ser Ser Tyr Leu Glu Gly
1               5                   10                  15

Gln Ala Ala Lys Glu Phe Ile Ala Trp Leu Xaa Lys Gly Arg
            20                  25                  30

<210> SEQ ID NO 30
```

<210> SEQ ID NO 30
<211> LENGTH: 30
<212> TYPE: PRT
<213> ORGANISM: Artificial Sequence
<220> FEATURE:
<223> OTHER INFORMATION: GLP-1 mutant 28
<220> FEATURE:
<221> NAME/KEY: MISC_FEATURE
<222> LOCATION: (28)..(28)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 30

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Xaa Gly Arg
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: GLP-1 mutant 29
<220> FEATURE:
<221> NAME/KEY: MISC_FEATURE
<222> LOCATION: (29)..(29)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 31

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Xaa Arg
            20                  25                  30

<210> SEQ ID NO 32
<211> LENGTH: 30
<212> TYPE: PRT
<213> ORGANISM: Artificial Sequence
<220> FEATURE:
<223> OTHER INFORMATION: GLP-1 mutant 30
<220> FEATURE:
<221> NAME/KEY: MISC_FEATURE
<222> LOCATION: (30)..(30)
<223> OTHER INFORMATION: Xaa is an O-glycosylated amino acid
<220> FEATURE:
<221> NAME/KEY: MOD_RES
<222> LOCATION: (30)..(30)
<223> OTHER INFORMATION: AMIDATION

<400> SEQUENCE: 32

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Xaa
            20                  25                  30

<210> SEQ ID NO 33
<211> LENGTH: 31
<212> TYPE: PRT
<213> ORGANISM: Artificial Sequence
<220> FEATURE:
<223> OTHER INFORMATION: GLP-1 mutant 31
<220> FEATURE:
<221> NAME/KEY: MISC_FEATURE

```
<222> LOCATION: (31)..(31)
<223> OTHER INFORMATION: Xaa is an O-glycosylated amino acid
<220> FEATURE:
<221> NAME/KEY: MOD_RES
<222> LOCATION: (31)..(31)
<223> OTHER INFORMATION: AMIDATION

<400> SEQUENCE: 33

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Xaa
            20                  25                  30

<210> SEQ ID NO 34
<211> LENGTH: 76
<212> TYPE: PRT
<213> ORGANISM: Artificial Sequence
<220> FEATURE:
<223> OTHER INFORMATION: oxyntomodulin-GLP-1 fusion

<400> SEQUENCE: 34

His Ser Gln Gly Thr Phe Thr Ser Asp Tyr Ser Lys Tyr Leu Asp Ser
 1               5                  10                  15

Arg Arg Ala Gln Asp Phe Val Gln Trp Leu Met Asn Thr Lys Arg Asn
            20                  25                  30

Arg Asn Asn Ile Ala Lys Arg His Asp Glu Phe Glu Arg His Ala Glu
35                  40                  45

Gly Thr Phe Thr Ser Asp Val Ser Ser Tyr Leu Glu Gly Gln Ala Ala
50                  55                  60

Lys Glu Phe Ile Ala Trp Leu Val Lys Gly Arg Gly
65                  70                  75

<210> SEQ ID NO 35
<211> LENGTH: 20
<212> TYPE: PRT
<213> ORGANISM: Artificial Sequence
<220> FEATURE:
<223> OTHER INFORMATION: oxyntomodulin-GLP-1 (OG1) fusion peptide

<400> SEQUENCE: 35

Thr Lys Arg Asn Arg Asn Asn Ile Ala Lys Arg His Asp Glu Phe Glu
 1               5                  10                  15

Arg His Ala Glu
            20

<210> SEQ ID NO 36
<211> LENGTH: 21
<212> TYPE: PRT
<213> ORGANISM: Artificial Sequence
<220> FEATURE:
<223> OTHER INFORMATION: OG1 mutant 1
<220> FEATURE:
<221> NAME/KEY: VARIANT
<222> LOCATION: (2)..(2)
<223> OTHER INFORMATION: Xaa is Asn, Lys, Ala, Gly, Ser, Thr, or Leu
<220> FEATURE:
<221> NAME/KEY: VARIANT
<222> LOCATION: (3)..(3)
<223> OTHER INFORMATION: Xaa is Arg, Gly, Ala, Ser, Thr, or Leu
<220> FEATURE:
<221> NAME/KEY: VARIANT
<222> LOCATION: (4)..(4)
<223> OTHER INFORMATION: Xaa is Asn, Ser, or Thr
<220> FEATURE:
<221> NAME/KEY: VARIANT
<222> LOCATION: (7)..(7)
<223> OTHER INFORMATION: Xaa is present or absent; when present, Xaa is
```

```
                Gly or Ala
<220> FEATURE:
<221> NAME/KEY: VARIANT
<222> LOCATION: (11)..(11)
<223> OTHER INFORMATION: Xaa is Lys or Pro
<220> FEATURE:
<221> NAME/KEY: VARIANT
<222> LOCATION: (12)..(12)
<223> OTHER INFORMATION: Xaa is Thr, Ser, or Lys
<220> FEATURE:
<221> NAME/KEY: VARIANT
<222> LOCATION: (13)..(13)
<223> OTHER INFORMATION: Xaa is His, Ala, Gln, Asn, Gly, or any
                uncharged amino acid
<220> FEATURE:
<221> NAME/KEY: VARIANT
<222> LOCATION: (14)..(14)
<223> OTHER INFORMATION: Xaa is Asp, Gly, Ala, Asn, Glu, or any
                uncharged amino acid
<220> FEATURE:
<221> NAME/KEY: VARIANT
<222> LOCATION: (15)..(15)
<223> OTHER INFORMATION: Xaa is Glu, Ala, Gly, Met, or any uncharged
                amino acid
<220> FEATURE:
<221> NAME/KEY: VARIANT
<222> LOCATION: (18)..(18)
<223> OTHER INFORMATION: Xaa is Arg, Ala, Gly, Ser, Thr, Val, Ile, Leu,
                or any uncharged amino acid

<400> SEQUENCE: 36

Thr Xaa Xaa Xaa Arg Asn Xaa Asn Ile Ala Xaa Xaa Xaa Xaa Xaa Phe
1               5                   10                  15

Glu Xaa His Ala Glu
            20

<210> SEQ ID NO 37
<211> LENGTH: 20
<212> TYPE: PRT
<213> ORGANISM: Artificial Sequence
<220> FEATURE:
<223> OTHER INFORMATION: OG1 mutant 2

<400> SEQUENCE: 37

Thr Asn Ala Asn Arg Asn Asn Ile Ala Pro Thr His Asp Glu Phe Glu
1               5                   10                  15

Ala His Ala Glu
            20

<210> SEQ ID NO 38
<211> LENGTH: 20
<212> TYPE: PRT
<213> ORGANISM: Artificial Sequence
<220> FEATURE:
<223> OTHER INFORMATION: OG1 mutant 3

<400> SEQUENCE: 38

Thr Asn Ala Asn Arg Asn Asn Ile Ala Pro Thr Gln Asp Glu Phe Glu
1               5                   10                  15

Ala His Ala Glu
            20

<210> SEQ ID NO 39
<211> LENGTH: 20
<212> TYPE: PRT
<213> ORGANISM: Artificial Sequence
<220> FEATURE:
<223> OTHER INFORMATION: OG1 mutant 4

<400> SEQUENCE: 39
```

```
Thr Asn Ala Asn Arg Asn Asn Ile Ala Pro Thr Thr Asp Glu Phe Glu
1               5                   10                  15

Ala His Ala Glu
            20

<210> SEQ ID NO 40
<211> LENGTH: 20
<212> TYPE: PRT
<213> ORGANISM: Artificial Sequence
<220> FEATURE:
<223> OTHER INFORMATION: OG1 mutant 5

<400> SEQUENCE: 40

Thr Asn Ala Asn Arg Asn Asn Ile Ala Pro Thr Gln Gly Glu Phe Glu
1               5                   10                  15

Ala His Ala Glu
            20

<210> SEQ ID NO 41
<211> LENGTH: 20
<212> TYPE: PRT
<213> ORGANISM: Artificial Sequence
<220> FEATURE:
<223> OTHER INFORMATION: OG1 mutant 6

<400> SEQUENCE: 41

Thr Asn Ala Asn Arg Asn Asn Ile Ala Pro Thr Gln Gly Ala Phe Glu
1               5                   10                  15

Ala His Ala Glu
            20

<210> SEQ ID NO 42
<211> LENGTH: 20
<212> TYPE: PRT
<213> ORGANISM: Artificial Sequence
<220> FEATURE:
<223> OTHER INFORMATION: OG1 mutant 7

<400> SEQUENCE: 42

Thr Asn Ala Asn Arg Asn Asn Ile Ala Pro Thr Gln Gly Ala Met Pro
1               5                   10                  15

Ala His Ala Glu
            20

<210> SEQ ID NO 43
<211> LENGTH: 20
<212> TYPE: PRT
<213> ORGANISM: Artificial Sequence
<220> FEATURE:
<223> OTHER INFORMATION: OG1 mutant 8

<400> SEQUENCE: 43

Thr Ala Arg Asn Arg Asn Asn Ile Ala Pro Thr Gln Gly Ala Met Glu
1               5                   10                  15

Ala His Ala Glu
            20

<210> SEQ ID NO 44
<211> LENGTH: 20
<212> TYPE: PRT
<213> ORGANISM: Artificial Sequence
<220> FEATURE:
<223> OTHER INFORMATION: OG1 mutant 9
```

```
<400> SEQUENCE: 44

Thr Asn Ala Asn Arg Asn Asn Ile Ala Pro Thr Ile Asn Thr Phe Glu
1               5                   10                  15

Ala His Ala Glu
            20

<210> SEQ ID NO 45
<211> LENGTH: 20
<212> TYPE: PRT
<213> ORGANISM: Artificial Sequence
<220> FEATURE:
<223> OTHER INFORMATION: OG1 mutant 10

<400> SEQUENCE: 45

Thr Asn Ala Asn Arg Asn Asn Ile Ala Pro Thr Gln Ala Tyr Ser Glu
1               5                   10                  15

Gly His Ala Glu
            20

<210> SEQ ID NO 46
<211> LENGTH: 20
<212> TYPE: PRT
<213> ORGANISM: Artificial Sequence
<220> FEATURE:
<223> OTHER INFORMATION: OG1 mutant 11

<400> SEQUENCE: 46

Thr Asn Ala Asn Arg Asn Asn Ile Ala Pro Thr Gln Ala Tyr Phe Glu
1               5                   10                  15

Gly His Ala Glu
            20

<210> SEQ ID NO 47
<211> LENGTH: 20
<212> TYPE: PRT
<213> ORGANISM: Artificial Sequence
<220> FEATURE:
<223> OTHER INFORMATION: OG1 mutant 12

<400> SEQUENCE: 47

Thr Asn Ala Asn Arg Asn Asn Ile Ala Pro Thr Thr Ala Ser Phe Glu
1               5                   10                  15

Gly His Ala Glu
            20

<210> SEQ ID NO 48
<211> LENGTH: 20
<212> TYPE: PRT
<213> ORGANISM: Artificial Sequence
<220> FEATURE:
<223> OTHER INFORMATION: OG1 mutant 13

<400> SEQUENCE: 48

Thr Asn Ala Asn Arg Asn Asn Ile Ala Pro Thr Thr Leu Tyr Val Glu
1               5                   10                  15

Gly His Ala Glu
            20

<210> SEQ ID NO 49
<211> LENGTH: 20
<212> TYPE: PRT
<213> ORGANISM: Artificial Sequence
<220> FEATURE:
<223> OTHER INFORMATION: OG1 mutant 14
```

```
<400> SEQUENCE: 49

Thr Ala Arg Asn Arg Asn Asn Ile Ala Pro Thr Ile Asn Thr Phe Glu
1               5                   10                  15

Gly His Ala Glu
            20

<210> SEQ ID NO 50
<211> LENGTH: 20
<212> TYPE: PRT
<213> ORGANISM: Artificial Sequence
<220> FEATURE:
<223> OTHER INFORMATION: OG1 mutant 15

<400> SEQUENCE: 50

Thr Asn Ala Asn Arg Asn Asn Ile Ala Pro Thr Ile Asn Thr Phe Glu
1               5                   10                  15

Gly His Ala Glu
            20

<210> SEQ ID NO 51
<211> LENGTH: 20
<212> TYPE: PRT
<213> ORGANISM: Artificial Sequence
<220> FEATURE:
<223> OTHER INFORMATION: OG1 mutant 16

<400> SEQUENCE: 51

Thr Asn Ala Asn Arg Ser Gly Asp Ile Pro Thr Ile Asn Thr Phe Glu
1               5                   10                  15

Gly His Ala Glu
            20

<210> SEQ ID NO 52
<211> LENGTH: 83
<212> TYPE: PRT
<213> ORGANISM: Artificial Sequence
<220> FEATURE:
<223> OTHER INFORMATION: GLP-1-GLP-2 fusion (G1G2)

<400> SEQUENCE: 52

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Arg
            20                  25                  30

Arg Asp Phe Pro Glu Glu Val Ala Ile Val Glu Leu Gly Arg Arg
        35                  40                  45

His Ala Asp Gly Ser Phe Ser Asp Glu Met Asn Thr Ile Leu Asp Asn
    50                  55                  60

Leu Ala Ala Arg Asp Phe Ile Asn Trp Leu Ile Gln Thr Lys Ile Thr
65                  70                  75                  80

Asp Arg Lys

<210> SEQ ID NO 53
<211> LENGTH: 85
<212> TYPE: PRT
<213> ORGANISM: Artificial Sequence
<220> FEATURE:
<223> OTHER INFORMATION: G1G2 mutant 1
<220> FEATURE:
<221> NAME/KEY: VARIANT
<222> LOCATION: (2)..(2)
<223> OTHER INFORMATION: Xaa is Ala, Gly, Ser, or Thr
```

```
<220> FEATURE:
<221> NAME/KEY: VARIANT
<222> LOCATION: (32)..(32)
<223> OTHER INFORMATION: Xaa is Arg, Ala, Gly, Val, Ile, Leu, Gln,
      or Pro
<220> FEATURE:
<221> NAME/KEY: VARIANT
<222> LOCATION: (33)..(33)
<223> OTHER INFORMATION: Xaa is Arg, Ala, Gly, Val, Ile, Leu, Gln, or
      Pro
<220> FEATURE:
<221> NAME/KEY: VARIANT
<222> LOCATION: (37)..(37)
<223> OTHER INFORMATION: Xaa is Thr, Ser, or Glu
<220> FEATURE:
<221> NAME/KEY: VARIANT
<222> LOCATION: (38)..(38)
<223> OTHER INFORMATION: Xaa is Glu, Ser, Thr, Gln, Ile, Val, Leu, or
      uncharged amino acid
<220> FEATURE:
<221> NAME/KEY: VARIANT
<222> LOCATION: (39)..(39)
<223> OTHER INFORMATION: Xaa is present or absent; when present, Xaa is
      Ser, Asn, Tyr, or Val
<220> FEATURE:
<221> NAME/KEY: VARIANT
<222> LOCATION: (40)..(40)
<223> OTHER INFORMATION: Xaa is present when Xaa at residue 39 is Ser
      or Asn; otherwise Xaa is absent; when present, Xaa is Leu when Xaa
      at residue 39 is Ser, and Xaa is Thr when Xaa at residue 39 is Asn
<220> FEATURE:
<221> NAME/KEY: VARIANT
<222> LOCATION: (41)..(41)
<223> OTHER INFORMATION: Xaa is present when Xaa at residue 39 is Ser
      and Xaa at residue 40 is Leu; otherwise Xaa is absent; when
      present, Xaa is Pro
<220> FEATURE:
<221> NAME/KEY: VARIANT
<222> LOCATION: (42)..(42)
<223> OTHER INFORMATION: Xaa is Pro, Ala, Ile, Val, or Gly
<220> FEATURE:
<221> NAME/KEY: VARIANT
<222> LOCATION: (43)..(43)
<223> OTHER INFORMATION: Xaa is Glu, Tyr, Ile, Asn, Ala, Phe, Gly, or
      any uncharged amino acid
<220> FEATURE:
<221> NAME/KEY: VARIANT
<222> LOCATION: (49)..(49)
<223> OTHER INFORMATION: Xaa is Arg, Ala, Gly, Ser, Thr, Val, Ile, Leu,
      or any uncharged amino acid
<220> FEATURE:
<221> NAME/KEY: VARIANT
<222> LOCATION: (50)..(50)
<223> OTHER INFORMATION: Xaa is Arg, Ala, Gly, Ser, Thr, Val, Ile, Leu,
      or any uncharged amino acid

<400> SEQUENCE: 53

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Xaa
            20                  25                  30

Xaa Asp Phe Pro Xaa Xaa Xaa Xaa Xaa Xaa Val Glu Glu Leu Gly
        35                  40                  45

Xaa Xaa His Ala Asp Gly Ser Phe Ser Asp Glu Met Asn Thr Ile Leu
    50                  55                  60

Asp Asn Leu Ala Ala Arg Asp Phe Ile Asn Trp Leu Ile Gln Thr Lys
65                  70                  75                  80

Ile Thr Asp Arg Lys
                85

<210> SEQ ID NO 54
<211> LENGTH: 86
```

```
<212> TYPE: PRT
<213> ORGANISM: Artificial Sequence
<220> FEATURE:
<223> OTHER INFORMATION: G1G2 mutant 2

<400> SEQUENCE: 54

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gln
            20                  25                  30

Pro Asp Phe Pro Glu Gly Ser Leu Pro Val Ala Ile Val Glu Glu Leu
        35                  40                  45

Gly Arg Gly His Ala Asp Gly Ser Phe Ser Asp Glu Met Asn Thr Ile
    50                  55                  60

Leu Asp Asn Leu Ala Ala Arg Asp Phe Ile Asn Trp Leu Ile Gln Thr
65                  70                  75                  80

Lys Ile Thr Asp Arg Lys
                85

<210> SEQ ID NO 55
<211> LENGTH: 86
<212> TYPE: PRT
<213> ORGANISM: Artificial Sequence
<220> FEATURE:
<223> OTHER INFORMATION: G1G2 mutant 3

<400> SEQUENCE: 55

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gln
            20                  25                  30

Pro Asp Phe Pro Thr Gly Ser Leu Pro Val Ala Ile Val Glu Glu Leu
        35                  40                  45

Gly Arg Gly His Ala Asp Gly Ser Phe Ser Asp Glu Met Asn Thr Ile
    50                  55                  60

Leu Asp Asn Leu Ala Ala Arg Asp Phe Ile Asn Trp Leu Ile Gln Thr
65                  70                  75                  80

Lys Ile Thr Asp Arg Lys
                85

<210> SEQ ID NO 56
<211> LENGTH: 86
<212> TYPE: PRT
<213> ORGANISM: Artificial Sequence
<220> FEATURE:
<223> OTHER INFORMATION: G1G2 mutant 4

<400> SEQUENCE: 56

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gln
            20                  25                  30

Pro Asp Phe Pro Thr Thr Ser Glu Pro Val Ala Ile Val Glu Glu Leu
        35                  40                  45

Gly Arg Gly His Ala Asp Gly Ser Phe Ser Asp Glu Met Asn Thr Ile
    50                  55                  60

Leu Asp Asn Leu Ala Ala Arg Asp Phe Ile Asn Trp Leu Ile Gln Thr
65                  70                  75                  80

Lys Ile Thr Asp Arg Lys
```

-continued

```
                85

<210> SEQ ID NO 57
<211> LENGTH: 86
<212> TYPE: PRT
<213> ORGANISM: Artificial Sequence
<220> FEATURE:
<223> OTHER INFORMATION: G1G2 mutant 5

<400> SEQUENCE: 57

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gln
            20                  25                  30

Pro Asp Phe Pro Thr Ala Val Ile Pro Val Ala Ile Val Glu Glu Leu
        35                  40                  45

Gly Arg Gly His Ala Asp Gly Ser Phe Ser Asp Glu Met Asn Thr Ile
    50                  55                  60

Leu Asp Asn Leu Ala Ala Arg Asp Phe Ile Asn Trp Leu Ile Gln Thr
65                  70                  75                  80

Lys Ile Thr Asp Arg Lys
                85

<210> SEQ ID NO 58
<211> LENGTH: 86
<212> TYPE: PRT
<213> ORGANISM: Artificial Sequence
<220> FEATURE:
<223> OTHER INFORMATION: G1G2 mutant 6

<400> SEQUENCE: 58

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gln
            20                  25                  30

Pro Asp Phe Pro Gly Ser Thr Ala Pro Val Ala Ile Val Glu Glu Leu
        35                  40                  45

Gly Arg Gly His Ala Asp Gly Ser Phe Ser Asp Glu Met Asn Thr Ile
    50                  55                  60

Leu Asp Asn Leu Ala Ala Arg Asp Phe Ile Asn Trp Leu Ile Gln Thr
65                  70                  75                  80

Lys Ile Thr Asp Arg Lys
                85

<210> SEQ ID NO 59
<211> LENGTH: 86
<212> TYPE: PRT
<213> ORGANISM: Artificial Sequence
<220> FEATURE:
<223> OTHER INFORMATION: G1G2 mutant 7

<400> SEQUENCE: 59

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gln
            20                  25                  30

Pro Asp Phe Pro Leu Thr Leu Glu Pro Val Ala Ile Val Glu Glu Leu
        35                  40                  45

Gly Arg Gly His Ala Asp Gly Ser Phe Ser Asp Glu Met Asn Thr Ile
    50                  55                  60
```

```
Leu Asp Asn Leu Ala Ala Arg Asp Phe Ile Asn Trp Leu Ile Gln Thr
 65                  70                  75                  80

Lys Ile Thr Asp Arg Lys
                85

<210> SEQ ID NO 60
<211> LENGTH: 86
<212> TYPE: PRT
<213> ORGANISM: Artificial Sequence
<220> FEATURE:
<223> OTHER INFORMATION: G1G2 mutant 8

<400> SEQUENCE: 60

His Ser Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Gly Gln
                 20                  25                  30

Pro Asp Phe Pro Thr Ser Gly Glu Pro Val Ala Ile Val Glu Glu Leu
             35                  40                  45

Gly Arg Gly His Ala Asp Gly Ser Phe Ser Asp Glu Met Asn Thr Ile
 50                  55                  60

Leu Asp Asn Leu Ala Ala Arg Asp Phe Ile Asn Trp Leu Ile Gln Thr
 65                  70                  75                  80

Lys Ile Thr Asp Arg Lys
                85

<210> SEQ ID NO 61
<211> LENGTH: 86
<212> TYPE: PRT
<213> ORGANISM: Artificial Sequence
<220> FEATURE:
<223> OTHER INFORMATION: G1G2 mutant 9

<400> SEQUENCE: 61

His Ser Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Gly Gln
                 20                  25                  30

Pro Asp Phe Pro Thr Ile Asn Thr Pro Val Ala Ile Val Glu Glu Leu
             35                  40                  45

Gly Arg Gly His Ala Asp Gly Ser Phe Ser Asp Glu Met Asn Thr Ile
 50                  55                  60

Leu Asp Asn Leu Ala Ala Arg Asp Phe Ile Asn Trp Leu Ile Gln Thr
 65                  70                  75                  80

Lys Ile Thr Asp Arg Lys
                85

<210> SEQ ID NO 62
<211> LENGTH: 86
<212> TYPE: PRT
<213> ORGANISM: Artificial Sequence
<220> FEATURE:
<223> OTHER INFORMATION: G1G2 mutant 10

<400> SEQUENCE: 62

His Ser Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Gly Gln
                 20                  25                  30
```

```
Pro Asp Phe Pro Thr Thr Leu Tyr Pro Val Ala Ile Val Glu Glu Leu
         35                  40                  45

Gly Arg Gly His Ala Asp Gly Ser Phe Ser Asp Glu Met Asn Thr Ile
 50                  55                  60

Leu Asp Asn Leu Ala Ala Arg Asp Phe Ile Asn Trp Leu Ile Gln Thr
 65                  70                  75                  80

Lys Ile Thr Asp Arg Lys
                 85

<210> SEQ ID NO 63
<211> LENGTH: 86
<212> TYPE: PRT
<213> ORGANISM: Artificial Sequence
<220> FEATURE:
<223> OTHER INFORMATION: G1G2 mutant 11

<400> SEQUENCE: 63

His Ser Glu Gly Thr Phe Thr Ser Asp Val Ser Ser Tyr Leu Glu Gly
 1                5                  10                  15

Gln Ala Ala Lys Glu Phe Ile Ala Trp Leu Val Lys Gly Arg Gly Gln
                 20                  25                  30

Pro Asp Phe Pro Glu Gly Ser Leu Pro Thr Ala Ile Val Glu Glu Leu
         35                  40                  45

Gly Arg Gly His Ala Asp Gly Ser Phe Ser Asp Glu Met Asn Thr Ile
 50                  55                  60

Leu Asp Asn Leu Ala Ala Arg Asp Phe Ile Asn Trp Leu Ile Gln Thr
 65                  70                  75                  80

Lys Ile Thr Asp Arg Lys
                 85

<210> SEQ ID NO 64
<211> LENGTH: 86
<212> TYPE: PRT
<213> ORGANISM: Artificial Sequence
<220> FEATURE:
<223> OTHER INFORMATION: G1G2 mutant 12

<400> SEQUENCE: 64

His Ser Glu Gly Thr Phe Thr Ser Asp Val Ser Ser Tyr Leu Glu Gly
 1                5                  10                  15

Gln Ala Ala Lys Glu Phe Ile Ala Trp Leu Val Lys Gly Arg Gly Gln
                 20                  25                  30

Pro Asp Phe Pro Glu Gly Ser Leu Pro Thr Ile Asn Thr Glu Glu Leu
         35                  40                  45

Gly Arg Gly His Ala Asp Gly Ser Phe Ser Asp Glu Met Asn Thr Ile
 50                  55                  60

Leu Asp Asn Leu Ala Ala Arg Asp Phe Ile Asn Trp Leu Ile Gln Thr
 65                  70                  75                  80

Lys Ile Thr Asp Arg Lys
                 85

<210> SEQ ID NO 65
<211> LENGTH: 86
<212> TYPE: PRT
<213> ORGANISM: Artificial Sequence
<220> FEATURE:
<223> OTHER INFORMATION: G1G2 mutant 13

<400> SEQUENCE: 65

His Ser Glu Gly Thr Phe Thr Ser Asp Val Ser Ser Tyr Leu Glu Gly
```

```
1               5                   10                  15
Gln Ala Ala Lys Glu Phe Ile Ala Trp Leu Val Lys Gly Arg Gly Gln
                20                  25                  30

Pro Asp Phe Pro Glu Gly Ser Leu Pro Thr Gln Ala Val Glu Glu Leu
                35                  40                  45

Gly Arg Gly His Ala Asp Gly Ser Phe Ser Asp Glu Met Asn Thr Ile
 50                  55                  60

Leu Asp Asn Leu Ala Ala Arg Asp Phe Ile Asn Trp Leu Ile Gln Thr
 65                  70                  75                  80

Lys Ile Thr Asp Arg Lys
                85

<210> SEQ ID NO 66
<211> LENGTH: 83
<212> TYPE: PRT
<213> ORGANISM: Artificial Sequence
<220> FEATURE:
<223> OTHER INFORMATION: G1G2 mutant 14

<400> SEQUENCE: 66

His Ser Glu Gly Thr Phe Thr Ser Asp Val Ser Ser Tyr Leu Glu Gly
 1               5                   10                  15

Gln Ala Ala Lys Glu Phe Ile Ala Trp Leu Val Lys Gly Arg Gly Gln
                20                  25                  30

Ala Asp Phe Pro Glu Glu Val Pro Thr Val Glu Glu Leu Gly Arg Gly
                35                  40                  45

His Ala Asp Gly Ser Phe Ser Asp Glu Met Asn Thr Ile Leu Asp Asn
 50                  55                  60

Leu Ala Ala Arg Asp Phe Ile Asn Trp Leu Ile Gln Thr Lys Ile Thr
 65                  70                  75                  80

Asp Arg Lys

<210> SEQ ID NO 67
<211> LENGTH: 83
<212> TYPE: PRT
<213> ORGANISM: Artificial Sequence
<220> FEATURE:
<223> OTHER INFORMATION: G1G2 mutant 15

<400> SEQUENCE: 67

His Ser Glu Gly Thr Phe Thr Ser Asp Val Ser Ser Tyr Leu Glu Gly
 1               5                   10                  15

Gln Ala Ala Lys Glu Phe Ile Ala Trp Leu Val Lys Gly Arg Gly Gln
                20                  25                  30

Ala Asp Phe Pro Glu Glu Val Pro Thr Ile Asn Thr Leu Gly Arg Gly
                35                  40                  45

His Ala Asp Gly Ser Phe Ser Asp Glu Met Asn Thr Ile Leu Asp Asn
 50                  55                  60

Leu Ala Ala Arg Asp Phe Ile Asn Trp Leu Ile Gln Thr Lys Ile Thr
 65                  70                  75                  80

Asp Arg Lys

<210> SEQ ID NO 68
<211> LENGTH: 83
<212> TYPE: PRT
<213> ORGANISM: Artificial Sequence
<220> FEATURE:
<223> OTHER INFORMATION: G1G2 mutant 16
```

<400> SEQUENCE: 68

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gln
            20                  25                  30

Ala Asp Phe Pro Glu Val Pro Thr Gln Gly Ala Leu Gly Arg Gly
        35                  40                  45

His Ala Asp Gly Ser Phe Ser Asp Glu Met Asn Thr Ile Leu Asp Asn
    50                  55                  60

Leu Ala Ala Arg Asp Phe Ile Asn Trp Leu Ile Gln Thr Lys Ile Thr
65                  70                  75                  80

Asp Arg Lys

<210> SEQ ID NO 69
<211> LENGTH: 83
<212> TYPE: PRT
<213> ORGANISM: Artificial Sequence
<220> FEATURE:
<223> OTHER INFORMATION: G1G2 mutant 17

<400> SEQUENCE: 69

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gln
            20                  25                  30

Ala Asp Phe Pro Glu Glu Val Pro Thr Thr Leu Tyr Leu Gly Arg Gly
        35                  40                  45

His Ala Asp Gly Ser Phe Ser Asp Glu Met Asn Thr Ile Leu Asp Asn
    50                  55                  60

Leu Ala Ala Arg Asp Phe Ile Asn Trp Leu Ile Gln Thr Lys Ile Thr
65                  70                  75                  80

Asp Arg Lys

<210> SEQ ID NO 70
<211> LENGTH: 83
<212> TYPE: PRT
<213> ORGANISM: Artificial Sequence
<220> FEATURE:
<223> OTHER INFORMATION: G1G2 mutant 18

<400> SEQUENCE: 70

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gln
            20                  25                  30

Ala Asp Phe Pro Thr Val Leu Pro Ile Val Glu Glu Leu Gly Arg Gly
        35                  40                  45

His Ala Asp Gly Ser Phe Ser Asp Glu Met Asn Thr Ile Leu Asp Asn
    50                  55                  60

Leu Ala Ala Arg Asp Phe Ile Asn Trp Leu Ile Gln Thr Lys Ile Thr
65                  70                  75                  80

Asp Arg Lys

<210> SEQ ID NO 71
<211> LENGTH: 83
<212> TYPE: PRT
<213> ORGANISM: Artificial Sequence
<220> FEATURE:

<223> OTHER INFORMATION: G1G2 mutant 19

<400> SEQUENCE: 71

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gln
            20                  25                  30

Ala Asp Phe Pro Thr Glu Ile Pro Ile Val Glu Glu Leu Gly Arg Gly
        35                  40                  45

His Ala Asp Gly Ser Phe Ser Asp Glu Met Asn Thr Ile Leu Asp Asn
    50                  55                  60

Leu Ala Ala Arg Asp Phe Ile Asn Trp Leu Ile Gln Thr Lys Ile Thr
65                  70                  75                  80

Asp Arg Lys

<210> SEQ ID NO 72
<211> LENGTH: 83
<212> TYPE: PRT
<213> ORGANISM: Artificial Sequence
<220> FEATURE:
<223> OTHER INFORMATION: G1G2 mutant 20

<400> SEQUENCE: 72

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gln
            20                  25                  30

Ala Asp Phe Pro Ser Asp Gly Pro Ile Val Glu Glu Leu Gly Arg Gly
        35                  40                  45

His Ala Asp Gly Ser Phe Ser Asp Glu Met Asn Thr Ile Leu Asp Asn
    50                  55                  60

Leu Ala Ala Arg Asp Phe Ile Asn Trp Leu Ile Gln Thr Lys Ile Thr
65                  70                  75                  80

Asp Arg Lys

<210> SEQ ID NO 73
<211> LENGTH: 83
<212> TYPE: PRT
<213> ORGANISM: Artificial Sequence
<220> FEATURE:
<223> OTHER INFORMATION: G1G2 mutant 21

<400> SEQUENCE: 73

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gln
            20                  25                  30

Ala Asp Phe Pro Thr Glu Val Pro Ile Val Glu Glu Leu Gly Arg Gly
        35                  40                  45

His Ala Asp Gly Ser Phe Ser Asp Glu Met Asn Thr Ile Leu Asp Asn
    50                  55                  60

Leu Ala Ala Arg Asp Phe Ile Asn Trp Leu Ile Gln Thr Lys Ile Thr
65                  70                  75                  80

Asp Arg Lys

<210> SEQ ID NO 74
<211> LENGTH: 128
<212> TYPE: PRT

<213> ORGANISM: Artificial Sequence
<220> FEATURE:
<223> OTHER INFORMATION: oxyntomodulin-GLP-1-GLP-2 fusion (OG1G2)

<400> SEQUENCE: 74

```
His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Lys Arg His Asp Glu Phe Glu Arg His Ala Glu
        35                  40                  45

Gly Thr Phe Thr Ser Asp Val Ser Ser Tyr Leu Glu Gly Gln Ala Ala
    50                  55                  60

Lys Glu Phe Ile Ala Trp Leu Val Lys Gly Arg Gly Arg Arg Asp Phe
65                  70                  75                  80

Pro Glu Glu Val Ala Ile Val Glu Glu Leu Gly Arg Arg His Ala Asp
                85                  90                  95

Gly Ser Phe Ser Asp Glu Met Asn Thr Ile Leu Asp Asn Leu Ala Ala
            100                 105                 110

Arg Asp Phe Ile Asn Trp Leu Ile Gln Thr Lys Ile Thr Asp Arg Lys
        115                 120                 125
```

<210> SEQ ID NO 75
<211> LENGTH: 131
<212> TYPE: PRT
<213> ORGANISM: Artificial Sequence
<220> FEATURE:
<223> OTHER INFORMATION: OG1G2 mutant 1
<220> FEATURE:
<221> NAME/KEY: VARIANT
<222> LOCATION: (30)..(30)
<223> OTHER INFORMATION: Xaa is Asn, Lys, Ala, Gly, Ser, Thr, or Leu
<220> FEATURE:
<221> NAME/KEY: VARIANT
<222> LOCATION: (31)..(31)
<223> OTHER INFORMATION: Xaa is Arg, Gly, Ala, Ser, Thr, or Leu
<220> FEATURE:
<221> NAME/KEY: VARIANT
<222> LOCATION: (32)..(32)
<223> OTHER INFORMATION: Xaa is Asn, Ser, or Thr
<220> FEATURE:
<221> NAME/KEY: VARIANT
<222> LOCATION: (35)..(35)
<223> OTHER INFORMATION: Xaa is present or absent; when present, Xaa is
      Gly or Ala
<220> FEATURE:
<221> NAME/KEY: VARIANT
<222> LOCATION: (39)..(39)
<223> OTHER INFORMATION: Xaa is Lys or Pro
<220> FEATURE:
<221> NAME/KEY: VARIANT
<222> LOCATION: (40)..(40)
<223> OTHER INFORMATION: Xaa is Thr or Ser
<220> FEATURE:
<221> NAME/KEY: VARIANT
<222> LOCATION: (41)..(41)
<223> OTHER INFORMATION: Xaa is His, Ala, Gln, Asn, Gly, or any
      uncharged amino acid
<220> FEATURE:
<221> NAME/KEY: VARIANT
<222> LOCATION: (42)..(42)
<223> OTHER INFORMATION: Xaa is Asp, Gly, Ala, Asn, Glu, or any
      uncharged amino acid
<220> FEATURE:
<221> NAME/KEY: VARIANT
<222> LOCATION: (43)..(43)
<223> OTHER INFORMATION: Xaa is Glu, Ala, Gly, Met, or any uncharged
      amino acid
<220> FEATURE:
<221> NAME/KEY: VARIANT

```
<222> LOCATION: (46)..(46)
<223> OTHER INFORMATION: Xaa is Arg, Ala, Gly, Ser, Thr, Val, Ile, Leu,
      or any uncharged amino acid
<220> FEATURE:
<221> NAME/KEY: VARIANT
<222> LOCATION: (78)..(78)
<223> OTHER INFORMATION: Xaa is Arg, Ala, Gly, Val, Ile, Leu, Gln, or
      Pro
<220> FEATURE:
<221> NAME/KEY: VARIANT
<222> LOCATION: (79)..(79)
<223> OTHER INFORMATION: Xaa is Arg, Ala, Gly, Val, Ile, Leu, Gln, or
      Pro
<220> FEATURE:
<221> NAME/KEY: VARIANT
<222> LOCATION: (83)..(83)
<223> OTHER INFORMATION: Xaa is Thr, Ser, or Glu
<220> FEATURE:
<221> NAME/KEY: VARIANT
<222> LOCATION: (84)..(84)
<223> OTHER INFORMATION: Xaa is Glu, Ser, Thr, Gln, Ile, Val, Leu, or
      uncharged amino acid
<220> FEATURE:
<221> NAME/KEY: VARIANT
<222> LOCATION: (85)..(85)
<223> OTHER INFORMATION: Xaa is present or absent; when present, Xaa is
      Ser, Asn, Tyr, or Val
<220> FEATURE:
<221> NAME/KEY: VARIANT
<222> LOCATION: (86)..(86)
<223> OTHER INFORMATION: Xaa is present when Xaa at residue 85 is Ser
      or Asn; otherwise Xaa is absent; when present, Xaa is Leu when
      Xaa at residue 85 is Ser, and Xaa is Thr when Xaa at residue 85
      is Asn
<220> FEATURE:
<221> NAME/KEY: VARIANT
<222> LOCATION: (87)..(87)
<223> OTHER INFORMATION: Xaa is present when Xaa at residue 85 is Ser
      and Xaa at residue 86 is Leu; otherwise Xaa is absent; when
      present, Xaa is Pro
<220> FEATURE:
<221> NAME/KEY: VARIANT
<222> LOCATION: (88)..(88)
<223> OTHER INFORMATION: Xaa is Pro, Ala, Ile, Val, or Gly
<220> FEATURE:
<221> NAME/KEY: VARIANT
<222> LOCATION: (89)..(89)
<223> OTHER INFORMATION: Xaa is Glu, Tyr, Ile, Asn, Ala, Phe, Gly, or
      any uncharged amino acid
<220> FEATURE:
<221> NAME/KEY: VARIANT
<222> LOCATION: (95)..(95)
<223> OTHER INFORMATION: Xaa is Arg, Ala, Gly, Ser, Thr, Val, Ile, Leu,
      or any uncharged amino acid
<220> FEATURE:
<221> NAME/KEY: VARIANT
<222> LOCATION: (96)..(96)
<223> OTHER INFORMATION: Xaa is Arg, Ala, Gly, Ser, Thr, Val, Ile, Leu,
      or any uncharged amino acid

<400> SEQUENCE: 75

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Xaa Xaa Xaa
            20                  25                  30

Arg Asn Xaa Asn Ile Ala Xaa Xaa Xaa Xaa Xaa Phe Glu Xaa His Ala
        35                  40                  45

Glu Gly Thr Phe Thr Ser Asp Val Ser Ser Tyr Leu Glu Gly Gln Ala
    50                  55                  60

Ala Lys Glu Phe Ile Ala Trp Leu Val Lys Gly Arg Gly Xaa Xaa Asp
65                  70                  75                  80

Phe Pro Xaa Xaa Xaa Xaa Xaa Xaa Xaa Val Glu Glu Leu Gly Xaa Xaa
                85                  90                  95
```

```
His Ala Asp Gly Ser Phe Ser Asp Glu Met Asn Thr Ile Leu Asp Asn
            100                 105                 110

Leu Ala Ala Arg Asp Phe Ile Asn Trp Leu Ile Gln Thr Lys Ile Thr
        115                 120                 125

Asp Arg Lys
    130

<210> SEQ ID NO 76
<211> LENGTH: 132
<212> TYPE: PRT
<213> ORGANISM: Artificial Sequence
<220> FEATURE:
<223> OTHER INFORMATION: OG1G2 mutant 2

<400> SEQUENCE: 76

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Asn Ala Asn
            20                  25                  30

Arg Ser Gly Asp Ile Pro Lys Ala His Asp Glu Phe Glu Ala His Ala
        35                  40                  45

Glu Gly Thr Phe Thr Ser Asp Val Ser Ser Tyr Leu Glu Gly Gln Ala
    50                  55                  60

Ala Lys Glu Phe Ile Ala Trp Leu Val Lys Gly Arg Gly Gln Pro Asp
65                  70                  75                  80

Phe Pro Glu Gly Ser Leu Pro Val Ala Ile Val Glu Glu Leu Gly Arg
                85                  90                  95

Gly His Ala Asp Gly Ser Phe Ser Asp Glu Met Asn Thr Ile Leu Asp
            100                 105                 110

Asn Leu Ala Ala Arg Asp Phe Ile Asn Trp Leu Ile Gln Thr Lys Ile
        115                 120                 125

Thr Asp Arg Lys
    130

<210> SEQ ID NO 77
<211> LENGTH: 131
<212> TYPE: PRT
<213> ORGANISM: Artificial Sequence
<220> FEATURE:
<223> OTHER INFORMATION: OG1G2 mutant 3

<400> SEQUENCE: 77

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Asn Ala Asn
            20                  25                  30

Arg Ser Asp Ile Pro Lys Ala His Asp Glu Phe Glu Ala His Ala Glu
        35                  40                  45

Gly Thr Phe Thr Ser Asp Val Ser Ser Tyr Leu Glu Gly Gln Ala Ala
    50                  55                  60

Lys Glu Phe Ile Ala Trp Leu Val Lys Gly Arg Gly Gln Pro Asp Phe
65                  70                  75                  80

Pro Glu Gly Ser Leu Pro Val Ala Ile Val Glu Glu Leu Gly Arg Gly
                85                  90                  95

His Ala Asp Gly Ser Phe Ser Asp Glu Met Asn Thr Ile Leu Asp Asn
            100                 105                 110

Leu Ala Ala Arg Asp Phe Ile Asn Trp Leu Ile Gln Thr Lys Ile Thr
```

Asp Arg Lys
    130

<210> SEQ ID NO 78
<211> LENGTH: 131
<212> TYPE: PRT
<213> ORGANISM: Artificial Sequence
<220> FEATURE:
<223> OTHER INFORMATION: OG1G2 mutant 4

<400> SEQUENCE: 78

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Asn Ala Asn
            20                  25                  30

Ala Asn Asn Ile Ala Lys Ala His Asp Glu Phe Glu Ala His Ala Glu
        35                  40                  45

Gly Thr Phe Thr Ser Asp Val Ser Ser Tyr Leu Glu Gly Gln Ala Ala
    50                  55                  60

Lys Glu Phe Ile Ala Trp Leu Val Lys Gly Arg Gly Gln Pro Asp Phe
65                  70                  75                  80

Pro Thr Gly Ser Leu Pro Val Ala Ile Val Glu Glu Leu Gly Arg Gly
                85                  90                  95

His Ala Asp Gly Ser Phe Ser Asp Glu Met Asn Thr Ile Leu Asp Asn
            100                 105                 110

Leu Ala Ala Arg Asp Phe Ile Asn Trp Leu Ile Gln Thr Lys Ile Thr
        115                 120                 125

Asp Arg Lys
    130

<210> SEQ ID NO 79
<211> LENGTH: 131
<212> TYPE: PRT
<213> ORGANISM: Artificial Sequence
<220> FEATURE:
<223> OTHER INFORMATION: OG1G2 mutant 5

<400> SEQUENCE: 79

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Asn Ala Asn
            20                  25                  30

Ala Asn Asn Ile Ala Lys Ala His Asp Glu Phe Glu Ala His Ala Glu
        35                  40                  45

Gly Thr Phe Thr Ser Asp Val Ser Ser Tyr Leu Glu Gly Gln Ala Ala
    50                  55                  60

Lys Glu Phe Ile Ala Trp Leu Val Lys Gly Arg Gly Gln Pro Asp Phe
65                  70                  75                  80

Pro Thr Thr Ser Glu Pro Val Ala Ile Val Glu Glu Leu Gly Arg Gly
                85                  90                  95

His Ala Asp Gly Ser Phe Ser Asp Glu Met Asn Thr Ile Leu Asp Asn
            100                 105                 110

Leu Ala Ala Arg Asp Phe Ile Asn Trp Leu Ile Gln Thr Lys Ile Thr
        115                 120                 125

Asp Arg Lys
    130

<210> SEQ ID NO 80
<211> LENGTH: 131
<212> TYPE: PRT
<213> ORGANISM: Artificial Sequence
<220> FEATURE:
<223> OTHER INFORMATION: OG1G2 mutant 6

<400> SEQUENCE: 80

```
His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Asn Ala Asn
            20                  25                  30

Ala Asn Asn Ile Ala Lys Ala His Asp Glu Phe Glu Ala His Ala Glu
        35                  40                  45

Gly Thr Phe Thr Ser Asp Val Ser Ser Tyr Leu Glu Gly Gln Ala Ala
    50                  55                  60

Lys Glu Phe Ile Ala Trp Leu Val Lys Gly Arg Gly Gln Pro Asp Phe
65                  70                  75                  80

Pro Thr Ala Val Ile Pro Val Ala Ile Val Glu Glu Leu Gly Arg Gly
                85                  90                  95

His Ala Asp Gly Ser Phe Ser Asp Glu Met Asn Thr Ile Leu Asp Asn
            100                 105                 110

Leu Ala Ala Arg Asp Phe Ile Asn Trp Leu Ile Gln Thr Lys Ile Thr
        115                 120                 125

Asp Arg Lys
    130
```

<210> SEQ ID NO 81
<211> LENGTH: 131
<212> TYPE: PRT
<213> ORGANISM: Artificial Sequence
<220> FEATURE:
<223> OTHER INFORMATION: OG1G2 mutant 7

<400> SEQUENCE: 81

```
His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Asn Ala Asn
            20                  25                  30

Ala Asn Asn Ile Ala Lys Ala His Asp Glu Phe Glu Ala His Ala Glu
        35                  40                  45

Gly Thr Phe Thr Ser Asp Val Ser Ser Tyr Leu Glu Gly Gln Ala Ala
    50                  55                  60

Lys Glu Phe Ile Ala Trp Leu Val Lys Gly Arg Gly Gln Pro Asp Phe
65                  70                  75                  80

Pro Gly Ser Thr Ala Pro Val Ala Ile Val Glu Glu Leu Gly Arg Gly
                85                  90                  95

His Ala Asp Gly Ser Phe Ser Asp Glu Met Asn Thr Ile Leu Asp Asn
            100                 105                 110

Leu Ala Ala Arg Asp Phe Ile Asn Trp Leu Ile Gln Thr Lys Ile Thr
        115                 120                 125

Asp Arg Lys
    130
```

<210> SEQ ID NO 82
<211> LENGTH: 131
<212> TYPE: PRT
<213> ORGANISM: Artificial Sequence

```
<220> FEATURE:
<223> OTHER INFORMATION: OG1G2 mutant 8

<400> SEQUENCE: 82

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Asn Ala Asn
            20                  25                  30

Ala Asn Asn Ile Ala Lys Ala His Asp Glu Phe Glu Ala His Ala Glu
        35                  40                  45

Gly Thr Phe Thr Ser Asp Val Ser Ser Tyr Leu Glu Gly Gln Ala Ala
    50                  55                  60

Lys Glu Phe Ile Ala Trp Leu Val Lys Gly Arg Gly Gln Pro Asp Phe
65                  70                  75                  80

Pro Leu Thr Leu Glu Pro Val Ala Ile Val Glu Glu Leu Gly Arg Gly
                85                  90                  95

His Ala Asp Gly Ser Phe Ser Asp Glu Met Asn Thr Ile Leu Asp Asn
            100                 105                 110

Leu Ala Ala Arg Asp Phe Ile Asn Trp Leu Ile Gln Thr Lys Ile Thr
        115                 120                 125

Asp Arg Lys
    130

<210> SEQ ID NO 83
<211> LENGTH: 131
<212> TYPE: PRT
<213> ORGANISM: Artificial Sequence
<220> FEATURE:
<223> OTHER INFORMATION: OG1G2 mutant 9

<400> SEQUENCE: 83

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Asn Ala Asn
            20                  25                  30

Ala Asn Asn Ile Ala Lys Ala His Asp Glu Phe Glu Ala His Ala Glu
        35                  40                  45

Gly Thr Phe Thr Ser Asp Val Ser Ser Tyr Leu Glu Gly Gln Ala Ala
    50                  55                  60

Lys Glu Phe Ile Ala Trp Leu Val Lys Gly Arg Gly Gln Pro Asp Phe
65                  70                  75                  80

Pro Thr Ser Gly Glu Pro Val Ala Ile Val Glu Glu Leu Gly Arg Gly
                85                  90                  95

His Ala Asp Gly Ser Phe Ser Asp Glu Met Asn Thr Ile Leu Asp Asn
            100                 105                 110

Leu Ala Ala Arg Asp Phe Ile Asn Trp Leu Ile Gln Thr Lys Ile Thr
        115                 120                 125

Asp Arg Lys
    130

<210> SEQ ID NO 84
<211> LENGTH: 131
<212> TYPE: PRT
<213> ORGANISM: Artificial Sequence
<220> FEATURE:
<223> OTHER INFORMATION: OG1G2 mutant 10

<400> SEQUENCE: 84
```

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Asn Ala Asn
            20                  25                  30

Ala Asn Asn Ile Ala Lys Ala His Asp Glu Phe Glu Ala His Ala Glu
            35                  40                  45

Gly Thr Phe Thr Ser Asp Val Ser Ser Tyr Leu Glu Gly Gln Ala Ala
        50                  55                  60

Lys Glu Phe Ile Ala Trp Leu Val Lys Gly Arg Gly Gln Pro Asp Phe
65                  70                  75                  80

Pro Thr Ile Asn Thr Pro Val Ala Ile Val Glu Glu Leu Gly Arg Gly
                85                  90                  95

His Ala Asp Gly Ser Phe Ser Asp Glu Met Asn Thr Ile Leu Asp Asn
            100                 105                 110

Leu Ala Ala Arg Asp Phe Ile Asn Trp Leu Ile Gln Thr Lys Ile Thr
            115                 120                 125

Asp Arg Lys
    130

<210> SEQ ID NO 85
<211> LENGTH: 131
<212> TYPE: PRT
<213> ORGANISM: Artificial Sequence
<220> FEATURE:
<223> OTHER INFORMATION: OG1G2 mutant 11

<400> SEQUENCE: 85

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Asn Ala Asn
            20                  25                  30

Ala Asn Asn Ile Ala Lys Ala His Asp Glu Phe Glu Ala His Ala Glu
            35                  40                  45

Gly Thr Phe Thr Ser Asp Val Ser Ser Tyr Leu Glu Gly Gln Ala Ala
        50                  55                  60

Lys Glu Phe Ile Ala Trp Leu Val Lys Gly Arg Gly Gln Pro Asp Phe
65                  70                  75                  80

Pro Thr Thr Leu Tyr Pro Val Ala Ile Val Glu Glu Leu Gly Arg Gly
                85                  90                  95

His Ala Asp Gly Ser Phe Ser Asp Glu Met Asn Thr Ile Leu Asp Asn
            100                 105                 110

Leu Ala Ala Arg Asp Phe Ile Asn Trp Leu Ile Gln Thr Lys Ile Thr
            115                 120                 125

Asp Arg Lys
    130

<210> SEQ ID NO 86
<211> LENGTH: 131
<212> TYPE: PRT
<213> ORGANISM: Artificial Sequence
<220> FEATURE:
<223> OTHER INFORMATION: OG1G2 mutant 12

<400> SEQUENCE: 86

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Asn Ala Asn
            20                  25                  30

```
Ala Asn Asn Ile Ala Lys Ala His Asp Glu Phe Glu Ala His Ala Glu
            35                  40                  45

Gly Thr Phe Thr Ser Asp Val Ser Ser Tyr Leu Glu Gly Gln Ala Ala
     50                  55                  60

Lys Glu Phe Ile Ala Trp Leu Val Lys Gly Arg Gly Gln Pro Asp Phe
 65                  70                  75                  80

Pro Glu Gly Ser Leu Pro Thr Ala Ile Val Glu Glu Leu Gly Arg Gly
                 85                  90                  95

His Ala Asp Gly Ser Phe Ser Asp Glu Met Asn Thr Ile Leu Asp Asn
                100                 105                 110

Leu Ala Ala Arg Asp Phe Ile Asn Trp Leu Ile Gln Thr Lys Ile Thr
                115                 120                 125

Asp Arg Lys
        130

<210> SEQ ID NO 87
<211> LENGTH: 131
<212> TYPE: PRT
<213> ORGANISM: Artificial Sequence
<220> FEATURE:
<223> OTHER INFORMATION: OG1G2 mutant 13

<400> SEQUENCE: 87

His Ser Gln Gly Thr Phe Thr Ser Asp Tyr Ser Lys Tyr Leu Asp Ser
 1               5                  10                  15

Arg Arg Ala Gln Asp Phe Val Gln Trp Leu Met Asn Thr Asn Ala Asn
             20                  25                  30

Ala Asn Asn Ile Ala Lys Ala His Asp Glu Phe Glu Ala His Ala Glu
            35                  40                  45

Gly Thr Phe Thr Ser Asp Val Ser Ser Tyr Leu Glu Gly Gln Ala Ala
     50                  55                  60

Lys Glu Phe Ile Ala Trp Leu Val Lys Gly Arg Gly Gln Pro Asp Phe
 65                  70                  75                  80

Pro Glu Gly Ser Leu Pro Thr Ile Asn Thr Glu Glu Leu Gly Arg Gly
                 85                  90                  95

His Ala Asp Gly Ser Phe Ser Asp Glu Met Asn Thr Ile Leu Asp Asn
                100                 105                 110

Leu Ala Ala Arg Asp Phe Ile Asn Trp Leu Ile Gln Thr Lys Ile Thr
                115                 120                 125

Asp Arg Lys
        130

<210> SEQ ID NO 88
<211> LENGTH: 131
<212> TYPE: PRT
<213> ORGANISM: Artificial Sequence
<220> FEATURE:
<223> OTHER INFORMATION: OG1G2 mutant 14

<400> SEQUENCE: 88

His Ser Gln Gly Thr Phe Thr Ser Asp Tyr Ser Lys Tyr Leu Asp Ser
 1               5                  10                  15

Arg Arg Ala Gln Asp Phe Val Gln Trp Leu Met Asn Thr Asn Ala Asn
             20                  25                  30

Ala Asn Asn Ile Ala Lys Ala His Asp Glu Phe Glu Ala His Ala Glu
            35                  40                  45

Gly Thr Phe Thr Ser Asp Val Ser Ser Tyr Leu Glu Gly Gln Ala Ala
```

```
                            50                  55                  60

Lys Glu Phe Ile Ala Trp Leu Val Lys Gly Arg Gly Gln Pro Asp Phe
 65                  70                  75                  80

Pro Glu Gly Ser Leu Pro Thr Gln Ala Val Glu Glu Leu Gly Arg Gly
                 85                  90                  95

His Ala Asp Gly Ser Phe Ser Asp Glu Met Asn Thr Ile Leu Asp Asn
            100                 105                 110

Leu Ala Ala Arg Asp Phe Ile Asn Trp Leu Ile Gln Thr Lys Ile Thr
            115                 120                 125

Asp Arg Lys
        130

<210> SEQ ID NO 89
<211> LENGTH: 128
<212> TYPE: PRT
<213> ORGANISM: Artificial Sequence
<220> FEATURE:
<223> OTHER INFORMATION: OG1G2 mutant 15

<400> SEQUENCE: 89

His Ser Gln Gly Thr Phe Thr Ser Asp Tyr Ser Lys Tyr Leu Asp Ser
 1               5                  10                  15

Arg Arg Ala Gln Asp Phe Val Gln Trp Leu Met Asn Thr Asn Ala Asn
             20                  25                  30

Ala Asn Asn Ile Ala Lys Ala His Asp Glu Phe Glu Ala His Ala Glu
         35                  40                  45

Gly Thr Phe Thr Ser Asp Val Ser Ser Tyr Leu Glu Gly Gln Ala Ala
     50                  55                  60

Lys Glu Phe Ile Ala Trp Leu Val Lys Gly Arg Gly Gln Ala Asp Phe
 65                  70                  75                  80

Pro Glu Glu Val Pro Thr Val Glu Glu Leu Gly Arg Gly His Ala Asp
                 85                  90                  95

Gly Ser Phe Ser Asp Glu Met Asn Thr Ile Leu Asp Asn Leu Ala Ala
            100                 105                 110

Arg Asp Phe Ile Asn Trp Leu Ile Gln Thr Lys Ile Thr Asp Arg Lys
            115                 120                 125

<210> SEQ ID NO 90
<211> LENGTH: 128
<212> TYPE: PRT
<213> ORGANISM: Artificial Sequence
<220> FEATURE:
<223> OTHER INFORMATION: OG1G2 mutant 16

<400> SEQUENCE: 90

His Ser Gln Gly Thr Phe Thr Ser Asp Tyr Ser Lys Tyr Leu Asp Ser
 1               5                  10                  15

Arg Arg Ala Gln Asp Phe Val Gln Trp Leu Met Asn Thr Asn Ala Asn
             20                  25                  30

Ala Asn Asn Ile Ala Lys Ala His Asp Glu Phe Glu Ala His Ala Glu
         35                  40                  45

Gly Thr Phe Thr Ser Asp Val Ser Ser Tyr Leu Glu Gly Gln Ala Ala
     50                  55                  60

Lys Glu Phe Ile Ala Trp Leu Val Lys Gly Arg Gly Gln Ala Asp Phe
 65                  70                  75                  80

Pro Glu Glu Val Pro Thr Ile Asn Thr Leu Gly Arg Gly His Ala Asp
                 85                  90                  95
```

```
Gly Ser Phe Ser Asp Glu Met Asn Thr Ile Leu Asp Asn Leu Ala Ala
            100                 105                 110

Arg Asp Phe Ile Asn Trp Leu Ile Gln Thr Lys Ile Thr Asp Arg Lys
        115                 120                 125
```

<210> SEQ ID NO 91
<211> LENGTH: 128
<212> TYPE: PRT
<213> ORGANISM: Artificial Sequence
<220> FEATURE:
<223> OTHER INFORMATION: OG1G2 mutant 17

<400> SEQUENCE: 91

```
His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Asn Ala Asn
            20                  25                  30

Ala Asn Asn Ile Ala Lys Ala His Asp Glu Phe Glu Ala His Ala Glu
        35                  40                  45

Gly Thr Phe Thr Ser Asp Val Ser Ser Tyr Leu Glu Gly Gln Ala Ala
    50                  55                  60

Lys Glu Phe Ile Ala Trp Leu Val Lys Gly Arg Gly Gln Ala Asp Phe
65                  70                  75                  80

Pro Glu Glu Val Pro Thr Gln Gly Ala Leu Gly Arg Gly His Ala Asp
            85                  90                  95

Gly Ser Phe Ser Asp Glu Met Asn Thr Ile Leu Asp Asn Leu Ala Ala
            100                 105                 110

Arg Asp Phe Ile Asn Trp Leu Ile Gln Thr Lys Ile Thr Asp Arg Lys
        115                 120                 125
```

<210> SEQ ID NO 92
<211> LENGTH: 128
<212> TYPE: PRT
<213> ORGANISM: Artificial Sequence
<220> FEATURE:
<223> OTHER INFORMATION: OG1G2 mutant 18

<400> SEQUENCE: 92

```
His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Asn Ala Asn
            20                  25                  30

Ala Asn Asn Ile Ala Lys Ala His Asp Glu Phe Glu Ala His Ala Glu
        35                  40                  45

Gly Thr Phe Thr Ser Asp Val Ser Ser Tyr Leu Glu Gly Gln Ala Ala
    50                  55                  60

Lys Glu Phe Ile Ala Trp Leu Val Lys Gly Arg Gly Gln Ala Asp Phe
65                  70                  75                  80

Pro Glu Glu Val Pro Thr Thr Leu Tyr Leu Gly Arg Gly His Ala Asp
            85                  90                  95

Gly Ser Phe Ser Asp Glu Met Asn Thr Ile Leu Asp Asn Leu Ala Ala
            100                 105                 110

Arg Asp Phe Ile Asn Trp Leu Ile Gln Thr Lys Ile Thr Asp Arg Lys
        115                 120                 125
```

<210> SEQ ID NO 93
<211> LENGTH: 128
<212> TYPE: PRT
<213> ORGANISM: Artificial Sequence

```
<220> FEATURE:
<223> OTHER INFORMATION: OG1G2 mutant 19

<400> SEQUENCE: 93

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Asn Ala Asn
            20                  25                  30

Ala Asn Asn Ile Ala Lys Ala His Asp Glu Phe Glu Ala His Ala Glu
        35                  40                  45

Gly Thr Phe Thr Ser Asp Val Ser Ser Tyr Leu Glu Gly Gln Ala Ala
    50                  55                  60

Lys Glu Phe Ile Ala Trp Leu Val Lys Gly Arg Gly Gln Ala Asp Phe
65                  70                  75                  80

Pro Thr Val Leu Pro Ile Val Glu Glu Leu Gly Arg Gly His Ala Asp
                85                  90                  95

Gly Ser Phe Ser Asp Glu Met Asn Thr Ile Leu Asp Asn Leu Ala Ala
            100                 105                 110

Arg Asp Phe Ile Asn Trp Leu Ile Gln Thr Lys Ile Thr Asp Arg Lys
        115                 120                 125

<210> SEQ ID NO 94
<211> LENGTH: 128
<212> TYPE: PRT
<213> ORGANISM: Artificial Sequence
<220> FEATURE:
<223> OTHER INFORMATION: OG1G2 mutant 20

<400> SEQUENCE: 94

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Asn Ala Asn
            20                  25                  30

Ala Asn Asn Ile Ala Lys Ala His Asp Glu Phe Glu Ala His Ala Glu
        35                  40                  45

Gly Thr Phe Thr Ser Asp Val Ser Ser Tyr Leu Glu Gly Gln Ala Ala
    50                  55                  60

Lys Glu Phe Ile Ala Trp Leu Val Lys Gly Arg Gly Gln Ala Asp Phe
65                  70                  75                  80

Pro Thr Glu Ile Pro Ile Val Glu Glu Leu Gly Arg Gly His Ala Asp
                85                  90                  95

Gly Ser Phe Ser Asp Glu Met Asn Thr Ile Leu Asp Asn Leu Ala Ala
            100                 105                 110

Arg Asp Phe Ile Asn Trp Leu Ile Gln Thr Lys Ile Thr Asp Arg Lys
        115                 120                 125

<210> SEQ ID NO 95
<211> LENGTH: 128
<212> TYPE: PRT
<213> ORGANISM: Artificial Sequence
<220> FEATURE:
<223> OTHER INFORMATION: OG1G2 mutant 21

<400> SEQUENCE: 95

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Asn Ala Asn
            20                  25                  30
```

```
Ala Asn Asn Ile Ala Lys Ala His Asp Glu Phe Glu Ala His Ala Glu
            35                  40                  45
Gly Thr Phe Thr Ser Asp Val Ser Ser Tyr Leu Glu Gly Gln Ala Ala
 50                      55                  60
Lys Glu Phe Ile Ala Trp Leu Val Lys Gly Arg Gly Gln Ala Asp Phe
65                  70                  75                  80
Pro Ser Asp Gly Pro Ile Val Glu Glu Leu Gly Arg Gly His Ala Asp
                85                  90                  95
Gly Ser Phe Ser Asp Glu Met Asn Thr Ile Leu Asp Asn Leu Ala Ala
                100                 105                 110
Arg Asp Phe Ile Asn Trp Leu Ile Gln Thr Lys Ile Thr Asp Arg Lys
                115                 120                 125

<210> SEQ ID NO 96
<211> LENGTH: 128
<212> TYPE: PRT
<213> ORGANISM: Artificial Sequence
<220> FEATURE:
<223> OTHER INFORMATION: OG1G2 mutant 22

<400> SEQUENCE: 96

His Ser Gln Gly Thr Phe Thr Ser Asp Tyr Ser Lys Tyr Leu Asp Ser
1               5                   10                  15
Arg Arg Ala Gln Asp Phe Val Gln Trp Leu Met Asn Thr Asn Ala Asn
            20                  25                  30
Ala Asn Asn Ile Ala Lys Ala His Asp Glu Phe Glu Ala His Ala Glu
            35                  40                  45
Gly Thr Phe Thr Ser Asp Val Ser Ser Tyr Leu Glu Gly Gln Ala Ala
 50                      55                  60
Lys Glu Phe Ile Ala Trp Leu Val Lys Gly Arg Gly Gln Ala Asp Phe
65                  70                  75                  80
Pro Thr Glu Val Pro Ile Val Glu Glu Leu Gly Arg Gly His Ala Asp
                85                  90                  95
Gly Ser Phe Ser Asp Glu Met Asn Thr Ile Leu Asp Asn Leu Ala Ala
                100                 105                 110
Arg Asp Phe Ile Asn Trp Leu Ile Gln Thr Lys Ile Thr Asp Arg Lys
                115                 120                 125
```

HS--T$^{29}$NANANNIAKAHDEFEAHAE--
R$^{75}$ GQADFPSDGPIVEELGRGHADG— (SEQ ID NO: 95), and
HS--T$^{29}$NANANNIAKAHDEFEAHAE--
R$^{75}$ GQADFPTEVPIVEELGRGHADG— (SEQ ID NO: 96).
IN THE CLAIMS
Claim 1, at column 165, line 53, "and" should read "or"
Claim 5, at column 166, lines 51-64,
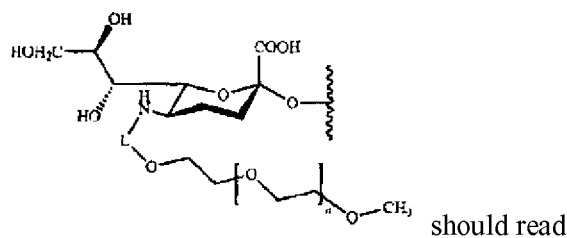 should read 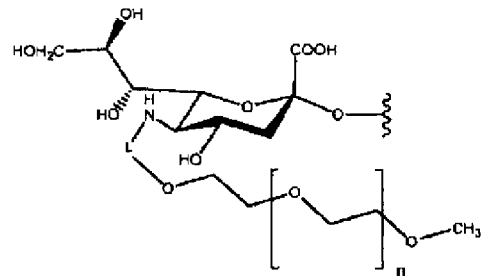

The invention claimed is:

1. A mutant glucagon-like peptide-1 (GLP-1)-glucagon-like peptide-2 (GLP-2) fusion peptide of formula

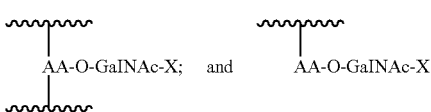

wherein AA is an amino acid with a side chain that comprises a hydroxyl moiety;
wherein X is a modifying group or a saccharyl moiety; and
wherein the mutant GLP-1-GLP-2 fusion peptide comprises an amino acid sequence selected from the group consisting of SEQ ID NOs: 54-73.

2. The mutant GLP-1-GLP-2 fusion peptide according to claim 1, wherein X comprises a group selected from sialyl, galactosyl and Gal-Sia moieties, wherein at least one of the sialyl, galactosyl and Gal-Sia comprises a modifying group.

3. The mutant GLP-1-GLP-2 fusion peptide according to claim 1, wherein X comprises poly(ethylene glycol).

4. The mutant GLP-1-GLP-2 fusion peptide according to claim 1, wherein X comprises monomethoxy-poly(ethylene glycol).

5. The mutant GLP-1-GLP-2 fusion peptide according to claim 4, wherein X comprises the structure:

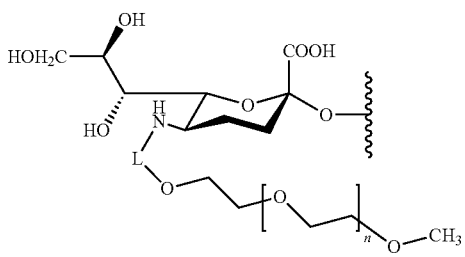

in which L is a substituted or unsubstituted alkyl or substituted or unsubstituted heteroalkyl group; and n is selected from the integers from 0 to about 500.

6. The mutant GLP-1-GLP-2 fusion peptide according to claim 4, wherein X comprises the structure:

[Chemical structure diagram]

in which s is selected from the integers from 0 to 20.

7. An isolated nucleic acid comprising a polynucleotide sequence encoding a mutant glucagon-like peptide-1 (GLP-1)-glucagon-like peptide-2 (GLP-2) fusion peptide, wherein the mutant GLP-1-GLP-2 fusion peptide comprises an O-linked glycosylation site that does not exist in the corresponding wild-type GLP-1 or GLP-2 peptide, and wherein the mutant GLP-1-GLP-2 fusion peptide comprises an amino acid sequence selected from the group consisting of SEQ ID NOs: 54-73.

8. The nucleic acid of claim 7, wherein the O-linked glycosylation site is present within the GLP-1 portion of the GLP-1-GLP-2 fusion peptide.

9. An expression cassette comprising the nucleic acid of claim 7.

10. A cell comprising the nucleic acid of claim 7.

11. A method for making a glycoconjugate of a mutant glucagon-like peptide-1 (GLP-1)-glucagon-like peptide-2 (GLP-2) fusion peptide, which comprises an O-linked glycosylation that does not exist in the corresponding wild-type GLP-1 or GLP-2 peptide, comprising the steps of:
(a) recombinantly producing the mutant GLP-1-GLP-2 fusion peptide, and
(b) enzymatically glycosylating the mutant GLP-1-GLP-2 fusion peptide with a modified sugar at the O-linked glycosylation site,
wherein the mutant GLP-1-GLP-2 fusion peptide comprises an amino acid sequence selected from the group consisting of SEQ ID NOs: 54-73.

12. A pharmaceutical composition of a mutant glucagon-like peptide-1 (GLP-1)-glucagon-like peptide-2 (GLP-2) fusion peptide comprising an effective amount of a mutant GLP-1-GLP-2 fusion peptide, which comprises an O-linked glycosylation site that does not exist in the corresponding wild-type GLP-1 or GLP-2 peptide, wherein the mutant GLP-1-GLP-2 fusion peptide is glycoconjugated with a modified sugar, and wherein the mutant GLP-1-GLP-2 fusion peptide comprises an amino acid sequence selected from the group consisting of SEQ ID NOs: 54-73.

13. The pharmaceutical composition according to claim 12, wherein the modified sugar is a sugar modified with a member selected from poly(ethylene glycol) and m-poly(ethylene glycol).

14. A method of providing glucagon-like peptide-1 (GLP-1) therapy to a subject in need of GLP-1 therapy, the method comprising, administering to the subject an amount of an O-linked glyco-PEG-ylated mutant glucagon-like peptide-1 (GLP-1)-glucagon-like peptide-2 (GLP-2) fusion peptide sufficient to provide a therapeutic effect, wherein the mutant GLP-1-GLP-2 fusion peptide comprises an amino acid sequence selected from the group consisting of SEQ ID NOs: 54-73, thereby providing GLP-1 therapy.

15. The method according to claim 14, wherein the O-linked glyco-PEG-ylated mutant GLP-1-GLP-2 fusion peptide is glyco-PEG-ylated on an amino acid residue not present in wild type GLP-1 or GLP-2 peptide.

16. The mutant GLP-1-GLP-2 fusion peptide according to claim 1, wherein AA has been introduced into GLP-1 or GLP-2 by mutation of a wild-type GLP-1 or GLP-2 amino acid sequence.

17. The mutant GLP-1-GLP-2 fusion peptide according to claim 1, wherein the mutant GLP-1-GLP-2 fusion peptide comprises the amino acid sequence of SEQ ID NO: 64.

* * * * *

UNITED STATES PATENT AND TRADEMARK OFFICE
CERTIFICATE OF CORRECTION

PATENT NO. : 8,791,066 B2
APPLICATION NO. : 13/541185
DATED : July 29, 2014
INVENTOR(S) : Shawn DeFrees Page 1 of 4

It is certified that error appears in the above-identified patent and that said Letters Patent is hereby corrected as shown below:

IN THE SPECIFICATION

Column 15, lines 40-41, (HGVTSAPDTRPAPGSTAPPA) should read (HGVTSAPDTRPAPGSTAPPA)

Column 15, line 52, (TAPPAHGVTSAPDTRPAPGSTAPP should read (TAPPAHGVTSAPDTRPAPGSTAPP Column 16, lines 41-56,

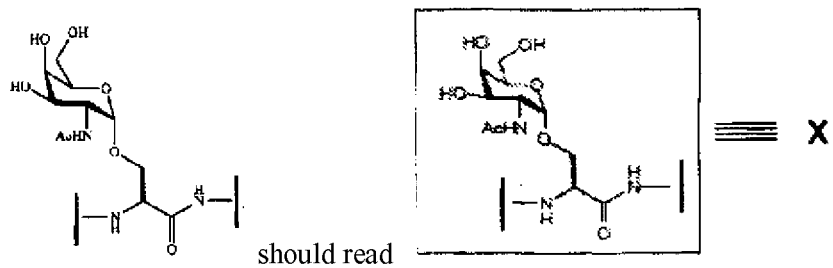

should read

Column 18, line 27, $T^{29}$BJJ'RN(Z')$_a$NIAOUXX'O'FEZHAE should read $T^{29}$BJJ'RN(Z')$_a$NIAOUXX'O'FEZHAE

Column 18, lines 47-62, the text should read as follows (wherein the threonine residue at amino acid position 39 of each of the sequences is in bold text)

--$T^{29}$NANRNNIAPTHDEFEAHAE (SEQ ID NO: 37)--,
--$T^{29}$NANRNNIAPTQDEFEAHAE (SEQ ID NO: 38)--,
--$T^{29}$NANRNNIAPTTDEFEAHAE (SEQ ID NO: 39)--,
--$T^{29}$NANRNNIAPTQGEFEAHAE (SEQ ID NO: 40)--,
--$T^{29}$NANRNNIAPTQGAFEAHAE (SEQ ID NO: 41)--,

Signed and Sealed this
Third Day of February, 2015

Michelle K. Lee
*Deputy Director of the United States Patent and Trademark Office*

--$T^{29}$NANRNNIAPTQGAMPAHAE (SEQ ID NO: 42)--,
--$T^{29}$ARNRNNIAPTQGAMEAHAE (SEQ ID NO: 43)--,
--$T^{29}$NANRNNIAPTINTFEAHAE (SEQ ID NO: 44)--,
--$T^{29}$NANRNNIAPTQAYSEGHAE (SEQ ID NO: 45)--,
--$T^{29}$NANRNNIAPTQAYFEGHAE (SEQ ID NO: 46)--,
--$T^{29}$NANRNNIAPTTASFEGHAE (SEQ ID NO: 47)--,
--$T^{29}$NANRNNIAPTTLYVEGHAE (SEQ ID NO: 48)--,
--$T^{29}$ARNRNNIAPTINTFEGHAE (SEQ ID NO: 49)--,
--$T^{29}$NANRNNIAPTINTFEGHAE (SEQ ID NO: 50)--, and
--$T^{29}$NANRSGDIPTINTFEGHAE (SEQ ID NO: 51)-.

Column 19, line 14, HX"--$R^{30}$GBB'DFPOU(O')$_a$JJ'VEELGZEHADG should read
HX"--$R^{30}$GBB'DFPOU(O')$_a$JJ'VEELGZZ'HADG Column 19, line 32, through column 20, line 4, the text should read as follows (wherein certain threonine and serine residues within the amino acid sequences are in bold text)

HS--$R^{30}$GQPDFPEGSLPVAIVEELGRGHADG— (SEQ ID NO: 54),
HS--$R^{30}$GQPDFPTGSLPVAIVEELGRGHADG— (SEQ ID NO: 55),
HS--$R^{30}$GQPDFPTTSEPVAIVEELGRGHADG— (SEQ ID NO: 56),
HS--$R^{30}$GQPDFPTAVIPVAIVEELGRGHADG— (SEQ ID NO: 57),
HS--$R^{30}$GQPDFPGSTAPVAIVEELGRGHADG— (SEQ ID NO: 58),
HS--$R^{30}$GQPDFPLTLEPVAIVEELGRGHADG— (SEQ ID NO: 59),
HS--$R^{30}$GQPDFPTSGEPVAIVEELGRGHADG— (SEQ ID NO: 60),
HS--$R^{30}$GQPDFPTINTPVAIVEELGRGHADG— (SEQ ID NO: 61),
HS--$R^{30}$GQPDFPTTLYPVAIVEELGRGHADG— (SEQ ID NO: 62),
HS--$R^{30}$GQPDFPEGSLPTAIVEELGRGHADG— (SEQ ID NO: 63),
HS--$R^{30}$GQPDFPEGSLPTINTEELGRGHADG— (SEQ ID NO: 64),
HS--$R^{30}$GQPDFPEGSLPTQAVEELGRGHADG— (SEQ ID NO: 65),
HS--$R^{30}$GQADFPEEVPTVEELGRGHADG— (SEQ ID NO: 66),
HS--$R^{30}$GQADFPEEVPTINTLGRGHADG— (SEQ ID NO: 67),
HS--$R^{30}$GQADFPEEVPTQGALGRGHADG— (SEQ ID NO: 68),
HS--$R^{30}$GQADFPEEVPTTLYLGRGHADG— (SEQ ID NO: 69),
HS--$R^{30}$GQADFPTVLPIVEELGRGHADG— (SEQ ID NO: 70),
HS--$R^{30}$GQADFPTEIPIVEELGRGHADG— (SEQ ID NO: 71),
HS--$R^{30}$GQADFPSDGPIVEELGRGHADG— (SEQ ID NO: 72), and
HS--$R^{30}$GQADFPTEVPIVEELGRGHADG— (SEQ ID NO: 73).

Column 20, lines 26-27,

HS--$T^{29}$BJJ'RN(Z')$_a$NIAOUXX'O'FEZHAE--
$R^{76}$GB'B"DFPO"U' (O'")$_a$J"J'"VEELGX'"Z"HADG-- should read

HS--$T^{29}$BJJ'RN(Z')$_a$NIAOUXX'O'FEZHAE--
$R^{76}$GB'B"DFPO"U' (O'")$_a$J"J'"VEELGX'"Z"HADG--

Column 20, line 55, through column 21, line 52, the text should read as follows (wherein certain amino acid residues within the amino acid sequences are in bold text)

HS--T$^{29}$NANRSGDIPKAHDEFEAHAE--
R$^{76}$GQPDFPEGSLPVAIVEELGRGHADG— (SEQ ID NO: 76),

HS--T$^{29}$NANRSDIPKAHDEFEAHAE--
R$^{75}$GQPDFPEGSLPVAIVEELGRGHADG— (SEQ ID NO: 77),

HS--T$^{29}$NANANNIAKAHDEFEAHAE--
R$^{75}$GQPDFPTGSLPVAIVEELGRGHADG— (SEQ ID NO: 78),

HS--T$^{29}$NANANNIAKAHDEFEAHAE--
R$^{75}$GQPDFPTTSEPVAIVEELGRGHADG— (SEQ ID NO: 79),

HS--T$^{29}$NANANNIAKAHDEFEAHAE--
R$^{75}$GQPDFPTAVIPVAIVEELGRGHADG— (SEQ ID NO: 80),

HS--T$^{29}$NANANNIAKAHDEFEAHAE--
R$^{75}$GQPDFPGSTAPVAIVEELGRGHADG— (SEQ ID NO: 81),

HS--T$^{29}$NANANNIAKAHDEFEAHAE--
R$^{75}$GQPDFPLTLEPVAIVEELGRGHADG— (SEQ ID NO: 82),

HS--T$^{29}$NANANNIAKAHDEFEAHAE--
R$^{75}$GQPDFPTSGEPVAIVEELGRGHADG— (SEQ ID NO: 83),

HS--T$^{29}$NANANNIAKAHDEFEAHAE--
R$^{75}$GQPDFPTINTPVAIVEELGRGHADG— (SEQ ID NO: 84),

HS--T$^{29}$NANANNIAKAHDEFEAHAE--
R$^{75}$GQPDFPTTLYPVAIVEELGRGHADG— (SEQ ID NO: 85),

HS--T$^{29}$NANANNIAKAHDEFEAHAE--
R$^{75}$GQPDFPEGSLPTAIVEELGRGHADG— (SEQ ID NO: 86),

HS--T$^{29}$NANANNIAKAHDEFEAHAE--
R$^{75}$GQPDFPEGSLPTINTEELGRGHADG— (SEQ ID NO: 87),

HS--T$^{29}$NANANNIAKAHDEFEAHAE--
R$^{75}$GQPDFPEGSLPTQAVEELGRGHADG— (SEQ ID NO: 88),

HS--T$^{29}$NANANNIAKAHDEFEAHAE--
R$^{75}$GQADFPEEVPTVEELGRGHADG— (SEQ ID NO: 89),

HS--T$^{29}$NANANNIAKAHDEFEAHAE--
R$^{75}$GQADFPEEVPTINTLGRGHADG— (SEQ ID NO: 90),

HS--T$^{29}$NANANNIAKAHDEFEAHAE--
R$^{75}$GQADFPEEVPTQGALGRGHADG— (SEQ ID NO: 91),

HS--T$^{29}$NANANNIAKAHDEFEAHAE--
R$^{75}$GQADFPEEVPTTLYLGRGHADG— (SEQ ID NO: 92),

HS--T$^{29}$NANANNIAKAHDEFEAHAE--
R$^{75}$GQADFPTVLPIVEELGRGHADG— (SEQ ID NO: 93),

HS--T$^{29}$NANANNIAKAHDEFEAHAE--
R$^{75}$GQADFPTEIPIVEELGRGHADG— (SEQ ID NO: 94),